US008048893B2

(12) United States Patent
Genevois-Borella et al.

(10) Patent No.: US 8,048,893 B2
(45) Date of Patent: Nov. 1, 2011

(54) PYRAZOLYL DERIVATIVES, PREPARATION PROCESS AND INTERMEDIATES OF THIS PROCESS AS MEDICINAL PRODUCTS AND PHARMACEUTICAL COMPOSITIONS CONTAINING THEM

(75) Inventors: Arielle Genevois-Borella, Thiais (FR); Jean-Luc Malleron, Marcoussis (FR); Jean Bouquerel, Drancy (FR); Gilles Doerflinger, Les Ullis (FR); Andrees Bohme, Paris (FR); Gaetan Touyer, Chelles (FR); Jean-Francois Sabuco, Paris (FR); Corrine Terrier, Livry Gargan (FR); Serge Mignani, Chatenay-Malabry (FR); Michel Evers, LaQueue En Brie (FR); Youssef El-Ahmad, Creteil (FR)

(73) Assignee: Aventis Pharma SA, Antony (FR)

( * ) Notice: Subject to any disclaimer, the term of this patent is extended or adjusted under 35 U.S.C. 154(b) by 8 days.

(21) Appl. No.: 12/394,589

(22) Filed: Feb. 27, 2009

(65) Prior Publication Data
US 2009/0170833 A1   Jul. 2, 2009

Related U.S. Application Data

(63) Continuation of application No. 10/997,736, filed on Nov. 24, 2004, now Pat. No. 7,524,838.

(60) Provisional application No. 60/537,046, filed on Jan. 16, 2004.

(30) Foreign Application Priority Data

Nov. 25, 2003   (FR) ..................... 03 13775

(51) Int. Cl.
*A61K 31/439* (2006.01)
*A61K 31/4155* (2006.01)
*C07D 231/20* (2006.01)
*C07D 453/02* (2006.01)

(52) U.S. Cl. .............. 514/305; 514/407; 548/364.1; 546/133

(58) Field of Classification Search .............. 546/133; 548/364.1; 514/407, 305
See application file for complete search history.

(56) References Cited

U.S. PATENT DOCUMENTS 5,409,946 A    4/1995  Garvey et al.
5,939,436 A *  8/1999  Carling et al. ............... 514/326

FOREIGN PATENT DOCUMENTS

DE   1 938 546       3/1970
EP   0427390         5/1991
EP   0525879         2/1993
EP   1 002 871 A1    5/2000
EP   1004592         5/2000
WO   WO 2004/048386 A2  6/2004

OTHER PUBLICATIONS

Aracava et al. The Journal of Pharmacology and Experimental Therapeutics 2005, 312(2), 1195-1205.*
Moore et al. Biorg. Med. Chem. Lett. 1999, 9(9), 1285-1290.*
J. G. Cannon, Chapter Nineteen in Burger's Medicinal Chemistry and Drug Discovery, Fifth Edition, vol. I: Principles and Practice, Wiley-Interscience 1995, pp. 783-802.*
Schafer et al. Drug Discovery Today 2008, 13 (21/22), 913-916.*
Horig et al. Journal of Translational Medicine 2004, 2(44).*
Kishimoto et al. Chem. Pharm. Bull. 1976, 24(12), 3001-3010.*
Haydar et al. Bioorganic & Medicinal Chemistry 2009, 17, 5247-5258.*
Amundsen et al, Beta-Dialkylaminoethyl Bromide Hydrobromides and Beta-Dialkylaminoethylamines, J. Am. Chem. Soc., 1941, 63 (1), pp. 305-307.
Cheng, et al, Relationship Between the Inhibition Constant (KI) and the Concentration of Inhibitor Which Causes 50 Per Cent Inhibition (I50) of an Enzymatic Reaction, Biochem. Pharmacol. (1973), 22, 3099-3108.
Dahlbom et al, Some 2-bromobenzyl and 2,6-dimethylphenoxyethyl substituted sterically hindered amines, Acta Pharm. Suecica, 1969 (6) pp. 413-418.
Davies et al, Characterisation of the binding of [3H]methyllycaconitine: a new radioligand for labelling alpha7-type neuronal nicotinic acetylcholine receptors, Neuropharmacology 1999 (38) pp. 670-690.
H Plumpe et al., Archiv Der Pharmazie Und Berichte Der Deutschen Pharmazeutischen Gesellschaft , Einige Neue in 4-Stellung Substituierte Pyrazole, (1967, pp. 704-708, vol. 388(8).
Hacksell et al, 3-Lithioquinuclidin-2-ene: A novel intermediate for the synthesis of muscarinic agonists and antagonists, Bioorganic & Med. Chem. Letters, 1994 (4)24, pp. 2837-2840.

(Continued)

Primary Examiner — Jason M Nolan
(74) Attorney, Agent, or Firm — Kelly L. Bender

(57) ABSTRACT

The present invention relates to the novel derivatives of formula (I) in which

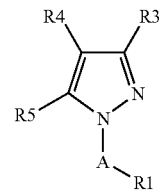

A is, if it is present, a (C1-C6) alkyl, a (C3-C6) alkenyl, a (C3-C6) alkynyl, a (C3-C7) cycloalkyl or a (C5-C7) cycloalkenyl, R1 is an NR6R7, (C4-C7) azacycloalkyl, (C5-C7) azacycloalkenyl, (C5-C9) azabicycloalkyl or (C5-C9) azabicycloalkenyl group; A-R1 is such that the nitrogen of R1 and the nitrogen in the 1-position of the pyrazole are necessarily separated by at least two carbon atoms, R3 is an H, halogen, OH, SH, $NH_2$, ORc, SRc, SORa, $SO_2Ra$, NHCHO, NRaRb, NHC(O)Ra, NHC(S)Ra or $NHSO_2Ra$, R4 is an aryl or heteroaryl; and R5 is an H, halogen, $CF_3$, $CHF_2$, $CH_2F$, linear or branched (C1-C6) alkyl or (C3-C7) cycloalkyl, to their racemates, enantiomers and diastereoisomers and to their mixtures, their tautomers and to their pharmaceutically acceptable salts.

17 Claims, No Drawings

OTHER PUBLICATIONS

Hartwig, John, Transition Metal Catalyzed Synthesis of Arylamines and Aryl Ethers from Aryl Halides and Triflates: Scope and Mechanism, Angew. Chem. (Int. Ed.) 1998, 37, 2046-2067.

Jenkins et al, Substituent Variation in Azabicyclic Triazole- and Tetrazole-Based Muscarinic Receptor Ligands, J. Med. Chem. 1992 (35) pp. 2392-2406.

Kabalka et al, A New Route to Iodine-Labeled N-Isopropyl Iodoamphetamine via Organoboranes, Tetrahedron Letters, 1986 (27) 33, pp. 3843-3844.

Kotha et al, Recent applications of the Suzuki-Miyaura cross-coupling reaction in organic synthesis, Tetrahedron 2002 (58) pp. 9633-9695.

Lamba et al, Imine-Bridged Planar Poly(p-phenylene) Derivatives for Maximization of Extended pi-Conjugation. The Common Intermediate Approach, J. Am. Chem. Soc., 1994 (116) pp. 11723-11736.

Lang et al, Synthesis of 4-(4-Phenyl-3-pyrazolyl)-4H-1,2,4-triazoles, J. Heterocyclic Chem., 1977 (14) 65 pp. 65-69.

Malpass et al, Reaction of Chlorosulphonyl Isocyanate with 1,3-Dienes. Control of 1,2-and 1,4-Addition Pathways and the Synthesis of Aza- and Oxa-bicyclic Systems, J.C.S. Perkin I, 1977 (8) pp. 874-884.

Muller et al, Syntheses of Phenothiazinylboronic Acid Derivatives—Suitable Starting Points for the Construction of Redox Active Materials, Synthesis, 2002 (9), pp. 1163-1170.

Selwood et al, Synthesis and Biological Evaluation of Novel Pyrazoles and Indazoles as Activators of the Nitric Oxide Receptor, Soluble Guanylate Cyclase, J. Med. Chem., 2001 (44) 1 pp. 78-93.

Villalgordo et al, A New Class of Fused Imidazoles by Intramolecular Nucleophillic ipso-Substitution in 2-Alkylsulfonylimidazoles: Synthesis of 2,3-Dihydroimidazo[2,1-b][1,3]oxazoles, Synthesis 1999 (9) pp. 1613-1624.

Wang et al, A General Synthesis of Beta-Aryl and Heteroarylpyrroles by Palladium-catalyzed Coupling Reaction of Beta-Tributylstannylpyrrole with Aryl and Heteroaryl Halides, Tetrahedron Letters, 1996 (37) 19 pp. 3247-3250.

Wong et al, Synthesis of Extended Chromogenic Tetra-(p-substituted-phenyl)-tetraethoxycalix[4]arenes, Tetrahedron Letters, 1993 (34) 51 pp. 8237-8240.

Yasuhara et al, Deprotection of N-Sulfonyl Nitrogen-Heteroaromatics with Tetrabutylammonium Fluoride, Tetrahedron Letters, 1998 (39) pp. 595-596.

Yokota et al, Isoquinuclidine-based expectorants. Synthesis and biological activities of N-alkoxybenzylisoquinuclidines, Eur. J. Med. Chem., 1997 (32) pp. 377-384.

Chemical Abstracts, CAS Registry No. 56824-22-7, Nov. 16, 1984.

Parham et al, 3-Amino-4-phenylpyrazole as an Intermediate, J. of Organic Chem., 1960 (25)7 pp. 1259-1260.

* cited by examiner

PYRAZOLYL DERIVATIVES, PREPARATION PROCESS AND INTERMEDIATES OF THIS PROCESS AS MEDICINAL PRODUCTS AND PHARMACEUTICAL COMPOSITIONS CONTAINING THEM

This application is continuation of U.S. patent application Ser. No. 10/997,736, filed Nov. 24, 2004, now allowed, which claims the benefit of U.S. Provisional Application No. 60/537,046 filed Jan. 16, 2004, both of which are incorporated herein by reference in their entirety; and the benefit of priority from French Application No. 03 13775, filed Nov. 25, 2003.

The present invention relates to novel ligands for acetylcholine receptors of the nicotinic type. These compounds are more particularly ligands for α7 nicotinic receptors. These properties suggest that the compounds of the invention may be useful, in animals including humans, as a curative and/or symptomatic treatment for the prevention, diagnosis and/or monitoring of the evolution of disorders or diseases which involve a disturbance of nicotinic receptor function or which respond favorably to a modulation of said receptors. More particularly, the compounds of the invention could be useful in psychiatric disorders or diseases or neurological disorders or diseases of the central nervous system involving the impairment of cognitive functions, of attention, of the ability to concentrate, to learn and to memorize, or of the processing of sensory information. They may also be useful in the treatment, prevention, diagnosis and/or monitoring of the evolution of diseases involving neurodegenerative processes which are spontaneous or which are subsequent to lesions, and of diseases involving inflammatory phenomena. The present invention also refers to the methods of treatment involving nicotinic receptors consisting of the administration, to animals including humans, of therapeutically effective doses of one or more compounds of the invention. The present invention also relates to the use, for diagnostic purposes, of analogs of these derivatives in which one or more atoms have been replaced with an isotope with an atomic mass or a mass number which is different to the atomic mass or to the mass number of the atoms usually encountered naturally.

A subject of the present invention is therefore the use of pyrazole derivatives of formula (I)

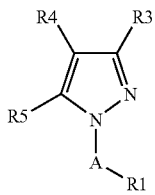

(I)

and their pharmaceutically acceptable salts, for preparing medicinal products and pharmaceutical compositions, as ligands for α7 nicotinic receptors.

Many disorders or diseases are associated with a nicotinic receptor dysfunction and may thus benefit from a modulation of said receptors using the compounds of the invention to correct the symptoms thereof and/or to slow down, stop or reverse the evolution thereof. In this regard, the compounds of the invention are more particularly advantageous in the case of psychiatric disorders or diseases or neurological disorders or diseases of the central nervous system, such as, for example, an impairment of the ability to learn, to concentrate or to memorize, slight cognitive impairments, senile dementia, vascular dementia, Levy body dementia, Alzheimer's disease, Parkinson's disease, Huntington's chorea, Tourette's syndrome, neuronal degeneration subsequent to a trauma, to strokes, to ischemia or to brain hypoxia, multisystem atrophy, progressive supranuclear paralysis, amyotrophic lateral sclerosis, peripheral neuropathies, motor disorders such as dyskinesia, tardive dyskinesia, hyperkinesia, dystonia and epilepsy, attention deficit hyperactivity disorders, schizophrenia, depression, manic depressive psychosis, anxiety, phobias, obsessive-compulsive disorders, post-traumatic stress syndrome, panic attacks, eating disorders such as anorexia, bulimia and obesity, or sleep disorders including those associated with jetlag. The compounds of the invention may be useful for establishing a decrease in the consumption of addictive substances, for helping to maintain an abstinence with respect to said substances or for reducing the symptoms of withdrawal therefrom. In the context of the present invention, the term "addictive substance" applies to licit or illicit substances, the consumption of which may give rise to abuse and/or dependency, such as, for example, nicotine and tobacco products, alcohol, cannabis derivatives, opiates, cocaine, barbiturates, benzodiazepines and pyschostimulants.

The compounds of the invention could also have an advantage in the treatment of acute or chronic pain, such as post-surgical pain, pain subsequent to amputation (phantom limb pain), pain associated with cancerous lesions, with migraines, with neuropathies and muscle pains such as fibromyalgia. In addition, the compounds of the invention could also be used in the context of the treatment of disorders or diseases involving inflammatory processes, such as, for example, in the gastrointestinal tract, ulcerative colitis, Crohn's disease, irritable bowel syndrome or diarrhea and, elsewhere in the body, arthritis (including rheumatoid arthritis) and skin inflammations such as acne. Finally, the compounds of the invention could be useful in endocrine disorders such as pheochromocytoma and smooth muscle contraction-related disorders.

The present invention also covers the use of the compounds of the invention for diagnostic purposes or for the purposes of medical imaging. It comprises the diagnostic and imaging methods consisting of the analysis, by noninvasive methods, of the distribution of a tracer compound within the intact body of an animal, including humans, using physical means such as positon emission tomography, single-photon tomography, magnetic resonance spectroscopy and nuclear magnetic resonance imaging, computed X-ray tomodensitometry (scanner) or a combination of these techniques. In the context of the present invention, the term "tracer compound" denotes the compounds of the invention, their enantiomers or their prodrugs which may or may not be used in a labeled form allowing them to be detected by physical means as described above. The labeling consists in replacing one or more atoms in the compounds of the invention with an isotope with an atomic mass or a mass number which is different to the atomic mass or to the mass number of these atoms such as they are usually encountered naturally. It may also consist in adding to the compounds of the invention chemical groups carrying such isotopes, by means, for example, of methylating reagents. The isotopes used may, for example, be radionuclide isotopes of hydrogen, of carbon, of nitrogen, of oxygen, of fluorine, of phosphorus, of sulfur, of chlorine, of iodine or of technetium, such as, respectively, $^2$H, $^3$H, $^{11}$C, $^{13}$C, $^{14}$C, $^{13}$N, $^{15}$O, $^{17}$O, $^{18}$F, $^{35}$S, $^{36}$Cl, $^{123}$I, $^{125}$I and $^{131}$I. The labeled compounds can be synthesized according to the methods described in the procedures of the present invention by substituting one or more reagents in the synthetic process with identical reagents containing the label isotope(s).

The present invention relates to derivatives of formula (I) in which:

A is a bond or (C1-C6) alkyl radical, a (C3-C6) alkenyl radical, a (C3-C6) alkynyl radical, a (C3-C7) cycloalkyl radical or a (C5-C7) cycloalkenyl radical; these radicals are optionally substituted with one or more substituents chosen from (C1-C5) alkyl, (C2-C5) alkenyl, (C2-C5) alkynyl, (C3-C7) cycloalkyl, (C5-C7) cycloalkenyl, arylalkyl, heteroarylalkyl, aryl, heteroaryl and halogen, R1 is an NR6R7, (C4-C7) azacycloalkyl, (C5-C7) azacycloalkenyl, (C5-C9) azabicycloalkyl or (C5-C9) azabicycloalkenyl group; these groups are optionally substituted with one or more substituents chosen from (C1-C5) alkyl, (C3-C5) cycloalkyl and halogen, A-R1 is such that the nitrogen of R1 and the nitrogen in the 1-position of the pyrazole are necessarily separated by at least two carbon atoms, R3 is an H, halogen, OH, SH, $NH_2$, ORc, SRc, SORa, $SO_2Ra$, NHCHO, NRaRb, NHC(O)Ra, NHC(S)Ra or $NHSO_2Ra$ radical, R4 is an aryl or heteroaryl radical being optionally substituted with one or more substituents chosen from halogen, CN, $NO_2$, $NH_2$, OH, SH, COOH, CHO, C(O)$NH_2$, C(S)$NH_2$, $SO_2H$, $SO_2NH_2$, NHCHO, C(O)Ra, C(O)ORa, C(O)NRaRb, C(S)NRaRb, S(O)Ra, $SO_2Ra$, $SO_2NRaRb$, ORc, SRc, O—C(O)Ra, —O—C(S)Ra, NRaRb, NHC(O)Ra, NHC(S)Ra, NHCO$NH_2$, NHCONRaRb, $NHSO_2Ra$, aryl, heteroaryl, (C4-C7) heterocycloalkyl, polyfluoroalkyl, trifluoromethyl-sulfanyl, trifluoromethoxy, linear or branched (C1-C6) alkyl, (C2-C6) alkenyl and (C2-C6) alkynyl, these substituents being optionally substituted with one or more alkyl, halogen, OH, methoxy, R5 is an H, halogen, $CF_3$, $CHF_2$, $CH_2F$, linear or branched (C1-C6) alkyl or (C3-C7) cycloalkyl radical, Ra is linear or branched (C1-C6) alkyl, alkenyl, alkynyl, (C3-C7) cycloalkyl, (C5-C7) cycloalkenyl, (C4-C7) heterocycloalkyl, (C4-C7)heterocycloalkyl, arylalkyl, heteroarylalkyl, aryl, heteroaryl or polyfluoroalkyl, Rb is, independently of Ra, a hydrogen, linear or branched (C1-C6) alkyl, alkenyl, alkynyl, (C3-C7) cycloalkyl, (C5-C7) cycloalkenyl, (C4-C7) hetero-cycloalkyl, (C4-C7) heterocycloalkyl, arylalkyl, heteroarylalkyl, aryl, heteroaryl or polyfluoroalkyl, Ra and Rb may form a saturated or unsaturated ring containing 5, 6 or 7 ring members, which may or may not have a hetero atom such as O, S or N, this ring being optionally substituted with one or more alkyl and/or halogen radicals, Rc is a linear or branched (C1-C6) alkyl, (C3-C6) alkenyl, (C3-C6) alkynyl, (C3-C7) cycloalkyl, (C5-C7) cycloalkenyl, (C4-C7) heterocycloalkyl (C4-C7)hetero-cycloalkyl, (hetero)arylalkyl, (hetero)aryl, (poly)-fluoroalkyl, C(O)R8, C(S)R8 or $SO_2R8$ radical, R6 and R7 are, independently of one another, a hydrogen, (C1-C6) alkyl, (C3-C6) alkenyl, (C3-C6) alkynyl, (C3-C7) cycloalkyl, (C5-C7) cycloalkenyl, (C4-C7) heterocycloalkyl, an arylalkyl or heteroarylalkyl, R6 and R7 may form a saturated or unsaturated ring with 5, 6 or 7 ring members, which may or may not have a hetero atom such as O, S or N and which is optionally substituted with one or more alkyls and/or halogens, R8 is an Ra or NRaRb radical, or the racemates, enantiomers or diastereoisomers or mixtures in any combination thereof, the tautomers or the pharmaceutically acceptable salts thereof, with the exception of 3-(3-pyridinyl)-1H-pyrazole-1-butanamine, 4-(3-pyridinyl)-1H-pyrazole-1-butanamine and N-(diethyl)-4-phenyl-1H-pyrazole-1-ethylamine.

Preferably, the present invention relates to derivatives of formula (I) in which:

A is a bond, a (C1-C6) alkyl radical, a (C3-C6) alkenyl radical, a (C3-C6) alkynyl radical, a (C3-C7) cycloalkyl radical or a (C5-C7) cycloalkenyl radical; these radicals are optionally substituted with one or more substituents chosen from (C1-C5) alkyl, (C2-C5) alkenyl, (C2-C5) alkynyl, (C3-C7) cycloalkyl, (C5-C7) cycloalkenyl, arylalkyl, heteroarylalkyl, aryl, heteroaryl and halogen, R1 is an NR6R7, (C4-C7) azacycloalkyl, (C5-C7) azacycloalkenyl, (C5-C9) azabicycloalkyl or (C5-C9) azabicycloalkenyl group; these groups are optionally substituted with one or more substituents chosen from (C1-C5) alkyl, (C3-C5) cycloalkyl and halogen, A-R1 is such that the nitrogen of R1 and the nitrogen in the 1-position of the pyrazole are necessarily separated by at least two carbon atoms, R3 is an OH, $NH_2$, OMe or H radical, R4 is an aryl or heteroaryl radical being optionally substituted with one or more substituents chosen from halogen, CN, $NO_2$, $NH_2$, OH, SH, COOH, CHO, C(O)$NH_2$, C(S)$NH_2$, $SO_2H$, $SO_2NH_2$, NHCHO, C(O)Ra, C(O)ORa, C(O)NRaRb, C(S)NRaRb, S(O)Ra, $SO_2Ra$, $SO_2NRaRb$, ORc, SRc, O—C(O)Ra, —O—C(S)Ra, NRaRb, NHC(O)Ra, NHC(S)Ra, NHCO$NH_2$, NHCONRaRb, $NHSO_2Ra$, aryl, heteroaryl, (C4-C7) heterocycloalkyl, polyfluoroalkyl, trifluoromethyl-sulfanyl, trifluoromethoxy, linear or branched (C1-C6) alkyl, (C2-C6) alkenyl and (C2-C6) alkynyl, these substituents being optionally substituted with one or more alkyl, halogen, OH, methoxy, R5 is a hydrogen or Me radical, Ra is linear or branched (C1-C6) alkyl, alkenyl, alkynyl, (C3-C7) cycloalkyl, (C5-C7) cycloalkenyl, (C4-C7) heterocycloalkyl, arylalkyl, heteroarylalkyl, aryl, heteroaryl or polyfluoroalkyl, Rb is, independently of Ra, a hydrogen, linear or branched (C1-C6) alkyl, alkenyl, alkynyl, (C3-C7) cycloalkyl, (C5-C7) cycloalkenyl, (C4-C7) hetero-cycloalkyl, arylalkyl, heteroarylalkyl, aryl, heteroaryl or polyfluoroalkyl, Ra and Rb may form a saturated or unsaturated ring containing 5, 6 or 7 ring members, which may or may not have a hetero atom such as O, S or N, this ring being optionally substituted with one or more alkyl and/or halogen radicals, Rc is a linear or branched (C1-C6) alkyl, (C3-C6) alkenyl, (C3-C6) alkynyl, (C3-C7) cycloalkyl, (C5-C7) cycloalkenyl, (C4-C7) heterocycloalkyl, (hetero)-arylalkyl, (hetero)aryl, (poly)fluoroalkyl, C(O)R8, C(S)R8 or $SO_2R8$ radical, R6 and R7 are, independently of one another, a hydrogen, (C1-C6) alkyl, (C3-C6) alkenyl, (C3-C6) alkynyl, (C3-C7) cycloalkyl, (C5-C7) cycloalkenyl, (C4-C7) heterocycloalkyl, an arylalkyl or heteroarylalkyl, R6 and R7 may form a saturated or unsaturated ring with 5, 6 or 7 ring members, which may or may not have a hetero atom such as O, S or N and which is optionally substituted with one or more alkyls and/or halogens, R8 is an Ra or NRaRb radical, or a racemate, an enantiomer or a diastereoisomer, or a mixture in any combination thereof, a tautomer or a pharmaceutically acceptable salt thereof, with the exception of 3-(3-pyridinyl)-1H-pyrazole-1-butanamine, 4-(3-pyridinyl)-1H-pyrazole-1-butanamine and N-(diethyl)-4-phenyl-1H-pyrazole-1-ethylamine.

More particularly, the present invention relates to derivatives of formula (I) in which:

A is a bond or (C1-C6) alkyl radical, a (C3-C6) alkenyl radical, a (C3-C6) alkynyl radical, a (C3-C7) cycloalkyl radical or a (C5-C7) cycloalkenyl radical; these radicals are optionally substituted with one or more substituents chosen from (C1-C5) alkyl, (C2-C5) alkenyl, (C2-C5) alkynyl, (C3-C7) cycloalkyl, (C5-C7) cycloalkenyl, arylalkyl, heteroarylalkyl, aryl, heteroaryl and halogen, R1 is an NR6R7, (C4-C7) azacycloalkyl, (C5-C7) azacycloalkenyl, (C5-C9) azabicycloalkyl or (C5-C9) azabicycloalkenyl group; these groups are optionally substituted with one or more substituents chosen from (C1-C5) alkyl, (C3-C5) cycloalkyl and halogen, A-R1 is such that the nitrogen of R1 and the nitrogen in the 1-position of the pyrazole are necessarily separated by at least two carbon atoms, R3 is an OH, NH$_2$, OMe or H radical, R4 is an aryl or heteroaryl radical being optionally substituted with one or more substituents chosen from halogen, CN, NO$_2$, NH$_2$, OH, SH, COOH, CHO, C(O)NH$_2$, C(S)NH$_2$, SO$_2$H, SO$_2$NH$_2$, NHCHO, C(O)Ra, C(O)ORa, C(O)NRaRb, C(S)NRaRb, S(O)Ra, SO$_2$Ra, SO$_2$NRaRb, ORc, SRc, O—C(O)Ra, —O—C(S)Ra, NRaRb, NHC(O)Ra, NHC(S)Ra, NHCONH$_2$, NHCONRaRb, NHSO$_2$Ra, aryl, heteroaryl, (C4-C7) heterocycloalkyl, polyfluoroalkyl, trifluoromethyl-sulfanyl, trifluoromethoxy, linear or branched (C1-C6) alkyl, (C2-C6) alkenyl and (C2-C6) alkynyl, these substituents being optionally substituted with one or more alkyl, halogen, OH, methoxy, R5 is a hydrogen, Ra is linear or branched (C1-C6) alkyl, alkenyl, alkynyl, (C3-C7) cycloalkyl, (C5-C7) cycloalkenyl, (C4-C7) heterocycloalkyl, arylalkyl, heteroarylalkyl, aryl, heteroaryl or polyfluoroalkyl, Rb is, independently of Ra, a hydrogen, linear or branched (C1-C6) alkyl, alkenyl, alkynyl, (C3-C7) cycloalkyl, (C5-C7) cycloalkenyl, (C4-C7) hetero-cycloalkyl, arylalkyl, heteroarylalkyl, aryl, heteroaryl or polyfluoroalkyl, Ra and Rb may form a saturated or unsaturated ring containing 5, 6 or 7 ring members, which may or may not have a hetero atom such as O, S or N, this ring being optionally substituted with one or more alkyl and/or halogen radicals, Rc is a linear or branched (C1-C6) alkyl, (C3-C6) alkenyl, (C3-C6) alkynyl, (C3-C7) cycloalkyl, (C5-C7) cycloalkenyl, (C4-C7) heterocycloalkyl, (hetero)arylalkyl, (hetero)aryl, (poly)fluoroalkyl, C(O)R8, C(S)R8 or SO$_2$R8 radical, R6 and R7 are, independently of one another, a hydrogen, (C1-C6) alkyl, (C3-C6) alkenyl, (C3-C6) alkynyl, (C3-C7) cycloalkyl, (C5-C7) cycloalkenyl, (C4-C7) heterocycloalkyl, an arylalkyl or heteroarylalkyl, R6 and R7 may form a saturated or unsaturated ring with 5, 6 or 7 ring members, which may or may not have a hetero atom such as O, S or N and which is optionally substituted with one or more alkyls and/or halogens, R8 is an Ra or NRaRb radical, or a racemate, an enantiomer or a diastereoisomer, or a mixture in any combination thereof, a tautomer or a pharmaceutically acceptable salt thereof, with the exception of 3-(3-pyridinyl)-1H-pyrazole-1-butanamine, 4-(3-pyridinyl)-1H-pyrazole-1-butanamine and N-(diethyl)-4-phenyl-1H-pyrazole-1-ethylamine.

In the definitions above and those which follow, the (C1-C6) alkyl radicals contain 1 to 6 carbon atoms in a straight or branched chain; the (C3-C7) cycloalkyl radicals contain 3 to 7 carbon atoms; the alkenyl radicals contain 2 to 6 carbon atoms and one to 2 conjugated or unconjugated double bonds in a straight or branched chain, the double bond not being in the alpha-position with respect to a hetero atom; the alkynyl radicals contain 2 to 6 carbon atoms and one to 2 conjugated or unconjugated triple bonds in a straight or branched chain, the triple bond not being in the alpha-position with respect to a hetero atom; the aryl radicals are chosen from phenyl, naphthyl or indenyl; the heteroaryl radicals contain 3 to 10 ring members, optionally containing one or more hetero atoms chosen from oxygen, sulfur and nitrogen, in particular thiazolyl, thienyl, pyrrolyl, pyrazolyl, pyridinyl, furyl, imidazolyl, oxazolyl, pyrazinyl, pyrimidyl, tetrazolyl, oxadiazolyl, thiadiazolyl, isoxadiazolyl, isothiadiazolyl, isothiazolyl, isoxazolyl, triazolyl, indolyl, benzofuranyl, benzothienyl, azaindolyl, pyrazolyl, indolyl; the halogen radical is either chlorine, iodine, fluorine or bromine; the (C4-C7) azacycloalkyl radicals contain a nitrogen and 4 to 7 carbon atoms and in particular azetidinyl, pyrrolidinyl, piperidinyl; the azacycloalkenyl radicals contain a nitrogen and 5 to 7 carbon atoms; the (C5-C9) azabicycloalkyl radicals contain 5 to 9 carbon atoms and are illustrated in a nonlimiting manner in list (A); the (C5-C9) azabicycloalkenyl radicals contain 5 to 9 carbon atoms and are illustrated in a nonlimiting manner in list (B); the (C4-C7) heterocycloalkyl radicals contain 5 to 7 carbon atoms and one or more hetero atoms chosen from oxygen, sulfur and nitrogen; the polyfluoroalkyl radicals contain 1 to 6 carbon atoms in a straight or branched chain, which are substituted with one or more fluorine atoms and in particular trifluoromethyl, difluoromethyl;

By way of illustration, below are structures of list (A); these structures may be linked to the main ring via any of their positions:

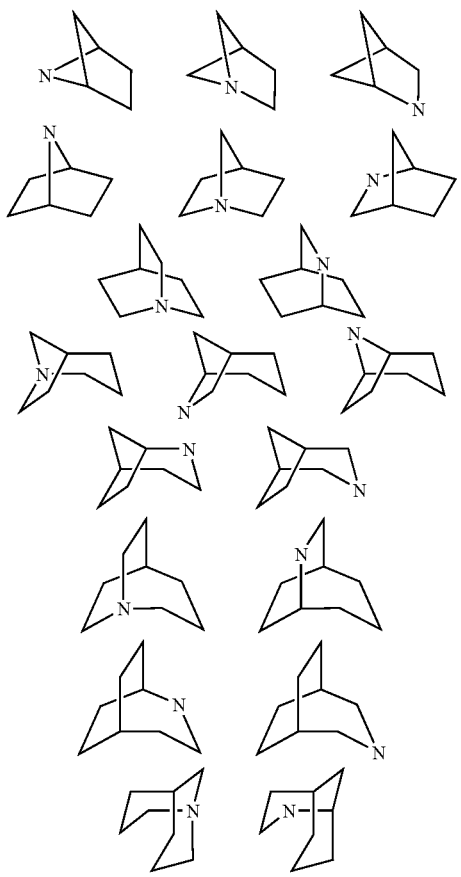

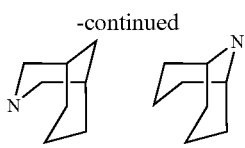

By way of illustration, below are structures of list (B); these structures may be linked to the main ring via any of their positions:

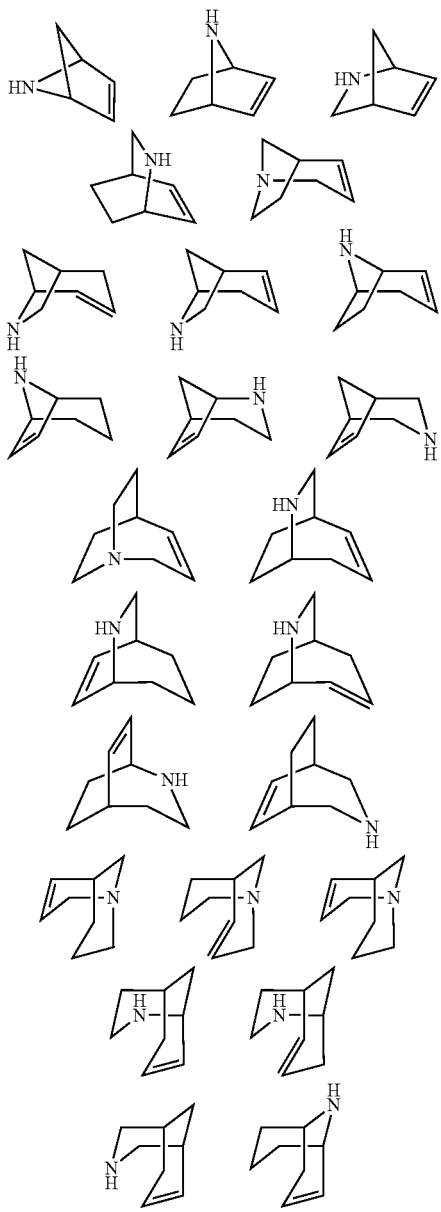

The compounds of formula (I) exhibit one or more asymmetric carbons and can therefore be in the form of isomers, of racemates, of enantiomers and of diastereoisomers; these are also part of the invention as are mixtures thereof.

The present invention also relates to the pharmaceutical compositions containing as active principle a derivative of formula (I) in which:

A is a bond or (C1-C6) alkyl radical, a (C3-C6) alkenyl radical, a (C3-C6) alkynyl radical, a (C3-C7) cycloalkyl radical or a (C5-C7) cycloalkenyl radical; these radicals are optionally substituted with one or more substituents chosen from (C1-C5) alkyl, (C2-C5) alkenyl, (C2-C5) alkynyl, (C3-C7) cycloalkyl, (C5-C7) cycloalkenyl, arylalkyl, heteroarylalkyl, aryl, heteroaryl and halogen, R1 is an NR6R7, (C4-C7) azacycloalkyl, (C5-C7) azacycloalkenyl, (C5-C9) azabicycloalkyl or (C5-C9) azabicycloalkenyl group; these groups are optionally substituted with one or more substituents chosen from (C1-C5) alkyl, (C3-C5) cycloalkyl and halogen, A-R1 is such that the nitrogen of R1 and the nitrogen in the 1-position of the pyrazole are necessarily separated by at least two carbon atoms, R3 is an H, halogen, OH, SH, $NH_2$, ORc, SRc, SORa, $SO_2Ra$, NHCHO, NRaRb, NHC(O)Ra, NHC(S)Ra or $NHSO_2Ra$ radical, R4 is an aryl or heteroaryl radical being optionally substituted with one or more substituents chosen from halogen, CN, $NO_2$, $NH_2$, OH, SH, COOH, CHO, $C(O)NH_2$, $C(S)NH_2$, $SO_2H$, $SO_2NH_2$, NHCHO, C(O)Ra, C(O)ORa, C(O)NRaRb, C(S)NRaRb, S(O)Ra, $SO_2Ra$, $SO_2NRaRb$, ORc, SRc, O—C(O)Ra, —O—C(S)Ra, NRaRb, NHC(O)Ra, NHC(S)Ra, $NHCONH_2$, NHCONRaRb, $NHSO_2Ra$, aryl, heteroaryl, (C4-C7) heterocycloalkyl, polyfluoroalkyl, trifluoromethyl-sulfanyl, trifluoromethoxy, linear or branched (C1-C6) alkyl, (C2-C6) alkenyl and (C2-C6) alkynyl, these substituents being optionally substituted with one or more alkyl, halogen, OH, methoxy, R5 is an H, halogen, $CF_3$, $CHF_2$, $CH_2F$, linear or branched (C1-C6) alkyl or (C3-C7) cycloalkyl radical, Ra is linear or branched (C1-C6) alkyl, alkenyl, alkynyl, (C3-C7) cycloalkyl, (C5-C7) cycloalkenyl, (C4-C7) heterocycloalkyl, arylalkyl, heteroarylalkyl, aryl, heteroaryl or polyfluoroalkyl, Rb is, independently of Ra, a hydrogen, linear or branched (C1-C6) alkyl, alkenyl, alkynyl, (C3-C7) cycloalkyl, (C5-C7) cycloalkenyl, (C4-C7) hetero-cycloalkyl, arylalkyl, heteroarylalkyl, aryl, heteroaryl or polyfluoroalkyl, Ra and Rb may form a saturated or unsaturated ring containing 5, 6 or 7 ring members, which may or may not have a hetero atom such as O, S or N, this ring being optionally substituted with one or more alkyl and/or halogen radicals, Rc is a linear or branched (C1-C6) alkyl, (C3-C6) alkenyl, (C3-C6) alkynyl, (C3-C7) cycloalkyl, (C5-C7) cycloalkenyl, (C4-C7) heterocycloalkyl, (hetero)-arylalkyl, (hetero)aryl, (poly)fluoroalkyl, C(O)R8, C(S)R8 or $SO_2R8$ radical, R6 and R7 are, independently of one another, a hydrogen, (C1-C6) alkyl, (C3-C6) alkenyl, (C3-C6) alkynyl, (C3-C7) cycloalkyl, (C5-C7) cycloalkenyl, (C4-C7) heterocycloalkyl, an arylalkyl or heteroarylalkyl, R6 and R7 may form a saturated or unsaturated ring with 5, 6 or 7 ring members, which may or may not have a hetero atom such as O, S or N and which is optionally substituted with one or more alkyls and/or halogens, R8 is an Ra or NRaRb radical, or a racemate, an enantiomer or a diastereoisomer, or a mixture in any combination thereof, a tautomer or a pharmaceutically acceptable salt thereof.

Preferably, the present invention also relates to pharmaceutical compositions containing as active principle a derivative of formula (I) in which:

A is a bond, a (C1-C6) alkyl radical, a (C3-C6) alkenyl radical, a (C3-C6) alkynyl radical, a (C3-C7) cycloalkyl radical or a (C5-C7) cycloalkenyl radical; these radicals are optionally substituted with one or more substituents chosen from (C1-C5) alkyl, (C2-C5) alkenyl, (C2-C5) alkynyl, (C3-C7) cycloalkyl, (C5-C7) cycloalkenyl, arylalkyl, heteroarylalkyl, aryl, heteroaryl and halogen, R1 is an NR6R7, (C4-C7) azacycloalkyl, (C5-C7) azacycloalkenyl, (C5-C9) azabicycloalkyl or (C5-C9) azabicycloalkenyl group; these groups are optionally substituted with one or more substituents chosen from (C1-C5) alkyl, (C3-C5) cycloalkyl and halogen, A-R1 is such that the nitrogen of R1 and the nitrogen in the 1-position of the pyrazole are necessarily separated by at least two carbon atoms, R3 is an OH, NH$_2$, OMe or H radical, R4 is an aryl or heteroaryl radical being optionally substituted with one or more substituents chosen from halogen, CN, NO$_2$, NH$_2$, OH, SH, COOH, CHO, C(O)NH$_2$, C(S)NH$_2$, SO$_2$H, SO$_2$NH$_2$, NHCHO, C(O)Ra, C(O)ORa, C(O)NRaRb, C(S)NRaRb, S(O)Ra, SO$_2$Ra, SO$_2$NRaRb, ORc, SRc, O—C(O)Ra, —O—C(S)Ra, NRaRb, NHC(O)Ra, NHC(S)Ra, NHCONH$_2$, NHCONRaRb, NHSO$_2$Ra, aryl, heteroaryl, (C4-C7) heterocycloalkyl, polyfluoroalkyl, trifluoromethyl-sulfanyl, trifluoromethoxy, linear or branched (C1-C6) alkyl, (C2-C6) alkenyl and (C2-C6) alkynyl, these substituents being optionally substituted with one or more alkyl, halogen, OH, methoxy, R5 is a hydrogen or Me radical, Ra is linear or branched (C1-C6) alkyl, alkenyl, alkynyl, (C3-C7) cycloalkyl, (C5-C7) cycloalkenyl, (C4-C7) heterocycloalkyl, arylalkyl, heteroarylalkyl, aryl, heteroaryl or polyfluoroalkyl, Rb is, independently of Ra, a hydrogen, linear or branched (C1-C6) alkyl, alkenyl, alkynyl, (C3-C7) cycloalkyl, (C5-C7) cycloalkenyl, (C4-C7) hetero-cycloalkyl, arylalkyl, heteroarylalkyl, aryl, heteroaryl or polyfluoroalkyl, Ra and Rb may form a saturated or unsaturated ring containing 5, 6 or 7 ring members, which may or may not have a hetero atom such as O, S or N, this ring being optionally substituted with one or more alkyl and/or halogen radicals, Rc is a linear or branched (C1-C6) alkyl, (C3-C6) alkenyl, (C3-C6) alkynyl, (C3-C7) cycloalkyl, (C5-C7) cycloalkenyl, (C4-C7) heterocycloalkyl, (hetero)-arylalkyl, (hetero)aryl, (poly)fluoroalkyl, C(O)R8, C(S)R8 or SO$_2$R8 radical, R6 and R7 are, independently of one another, a hydrogen, (C1-C6) alkyl, (C3-C6) alkenyl, (C3-C6) alkynyl, (C3-C7) cycloalkyl, (C5-C7) cycloalkenyl, (C4-C7) heterocycloalkyl, an arylalkyl or heteroarylalkyl, R6 and R7 may form a saturated or unsaturated ring with 5, 6 or 7 ring members, which may or may not have a hetero atom such as O, S or N and which is optionally substituted with one or more alkyls and/or halogens, R8 is an Ra or NRaRb radical, or a racemate, an enantiomer or a diastereoisomer, or a mixture in any combination thereof, a tautomer or a pharmaceutically acceptable salt thereof.

More particularly, the present invention also relates to the pharmaceutical compositions containing as active principle a derivative of formula (I) in which:

A is a bond, or (C1-C6) alkyl radical, a (C3-C6) alkenyl radical, a (C3-C6) alkynyl radical, a (C3-C7) cycloalkyl radical or a (C5-C7) cycloalkenyl radical; these radicals are optionally substituted with one or more substituents chosen from (C1-C5) alkyl, (C2-C5) alkenyl, (C2-C5) alkynyl, (C3-C7) cycloalkyl, (C5-C7) cycloalkenyl, arylalkyl, heteroarylalkyl, aryl, heteroaryl and halogen, R1 is an NR6R7, (C4-C7) azacycloalkyl, (C5-C7) azacycloalkenyl, (C5-C9) azabicycloalkyl or (C5-C9) azabicycloalkenyl group; these groups are optionally substituted with one or more substituents chosen from (C1-C5) alkyl, (C3-C5) cycloalkyl and halogen, A-R1 is such that the nitrogen of R1 and the nitrogen in the 1-position of the pyrazole are necessarily separated by at least two carbon atoms, R3 is an OH, NH$_2$, OMe or H radical, R4 is an aryl or heteroaryl radical being optionally substituted with one or more substituents chosen from halogen, CN, NO$_2$, NH$_2$, OH, SH, COOH, CHO, C(O)NH$_2$, C(S)NH$_2$, SO$_2$H, SO$_2$NH$_2$, NHCHO, C(O)Ra, C(O)ORa, C(O)NRaRb, C(S)NRaRb, S(O)Ra, SO$_2$Ra, SO$_2$NRaRb, ORc, SRc, O—C(O)Ra, —O—C(S)Ra, NRaRb, NHC(O)Ra, NHC(S)Ra, NHCONH$_2$, NHCONRaRb, NHSO$_2$Ra, aryl, heteroaryl, (C4-C7) heterocycloalkyl, polyfluoroalkyl, trifluoromethyl-sulfanyl, trifluoromethoxy, linear or branched (C1-C6) alkyl, (C2-C6) alkenyl and (C2-C6) alkynyl, these substituents being optionally substituted with one or more alkyl, halogen, OH, methoxy, R5 is a hydrogen, Ra is linear or branched (C1-C6) alkyl, alkenyl, alkynyl, (C3-C7) cycloalkyl, (C5-C7) cycloalkenyl, (C4-C7) heterocycloalkyl, arylalkyl, heteroarylalkyl, aryl, heteroaryl or polyfluoroalkyl, Rb is, independently of Ra, a hydrogen, linear or branched (C1-C6) alkyl, alkenyl, alkynyl, (C3-C7) cycloalkyl, (C5-C7) cycloalkenyl, (C4-C7) hetero-cycloalkyl, arylalkyl, heteroarylalkyl, aryl, heteroaryl or polyfluoroalkyl, Ra and Rb may form a saturated or unsaturated ring containing 5, 6 or 7 ring members, which may or may not have a hetero atom such as O, S or N, this ring being optionally substituted with one or more alkyl and/or halogen radicals, Rc is a linear or branched (C1-C6) alkyl, (C3-C6) alkenyl, (C3-C6) alkynyl, (C3-C7) cycloalkyl, (C5-C7) cycloalkenyl, (C4-C7) heterocycloalkyl, (hetero)aryl-alkyl, (hetero)aryl, (poly)fluoroalkyl, C(O)R8, C(S)R8 or SO$_2$R8 radical, R6 and R7 are, independently of one another, a hydrogen, (C1-C6) alkyl, (C3-C6) alkenyl, (C3-C6) alkynyl, (C3-C7) cycloalkyl, (C5-C7) cycloalkenyl, (C4-C7) heterocycloalkyl, an arylalkyl or heteroarylalkyl, R6 and R7 may form a saturated or unsaturated ring with 5, 6 or 7 ring members, which may or may not have a hetero atom such as O, S or N and which is optionally substituted with one or more alkyls and/or halogens, R8 is an Ra or NRaRb radical, or a racemate, an enantiomer or a diastereoisomer, or a mixture in any combination thereof, a tautomer or a pharmaceutically acceptable salt thereof.

The present invention also relates to the use as a medicinal product of the pyrazole derivatives of formula (I) in which:

A is a bond, or (C1-C6) alkyl radical, a (C3-C6) alkenyl radical, a (C3-C6) alkynyl radical, a (C3-C7) cycloalkyl radical or a (C5-C7) cycloalkenyl radical; these radicals are optionally substituted with one or more substituents chosen from (C1-C5) alkyl, (C2-C5) alkenyl, (C2-C5) alkynyl, (C3-C7) cycloalkyl, (C5-C7) cycloalkenyl, arylalkyl, heteroarylalkyl, aryl, heteroaryl and halogen, R1 is an NR6R7, (C4-C7) azacycloalkyl, (C5-C7) azacycloalkenyl, (C5-C9) azabicycloalkyl or (C5-C9) azabicycloalkenyl group; these groups are optionally substituted with one or more substituents chosen from (C1-C5) alkyl, (C3-C5) cycloalkyl and halogen, A-R1 is such that the nitrogen of R1 and the nitrogen in the 1-position of the pyrazole are necessarily separated by at least two carbon atoms, R3 is an H, halogen, OH, SH, $NH_2$, ORc, SRc, SORa, $SO_2Ra$, NHCHO, NRaRb, NHC(O)Ra, NHC(S)Ra or $NHSO_2Ra$ radical, R4 is an aryl or heteroaryl radical being optionally substituted with one or more substituents chosen from halogen, CN, $NO_2$, $NH_2$, OH, SH, COOH, CHO, $C(O)NH_2$, $C(S)NH_2$, $SO_2H$, $SO_2NH_2$, NHCHO, C(O)Ra, C(O)ORa, C(O)NRaRb, C(S)NRaRb, S(O)Ra, $SO_2Ra$, $SO_2NRaRb$, ORc, SRc, O—C(O)Ra, —O—C(S)Ra, NRaRb, NHC(O)Ra, NHC(S)Ra, $NHCONH_2$, NHCONRaRb, $NHSO_2Ra$, aryl, heteroaryl, (C4-C7) heterocycloalkyl, polyfluoroalkyl, trifluoromethyl-sulfanyl, trifluoromethoxy, linear or branched (C1-C6) alkyl, (C2-C6) alkenyl and (C2-C6) alkynyl, these substituents being optionally substituted with one or more alkyl, halogen, OH, methoxy, R5 is an H, halogen, $CF_3$, $CHF_2$, $CH_2F$, linear or branched (C1-C6) alkyl or (C3-C7) cycloalkyl radical, Ra is linear or branched (C1-C6) alkyl, alkenyl, alkynyl, (C3-C7) cycloalkyl, (C5-C7) cycloalkenyl, (C4-C7) heterocycloalkyl, arylalkyl, heteroarylalkyl, aryl, heteroaryl or polyfluoroalkyl, Rb is, independently of Ra, a hydrogen, linear or branched (C1-C6) alkyl, alkenyl, alkynyl, (C3-C7) cycloalkyl, (C5-C7) cycloalkenyl, (C4-C7) hetero-cycloalkyl, arylalkyl, heteroarylalkyl, aryl, heteroaryl or polyfluoroalkyl, Ra and Rb may form a saturated or unsaturated ring containing 5, 6 or 7 ring members, which may or may not have a hetero atom such as O, S or N, this ring being optionally substituted with one or more alkyl and/or halogen radicals, Rc is a linear or branched (C1-C6) alkyl, (C3-C6) alkenyl, (C3-C6) alkynyl, (C3-C7) cycloalkyl, (C5-C7) cycloalkenyl, (C4-C7) heterocycloalkyl, (hetero)-arylalkyl, (hetero)aryl, (poly)fluoroalkyl, C(O)R8, C(S)R8 or $SO_2R8$ radical, R6 and R7 are, independently of one another, a hydrogen, (C1-C6) alkyl, (C3-C6) alkenyl, (C3-C6) alkynyl, (C3-C7) cycloalkyl, (C5-C7) cycloalkenyl, (C4-C7) heterocycloalkyl, an arylalkyl or heteroarylalkyl, R6 and R7 may form a saturated or unsaturated ring with 5, 6 or 7 ring members, which may or may not have a hetero atom such as O, S or N and which is optionally substituted with one or more alkyls and/or halogens, R8 is an Ra or NRaRb radical, or a racemate, an enantiomer or a diastereoisomer, or a mixture in any combination thereof, a tautomer or a pharmaceutically acceptable salt thereof.

Preferably, the present invention relates to the use as medicinal product of the pyrazole derivatives of formula (I) in which:

A is a bond, or (C1-C6) alkyl radical, a (C3-C6) alkenyl radical, a (C3-C6) alkynyl radical, a (C3-C7) cycloalkyl radical or a (C5-C7) cycloalkenyl radical; these radicals are optionally substituted with one or more substituents chosen from (C1-C5) alkyl, (C2-C5) alkenyl, (C2-C5) alkynyl, (C3-C7) cycloalkyl, (C5-C7) cycloalkenyl, arylalkyl, heteroarylalkyl, aryl, heteroaryl and halogen, R1 is an NR6R7, (C4-C7) azacycloalkyl, (C5-C7) azacycloalkenyl, (C5-C9) azabicycloalkyl or (C5-C9) azabicycloalkenyl group; these groups are optionally substituted with one or more substituents chosen from (C1-C5) alkyl, (C3-C5) cycloalkyl and halogen, A-R1 is such that the nitrogen of R1 and the nitrogen in the 1-position of the pyrazole are necessarily separated by at least two carbon atoms, R3 is an OH, $NH_2$, OMe or H radical, R4 is an aryl or heteroaryl radical being optionally substituted with one or more substituents chosen from halogen, CN, $NO_2$, $NH_2$, OH, SH, COOH, CHO, $C(O)NH_2$, $C(S)NH_2$, $SO_2H$, $SO_2NH_2$, NHCHO, C(O)Ra, C(O)ORa, C(O)NRaRb, C(S)NRaRb, S(O)Ra, $SO_2Ra$, $SO_2NRaRb$, ORc, SRc, O—C(O)Ra, —O—C(S)Ra, NRaRb, NHC(O)Ra, NHC(S)Ra, $NHCONH_2$, NHCONRaRb, $NHSO_2Ra$, aryl, heteroaryl, (C4-C7) heterocycloalkyl, polyfluoroalkyl, trifluoromethyl-sulfanyl, trifluoromethoxy, linear or branched (C1-C6) alkyl, (C2-C6) alkenyl and (C2-C6) alkynyl, these substituents being optionally substituted with one or more alkyl, halogen, OH, methoxy, R5 is a hydrogen or Me radical, Ra is linear or branched (C1-C6) alkyl, alkenyl, alkynyl, (C3-C7) cycloalkyl, (C5-C7) cycloalkenyl, (C4-C7) heterocycloalkyl, arylalkyl, heteroarylalkyl, aryl, heteroaryl or polyfluoroalkyl, Rb is, independently of Ra, a hydrogen, linear or branched (C1-C6) alkyl, alkenyl, alkynyl, (C3-C7) cycloalkyl, (C5-C7) cycloalkenyl, (C4-C7) hetero-cycloalkyl, arylalkyl, heteroarylalkyl, aryl, heteroaryl or polyfluoroalkyl, Ra and Rb may form a saturated or unsaturated ring containing 5, 6 or 7 ring members, which may or may not have a hetero atom such as O, S or N, this ring being optionally substituted with one or more alkyl and/or halogen radicals, Rc is a linear or branched (C1-C6) alkyl, (C3-C6) alkenyl, (C3-C6) alkynyl, (C3-C7) cycloalkyl, (C5-C7) cycloalkenyl, (C4-C7) heterocycloalkyl, (hetero)-arylalkyl, (hetero)aryl, (poly)fluoroalkyl, C(O)R8, C(S)R8 or $SO_2R8$ radical, R6 and R7 are, independently of one another, a hydrogen, (C1-C6) alkyl, (C3-C6) alkenyl, (C3-C6) alkynyl, (C3-C7) cycloalkyl, (C5-C7) cycloalkenyl, (C4-C7) heterocycloalkyl, an arylalkyl or heteroarylalkyl, R6 and R7 may form a saturated or unsaturated ring with 5, 6 or 7 ring members, which may or may not have a hetero atom such as O, S or N and which is optionally substituted with one or more alkyls and/or halogens, R8 is an Ra or NRaRb radical, or a racemate, an enantiomer or a diastereoisomer, or a mixture in any combination thereof, a tautomer or a pharmaceutically acceptable salt thereof.

More particularly, the present invention relates to the use as a medicinal product of pyrazole derivatives of formula (I) in which:

A is a bond, or (C1-C6) alkyl radical, a (C3-C6) alkenyl radical, a (C3-C6) alkynyl radical, a (C3-C7) cycloalkyl radical or a (C5-C7) cycloalkenyl radical; these radicals are optionally substituted with one or more substituents chosen from (C1-C5) alkyl, (C2-C5) alkenyl, (C2-C5) alkynyl, (C3-C7) cycloalkyl, (C5-C7) cycloalkenyl, arylalkyl, heteroarylalkyl, aryl, heteroaryl and halogen, R1 is an NR6R7, (C4-C7) azacycloalkyl, (C5-C7) azacycloalkenyl, (C5-C9) azabicycloalkyl or (C5-C9) azabicycloalkenyl group; these groups are optionally substituted with one or more substituents chosen from (C1-C5) alkyl, (C3-C5) cycloalkyl and halogen, A-R1 is such that the nitrogen of R1 and the nitrogen in the 1-position of the pyrazole are necessarily separated by at least two carbon atoms, R3 is an OH, $NH_2$, OMe or H radical, R4 is an aryl or heteroaryl radical being optionally substituted with one or more substituents chosen from halogen, CN, $NO_2$, $NH_2$, OH, SH, COOH, CHO, $C(O)NH_2$, $C(S)NH_2$, $SO_2H$, $SO_2NH_2$, NHCHO, C(O)Ra, C(O)ORa, C(O)NRaRb, C(S)NRaRb, S(O)Ra, $SO_2Ra$, $SO_2NRaRb$, ORc, SRc, O—C(O)Ra, —O—C(S)Ra, NRaRb, NHC(O)Ra, NHC(S)Ra, $NHCONH_2$, NHCONRaRb, $NHSO_2Ra$, aryl, heteroaryl, (C4-C7) heterocycloalkyl, polyfluoroalkyl, trifluoromethyl-sulfanyl, trifluoromethoxy, linear or branched (C1-C6) alkyl, (C2-C6) alkenyl and (C2-C6) alkynyl, these substituents being optionally substituted with one or more alkyl, halogen, OH, methoxy, R5 is a hydrogen, Ra is linear or branched (C1-C6) alkyl, alkenyl, alkynyl, (C3-C7) cycloalkyl, (C5-C7) cycloalkenyl, (C4-C7) heterocycloalkyl, arylalkyl, heteroarylalkyl, aryl, heteroaryl or polyfluoroalkyl, Rb is, independently of Ra, a hydrogen, linear or branched (C1-C6) alkyl, alkenyl, alkynyl, (C3-C7) cycloalkyl, (C5-C7) cycloalkenyl, (C4-C7) hetero-cycloalkyl, arylalkyl, heteroarylalkyl, aryl, heteroaryl or polyfluoroalkyl, Ra and Rb may form a saturated or unsaturated ring containing 5, 6 or 7 ring members, which may or may not have a hetero atom such as O, S or N, this ring being optionally substituted with one or more alkyl and/or halogen radicals, Rc is a linear or branched (C1-C6) alkyl, (C3-C6) alkenyl, (C3-C6) alkynyl, (C3-C7) cycloalkyl, (C5-C7) cycloalkenyl, (C4-C7) heterocycloalkyl, (hetero)aryl-alkyl, (hetero)aryl, (poly)fluoroalkyl, C(O)R8, C(S)R8 or SO$_2$R8 radical, R6 and R7 are, independently of one another, a hydrogen, (C1-C6) alkyl, (C3-C6) alkenyl, (C3-C6) alkynyl, (C3-C7) cycloalkyl, (C5-C7) cycloalkenyl, (C4-C7) heterocycloalkyl, an arylalkyl or heteroarylalkyl, R6 and R7 may form a saturated or unsaturated ring with 5, 6 or 7 ring members, which may or may not have a hetero atom such as O, S or N and which is optionally substituted with one or more alkyls and/or halogens, R8 is an Ra or NRaRb radical, or a racemate, an enantiomer or a diastereoisomer, or a mixture in any combination thereof, a tautomer or a pharmaceutically acceptable salt thereof, Among the compounds of formula (I) which are useful according to the invention, mention may be made of the following compounds:

1-[2-(3-Methoxy-4-phenylpyrazol-1-yl)ethyl]piperidine;
1-(1-Azabicyclo[2.2.2]oct-3-ylmethyl)-4-phenyl-1H-pyrazol-1-ol;
3-(3-Benzyloxy-4-phenylpyrazol-1-ylmethyl)-1-azabicyclo[2.2.2]octane;
3-(3-Methoxy-4-phenylpyrazol-1-ylmethyl)-1-azabicyclo[2.2.2]octane;
1-(1-Azabicyclo[2.2.2]oct-3-yl)-4-phenyl-1H-pyrazol-3-ol;
1-(2-Perhydroazepin-1-ylethyl)-4-phenyl-1H-pyrazol-3-ol;
1-[2-(2-Methylpiperidin-1-yl)ethyl]-4-phenyl-1H-pyrazol-3-ol;
1-[2-(4-Fluoropiperidin-1-yl)ethyl]-4-phenyl-1H-pyrazol-3-ol;
1-[2-(3-Methylpiperidin-1-yl)ethyl]-4-phenyl-1H-pyrazol-3-ol;
1-[2-(3,6-Dihydro-2H-pyridin-1-yl)ethyl]-4-phenyl-1H-pyrazol-3-ol;
1-[2-(7-Azabicyclo[2.2.1]hept-7-yl)ethyl]-4-phenyl-1H-pyrazol-3-ol;
1-[2-(2-Azabicyclo[2.2.2]oct-2-yl)ethyl]-4-phenyl-1H-pyrazol-3-ol;
1-[2-(2-Azabicyclo[2.2.1]hept-2-yl)ethyl]-4-phenyl-1H-pyrazol-3-ol;
1-[2-Dimethylaminoethyl]-4-phenyl-1H-pyrazol-3-ol;
1-[3-Dimethylaminopropyl]-4-phenyl-1H-pyrazol-3-ol;
1-[2-((2S,6R)-2,6-Dimethylpiperidin-1-yl)ethyl]-4-phenyl-1H-pyrazol-3-ol;
1-[2-Diethylaminoethyl]-4-phenyl-1H-pyrazol-3-ol;
1-(2-Diisopropylaminoethyl)-4-phenyl-1H-pyrazol-3-ol;
4-Phenyl-1-(2-pyrrolidin-1-ylethyl)-1H-pyrazol-3-ol;
3-(3-Methoxy-4-phenylpyrazol-1-yl)-1-azabicyclo-[2.2.2]octane;
1-[2-(3-Difluoromethoxy-4-phenylpyrazol-1-yl)ethyl]-piperidine;
4-Phenyl-1-(2-piperidin-1-ylethyl)-1H-pyrazol-3-ylamine;
4-Phenyl-1-(2-piperidin-1-ylethyl)-1H-pyrazol-3-ylamine;
N-[4-Phenyl-1-(2-piperidin-1-ylethyl)-1H-pyrazol-3-yl]acetamide;
N-[4-Phenyl-1-(2-piperidin-1-ylethyl)-1H-pyrazol-3-yl]methanesulfonamide;
1-(2-Dimethylaminopropyl)-4-phenyl-1H-pyrazol-3-ol;
1-(1-Methylpiperidin-3-ylmethyl)-4-phenyl-1H-pyrazol-3-ol;
5-Methyl-4-phenyl-1-(2-piperidin-1-ylethyl)-1H-pyrazol-3-ol;
4-(3-Aminophenyl)-1-(2-dimethylaminoethyl)-1H-pyrazol-3-ol;
N-{3-[3-Hydroxy-1-(2-dimethylaminoethyl)-1H-pyrazol-4-yl]phenyl}acetamide;
4-(4-Aminophenyl)-1-(2-dimethylaminoethyl)-1H-pyrazol-3-ol;
1-(2-Dimethylaminoethyl)-4-(4'-fluorobiphenyl-3-yl)-1H-pyrazol-3-ol;
4-Biphenyl-3-yl-1-(2-dimethylaminoethyl)-1H-pyrazol-3-ol;
1-(2-Dimethylaminoethyl)-4-(4'-fluorobiphenyl-4-yl)-1H-pyrazol-3-ol;
1-(2-Piperidin-1-ylethyl)-4-pyridin-2-yl-1H-pyrazol-3-ol;
1-(2-Piperidin-1-ylethyl)-4-pyridin-4-yl-1H-pyrazol-3-ol;
4-(4-Fluorophenyl)-1-(2-piperidin-1-ylethyl)-1H-pyrazol-3-ol;
4-(4-Trifluoromethoxyphenyl)-1-(2-piperidin-1-ylethyl)-1H-pyrazol-3-ol;
4-Phenyl-1-(2-piperidin-1-ylpropyl)-1H-pyrazol-3-ol;
3-(4-Phenylpyrazol-1-ylmethyl)-1-azabicyclo[2.2.2]-octane;
4-(5-Chlorothiophen-2-yl)-1-(2-piperidin-1-ylethyl)-1H-pyrazol-3-ol;
4-(3-Methoxyphenyl)-1-(2-piperidin-1-ylethyl)-1H-pyrazol-3-ol;
4-(2-Methoxyphenyl)-1-(2-piperidin-1-ylethyl)-1H-pyrazol-3-ol;
4-(3-Hydroxyphenyl)-1-(2-piperidin-1-ylethyl)-1H-pyrazol-3-ol;
4-(4-Hydroxyphenyl)-1-(2-piperidin-1-ylethyl)-1H-pyrazol-3-ol;
4-(4-Methoxyphenyl)-1-(2-piperidin-1-ylethyl)-1H-pyrazol-3-ol;
4-(3-Fluorophenyl)-1-(2-piperidin-1-ylethyl)-1H-pyrazol-3-ol;
1-(2-Piperidin-1-ylethyl)-4-(3-trifluoromethylphenyl)-1H-pyrazol-3-ol;
1-(2-Piperidin-1-ylethyl)-4-pyridin-3-yl-1H-pyrazol-3-ol;
4-(4-Chlorophenyl)-1-(2-piperidin-1-ylethyl)-1H-pyrazol-3-ol;
4-(3-Chlorophenyl)-1-(2-piperidin-1-ylethyl)-1H-pyrazol-3-ol;
4-(2-Fluorophenyl)-1-(2-piperidin-1-ylethyl)-1H-pyrazol-3-ol;
4-(2-Chlorophenyl)-1-(2-piperidin-1-ylethyl)-1H-pyrazol-3-ol;
1-(1-Azabicyclo[2.2.2]oct-3-yl)-4-(4-chlorophenyl)-1H-pyrazol-3-ol;
1-(1-Azabicyclo[2.2.2]oct-3-yl)-4-(3-chlorophenyl)-1H-pyrazol-3-ol;
1-(1-Azabicyclo[2.2.2]oct-3-yl)-4-(3-fluorophenyl)-1H-pyrazol-3-ol;

1-(1-Methylpyrrolidin-3-yl)-4-phenyl-1H-pyrazol-3-ol;
1-[2-(1-Methylpyrrolidin-2-yl)ethyl]-4-phenyl-1H-pyrazol-3-ol;
1-(Pyrrolidin-3-yl)-4-phenyl-1H-pyrazol-3-ol;
1-[(1-Methylpyrrolidin-2-(S)-yl)methyl]-4-phenyl-1H-pyrazol-3-ol;
4-Phenyl-1-(2-piperidin-1-ylethyl)-1H-pyrazol-3-ol;
1-[2-(4-Phenylpyrazol-1-yl)ethyl]piperidine;
1-[2-(4-Methylpiperidin-1-yl)ethyl]-4-phenyl-1H-pyrazol-3-ol;
3-(3-Difluoromethoxy-4-phenylpyrazol-1-ylmethyl)-1-azabicyclo[2.2.2]octane;
3-(4-Phenylpyrazol-1-yl)-1-azabicyclo[2.2.2]octane;
4-Benzo[b]thiophen-2-yl-1-(2-piperidin-1-ylethyl)-1H-pyrazol-3-ol;
4-Phenyl-1-piperidin-3-yl-1H-pyrazol-3-ol;
1-(2-Piperidin-1-ylethyl)-4-thiophen-3-yl-1H-pyrazol-3-ol;
1-(2-Piperidin-1-ylethyl)-4-p-tolyl-1H-pyrazol-3-ol;
1-(1-Azabicyclo[2.2.2]oct-2-ylmethyl)-4-phenyl-1H-pyrazol-3-ol;
(S)-1-(1-Azabicyclo[2.2.2]oct-3-yl)-4-phenyl-1H-pyrazol-3-ol;
(R)-1-(1-Azabicyclo[2.2.2]oct-3-yl)-4-phenyl-1H-pyrazol-3-ol;
4-Phenyl-1-pyrrolidin-3-ylmethyl-1H-pyrazol-3-ol;
1-(2-Piperidin-1-ylethyl)-4-thiophen-2-yl-1H-pyrazol-3-ol;
4-[3-Hydroxy-1-(2-piperidin-1-ylethyl)-1H-pyrazol-4-yl]benzamide;
3-[3-Hydroxy-1-(2-piperidin-1-ylethyl)-1H-pyrazol-4-yl]benzamide;
1-[(S)-1-(1-Azabicyclo[2.2.2]oct-3-yl)methyl]-4-phenyl-1H-pyrazol-3-ol;
1-[(R)-1-(1-Azabicyclo[2.2.2]oct-3-yl)methyl]-4-phenyl-1H-pyrazol-3-ol;
1-[(1S,4R)-2-(2-Azabicyclo[2.2.1]hept-2-yl)ethyl]-4-phenyl-1H-pyrazol-3-ol;
1-[(1R,4S)-2-(2-Azabicyclo[2.2.1]hept-2-yl)ethyl]-4-phenyl-1H-pyrazol-3-ol;
1-((R)-1-Methylpyrrolidin-2-ylmethyl)-4-phenyl-1H-pyrazol-3-ol;
1-((S)-1-Methylpyrrolidin-3-yl)-4-phenyl-1H-pyrazol-3-ol;
1-((R)-1-Methylpyrrolidin-3-yl)-4-phenyl-1H-pyrazol-3-ol;
1-[1-(7-Azabicyclo[2.2.1]hept-2-yl)ethyl]-4-phenyl-1H-pyrazol-3-ol;
1-(1-Azabicyclo[2.2.1]hept-3-yl)-4-phenyl-1H-pyrazol-3-ol;
4-Phenyl-1-piperidin-2-ylmethyl-1H-pyrazol-3-ol;
1-(1-Methylpiperidin-2-ylmethyl)-4-phenyl-1H-pyrazol-3-ol;
1-(1-Ethylpyrrolidin-2-ylmethyl)-4-phenyl-1H-pyrazol-3-ol;
1-(1-Methyl-2-piperidin-1-ylethyl)-4-phenyl-1H-pyrazol-3-ol;
1-[2-(2-Azabicyclo[2.2.1]hept-2-yl)-1-methylethyl]-4-phenyl-1H-pyrazol-3-ol;
1-(2-Dimethylaminocyclopentyl)-4-phenyl-1H-pyrazol-3-ol;
1-(R)-1-Azabicyclo[2.2.2]oct-3-yl-4-(4-chlorophenyl)-1H-pyrazol-3-ol;
1-(S)-1-Azabicyclo[2.2.2]oct-3-yl-4-(4-chlorophenyl)-1H-pyrazol-3-ol;
1-(R)-1-Azabicyclo[2.2.2]oct-3-yl-4-(3-chlorophenyl)-1H-pyrazol-3-ol;
1-(S)-1-Azabicyclo[2.2.2]oct-3-yl-4-(3-chlorophenyl)-1H-pyrazol-3-ol;
1-(R)-1-Azabicyclo[2.2.2]oct-3-yl-4-(3-fluorophenyl)-1H-pyrazol-3-ol;
1-(S)-1-Azabicyclo[2.2.2]oct-3-yl-4-(3-fluorophenyl)-1H-pyrazol-3-ol;
4-(5-Bromothiophen-2-yl)-1-(2-piperidin-1-ylethyl)-1H-pyrazol-3-ol;
4-(5-Phenylthiophen-2-yl)-1-(2-piperidin-1-ylethyl)-1H-pyrazol-3-ol;
1-(2-Piperidin-1-ylethyl)-4-(5-pyridin-2-ylthiophen-2-yl)-1H-pyrazol-3-ol;
4-(4-Chlorothiophen-2-yl)-1-(2-piperidin-1-ylethyl)-1H-pyrazol-3-ol;
4-(4-Bromophenyl)-1-(2-piperidin-1-ylethyl)-1H-pyrazol-3-ol;
1-(2-Piperidin-1-ylethyl)-4-(3-trifluoromethoxyphenyl)-1H-pyrazol-3-ol;
4-(3,4-Dichlorophenyl)-1-(2-piperidin-1-ylethyl)-1H-pyrazol-3-ol;
4-(3,5-Dichlorophenyl)-1-(2-piperidin-1-ylethyl)-1H-pyrazol-3-ol;
4-(6-Chloropyridin-2-yl)-1-(2-piperidin-1-ylethyl)-1H-pyrazol-3-ol;
4-(1H-Indol-6-yl)-1-(2-piperidin-1-ylethyl)-1H-pyrazol-3-ol;
4-(1H-Indol-5-yl)-1-(2-piperidin-1-ylethyl)-1H-pyrazol-3-ol;
4-(1H-Indol-3-yl)-1-(2-piperidin-1-ylethyl)-1H-pyrazol-3-ol;
4-(1-Methyl-1H-indol-3-yl)-1-(2-piperidin-1-ylethyl)-1H-pyrazol-3-ol;
N-{4-[3-Hydroxy-1-(2-piperidin-1-ylethyl)-1H-pyrazol-4-yl]phenyl}methanesulfonamide;
N-{3-[3-Hydroxy-1-(2-piperidin-1-ylethyl)-1H-pyrazol-4-yl]phenyl}methanesulfonamide;
4-[3-(1H-Imidazol-2-yl)phenyl]-1-(2-piperidin-1-yl-ethyl)-1H-pyrazol-3-ol;
4-[4-(1H-Imidazol-2-yl)phenyl]-1-(2-piperidin-1-yl-ethyl)-1H-pyrazol-3-ol;
4-(3-Chloro-4-hydroxyphenyl)-1-(2-piperidin-1-ylethyl)-1H-pyrazol-3-ol;
4-(4-Hydroxy-3-methylphenyl)-1-(2-piperidin-1-ylethyl)-1H-pyrazol-3-ol;
4-(4-Amino-3-chlorophenyl)-1-(2-piperidin-1-ylethyl)-1H-pyrazol-3-ol;
1-(1-Azabicyclo[2.2.2]oct-3-yl)-4-(5-chlorothiophen-2-yl)-1H-pyrazol-3-ol;
1-(1-Azabicyclo[2.2.2]oct-3-ylmethyl)-4-(5-chlorothiophen-2-yl)-1H-pyrazol-3-ol;
1-(1-Azabicyclo[2.2.2]oct-3-ylmethyl)-4-(4-chloro-phenyl)-1H-pyrazol-3-ol;
1-(1-Azabicyclo[2.2.2]oct-3-ylmethyl)-4-(3-chloro-phenyl)-1H-pyrazol-3-ol;
1-(1-Azabicyclo[2.2.2]oct-3-ylmethyl)-4-(3-fluoro-phenyl)-1H-pyrazol-3-ol;
1-(1-Azabicyclo[2.2.2]oct-3-ylmethyl)-4-(3-hydroxyphenyl)-1H-pyrazol-3-ol;
1-(1-Azabicyclo[2.2.2]oct-3-ylmethyl)-4-(4-hydroxy-phenyl)-1H-pyrazol-3-ol;
1-[2-(2-Azabicyclo[2.2.1]hept-2-yl)ethyl]-4-(5-chloro-thiophen-2-yl)-1H-pyrazol-3-ol;
1-[2-(2-Azabicyclo[2.2.1]hept-2-yl)ethyl]-4-(4-chloro-phenyl)-1H-pyrazol-3-ol;
1-[2-(2-Azabicyclo[2.2.1]hept-2-yl)ethyl]-4-(3-chloro-phenyl)-1H-pyrazol-3-ol;
1-[2-(2-Azabicyclo[2.2.1]hept-2-yl)ethyl]-4-(3-fluoro-phenyl)-1H-pyrazol-3-ol;
1-[2-(2-Azabicyclo[2.2.1]hept-2-yl)ethyl]-4-(3-hydroxyphenyl)-1H-pyrazol-3-ol;

1-[2-(2-Azabicyclo[2.2.1]hept-2-yl)ethyl]-4-(4-hydroxyphenyl)-1H-pyrazol-3-ol;
1-[2-(2-Azabicyclo[2.2.1]hept-2-yl)ethyl]-4-(3-chloro-4-hydroxyphenyl)-1H-pyrazol-3-ol;
1-(1-Azabicyclo[2.2.2]oct-3-ylmethyl)-4-(3-chloro-4-hydroxyphenyl)-1H-pyrazol-3-ol;
1-(1-Azabicyclo[2.2.2]oct-3-yl)-4-(3-hydroxyphenyl)-1H-pyrazol-3-ol;
1-(1-Azabicyclo[2.2.2]oct-3-yl)-4-(4-hydroxyphenyl)-1H-pyrazol-3-ol;
1-(1-Azabicyclo[2.2.2]oct-3-yl)-4-(3-chloro-4-hydroxyphenyl)-1H-pyrazol-3-ol;
2-[1-(2-Piperidin-1-ylethyl)-1H-pyrazol-4-yl]benzamide;
N-Methyl-2-[1-(2-piperidin-1-ylethyl)-1H-pyrazol-4-yl]benzamide;
2-[1-(2-Piperidin-1-ylethyl)-1H-pyrazol-4-yl]benzene-sulfonamide;
N-Methyl-2-[1-(2-piperidin-1-ylethyl)-1H-pyrazol-4-yl]benzenesulfonamide;
{2-[1-(2-Piperidin-1-ylethyl)-1H-pyrazol-4-yl]phenyl}-methanol;
4-Phenyl-1-(2-piperidin-1-ylethyl)-1H-pyrazole-3-thiol;
1-(1-Azabicyclo[2.2.2]oct-3-yl)-4-phenyl-1H-pyrazol-3-ylamine;
N-[1-(1-Azabicyclo[2.2.2]oct-3-yl)-4-phenyl-1H-pyrazol-3-yl]methanesulfonamide;
1-(1-Azabicyclo[2.2.2]oct-3-yl)-4-phenyl-1H-pyrazole-3-thiol;
4-[1-(1-Azabicyclo[2.2.2]oct-3-yl)-1H-pyrazol-4-yl]-2-chlorophenol;
4-[1-(1-Azabicyclo[2.2.2]oct-3-yl)-1H-pyrazol-4-yl]-phenol;
3-[4-(4-Chlorophenyl)pyrazol-1-ylmethyl]-1-azabicyclo[2.2.2]octane;
4-[1-(1-Azabicyclo[2.2.2]oct-3-ylmethyl)-1H-pyrazol-4-yl]phenol;
4-[1-(1-Azabicyclo[2.2.2]oct-3-ylmethyl)-1H-pyrazol-4-yl]-2-chlorophenol;
3-(3-Cyclopropylmethoxy-4-phenylpyrazol-1-ylmethyl)-1-azabicyclo[2.2.2]octane;
3-[4-(4-Chlorophenyl)-3-cyclopropylmethoxypyrazol-1-ylmethyl]-1-azabicyclo[2.2.2]octane;
4-[1-(1-Azabicyclo[2.2.2]oct-3-ylmethyl)-3-cyclopropylmethoxy-1H-pyrazol-4-yl]phenol;
4-[1-(1-Azabicyclo[2.2.2]oct-3-ylmethyl)-3-cyclopropylmethoxy-1H-pyrazol-4-yl]-2-chlorophenol;
3-[4-Phenyl-3-(2,2,2-trifluoroethoxy)pyrazol-1-yl-methyl]-1-azabicyclo[2.2.2]octane;
3-[4-(4-Chlorophenyl)-3-(2,2,2-trifluoroethoxy)pyrazol-1-ylmethyl]-1-azabicyclo[2.2.2]octane;
4-[1-(1-Azabicyclo[2.2.2]oct-3-ylmethyl)-3-(2,2,2-trifluoroethoxy)-1H-pyrazol-4-yl]phenol;
4-[1-(1-Azabicyclo[2.2.2]oct-3-ylmethyl)-3-(2,2,2-trifluoroethoxy)-1H-pyrazol-4-yl]-2-chlorophenol;
N-[1-(1-Azabicyclo[2.2.2]oct-3-ylmethyl)-4-phenyl-1H-pyrazol-3-yl]methanesulfonamide;
1-(1-Azabicyclo[2.2.2]oct-3-ylmethyl)-4-phenyl-1H-pyrazole-3-thiol;
1-(1-Azabicyclo[2.2.2]oct-3-ylmethyl)-4-phenyl-1H-pyrazol-3-ylamine;
2-[2-(4-Phenylpyrazol-1-yl)ethyl]-2-azabicyclo-[2.2.1]heptane;
2-{2-[4-(4-Chlorophenyl)pyrazol-1-yl]ethyl}-2-aza-bicyclo[2.2.1]heptane;
4-{1-[2-(2-Azabicyclo[2.2.1]hept-2-yl)ethyl]-1H-pyrazol-4-yl}phenol;
4-{1-[2-(2-Azabicyclo[2.2.1]hept-2-yl)ethyl]-1H-pyrazol-4-yl}-2-chlorophenol;
1-[2-(2-Ethyl-4-methylpyrrolidin-1-yl)ethyl]-4-phenyl-1H-pyrazole-3-thiol;
N-{1-[2-(2-Azabicyclo[2.2.1]hept-2-yl)ethyl]-4-phenyl-1H-pyrazol-3-yl}methanesulfonamide;
1-[2-(2-Azabicyclo[2.2.1]hept-2-yl)ethyl]-4-phenyl-1H-pyrazol-3-ylamine;
4-(4-Chlorophenyl)-1-[2-(2-ethyl-4-methylpyrrolidin-1-yl)ethyl]-1H-pyrazole-3-thiol;
N-[1-[2-(2-Azabicyclo[2.2.1]hept-2-yl)ethyl]-4-(4-chlorophenyl)-1H-pyrazol-3-yl]methanesulfonamide;
1-[2-(2-Azabicyclo[2.2.1]hept-2-yl)ethyl]-4-(4-chloro-phenyl)-1H-pyrazol-3-ylamine;
1-(1-Azabicyclo[2.2.2]oct-3-yl)-4-(4-chlorophenyl)-1H-pyrazole-3-thiol;
N-[1-(1-Azabicyclo[2.2.2]oct-3-ylmethyl)-4-(4-chloro-phenyl)-1H-pyrazol-3-yl]methanesulfonamide;
1-(1-Azabicyclo[2.2.2]oct-3-ylmethyl)-4-(4-chloro-phenyl)-1H-pyrazol-3-ylamine;
1-(1-Azabicyclo[2.2.2]oct-3-ylmethyl)-4-(4-chloro-phenyl)-1H-pyrazole-3-thiol;
1-(1-Methylperhydroazepin-3-yl)-4-phenyl-1H-pyrazol-3-ol;
1-(2-Methylaminocyclopentyl)-4-phenyl-1H-pyrazol-3-ol;
1-(3-Dimethylaminocyclopentyl)-4-phenyl-1H-pyrazol-3-ol;
1-(3-Methylaminocyclopentyl)-4-phenyl-1H-pyrazol-3-ol;
1-(2-Dimethylaminocyclohexyl)-4-phenyl-1H-pyrazol-3-ol;
1-(2-Methylaminocyclohexyl)-4-phenyl-1H-pyrazol-3-ol;
1-(3-Dimethylaminocyclohexyl)-4-phenyl-1H-pyrazol-3-ol;
1-(3-Methylaminocyclohexyl)-4-phenyl-1H-pyrazol-3-ol;
1-(Octahydroindolizin-3-ylmethyl)-4-phenyl-1H-pyrazol-3-ol;
1-((S)-1-Ethylpyrrolidin-2-ylmethyl)-4-phenyl-1H-pyrazol-3-ol;
4-Phenyl-1-pyrrolidin-3-ylmethyl-1H-pyrazol-3-ol;
1-((2R)1-Methylpyrrolidin-2-ylmethyl)-4-phenyl-1H-pyrazol-3-ol;
4-Phenyl-1-(piperidin-3-yl)-1H-pyrazol-3-ol;
1-(1-Methylpiperidin-2-ylmethyl)-4-phenyl-1H-pyrazol-3-ol;
1-(1-Methylazepan-3-yl)-4-phenyl-1H-pyrazol-3-ol;
4-Phenyl-1-(2-piperidin-1-ylethyl)-1H-pyrazol-3-ol;
4-(Thiophen-2-yl)-1-(2-piperidin-1-ylethyl)-1H-pyrazol-3-ol;
4-(3,4-Dichlorophenyl)-1-(2-piperidin-1-ylethyl)-1H-pyrazol-3-ol;
4-(4-Bromophenyl)-1-(2-piperidin-1-ylethyl)-1H-pyrazol-3-ol;
4-(1H-Indol-5-yl)-1-(2-piperidin-1-ylethyl)-1H-pyrazol-3-ol;
4-(5-Bromothiophen-2-yl)-1-(2-piperidin-1-ylethyl)-1H-pyrazol-3-ol;
2-[1-(2-Piperidin-1-ylethyl)-1H-pyrazol-4-yl]benzamide;
4-(2-Hydroxyphenyl)-1-(2-piperidin-1-ylethyl)-1H-pyrazole;
4-(1H-Indol-5-yl)-1-(2-piperidin-1-ylethyl)-1H-pyrazole;
4-(4-Methylphenyl)-1-(2-piperidin-1-ylethyl)-1H-pyrazol-3-ol;
1-(1-Azabicyclo[2.2.2]oct-3-yl)-4-(1H-indol-5-yl)-1H-pyrazole;
(+)-1-(Azabicyclo[2.2.2]oct-3-yl)-4-(1H-indol-5-yl)-1H-pyrazole;
(−)-1-(Azabicyclo[2.2.2]oct-3-yl)-4-(1H-indol-5-yl)-1H-pyrazole;

1-(1-Azabicyclo[2.2.2]oct-3-yl)-4-(5-chlorothiophen-2-yl)-1H-pyrazol-3-ol;
1-(1-Azabicyclo[2.2.2]oct-3-yl)-4-(5-chlorothiophen-2-yl)-1H-pyrazol-3-ol;
1-(1-Azabicyclo[2.2.2]oct-2-ylmethyl)-4-phenyl-1H-pyrazol-3-ol;
3-[4-(3,5-Difluorophenyl)pyrazol-1-yl]-1-azabicyclo[2.2.2]octane;
4-Benzo[b]thiophen-2-yl-1-(2-piperidin-1-ylethyl)-1H-pyrazol-3-ol;
1-(2-Piperidin-1-ylethyl)-4-thiophen-3-yl-1H-pyrazol-3-ol;
4-[3-Hydroxy-1-(2-piperidin-1-ylethyl)-1H-pyrazol-4-yl]benzamide;
3-[3-Hydroxy-1-(2-piperidin-1-ylethyl)-1H-pyrazol-4-yl]benzamide;
(−)-1-(1-Azabicyclo[2.2.2]oct-3-yl)-4-phenyl-1H-pyrazol-3-ol;
(+)-1-(1-Azabicyclo[2.2.2]oct-3-yl)-4-phenyl-1H-pyrazol-3-ol;
(−)-1-(1-Azabicyclo[2.2.2]oct-3-ylmethyl)-4-phenyl-1H-pyrazol-1-ol;
(+)-1-(1-Azabicyclo[2.2.2]oct-3-ylmethyl)-4-phenyl-1H-pyrazol-1-ol;
1-(1-Azabicyclo[2.2.2]oct-3-ylmethyl)-4-(4-chlorophenyl)-1H-pyrazol-3-ol;
(−)-1-(1-Azabicyclo[2.2.2]oct-3-yl)-4-(4-chlorophenyl)-1H-pyrazol-3-ol;
(+)-1-(1-Azabicyclo[2.2.2]oct-3-yl)-4-(4-chlorophenyl)-1H-pyrazol-3-ol;
(−)-1-(1-Azabicyclo[2.2.2]oct-3-yl)-4-(4-fluorophenyl)-1H-pyrazol-3-ol;
(+)-1-(1-Azabicyclo[2.2.2]oct-3-yl)-4-(4-fluorophenyl)-1H-pyrazol-3-ol;
3-[4-(4-Chlorophenyl)pyrazol-1-yl]-1-azabicyclo-[2.2.2]octane;
3-[4-(4-Chlorophenyl)pyrazol-1-ylmethyl]-1-azabicyclo[2.2.2]octane;
3-[4-(3-Chloro-4-methoxyphenyl)pyrazol-1-ylmethyl]-1-azabicyclo[2.2.2]octane;
4-[1-(1-Azabicyclo[2.2.2]oct-3-ylmethyl)-1H-pyrazol-4-yl]-2-chlorophenol;
4-[1-(1-Azabicyclo[2.2.2]oct-3-yl)-1H-pyrazol-4-yl]-2-chlorophenol;
(−)-4-[1-(1-Azabicyclo[2.2.2]oct-3-yl)-1H-pyrazol-4-yl]-2-chlorophenol;
(+)-4-[1-(1-Azabicyclo[2.2.2]oct-3-yl)-1H-pyrazol-4-yl]-2-chlorophenol;
(+)-1-(1-Azabicyclo[2.2.2]oct-3-yl)-4-pyridin-2-yl-1H-pyrazol-3-ol;
(−)-1-(1-Azabicyclo[2.2.2]oct-3-yl)-4-pyridin-2-yl-1H-pyrazol-3-ol;
(+)-1-(1-Azabicyclo[2.2.2]oct-3-yl)-4-phenyl-1H-pyrazol-3-ylamine;
(−)-1-(1-Azabicyclo[2.2.2]oct-3-yl)-4-phenyl-1H-pyrazol-3-ylamine;
(+)-1-(1-Azabicyclo[2.2.2]oct-3-yl)-4-(1H-indol-4-yl)-1H-pyrazole; and
(−)-1-(1-Azabicyclo[2.2.2]oct-3-yl)-4-(1H-indol-4-yl)-1H-pyrazole;
their racemates, enantiomers and diastereoisomers and their mixtures, their tautomers and their pharmaceutically acceptable salt.

The methods of obtaining the derivatives of the present invention are illustrated below and, in order for it to be easier to read the processes, the compounds of formula (I) are divided up into eight subfamilies (Ia) for R3=OH, (Ib) for R3=ORc, (Ic) for R3=H, (Id) for R3=NH$_2$, (Ie) for R3=NHCHO, NRaRb, NHC(O)Ra, NHC(S)Ra, NHSO$_2$Ra, (If) for R3=SH, (Ig) for R3=SRc, and (Ih) for R3=S(O)Ra, SO$_2$Ra. The definitions of various substituents are the same as those of formula (I), unless otherwise indicated.

For easy reading, groups GP, GP', GP'', GP''', GP$^{iv}$ and GP$^{v}$ are groups which protect functions sensitive to the reaction conditions and are introduced as defined in T. W. Greene et al., Protective Groups in Organic Synthesis, Wiley-Interscience, third edition (1999), capable of being unaffected by the subsequent steps of the synthesis and of being deprotected under conditions which do not affect the rest of the molecule.

The derivatives of formula (I) for which R3 is a hydroxyl (Ia) can be obtained from derivatives of formula (II) (I with R3=OGP) for which GP is a hydroxyl function-protecting group.

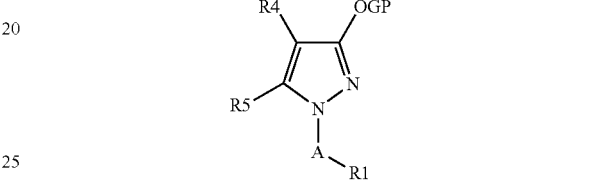

The term "GP" is intended to mean a hydroxyl function-protecting group, as defined in T. W. Greene et al., Protective Groups in Organic Synthesis, Wiley-Interscience, third edition (1999), capable of being unaffected by the subsequent steps of the synthesis and of being deprotected under conditions which do not affect the rest of the molecule. For example, the GP group may be a silyl-containing group such as tert-butyldimethylsilyl, triisopropylsilyl or diphenyl-methylsilyl, or an alkyl, aralkyl, alkylidene, cycloalkylidene, heteroalkyl or heterocycloalkyl residue such as methyl, allyl, cyclohex-2-enyl, benzyl or tetrahydropyran-2-yl. The GP group is preferably a benzyl or a cyclohex-2-enyl. The deprotection of the GP group is carried out according to the methods described in T. W. Greene et al., Protective Groups in Organic Synthesis, Wiley-Interscience, third edition (1999).

For example, when the GP group is a benzyl, the deprotection is carried out by hydrolysis in the presence of concentrated hydrochloric acid in an alcohol such as ethanol, methanol or isopropanol at a temperature of between 20° C. and the boiling temperature of the reaction medium, preferably in ethanol, at the boiling temperature of the reaction medium.

Alternatively, the debenzylation can be carried out by the following successive operations:

a) Formation of the hydrochloride of the compound to be deprotected in the presence of hydrochloric acid in aqueous solution or in solution in an organic solvent such as ethanol, methanol, dioxane or diethyl ether, at a temperature in the region of 20° C.;

b) Hydrogenation in the presence of a catalyst such as palladium-on-charcoal, in an alcohol such as ethanol, methanol or isopropanol, at a hydrogen pressure of between 1 bar and 20 bar and at a temperature of between 20° C. and the boiling temperature of the reaction medium.

The hydrogenolysis of the benzyl group can also be carried out in the presence of a catalyst such as palladium-on-charcoal, in the presence of concentrated hydrochloric acid, in an alcohol such as ethanol, methanol or isopropanol, at a hydrogen pressure of between 1 bar and 30 bar and at a temperature of between 20° C. and the boiling temperature of the reaction medium. The reaction can also be carried out with ammonium formate, in the presence of a catalyst such as palladium-on-charcoal, in an alcohol such as ethanol, methanol or isopropanol, at a temperature between 20° C. and the boiling temperature of the reaction medium, preferably in methanol at the boiling temperature of the reaction medium.

When the GP group is a cyclohexenyl, the deprotection is carried out by hydrolysis in acid medium, for example in the presence of a solution of hydrochloric acid in an ether or an alcohol, in a solvent such as methanol or ethanol at a temperature of between 20° C. and the boiling temperature of the reaction medium.

The derivatives of formula I for which R3 is ORc (Rc being different to C(O)R8, C(S)R8, SO$_2$R8), H, NH$_2$ or OGP (Ib), (Ic), (Id) or (II) can be obtained according to three different synthetic pathways.

The first synthetic pathway consists in using compounds of formula (III):

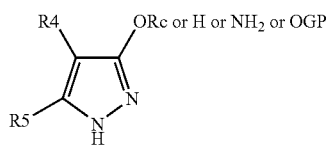

The compounds of formula (Ib), (Ic), (Id) or (II) can be obtained from a pyrazole of formula (III) and a compound of formula (IV) R1-A-X for which X=a function such as Cl, Br, I, OTs, OMs or OTf. The alkylation is carried out under an inert atmosphere, for example under argon or under nitrogen, in basic medium in an aprotic solvent, for example in the presence of sodium hydride, in an aprotic solvent such as dimethylformamide, at a temperature of between 20° C. and the boiling temperature of the reaction medium, or in the presence of potassium tert-butoxide, in a solvent such as dimethylformamide, at a temperature of between 20° C. and the boiling temperature of the reaction medium. The reaction can also be carried out in the presence of potassium carbonate and, optionally, of potassium iodide, in a solvent such as acetone, methyl ethyl ketone, acetonitrile or dimethylformamide, preferably in methyl ethyl ketone, at the boiling temperature of the reaction medium.

The compounds (IV) are commercial or can be obtained from the corresponding alcohols of formula R1-A-OH by methods known to those skilled in the art such as those described in J. March, Advanced Organic Chemistry, Wiley-Interscience, fourth edition (1992) or R.C. Larock, Comprehensive Organic Transformations, VCH Publishers (1989). The alcohols of formula R1-A-OH are commercial or can be obtained by adapting methods described in the literature using the basic general knowledge of those skilled in the art.

The second synthetic pathway can be used for the compounds of formula (I) for which R3 is ORc (Rc being different to C(O)R8, C(S)R8, SO$_2$R8), H or OGP, and R1-A is a group in which the radical A is connected to R1 by a nitrogen atom.

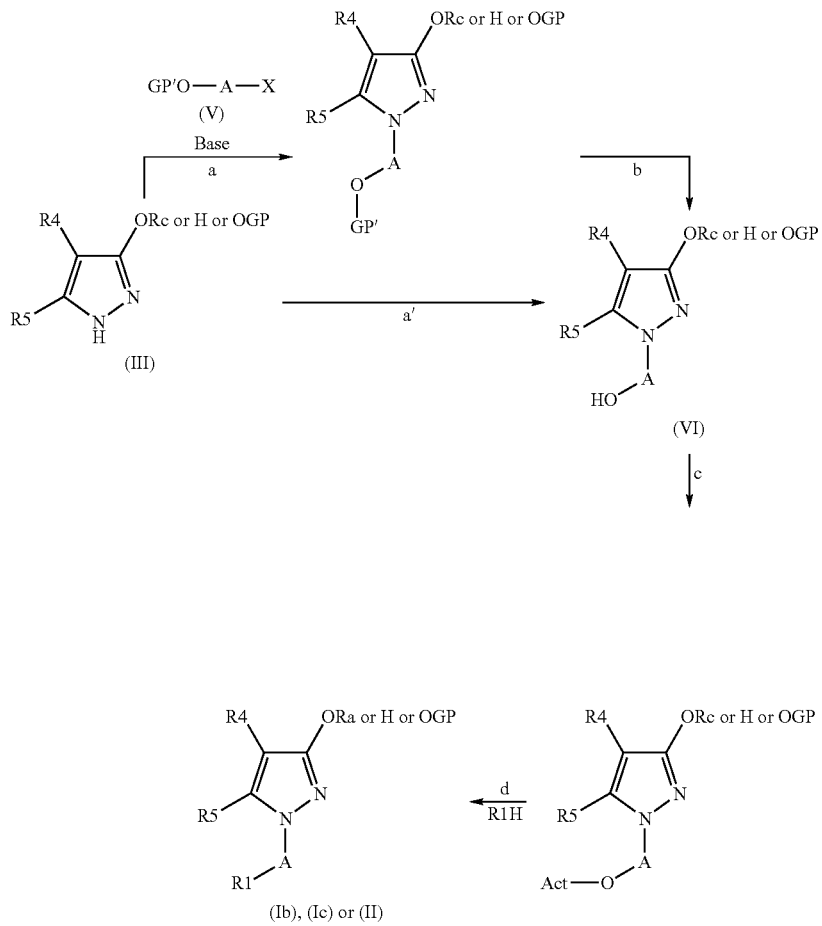

The compounds of formula (Ib), (IC) or (II) can be obtained in three or four steps from the pyrazoles of formula (III) according to the following protocol:

a) Alkylation of the pyrazole (III) with a compound of formula (V) GP'O-A-X in which GP' is a hydroxyl function-protecting group, as defined in T. W. Greene and al., Protective Groups in Organic Synthesis, Wiley-Interscience, third edition (1999), capable of being unaltered during the alkylation step and of being deprotected under conditions which do not affect the rest of the molecule (for example, the GP' group may be a silyl-containing group such as tert-butyldimethyl-silyl, triisopropylsilyl or diphenylmethylsilyl, or an aralkyl, alkylidene, cycloalkylidene, heteroalkyl, or heterocycloalkyl residue such as allyl, cyclohex-2-enyl, benzyl or tetrahydropyran-2-yl); the GP' group is preferably a tetrahydropyran-2-yl or tert-butyldi-methylsilyl group; the radical X is a function such as Cl, Br, I, OTs, OMs or OTf. The alkylation is carried out under an inert atmosphere, for example under argon or under nitrogen, in basic medium in an aprotic solvent, for example in the presence of sodium hydride, in an aprotic solvent such as dimethylformamide, at a temperature of between 20° C. and the boiling temperature of the reaction medium, or in the presence of potassium tert-butoxide, in a solvent such as dimethylformamide, at a temperature of between 20° C. and the boiling temperature of the reaction medium. The reaction may also be carried out in the presence of potassium carbonate and, optionally, of potassium iodide, in a solvent such as acetone, methyl ethyl ketone, acetonitrile or dimethylformamide, preferably in methyl ethyl ketone, at the boiling temperature of the reaction medium.

b) Production of the intermediates of formula (VI) after cleavage of the GP' protective group according to the methods described in T. W. Greene and al., Protective Groups in Organic Synthesis, Wiley-Interscience, third edition (1999), and not affecting the other functions carried by the molecule. For example, when the GP' group is a tetrahydropyran-2-yl, the deprotection of the alcohol may be carried out in acid medium, for example in the presence of aqueous hydrochloric acid, in a solvent such as ethanol or methanol, at a temperature of between 20° C. and the boiling temperature of the reaction medium, preferably in the presence of aqueous hydrochloric acid, in ethanol, at a temperature in the region of 20° C.

a') Alternatively, when A is an ethyl or (C5-C7) cycloalkyl radical, these radicals being optionally substituted with one or more substituents chosen from (C1-C5) alkyl, (C3-C7) cycloalkyl, arylalkyl, heteroarylalkyl, aryl and heteroaryl, the intermediates of formula (VI) can be obtained by reaction between a compound of formula (III) and a suitable epoxide in the presence of a base such as potassium tert-butoxide, in an aprotic solvent such as dimethylformamide, at a temperature between 20° C. and the boiling temperature of the reaction medium, according to J. M. Villalgordo, Synthesis 1999, 1613.

c) Activation of the alcohol residue of the compounds of formula (VI), for example by formation of a tosylate or of a mesylate designated "Act" in the synthesis scheme. The reaction is then carried out with tosyl chloride or mesyl chloride in basic medium, for example in the presence of pyridine, in a solvent such as dichloromethane, at a temperature of between −20° C. and the boiling temperature of the reaction medium, preferably at a temperature of between −10° C. and a temperature in the region of 20° C.

d) Substitution of the activated alcohol residue with a primary or secondary amine of formula R1H. The reaction is carried out in basic medium, for example in the presence of potassium carbonate, in a polar solvent, such as dimethylformamide or acetonitrile, at a temperature of between 20° C. and the boiling temperature of the reaction medium, preferably in dimethylformamide, at a temperature in the region of 80° C.

The compounds (V) are commercial or can be obtained from the corresponding alcohols of formula GP'O-A-OH by methods known to those skilled in the art as described in J. March, Advanced Organic Chemistry, Wiley-Interscience, fourth edition (1992) or R.C. Larock, Comprehensive Organic Transformations, VCH Publishers (1989). The alcohols of formula GP'O-A-OH are commercial or can be obtained, for example, by monoprotection of a dialcohol of formula HO-A-OH according to methods known to those skilled in the art as described in J. March, Advanced Organic Chemistry, Wiley-Interscience, fourth edition (1992) or R.C. Larock, Comprehensive Organic Transformations, VCH Publishers (1989). The compounds of formula HO-A-OH are commercial or available to those skilled in the art using or adapting methods described in the literature.

A third synthetic pathway consists, when R3 is ORc (Rc being different to C(O)R8, C(S)R8, SO₂R8), H or OGP, in carrying out the synthesis from a derivative of formula (VII) according to the synthesis scheme described below.

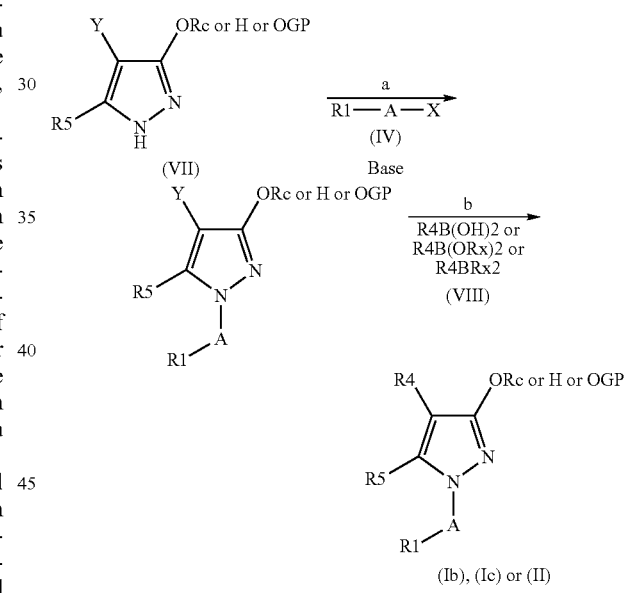

The compounds of formula (Ib), (Ic), and (II) can be obtained in two steps from the compounds of formula (VII) for which Y=Br, I or Cl (preferably Br or I):

a) Alkylation of the 4-halopyrazole of formula (VII) with a compound of formula (IV) as defined above. The reaction is carried out under an inert atmosphere, for example under argon or under nitrogen, in basic medium in an aprotic solvent, for example in the presence of sodium hydride, in an aprotic solvent such as dimethylformamide, at a temperature of between 20° C. and the boiling temperature of the reaction medium, or in the presence of potassium tert-butoxide, in a solvent such as dimethylformamide, at a temperature of between 20° C. and the boiling temperature of the reaction medium. The reaction can also be carried out in the presence of potassium carbonate and, optionally, in the presence of potassium iodide, in a solvent such as acetone, methyl ethyl ketone, acetonitrile or dimethylformamide, preferably in methyl ethyl ketone, at the boiling temperature of the reaction medium.

b) Suzuki coupling of the intermediate obtained and of a boronic acid, of an alkyl or cycloalkyl boronate or of a (hetero)aryldialkyl boron of formula (VIII) for which Rx is an alkyl or cycloalkyl radical. The reaction is carried out under an inert atmosphere in the presence of an inorganic base such as $K_3PO_4$, $Na_2CO_3$ or $Ba(OH)_2$, and of a palladium salt (catalyst) such as dichlorobis(triphenylphosphine)palladium ($PdCl_2(PPh_3)_2$), tetrakis(triphenylphosphine)palladium ($Pd(PPh_3)_4$) or (diphenylphosphino) ferrocenyl palladium ($PdCl_2dppf$), in a solvent such as dimethylformamide, dimethoxyethane, tetrahydrofuran, dioxane, toluene, xylene or ethanol, optionally in the presence of water, at a temperature of between 20° C. and the boiling temperature of the reaction medium (Kotha S. et al., Tetrahedron 2002, 58, 9633).

The boronic acids, alkyl or cycloalkyl boronates or (hetero)aryldialkyl boron of formula (VIII) are commercial or are obtained using or adapting methods described in the literature, for example in G. W. Kabalka et al., Tetrahedron Letters 1986, 27, 3843, J. F. Nicoud et al., Tetrahedron Letters 1993, 34, 8237, J. M. Tour et al., J. Amer. Chem. Soc. 1994, 116, 11723, or T. J. J. Mueller et al., Synthesis 2002, 9, 1163.

The intermediates of formula (III), when there is a radical ORc (Rc being different to C(O)R8, C(S)R8, $SO_2R8$) and OGP in the 3-position of the pyrazole, are obtained according to the reaction scheme represented below:

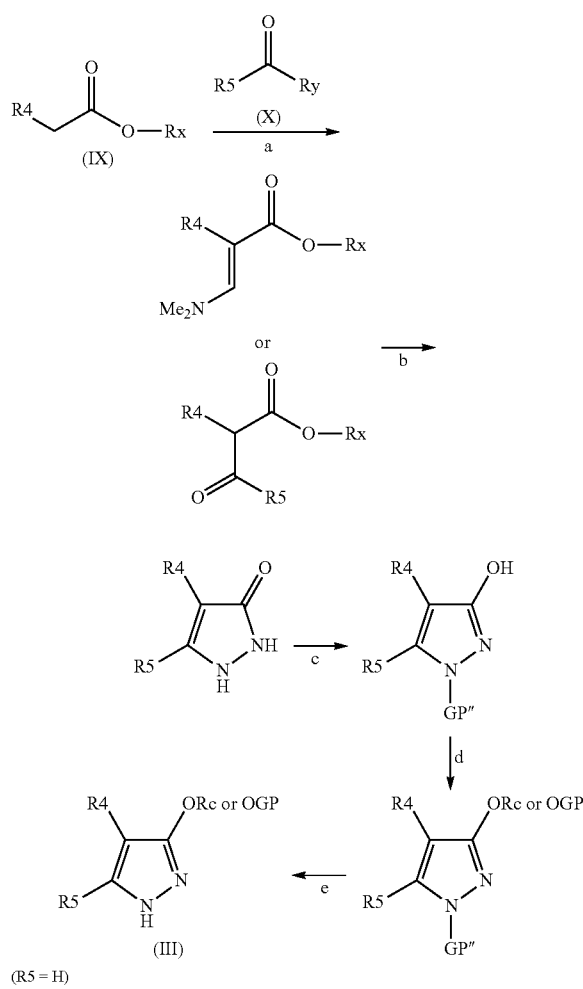

The pyrazoles of formula (III) can be obtained in four steps from the compounds of formula (IX) according to the following protocol:

a) Condensation of an (aryl)alkyl(hetero)aryl acetate for which Rx=alkyl or aralkyl, of formula (IX), with an aminomethylenation agent or a carbonylation agent of formula (X) for which Ry is a Cl, O-alkyl, O-aralkyl or O—CO-alkyl radical, preferably for which Ry is an O-alkyl radical. The aminomethylenation reaction can be carried out in the presence of a reagent such as N,N,N',N',N'',N''-hexamethylmethanetriamine, C-methoxy-N,N,N',N'-tetramethyl-methanediamine or C-tert-butoxy-N,N,N',N'-tetramethyl-methanediamine, in the absence of solvent or in a solvent such as tetrahydrofuran or dioxane at a temperature of between 20° C. and the boiling temperature of the reaction medium, preferably in the presence of C-tert-butoxy-N,N,N',N'-tetramethyl-methanediamine in tetrahydrofuran at a temperature of between 20° C. and the boiling temperature of the reaction medium. The carbonylation reaction between an (aryl)alkyl(hetero)aryl acetate and a carbonylation agent of formula (X) is carried out under an inert atmosphere, for example under argon or under nitrogen, in basic medium, for example in the presence of sodium hydride, in an aprotic solvent such as dimethylformamide, at a temperature of between –20° C. and the boiling temperature of the solvent, preferably at a temperature in the region of 20° C.

b) Formation of the 1H-pyrazol-3-ol ring by reaction of the intermediate obtained in the preceding step with hydrazine, generally in monohydrate form, in an alcohol such as ethanol, propanol or isopropanol, at a temperature of between 20° C. and the boiling temperature of the reaction medium, preferably in ethanol, at the boiling temperature of the reaction medium.

c) Protection of the nitrogen in the 1-position of the 1H-pyrazol-3-ol with a protective group such as an acetyl, alkyloxycarbonyl or tosyl, preferably with an acetyl group. The reaction is carried out with an acetylating, alkyloxycarbonylating or tosylating agent, preferably with acetic anhydride without solvent or in the presence of a solvent such as pyridine, at a temperature of between 20° C. and the boiling temperature of the reaction medium, preferably at a temperature in the region of 100° C.

d) Protection of the hydroxyl group of the pyrazole or introduction of the —Rc residue onto the hydroxyl of the pyrazole, followed by deprotection of the nitrogen in the 1-position of the pyrazole. The protection of the hydroxyl group of the pyrazole and the introduction of the —Rc residue onto the hydroxyl of the pyrazole can be carried out, for example, by alkylation of the hydroxyl group of the pyrazole with the compounds of formula GP-X or Rc-X for which X is a function such as Cl, Br, I, OTs, OMs or OTf. When Rc=Me or Et, dimethyl sulfate or diethyl sulfate can also be used as alkylating agent and will preferably be chosen. The reaction is carried out in basic medium, for example in the presence of a base such as potassium carbonate, in a solvent such as acetone, methyl ethyl ketone, acetonitrile or dimethylformamide, at a temperature of between 20° C. and the boiling temperature of the reaction medium, preferably in methyl ethyl ketone, at the boiling temperature of the reaction medium. When Rc=—$CHF_2$, the alkylation can be carried out with methyl chlorodifluoroacetate, in basic medium, for example in the presence of a base such as potassium carbonate, in a solvent such as dimethylformamide, at a temperature of between 20° C. and the boiling temperature of the reaction medium, preferably at a temperature in the region of 65° C. The deprotection of the nitrogen in the 1-position of the pyrazole is carried out according to the methods described in T. W. Greene et al., Protective Groups in Organic Synthesis, Wiley-Interscience, third edition (1999). For example, when the protective group is an acetyl, the deprotection can be carried out in the presence of a base such as sodium hydroxide or potassium carbonate, in an alcohol such as ethanol or methanol, to which a solvent such as tetrahydrofuran or dioxane is optionally added, at a temperature of between 20° C. and the boiling temperature of the reaction medium, preferably in the presence of sodium hydroxide in a mixture of ethanol and tetrahydrofuran, at a temperature in the region of 20° C.

The compounds of formula (IX) are commercial or can be obtained using or adapting methods described in the literature.

The compounds of formula (X) are commercial or can be obtained using or adapting methods described in the literature.

The compounds of formula GP-X are commercial. The compounds of formula Rc-X are commercial or can be obtained from the corresponding alcohols of formula Rc—OH by the methods known to those skilled in the art as described in J. March, Advanced Organic Chemistry, Wiley-Interscience, fourth edition (1992) or R.C. Larock, Comprehensive Organic Transformations, VCH Publishers (1989). The alcohols of formula Rc—OH are commercial or can be obtained using or adapting methods described in the literature.

The intermediates of formula (III), when there is a hydrogen in the 3-position of the pyrazole, are obtained according to the reaction scheme represented below:

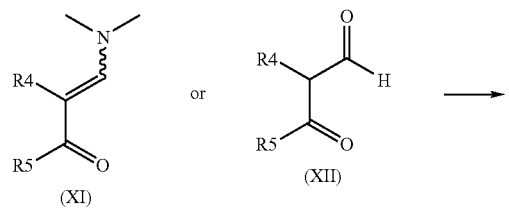

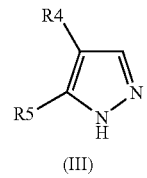

The compounds of formula (III) can be obtained from the compounds of formula (XI) or (XII) and hydrazine, generally in monohydrate form. The reaction is carried out, for example, in an alcohol such as ethanol, propanol or isopropanol, at a temperature in the region of 20° C. and the boiling temperature of the reaction medium, preferably in ethanol, at the boiling temperature of the reaction medium.

The compounds of formula (XI) or (XII) are commercial or can be obtained using or adapting methods described in the literature.

The intermediates of formula (III), when there is a radical ORc (Rc being different to C(O)R8, C(S)R8, SO$_2$R8) or OGP or H in the 3-position of the pyrazole, can also be obtained according to the reaction scheme represented below:

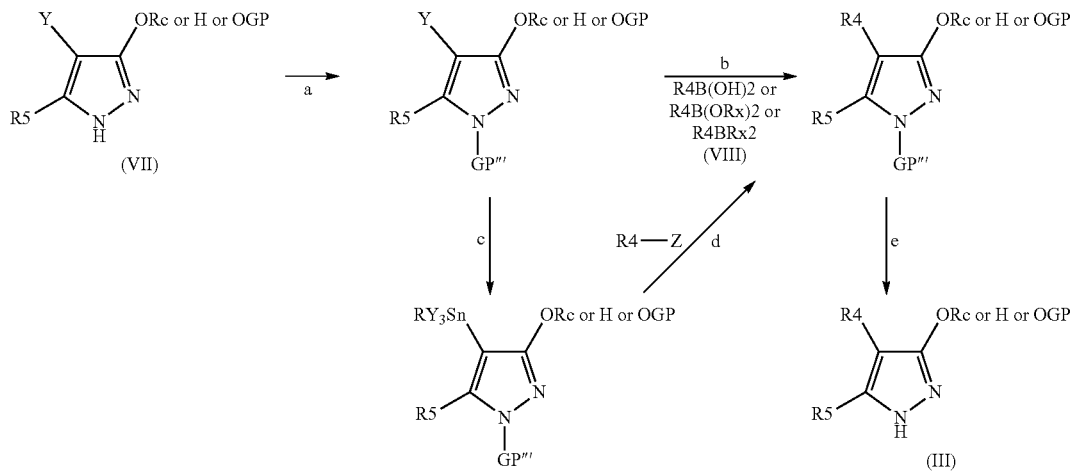

The compounds of formula (III) can be prepared in three or four steps from compounds of formula (VII):

a) Protection of the compounds of formula (VII), for example with a tosyl, mesyl or acetyl group, preferably with a tosyl group. This reaction is carried out according to the processes known to those skilled in the art and described in T. W. Greene et al., Protective Groups in Organic Synthesis, Wiley-Interscience, third edition (1999). For example, when the protective group is a tosyl, the reaction is carried out with tosyl chloride in basic medium, for example in the presence of sodium hydride or of potassium tert-butoxide in an aprotic solvent such as dimethylformamide at a temperature between −10° C. and the boiling temperature of the reaction medium.

b) Introduction of the R4 group by Suzuki coupling or by two consecutive Stille reactions. The introduction of the R4 group by Suzuki coupling is carried out using the protected 4-halopyrazole obtained in the preceding step and a boronic acid, an alkyl or cycloalkyl boronate or a (hetero)aryldialkyl boron of formula (VIII) for which Rx is an alkyl or cycloalkyl radical, under an inert atmosphere, in the presence of an inorganic base such as K$_3$PO$_4$, Na$_2$CO$_3$ or Ba(OH)$_2$, of a palladium salt (catalyst) such as dichlorobis- (triphenylphosphine)palladium ($PdCl_2(PPh_3)_2$), tetrakis-(triphenylphosphine)palladium ($Pd(PPh_3)_4$) or (diphenylphosphino)ferrocenyl palladium ($PdCl_2dppf$), in a solvent such as dimethylformamide, dimethoxyethane, tetra-hydrofuran, dioxane, toluene, xylene or ethanol, optionally in the presence of water, at a temperature of between 20° C. and the boiling temperature of the reaction medium. Alternatively, the introduction of the R4 group can be carried out with two consecutive Stille reactions. The first Stille reaction is carried out under an inert atmosphere using the protected 4-halopyrazole obtained in the preceding step and bis(tributyltin) in the presence of cuprous iodide, of a palladium salt (catalyst) such as palladium diacetate (Pd(OAc)$_2$) and of triphenylphosphine, in a solvent such as tetrahydrofuran at a temperature of between 20° C. and the boiling temperature of the reaction medium, according to A. I. Scott et al., Tetrahedron Lett. 1996, 37, 3247. The second Stille reaction is carried out using the organotin above and a halogenated aromatic derivative of formula R4-Z for which Z is a Br, I or Cl radical (preferably Br or I), with a palladium salt (catalyst) such as tris(dibenzylidene)dipalladium (Pd2dba3) and tristrifurylphosphine, in a solvent such as dioxane at a temperature of between 20° C. and the boiling temperature of the reaction medium, according to U. Hacksell et al., Bioorg. & Med. Chem. Lett., 1994, 2837.

c) Cleavage of the protective group introduced in the first step. This reaction is carried out according to the processes known to those skilled in the art and described in T. W. Greene et al., Protective Groups in Organic Synthesis, Wiley-Interscience, third edition (1999). For example, when the protective group is a tosyl, the reaction can be carried out with tetrabutylammonium fluoride in a solvent such as tetrahydrofuran or dioxane at a temperature between 20° C. and the boiling temperature of the reaction medium according to T. Sakamoto et al., Tetrahedron Lett. 1998, 39, 595.

The intermediates (III), when there is an NH$_2$ radical in the 3-position of the pyrazole, can be obtained according to the following scheme:

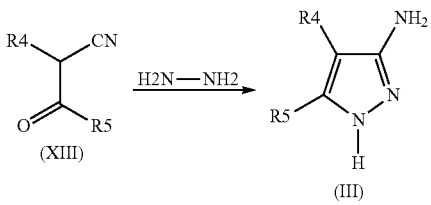

The compounds of formula (III) can be obtained by condensation of hydrazine, generally in monohydrate form, with a 2-(hetero)aryl-3-oxopropionitrile of formula (XIII) in acid medium, for example in the presence of acetic acid, in an alcohol such as ethanol, propanol or isopropanol, at a temperature of between 20° C. and the boiling temperature of the reaction medium, preferably in ethanol, at the boiling temperature of the reaction medium.

The compounds of formula (XIII) can be obtained using or adapting methods described in the literature.

The intermediates (VII) for which there is an H, OGP or ORc (Rc being different to C(O)R8, C(S)R8, SO$_2$R8) in the 3-position of the pyrazole are obtained from the derivative of formula (XIV)

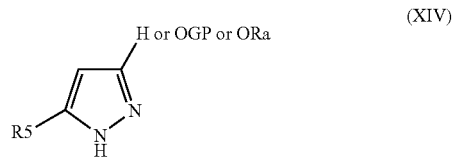

The intermediates (VII) for which Y=Br, I or Cl (preferably Br or I) are commercial or can be obtained from intermediates of formula (XIV). The reaction is carried out with a halogenating agent such as bromine or iodine chloride in a solvent such as dichloromethane or chloroform, in the presence of a base such as potassium carbonate, at a temperature of between –10° C. and the boiling temperature of the reaction medium, preferably with bromine, in dichloromethane, at a temperature in the region of 20° C.

The intermediates (XIV) for which there is a hydrogen in the 3-position of the pyrazole are commercial or are obtained using or adapting the methods described in the literature.

The intermediates (XIV) for which there is an OGP radical or an ORc radical (Rc being different to C(O)R8, C(S)R8, SO$_2$R8) in the 3-position of the pyrazole can be obtained in two steps from compounds of formula (XV) according to the following protocol:

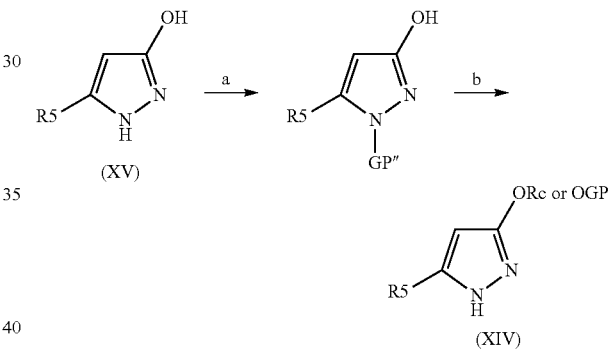

a) Protection of the nitrogen in the 1-position of the 1H-pyrazol-3-ol with a protective group such as an acetyl, alkyloxycarbonyl or tosyl, preferably with an acetyl group. The reaction is carried out with an acetylating, alkyloxycarbonylating or tosylating agent, preferably with acetic anhydride without solvent or in the presence of a solvent such as pyridine, at a temperature of between 20° C. and the boiling temperature of the reaction medium, preferably at a temperature in the region of 100° C.

b) Protection of the hydroxyl group of the pyrazole or introduction of the —Rc residue onto the hydroxyl of the pyrazole, followed by deprotection of the nitrogen in the 1-position of the pyrazole. The protection of the hydroxyl group of the pyrazole and the introduction of the —Rc residue onto the hydroxyl of the pyrazole can be carried out by alkylation of the hydroxyl group of the pyrazole with the compounds of formula GP-X or Rc-X for which X is a function such as Cl, Br, I, OTs, OMs or OTf. When Rc is a methyl or ethyl group, dimethyl sulfate or diethyl sulfate can also be used as alkylating agent and will preferably be chosen. The reaction is carried out in basic medium, for example in the presence of a base such as potassium carbonate, in a solvent such as acetone, methyl ethyl ketone, acetonitrile or dimethylformamide, at a temperature of between 20° C. and the boiling temperature of the reaction medium, preferably in methyl ethyl ketone, at the boiling temperature of the reaction medium. When Rc is a $CHF_2$ group, the alkylation can be carried out with methyl chlorodifluoroacetate, in basic medium, for example in the presence of a base such as potassium carbonate, in a solvent such as dimethylformamide, at a temperature of between 20° C. and the boiling temperature of the reaction medium, preferably at a temperature in the region of 65° C. The deprotection of the nitrogen of the pyrazole is carried out according to the methods described in T. W. Greene et al., in Protective Groups in Organic Synthesis, Wiley-Interscience, third edition (1999). For example, when the protective group is an acetyl, the deprotection can be carried out in the presence of a base such as sodium hydroxide or potassium carbonate, in an alcohol such as ethanol or methanol, with a solvent such as tetrahydrofuran or dioxane being optionally added, at a temperature of between 20° C. and the boiling temperature of the reaction medium, preferably in the presence of sodium hydroxide in a mixture of ethanol and tetrahydrofuran, at a temperature in the region of 20° C.

The compounds of formula (XV) are obtained using or adapting the methods described in the literature.

The compounds of formula (Id) can also be obtained in seven or eight steps from the compounds of formula (XVI) for which Y=Br, I or Cl (preferably Br or I), according to the following protocol:

ence of sodium hydride in an aprotic solvent such as dimethylformamide at a temperature of between −10° C. and the boiling temperature of the reaction medium.

b) Introduction of the R4 group by means of Suzuki coupling or by means of two consecutive Stille reactions. The introduction of the R4 group by means of Suzuki coupling is carried out using the protected 4-halo-3-nitropyrazole obtained in the preceding step and a boronic acid, an alkyl or cycloalkyl boronate or a (hetero)aryldialkyl boron of formula (VIII) for which Rx is an alkyl or cycloalkyl radical, under an inert atmosphere, in the presence of an inorganic base such as $K_3PO_4$, $Na_2CO_3$ or $Ba(OH)_2$, and of a palladium salt (catalyst) such as dichlorobis(triphenylphosphine)-palladium ($PdCl_2$ $(PPh_3)_2$), tetrakistriphenylphosphine palladium ($Pd(PPh_3)_4$) or diphenylphosphinoferroceynyl palladium ($PdCl_2dppf$), in a solvent such as dimethylformamide, dimethoxyethane, tetrahydrofuran, dioxane, toluene, xylene or ethanol, optionally in the presence of water at a temperature of between 20° C. and the boiling temperature of the reaction medium. Alternatively, the introduction of the R4 group can be carried out by means of two consecutive Stille reactions. The first Stille reaction is carried out under an inert atmosphere using the protected 4-halo-3-nitropyrazole obtained in the preceding step and bis(tributyltin) in the presence of cuprous iodide, of a palladium salt (catalyst) such as palladium diacetate ($Pd(OAc)_2$) and of triphenylphosphine, in

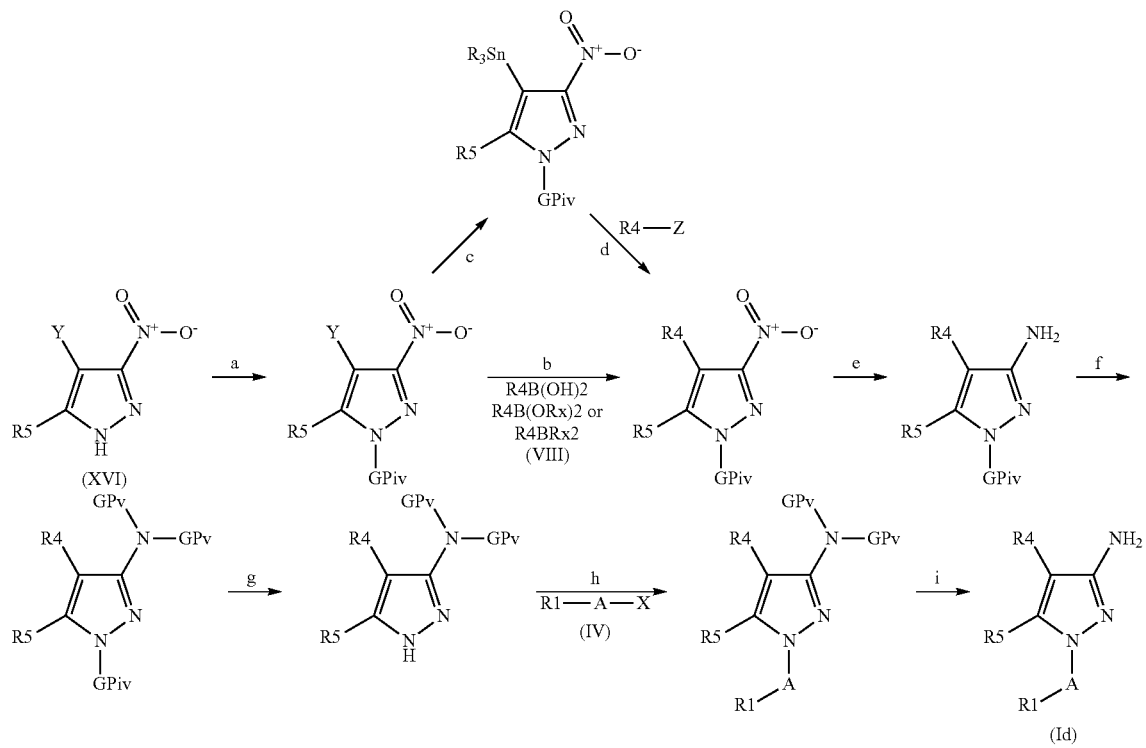

a) Protection of the 4-halo-3-nitropyrazoles of formula (XVI), for example with a 2-trimethylsilanylethoxy-methyl group. This reaction is carried out according to the processes known to those skilled in the art and described in T. W. Greene et al., Protective Groups in Organic Synthesis, Wiley-Interscience, third edition (1999). For example, the reaction is carried out with 2-trimethylsilanylethoxymethyl chloride in basic medium, for example in the presa solvent such as tetrahydrofuran, at a temperature of between 20° C. and the boiling temperature of the reaction medium, according to A. I. Scott et al., Tetrahedron Lett. 1996, 37, 3247. The second Stille reaction is carried out using the preceding organotin and a halogenated aromatic derivative of formula R4-Z for which Z is a Br, I or Cl radical (preferably Br or I), with a palladium salt (catalyst) such as tris(dibenzylidene)-dipalladium ($Pd_2$ $dba_3$) and tristrifurylphosphine, in a solvent such as dioxane at a temperature of between 20° C. and the boiling temperature of the reaction medium, according to U. Hacksell et al., Bioorg. & Med. Chem. Lett., 1994, 2837.

e) Reduction of the nitro function according to a protocol as described in J. March, Advanced Organic Chemistry, Wiley-Interscience, fourth edition (1992) or R.C. Larock, Comprehensive Organic Transformations, VCH Publishers (1989). For example, this reaction can be carried out using iron in the presence of ammonium chloride in a mixture of an alcohol such as ethanol and of water at a temperature of between 20° C. and the boiling temperature of the reaction medium.

f) Double protection of the amino residue obtained in the preceding step with a protective group $GP^v$. The group $GP^v$ is an amine-protecting group as defined in T. W. Greene et al., Protective Groups in Organic Synthesis, Wiley-Interscience, third edition (1999) and resistant to the conditions for deprotecting the group $GP^{iv}$. For example, the group $GP^v$ may be an allyl, a benzyl or a para-methoxybenzyl. The group $GP^v$ is introduced according to the processes known to those skilled in the art and described in T. W. Greene et al., Protective Groups in Organic Synthesis, Wiley-Interscience, third edition (1999). For example, when the protective group $GP^v$ is an allyl, the reaction is carried out with allyl bromide in the presence of a base such as cesium carbonate, in an aprotic solvent such as acetonitrile or dimethylformamide, at a temperature of between 20° C. and the boiling temperature of the reaction medium.

g) Cleavage of the protective group $GP^{iv}$ introduced in the first step, according to the processes known to those skilled in the art and described in T. W. Greene et al., Protective Groups in Organic Synthesis, Wiley-Interscience, third edition (1999). For example, when the protective group $GP^{iv}$ is a 2-trimethylsilanylethoxy-methyl, the reaction can be carried out with tetrabutylammonium fluoride in a solvent such as tetrahydrofuran or dioxane, at a temperature of between 20° C. and the boiling temperature of the reaction medium.

h) Alkylation of the compound obtained in the preceding step with a compound of formula (IV) R1-A-X, as defined above. The reaction is carried out under an inert atmosphere, for example under argon or under nitrogen, in basic medium in an aprotic solvent, for example in the presence of sodium hydride, in an aprotic solvent such as dimethylformamide, at a temperature of between 20° C. and the boiling temperature of the reaction medium, or in the presence of potassium tert-butoxide, in a solvent such as dimethylformamide, at a temperature of between 20° C. and the boiling temperature of the reaction medium. The reaction can also be carried out in the presence of potassium carbonate and, optionally, in the presence of potassium iodide, in a solvent such as acetone, methyl ethyl ketone, acetonitrile or dimethylformamide, preferably in methyl ethyl ketone, at the boiling temperature of the reaction medium.

i) Cleavage of the protective group $GP^v$ introduced in step f), according to the processes known to those skilled in the art and described in T. W. Greene et al., Protective Groups in Organic Synthesis, Wiley-Interscience, third edition (1999). For example, when the protective group $GP^v$ is an allyl, the reaction can be carried out with a palladium salt such as tetrakistriphenylphosphine palladium $(Pd(PPh_3)_4)$ in the presence of an acid such as N,N-dimethylbarbituric acid, in an aprotic solvent such as dichloromethane, at a temperature of between 20° C. and the boiling temperature of the reaction medium.

The compounds of formula (XVI) are commercially available or are obtained by analogy with methods described in the literature.

The compounds (Ib) for which Rc is a C(O)R8, C(S)R8 or $SO_2R8$ radical can be obtained from the compounds (Ia) according to the protocols known to those skilled in the art and described, for example, in J. March, Advanced Organic Chemistry, Wiley-Interscience, fourth edition (1992), R.C. Larock, Comprehensive Organic Transformations, VCH Publishers (1989) or Bradford P. Mundy and Michael G. Ellerd, Name Reactions and Reagents in Organic Synthesis, A. Wiley-Interscience Publication (1988).

The compounds (Ie) can be obtained from the compounds (Id) according to the protocols known to those skilled in the art and described, for example, in J. March, Advanced Organic Chemistry, Wiley-Interscience, fourth edition (1992), R.C. Larock, Comprehensive Organic Transformations, VCH Publishers (1989) or Bradford P. Mundy and Michael G. Ellerd, Name Reactions and Reagents in Organic Synthesis, A. Wiley-Interscience Publication (1988).

The compounds (If) can be obtained from the compounds (Ia) by reaction with a thionating agent, such as, for example, Lawesson's reagent, and according to the protocols described, for example, in J. March, Advanced Organic Chemistry, Wiley-Interscience, fourth edition (1992).

The compounds (Ig) can be obtained from the compounds (If) according to the protocols known to those skilled in the art and described, for example, in J. March, Advanced Organic Chemistry, Wiley-Interscience, fourth edition (1992), R.C. Larock, Comprehensive Organic Transformations, VCH Publishers (1989) or Bradford P. Mundy and Michael G. Ellerd, Name Reactions and Reagents in Organic Synthesis, A. Wiley-Interscience Publication (1988).

The compounds (Ih) can be obtained by oxidation of the compounds (Ig) for which Rc=Ra using reagents such as, for example, hydrogen peroxide, potassium permanganate or oxone, and according to the protocols described, for example, in J. March, Advanced Organic Chemistry, Wiley-Interscience, fourth edition (1992).

The compounds of formula (I) for which the R4 group is substituted with one or more OH radicals can be obtained by demethylation of the corresponding methoxylated compounds according to a protocol which does not affect the rest of the molecule, as described in Protective Groups in Organic Synthesis, T. W. Greene, Ed. by Wiley, third edition (1999). This reaction can, for example, be carried out with boron tribromide in a solvent such as dichloromethane at a temperature of between −5° C. and the boiling temperature of the reaction medium.

The compounds of formula (I) for which the R4 group is substituted with one or more $NH_2$ radicals can be obtained by reduction of the corresponding nitro compounds according to a protocol as described in J. March, Advanced Organic Chemistry, Wiley-Interscience, fourth edition (1992) or R.C. Larock, Comprehensive Organic Transformations, VCH Publishers (1989). For example, this reaction can be carried out by hydrogenation in the presence of a catalyst such as palladium-on-charcoal and, optionally, of an acid such as hydrochloric acid, in an alcohol such as ethanol, methanol or isopropanol, at a hydrogen pressure of between 1 bar and 20 bar and at a temperature of between 20° C. and the boiling temperature of the reaction medium.

The compounds of formula (Ib), (Ic) or (II) for which the R4 group is substituted with one or more NRaRb, NHC(O)Ra, C(O)NRaRb, $NHSO_2Ra$ or NHC(S)Ra radicals can be obtained by reduction of the corresponding nitro compounds, followed by appropriate functionalization of the amino derivatives obtained. The reduction of the nitro compounds is carried out according to a protocol which does not affect the rest of the molecule, as described in J. March, Advanced Organic Chemistry, Wiley-Interscience, fourth edition (1992) or R.C. Larock, Comprehensive Organic Transformations, VCH Publishers (1989). For example, this reaction can be carried out with a reducing agent such as iron powder, in the presence of ammonium chloride in a mixture of water and of an alcohol such as methanol or ethanol, at a temperature between 20° C. and the boiling temperature of the reaction medium, preferably in ethanol at the boiling temperature of the reaction medium. The functionalization of the resulting amino derivatives is carried out according to methods which do not affect the rest of the molecule, known to those skilled in the art and described, for example, in J. March, Advanced Organic Chemistry, Wiley-Interscience, fourth edition (1992), R.C. Larock, Comprehensive Organic Transformations, VCH Publishers (1989), Bradford P. Mundy and Michael G. Ellerd, Name Reactions and Reagents in Organic Synthesis, A. Wiley-Interscience Publication (1988) or Hartwig J. F., Angew. Chem. Int. Ed. Engl. 1998, 2047.

The compounds of formula (Ib), (Ic) or (II) for which the R4 group is substituted with one or more aryl or heteroaryl radicals can be obtained from the corresponding halogenated compounds (preferably brominated or iodinated) and from suitable boronic acids, alkyl or cycloalkyl boronates or (hetero)aryldialkyl borons by Suzuki coupling. This reaction is carried out under an inert atmosphere in the presence of an inorganic base such as $K_3PO_4$, $Na_2CO_3$ or $Ba(OH)_2$, of a palladium salt (catalyst) such as dichlorobis(triphenylphosphine)palladium ($PdCl_2$ $(PPh_3)_2$), tetrakis(triphenylphosphine)palladium ($Pd(PPh_3)_4$) or (diphenylphosphino)ferrocenyl palladium ($PdCl_2dppf$), in a solvent such as dimethylformamide, dimethoxyethane, tetrahydrofuran, dioxane, toluene, xylene or ethanol, optionally in the presence of water, at a temperature of between 20° C. and the boiling temperature of the reaction medium.

The compounds of formula (I) are isolated and can be purified by conventional known methods, for example by crystallization, chromatography or extraction.

The compounds of formula (I) can be optionally transformed into addition salts with an inorganic or organic acid by reaction of such an acid in an organic solvent such as an alcohol, a ketone or an ether or a chlorinated solvent. These salts are also part of the invention.

As examples of pharmaceutically acceptable salts, mention may be made of the following salts: benzenesulfonate, hydrobromide, hydrochloride, citrate, ethanesulfonate, fumarate, gluconate, iodate, maleate, isethionate, methanesulfonate, nitrate, oxalate, palmoate, phosphate, salicylate, succinate, sulfate, tartrate, theophylline acetate and p-toluenesulfonate.

The compounds of the invention have been tested with regard to their ability to bind nicotinic receptors containing the α7 subunit by means of a binding assay on rat brain membrane preparations according to the methods described below:

Membrane Preparations:

Frozen samples of Sprague-Dawley female rat brain hippocampus were conserved at −20° C. until use. The hippocampi from 10 rats were grouped together and homogenized using a Polytron grinder in 10 volumes of a buffer, cooled in ice, having the following composition: KCl (11 mM); $KH_2PO_4$ (6 mM); NaCl (137 mM); $Na_2HPO_4$ (8 mM); HEPES (20 mM); iodoacetamide (5 mM); EDTA (1.5 mM); PMSF (0.1 mM). The pH was adjusted to 7.4 using NaOH. The mixture obtained was centrifuged at 24 000 g for 20 minutes at 4° C. and the pellet was resuspended in 20 volumes of ice-cold water. After incubation for 60 minutes at 4° C., a further pellet was obtained by centrifugation at 24 000 g for 20 minutes at 4° C. The latter was resuspended in buffer having the above composition and frozen at −20° C. On the day of the assay, the membranes were thawed, centrifuged at 24 000 g for 20 minutes, and then resuspended at a final concentration of 2-5 mg of proteins/ml in Dulbecco phosphate buffer at pH 7.4 containing 0.05% of bovine serum albumin.

Measurement of the Affinity for Receptors Containing the α7 Subunit:

The binding of the compounds of the invention to receptors containing the α7 subunit was measured by competition with respect to [$^3$H]-methyllycaconitine ([$^3$H]-MLA), a radiolabeled tracer which recognizes α7 receptors (Davies et al., Neuropharmacology 1999, 38, 679-690), according to conventional methods adapted to the 96-well-plate format. The ability of the compounds of the invention to displace the binding of [$^3$H]-MLA to rat hippocampal membranes was determined in duplicate after incubation for 2 hours at ambient temperature. Each well contained a sample of approximately 150 μg of membrane proteins, 5 nM of [$^3$H]-MLA and one of the compounds of the invention diluted to a given concentration in Dulbecco phosphate buffer at pH 7.4 containing 0.05% of bovine serum albumin, for a final volume of 150 μL. The nonspecific binding was determined in specific wells containing 10 μM of non-radiolabeled MLA. The incubation was stopped by filtering the content of each well through glass fiber filters (Whatman GF/B) presoaked in a solution of polyethylenimine at 0.33% in Dulbecco phosphate buffer so as to decrease the nonspecific binding. The filters were then washed 3 times with Dulbecco phosphate buffer, and then dried at 50° C. for approximately 2 hours. The radioactivity retained on the filters was measured by applying scintillant (MeltiLex A, Perkin Elmer) followed by counting by luminometry (Trilux 1450 microbeta, Perkin-Elmer).

Data Analysis

For each compound tested, the residual radioactivity on the filters was expressed in counts per minutes. The determinations in duplicate were averaged and the concentration of compound which inhibits by half the specific binding of the radioactive tracer ($IC_{50}$) was calculated by curvilinear regression using specific software (GraphPad Prism). The apparent affinity constants Ki for the compounds of the invention were calculated using the Cheng and Prusoff equation (Cheng and Prusoff, Biochem. Pharmacol. 1973, 22, 3099-3108).

The compounds of the invention which were studied in this assay exhibit a $K_i$ value of less than 10 μM.

The following examples illustrate the invention in a non-limiting manner.

EXAMPLE 1

1-[2-(3-Methoxy-4-phenylpyrazol-1-yl)ethyl]piperidine Dihydrochloride 0.303 g of sodium hydride (at 75% by mass in liquid petroleum jelly) is added gradually, under an argon atmosphere and at ambient temperature, to a solution of 0.25 g of 3-methoxy-4-phenylpyrazole in 20 cm³ of anhydrous dimethylformamide. After stirring for three quarters of an hour at a temperature in the region of 50° C., 0.793 g of 1-(2-chloroethyl)piperidine is added in small portions, and the mixture is then heated for 8 hours at a temperature in the region of 50° C. The mixture is cooled to ambient temperature, 10 cm³ of water are then added, and the mixture is concentrated to dryness under reduced pressure (3 kPa). The evaporation residue is taken up in 25 cm³ of water and extracted with 250 cm³ of ethyl acetate. The organic phase is washed with 3 times 25 cm³ of water, and is then dried over anhydrous magnesium sulfate, filtered and concentrated to dryness under reduced pressure (3 kPa), so as to give an oily residue which is purified by chromatography on silica gel (particle size 15-35 µm), eluting with a mixture of ethyl acetate and cyclohexane (67/33 by volume). After concentration of the fractions under reduced pressure, 0.3 g of a colorless oil is obtained, which is dissolved in 15 cm³ of acetone and 30 cm³ of an approximately 3M solution of hydrochloric ether are added. The white precipitate formed is filtered and then dried under vacuum (70 Pa) at a temperature of 60° C. 0.325 g of 1-[2-(3-methoxy-4-phenylpyrazol-1-yl)ethyl]piperidine dihydrochloride is thus obtained in the form of a white solid which melts at 208° C. (with decomposition).

$^1$H NMR spectrum (300 MHz, $(CD_3)_2SO$ d6, δ in ppm): 1.40 (mt: 1H); from 1.60 to 1.90 (mt: 5H); 2.94 (mt: 2H); from 3.40 to 3.60 (mt: 4H); 3.95 (s: 3H); 4.47 (t, J=6.5 Hz: 2H); 7.29 (broad t, J=7.5 Hz: 1H); 7.36 (broad t, J=7.5 Hz: 2H); 7.62 (broad d, J=7.5 Hz: 2H); 8.14 (s: 1H); 10.03 (unresolved peak: 1H).

IR spectrum (KBr): 3031; 2945; 2632; 2540; 1606; 1579; 1518; 1456; 1411; 1047; 1030; 764 and 697 cm$^{-1}$.

The 3-methoxy-4-phenylpyrazole can be prepared in the following way:

A suspension of 2 g of 1-(3-hydroxy-4-phenylpyrazol-1-yl)ethanone, 1.37 g of potassium carbonate and 1.13 cm³ (1.5 g) of dimethyl sulfate in 70 cm³ of 2-butanone is stirred at a temperature of 70° C. for 4 hours. 24 cm³ of a 1.66N sodium hydroxide solution are added to the mixture, which is stirred for 4 hours at ambient temperature and then partially concentrated under reduced pressure (3 kPa) in order to drive off the 2-butanone. The residue is taken up with 10 cm³ of water and extracted with 250 cm³ of ethyl acetate. The organic phase is washed with 3 times 25 cm³ of water, and is then dried over anhydrous magnesium sulfate, filtered and concentrated to dryness under reduced pressure (3 kPa), so as to give a light brown solid residue, which is purified by chromatography on silica gel (particle size 15-35 µm), eluting with a mixture of dichloromethane and methanol (98.5/1.5 by volume). After concentration of the fractions under reduced pressure, 0.3 g of 3-methoxy-4-phenylpyrazole is obtained in the form of a pale yellow powder which melts at 150° C.

The 1-(3-hydroxy-4-phenylpyrazol-1-yl)ethanone can be prepared in the following way:

3.4 cm³ of acetic anhydride are added, over 10 minutes, to a solution of 6.4 g of 4-phenyl-1H-pyrazol-3-ol in 64 cm³ of pyridine preheated to 100° C. After a further 30 minutes at 100° C., the mixture is cooled and poured into 600 cm³ of a water-ice mixture. The precipitate which appears is filtered, washed with 4 times 100 cm³ of ice-water then with 4 times 100 cm³ of heptane, and then dried under vacuum (70 Pa) at a temperature of 60° C. 5.09 g of 1-(3-hydroxy-4-phenylpyrazol-1-yl)-ethanone are thus obtained in the form of a beige powder which melts at 215° C.

The 4-phenyl-1H-pyrazol-3-ol can be obtained according to the method described by D. L. Selwood et al., J. Med. Chem. 2001, 44, 78-93.

EXAMPLE 2

1-(1-Azabicyclo[2.2.2]oct-3-ylmethyl)-4-phenyl-1H-pyrazol-1-ol Dihydrochloride

A suspension of 0.67 g of 3-(3-benzyloxy-4-phenyl-pyrazol-1-ylmethyl)-1-azabicyclo[2.2.2]octane and 0.08 g of palladium-on-charcoal (10%) in 20 cm³ of ethanol is stirred in an autoclave under a hydrogen pressure of 500 kPa, at a temperature of 20° C., for 20 hours. The reaction medium is then filtered over Celite® and concentrated to dryness under reduced pressure (3 kPa), so as to give a pasty residue, which is covered with 50 cm³ of acetone and triturated overnight. After filtration of the solid which has appeared and drying under vacuum (70 Pa) at a temperature of 60° C., 0.265 g of 1-(1-azabicyclo[2.2.2]oct-3-ylmethyl)-4-phenyl-1H-pyrazol-1-ol dihydrochloride is obtained in the form of hygroscopic beige crystals which melt at around 240° C. (with decomposition).

$^1$H NMR spectrum (300 MHz, $(CD_3)_2SO$ d6, δ in ppm): from 1.65 to 1.95 (mt: 4H); from 1.95 to 2.15 (mt: 1H); from 2.40 to 2.60 (mt: 1H); 2.96 (broad dd, J=12.5 and 7.5 Hz: 1H); from 3.10 to 3.40 (mt: 5H); 4.03 (dd, J=13.5 and 7.5 Hz: 1H); 4.10 (dd, J=13.5 and 7.5 Hz: 1H); 7.15 (broad t, J=7.5 Hz: 1H); 7.34 (broad t, J=7.5 Hz: 2H); 7.66 (broad d, J=7.5 Hz: 2H); 8.00 (s: 1H); 10.51 (unresolved peak: 1H).

IR spectrum (KBr): 3417; 2940; 2546; 1601; 1474; 1388; 1189; 768; 702 and 611 cm$^{-1}$.

EXAMPLE 3

3-(3-Benzyloxy-4-phenylpyrazol-1-ylmethyl)-1-azabicyclo[2.2.2]octane Dihydrochloride A solution of 5 g of 3-benzyloxy-4-phenylpyrazole in 30 cm³ of anhydrous dimethylformamide are added gradually, under an argon atmosphere and at ambient temperature, to a suspension of 3.84 g of sodium hydride (75% by mass in liquid petroleum jelly) in 20 cm³ of anhydrous dimethylformamide. After stirring for three quarters of an hour at a temperature in the region of 50° C., 11.78 g of 3-chloromethyl-1-azabicyclo[2.2.2]octane hydrochloride are added in small portions, and the mixture is then heated for 18 hours at a temperature in the region of 50° C. The mixture is cooled to ambient temperature and 25 cm³ of water are then added slowly, and the mixture is then run into 300 cm³ of water and extracted with two times 300 cm³ of ethyl acetate. The pooled organic phases are washed with 3 times 100 cm³ of water, and then dried over anhydrous magnesium sulfate, filtered and concentrated to dryness under reduced pressure (3 kPa). The oily residue obtained is purified by chromatography on alumina, eluting with a mixture of ethyl acetate and methanol (90/10 by volume). After concentration of the fractions under reduced pressure, 2.81 g of a brown oil are obtained, which oil is dissolved in 200 cm³ of ethanol and 6.25 cm³ of an approximately 6M aqueous hydrochloric acid solution are added. The solution is concentrated to dryness under reduced pressure (3 kPa). The residue is taken up with 200 cm³ of ethanol and redried, twice. 3.01 g of 3-(3-benzyloxy-4-phenylpyrazol-1-ylmethyl)-1-azabicyclo[2.2.2]octane dihydrochloride are thus obtained in the form of a beige foam.

$^1$H NMR spectrum (400 MHz, $(CD_3)_2SO$ d6, δ in ppm): from 1.65 to 1.90 (mt: 4H); 2.06 (mt: 1H); from 2.50 to 2.65 (mt: 1H); 2.94 (dd, J=10 and 5 Hz: 1H); from 3.10 to 3.40 (mt: 5H); 4.11 (dd, J=10.5 and 6 Hz: 1H); 4.16 (dd J=10.5 and 6 Hz: 1H); 5.33 (s: 2H); 7.07 (broad t, J=7.5 Hz: 1H); 7.36 (broad t, J=7.5 Hz: 3H); 7.43 (broad t, J=7.5 Hz: 2H); 7.50 (broad d, J=7.5 Hz: 2H); 7.65 (broad d, J=7.5 Hz: 2H); 8.14 (s: 1H); 10.51 (unresolved peak: 1H).

IR spectrum (KBr): 3031; 2936; 2803; 2564; 1606; 1578; 1569; 1510; 1454; 1435; 1360; 1046; 1024; 764; 697; 615 and 511 cm$^{-1}$.

The 3-benzyloxy-4-phenylpyrazole can be prepared in the following way:

A suspension of 5.7 g of 1-(3-hydroxy-4-phenylpyrazol-1-yl)ethanone, 3.9 g of potassium carbonate and 3.7 cm³ (5.3 g) of benzyl bromide in 250 cm³ of 2-butanone is stirred at the boiling temperature of the reaction medium for two and a quarter hours. The insoluble inorganic material is removed by filtration and the filtrate is concentrated to dryness under reduced pressure (3 kPa). The residue is dissolved in 50 cm³ of tetrahydrofuran, 50 cm³ of methanol and 1 cm³ of a 10N sodium hydroxide solution are added and the mixture is stirred for a quarter of an hour at ambient temperature and then concentrated to dryness under reduced pressure (3 kPa). The residue is taken up with 5 cm³ of water and extracted with 250 cm³ of ethyl acetate. The organic phase is dried over anhydrous magnesium sulfate, filtered and concentrated to dryness under reduced pressure (3 kPa), so as to give a white solid residue, which is triturated in a mixture of isopropyl ether and petroleum ether. After filtration and air-drying, 4.43 g of 3-benzyloxy-4-phenylpyrazole are obtained in the form of a white solid which melts at 163° C.

EXAMPLE 4

3-(3-Methoxy-4-phenylpyrazol-1-ylmethyl)-1-azabicyclo[2.2.2]octane Hydrochloride Monohydrate 0.99 g of sodium hydride (75% by mass in liquid petroleum jelly) is added gradually, under an argon atmosphere and at ambient temperature, to a solution of 0.9 g of 3-methoxy-4-phenylpyrazole in 15 cm³ of anhydrous dimethylformamide. After stirring for three quarters of an hour at a temperature in the region of 50° C., 3.04 g of 3-chloromethyl-1-azabicyclo[2.2.2]-octane hydrochloride are added in small portions, and the mixture is then heated for 16 hours at a temperature in the region of 50° C. The mixture is cooled to ambient temperature, 10 cm³ of water are then added slowly, and the mixture is concentrated under reduced pressure (3 kPa). The residue is taken up with 25 cm³ of water and extracted with 3 times 100 cm³ of ethyl acetate. The pooled organic phases are washed with 3 times 25 cm³ of water, and then dried, filtered and concentrated to dryness under reduced pressure (3 kPa). The oily residue obtained is purified by chromatography on alumina, eluting with a mixture of ethyl acetate and methanol (90/10 by volume). After concentration of the fractions under reduced pressure, 0.3 g of a brown oil is obtained, which is dissolved in 40 cm³ of acetone, and 35 cm³ of approximately 3M hydrochloric ether are added. The solution is concentrated to dryness under reduced pressure (3 kPa) and the pasty residue is washed with two times 50 cm³ of ethyl ether and then triturated in 50 cm³ of ethyl ether overnight. After filtration of the solid obtained and drying under vacuum (70 Pa) at a temperature of 60° C., 0.25 g of 3-(3-methoxy-4-phenylpyrazol-1-ylmethyl)-1-azabicyclo[2.2.2]octane hydrochloride monohydrate is obtained in the form of a white powder which melts at around 125° C. (with decomposition).
$^1$H NMR spectrum (300 MHz, (CD$_3$)$_2$SO d6, δ in ppm): from 1.60 to 1.90 (mt: 4H); 2.05 (unresolved peak: 1H); from 2.45 to 2.60 (mt: 1H); 2.94 (broad dd, J=13 and 7 Hz: 1H); from 3.05 to 3.40 (mt: 5H); 3.93 (s: 3H); 4.12 (mt: 2H); 7.17 (broad t, J=7.5 Hz: 1H); 7.35 (broad t, J=7.5 Hz: 2H); 7.62 (broad d, J=7.5 Hz: 2H); 8.10 (s: 1H); from 9.40 to 9.90 (very broad unresolved peak: 1H).

IR spectrum (KBr): 2942; 2562; 1609; 1579; 1517; 1458; 1406; 1048; 1030; 759; 698; 601 and 508 cm$^{-1}$.

EXAMPLE 5

1-(1-Azabicyclo[2.2.2]oct-3-yl)-4-phenyl-1H-pyrazol-3-ol Dihydrochloride

A suspension of 0.163 g of 3-(3-benzyloxy-4-phenyl-pyrazol-1-yl)-1-azabicyclo[2.2.2]octane, 0.38 cm³ of 6M hydrochloric acid and 0.024 g of palladium-on-charcoal (at 10%) in 20 cm³ of ethanol is stirred in an autoclave under a hydrogen pressure of 1 000 kPa, at a temperature of 20° C. for 8 hours. The reaction medium is then filtered over Celite® and concentrated to dryness under reduced pressure (3 kPa), so as to give a hygroscopic oily residue, which is dissolved in 10 cm³ of water and lyophilized. 0.083 g of 1-(1-azabicyclo-[2.2.2]oct-3-yl)-4-phenyl-1H-pyrazol-1-ol dihydro-chloride is thus obtained in the form of an amorphous brown solid.
$^1$H NMR spectrum (300 MHz, (CD$_3$)$_2$SO d6, δ in ppm): from 1.65 to 2.05 (mt: 4H); 2.41 (mt: 1H); 3.26 (mt: 3H); 3.40 (mt: 1H); 3.77 (mt: 2H); 4.68 (mt: 1H); 7.15 (broad t, J=7.5 Hz: 1H); 7.34 (broad t, J=7.5 Hz: 2H); 7.69 (broad d, J=7.5 Hz: 2H); 8.22 (s: 1H); from 10.15 to 10.75 (broad unresolved peak: 1H); 11.07 (unresolved peak: 1H).

IR spectrum (KBr): 3417; 2956; 2806; 2666; 1607; 1580; 1522; 1450; 1168; 995; 762; 697; 671 and 513 cm$^{-1}$.

The 3-(3-benzyloxy-4-phenylpyrazol-1-yl)-1-azabicyclo-[2.2.2]octane can be prepared in the following way:

0.96 g of sodium hydride (at 75% by mass in liquid petroleum jelly) is added gradually, under an argon atmosphere and at ambient temperature, to a solution of 0.5 g of 3-benzyloxy-4-phenylpyrazole in 30 cm³ of anhydrous dimethylformamide. After stirring for three quarters of an hour at a temperature in the region of 50° C., a solution of 0.725 g of 3-[(methanesulfonyl)-oxy]-1-azabicyclo[2.2.2]octane in 5 cm³ of anhydrous dimethylformamide is added dropwise, and the mixture is then heated for 20 hours at a temperature in the region of 110° C. The mixture is cooled to ambient temperature, 5 cm³ of water are then added slowly, and the mixture is concentrated under reduced pressure (3 kPa). The residue is taken up with 10 cm³ of water and extracted with 50 cm³ of ethyl acetate. The organic phase is washed with 3 times 10 cm³ of water, and is then dried, filtered and concentrated to dryness under reduced pressure (3 kPa). The oily residue obtained is purified by preparative HPLC on 10μ C8 Kromasil, eluting with a mixture of acetonitrile and water (50/50 by volume) and then of acetonitrile and ammoniacal methanol (7M) (98/2 by volume). After concentration of the fractions under reduced pressure, 0.163 g of 3-(3-benzyloxy-4-phenylpyrazol-1-yl)-1-azabicyclo[2.2.2]octane is obtained in the form of a yellow oil, which is used as it is in the following step.

The 3-[(methanesulfonyl)oxy]-1-azabicyclo[2.2.2]octane can be obtained according to the method described by S. M. Jenkins et al., J. Med. Chem. 1992, 35, 2392-2406.

EXAMPLE 6

1-(2-Perhydroazepin-1-ylethyl)-4-phenyl-1H-pyrazol-3-ol Dihydrochloride

A suspension of 0.65 g of 1-[2-(3-benzyloxy-4-phenylpyrazol-1-yl)ethyl]perhydroazepine, 1.44 cm³ of 6M hydrochloric acid and 0.092 g of palladium-on-charcoal (at 10%) in 20 cm³ of ethanol is stirred in an autoclave under a hydrogen pressure of 1 000 kPa, at a temperature of 20° C. for 8 hours. The reaction medium is then filtered over Celite® and concentrated to dryness under reduced pressure (3 kPa). The residue is triturated in 40 cm³ of acetone and isolated by filtration. 0.541 g of 1-(2-perhydroazepin-1-ylethyl)-4-phenyl-1H-pyrazol-3-ol dihydrochloride is thus obtained in the form of a beige powder which melts at 228° C. (with decomposition).

$^1$H NMR spectrum (300 MHz, (CD$_3$)$_2$SO d6, δ in ppm): 1.64 (mt: 4H); 1.84 (mt: 4H); 3.17 (mt: 2H); from 3.25 to 3.55 (mt: 4H); 4.41 (t, J=6.5 Hz: 2H); 7.15 (broad t, J=7.5 Hz: 1H); 7.34 (broad t, J=7.5 Hz: 2H); 7.65 (broad d, J=7.5 Hz: 2H); 8.05 (s: 1H); 10.35 (unresolved peak: 1H); 10.49 (unresolved peak: 1H).

IR spectrum (KBr): 3431; 2934; 2638; 2422; 1608; 1582; 1572; 1528; 1452; 1210; 1179; 1013; 760; 692; 673 and 511 cm$^{-1}$.

The 1-[2-(3-benzyloxy-4-phenylpyrazol-1-yl)ethyl]perhydroazepine can be prepared in the following way:

A suspension of 1 g of 1-[(toluene-4-sulfonyl)oxy]-2-(3-benzyloxy-4-phenylpyrazol-1-yl)ethyl, 0.29 cm$^3$ of perhydroazepine and 0.88 g of potassium carbonate in 25 cm$^3$ of acetonitrile is stirred for 3 hours at a temperature in the region of 80° C., and then 0.15 cm$^3$ of perhydroazepine is added and the heating is continued for 2 hours. The mixture is concentrated to dryness under reduced pressure (3 kPa). The residue is taken up with 50 cm$^3$ of water and extracted with 200 cm$^3$ of ethyl acetate. The organic phase is washed with 3 times 25 cm$^3$ of water, and is then dried, filtered and concentrated to dryness under reduced pressure (3 kPa). The oily residue obtained is purified by chromatography on silica gel (particle size 15-35 μm), eluting with a mixture of dichloromethane and methanol (96/4 by volume). After concentration of the fractions under reduced pressure, 0.72 g of 1-[2-(3-benzyloxy-4-phenylpyrazol-1-yl)ethyl]perhydroazepine is obtained in the form of a colorless viscous oil, which is used as it is in the following step. Mass spectrum (EI): m/z 375 (M$^{+\cdot}$), m/z 112 (base peak).

The 1-[(toluene-4-sulfonyl)oxy]-2-(3-benzyloxy-4-phenylpyrazol-1-yl)ethyl can be prepared in the following way:

59 cm$^3$ of triethylamine are added dropwise, at ambient temperature, to a suspension of 13.7 g of 2-(3-benzyloxy-4-phenylpyrazol-1-yl)ethanol hydro-chloride in 400 cm$^3$ of dichloromethane. The reaction mixture is cooled to around 5° C. and a solution of 22.5 g of toluene-4-sulfonyl chloride in 200 cm$^3$ of dichloromethane is added, over 0.5 hours. After stirring for 16 hours at ambient temperature, the mixture is concentrated to dryness under reduced pressure (3 kPa). The residue is taken up with 100 cm$^3$ of water and extracted with (500+250) cm$^3$ of ethyl acetate. The pooled organic phases are washed with 3 times 100 cm$^3$ of water, and then dried over anhydrous magnesium sulfate, filtered and concentrated to dryness under reduced pressure (3 kPa). The oily residue obtained is purified by chromatography on silica gel (particle size 15-35 μm), eluting with dichloromethane and then a mixture of dichloromethane and methanol (95/5 by volume). After concentration of the fractions under reduced pressure, 19 g of 1-[(toluene-4-sulfonyl)oxy]-2-(3-benzyloxy-4-phenylpyrazol-1-yl)ethyl are obtained in the form of a colorless viscous oil, which is used as it is in the following step. Mass spectrum (EI): m/z 448 (M$^{+\cdot}$), m/z 91 (base peak).

The 2-(3-benzyloxy-4-phenylpyrazol-1-yl)ethanol can be prepared in the following way:

750 cm$^3$ of 37% hydrochloric acid are added, at ambient temperature, to a solution of 17 g of 3-benzyloxy-4-phenyl-1-[2-(tetrahydropyran-2-yloxy)ethyl]-1H-pyrazole in 750 cm$^3$ of ethanol. After stirring for 2 hours at ambient temperature, the mixture is concentrated to dryness under reduced pressure (3 kPa). The residue is taken up with 1 dm$^3$ of ethanol and concentrated to dryness, 3 times, so as to give 13.8 g of 2-(3-benzyloxy-4-phenylpyrazol-1-yl)ethanol in the form of a solid which melts at 115° C., which is used as it is in the following step.

The 3-benzyloxy-4-phenyl-1-[2-(tetrahydropyran-2-yloxy)ethyl]-1H-pyrazole can be prepared in the following way:

3.07 g of sodium hydride (at 75% by mass in liquid petroleum jelly) are added gradually, under an argon atmosphere and at ambient temperature, to a solution of 16 g of 3-benzyloxy-4-phenylpyrazole in 110 cm$^3$ of anhydrous dimethylformamide. After stirring for three quarters of an hour at a temperature in the region of 50° C., a solution of 11.06 cm$^3$ (15.31 g) of 2-(2-bromo-ethoxy)tetrahydropyran in 40 cm$^3$ of anhydrous dimethylformamide is added dropwise, and the mixture is then heated for three quarters of an hour at a temperature in the region of 50° C. 25 cm$^3$ of water are then added slowly to the mixture, which is then run into 90 cm$^3$ of water and extracted with 3 times 300 cm$^3$ of ethyl acetate. The pooled organic phases are washed with 3 times 100 cm$^3$ of water, and then dried, filtered and concentrated to dryness under reduced pressure (3 kPa). The oily residue obtained is purified by chromatography on silica gel (particle size 20-45 μm), eluting with a mixture of dichloromethane and ethyl acetate (90/10 by volume). After concentration of the fractions under reduced pressure, 17.35 g of 3-benzyloxy-4-phenyl-1-[2-(tetrahydropyran-2-yloxy)ethyl]-1H-pyrazole are obtained in the form of a colorless pasty solid, which is used as it is in the following step.

$^1$H NMR spectrum (300 MHz, (CD$_3$)$_2$SO d6, δ in ppm): from 1.25 to 1.75 (mt: 6H); from 3.25 to 3.45 (mt: 1H); 3.60 (ddd, J=11.5-8.5 and 3 Hz: 1H); 3.72 (mt: 1H); 3.94 (ddd, J=10.5-6 and 4.5 Hz: 1H); 4.16 (mt: 2H); 4.55 (mt: 1H); 5.32 (s: 2H); 7.14 (tt, J=7.5 and 1.5 Hz: 1H); from 7.25 to 7.45 (mt: 3H); 7.33 (broad t, J=7.5 Hz: 2H); 7.50 (broad d, J=7.5 Hz: 2H); 7.63 (broad d, J=7.5 Hz: 2H); 8.05 (s: 1H).

EXAMPLE 7

1-[2-(2-Methylpiperidin-1-yl)ethyl]-4-phenyl-1H-pyrazol-3-ol Dihydrochloride

A suspension of 0.58 g of 1-[2-(3-benzyloxy-4-phenylpyrazol-1-yl)ethyl]-2-methylpiperidine, 1.29 cm$^3$ of 6M hydrochloric acid and 0.082 g of palladium-on-charcoal (at 10%) in 20 cm$^3$ of ethanol is stirred in an autoclave under a hydrogen pressure of 1 000 kPa, at a temperature of 20° C. for 8 hours. The reaction medium is then filtered over Celite® and concentrated to dryness under reduced pressure (3 kPa). The residue is triturated in 40 cm$^3$ of acetone and isolated by filtration. 0.54 g of 1-[2-(2-methylpiperidin-1-yl)-ethyl]-4-phenyl-1H-pyrazol-3-ol dihydrochloride is thus obtained in the form of a beige powder which melts at 118° C. (with decomposition).

$^1$H NMR spectrum (300 MHz, (CD$_3$)$_2$SO d6 with addition of a few drops of CD$_3$COOD d4, δ in ppm): 1.29 (d, J=6.5 Hz: 3H); from 1.35 to 1.95 (mt: 6H); 3.04 (ddd, J=12-9 and 3.5 Hz: 1H); from 3.30 to 3.50 (mt: 3H); from 3.50 to 3.65 (mt: 1H); 4.37 (t, J=6.5 Hz: 2H); 7.14 (broad t, J=7.5 Hz: 1H); 7.33 (broad t, J=7.5 Hz: 2H); 7.64 (broad d, J=7.5 Hz: 2H); 8.02 (s: 1H).

IR spectrum (KBr): 3051; 2949; 2653; 2565; 1606; 1581; 1522; 1441; 1228; 1171; 995; 768; 700; 671 and 587 cm$^{-1}$.

The 1-[2-(3-benzyloxy-4-phenylpyrazol-1-yl)ethyl]-2-methylpiperidine can be prepared in the following way:

A suspension of 1 g of 1-[(toluene-4-sulfonyl)oxy]-2-(3-benzyloxy-4-phenylpyrazol-1-yl)ethyl, 0.46 cm$^3$ of 2-methylpiperidine and 0.88 g of potassium carbonate in 25 cm$^3$ of acetonitrile is stirred for 6 hours at a temperature in the region of 80° C. The mixture is concentrated to dryness under reduced pressure (3 kPa). The residue is taken up with 50 cm³ of water and extracted with 200 cm³ of ethyl acetate. The organic phase is washed with 3 times 25 cm³ of water, and is then dried, filtered and concentrated to dryness under reduced pressure (3 kPa). The oily residue obtained is purified by chromatography on silica gel (particle size 15-35 µm), eluting with a mixture of dichloromethane and methanol (97/3 by volume). After concentration of the fractions under reduced pressure, 0.65 g of 1-[2-(3-benzyloxy-4-phenylpyrazol-1-yl)ethyl]-2-methyl-piperidine is obtained in the form of a colorless viscous oil, which is used as it is in the following step.

Mass spectrum (EI): m/z 375 ($M^{+ \cdot}$), m/z 112 (base peak).

EXAMPLE 8

1-[2-(4-Fluoropiperidin-1-yl)ethyl]-4-phenyl-1H-pyrazol-3-ol Dihydrochloride

A suspension of 0.5 g of 1-[2-(3-benzyloxy-4-phenylpyrazol-1-yl)ethyl]-4-fluoropiperidine, 1.1 cm³ of 6M hydrochloric acid and 0.071 g of palladium-on-charcoal (at 10%) in 20 cm³ of ethanol is stirred in an autoclave under a hydrogen pressure of 1 000 kPa, at a temperature of 20° C. for 8 hours. The reaction medium is then filtered through Celite® and concentrated to dryness under reduced pressure (3 kPa). The residue is triturated in 40 cm³ of acetone and isolated by filtration. 0.54 g of 1-[2-(4-fluoropiperidin-1-yl)-ethyl]-4-phenyl-1H-pyrazol-3-ol dihydrochloride is thus obtained in the form of a beige powder which melts at 228° C. (with decomposition).

$^1$H NMR spectrum (400 MHz, $(CD_3)_2SO$ d6 with addition of a few drops of $CD_3COOD$ d4, δ in ppm): from 2.00 to 2.25 (mt: 4H); 3.29 (unresolved peak: 4H); 3.52 (t, J=6 Hz: 2H); 4.40 (t, J=6 Hz: 2H); 4.94 (broad d, J=48 Hz: 1H); 7.14 (broad t, J=7.5 Hz: 1H); 7.33 (broad t, J=7.5 Hz: 2H); 7.65 (broad d, J=7.5 Hz: 2H); 7.99 (s: 1H).

IR spectrum (KBr): 3054; 2963; 2633; 2531; 1608; 1582; 1528; 1452; 1177; 1031; 1015; 764; 698 and 509 cm⁻¹.

The 1-[2-(3-benzyloxy-4-phenylpyrazol-1-yl)ethyl]-4-fluoropiperidine can be prepared in the following way:

A suspension of 1 g of 1-[(toluene-4-sulfonyl)oxy]-2-(3-benzyloxy-4-phenylpyrazol-1-yl)ethyl, 0.702 g of 4-fluoropiperidine hydrobromide and 1.18 g of potassium carbonate in 25 cm³ of acetonitrile is stirred for 6 hours at a temperature in the region of 80° C. The mixture is concentrated to dryness under reduced pressure (3 kPa). The residue is taken up with 50 cm³ of water and extracted with 200 cm³ of ethyl acetate. The organic phase is washed with 3 times 25 cm³ of water, and is then dried, filtered and concentrated to dryness under reduced pressure (3 kPa). The oily residue obtained is purified by chromatography on silica gel (particle size 15-35 µm), eluting with a mixture of dichloromethane and methanol (98.5/1.5 by volume). After concentration of the fractions under reduced pressure, 0.61 g of 1-[2-(3-benzyloxy-4-phenylpyrazol-1-yl)ethyl]-4-fluoropiperidine is obtained in the form of a colorless viscous oil, which is used as it is in the following step.

Mass spectrum (EI): m/z 379 ($M^{+ \cdot}$), m/z 250 and m/z 116 (base peak).

EXAMPLE 9

1-[2-(3-Methylpiperidin-1-yl)ethyl]-4-phenyl-1H-pyrazol-3-ol Dihydrochloride

A suspension of 0.57 g of 1-[2-(3-benzyloxy-4-phenylpyrazol-1-yl)ethyl]-3-methylpiperidine, 1.27 cm³ of 6M hydrochloric acid and 0.081 g of palladium-on-charcoal (at 10%) in 20 cm³ of ethanol is stirred in an autoclave under a hydrogen pressure of 1 000 kPa, at a temperature of 20° C. for 8 hours. The reaction medium is then filtered over Celite® and concentrated to dryness under reduced pressure (3 kPa). The residue is triturated in 75 cm³ of acetone and isolated by filtration. 0.198 g of 1-[2-(3-methylpiperidin-1-yl)-ethyl]-4-phenyl-1H-pyrazol-3-ol dihydrochloride is thus obtained in the form of a pale yellow powder which melts at 220° C. (with decomposition).

$^1$H NMR spectrum (300 MHz, $(CD_3)_2SO$ d6 with addition of a few drops of $CD_3COOD$, δ in ppm): 0.89 (d, J=7 Hz: 3H); 1.05 (mt: 1H); from 1.60 to 2.00 (mt: 4H); 2.58 (mt: 1H); 2.83 (very broad t, J=12 Hz: 1H); from 3.30 to 3.55 (mt: 4H); 4.39 (t, J=6.5 Hz: 2H); 7.13 (broad t, J=7.5 Hz: 1H); 7.32 (broad t, J=7.5 Hz: 2H); 7.63 (broad d, J=7.5 Hz: 2H); 7.99 (s: 1H).

IR spectrum (KBr): 3057; 2960; 2651; 2550; 1607; 1581; 1523; 454; 1179; 761; 697; 614 and 513 cm⁻¹.

The 1-[2-(3-benzyloxy-4-phenylpyrazol-1-yl)ethyl]-3-methylpiperidine can be prepared in the following way:

A suspension of 1 g of 1-[(toluene-4-sulfonyl)oxy]-2-(3-benzyloxy-4-phenylpyrazol-1-yl)ethyl, 0.46 cm³ of 3-methylpiperidine and 0.88 g of potassium carbonate in 25 cm³ of acetonitrile is stirred for 6 hours at a temperature in the region of 80° C. The mixture is concentrated to dryness under reduced pressure (3 kPa). The residue is taken up with 50 cm³ of water and extracted with 200 cm³ of ethyl acetate. The organic phase is washed with 3 times 25 cm³ of water, and is then dried, filtered and concentrated to dryness under reduced pressure (3 kPa). The oily residue obtained is purified by chromatography on silica gel (particle size 15-35 µm), eluting with a mixture of dichloromethane and methanol (97/3 by volume). After concentration of the fractions under reduced pressure, 0.58 g of 1-[2-(3-benzyloxy-4-phenylpyrazol-1-yl)ethyl]-3-methyl-piperidine is obtained in the form of a colorless viscous oil, which is used as it is in the following step.

Mass spectrum (EI): m/z 375 ($M^{+ \cdot}$), m/z 112 (base peak).

EXAMPLE 10

1-[2-(3,6-Dihydro-2H-pyridin-1-yl)ethyl]-4-phenyl-1H-pyrazol-3-ol Dihydrochloride A solution of 0.6 g of 1-[2-(3-benzyloxy-4-phenyl-pyrrol-1-yl)ethyl]-1,2,3,6-tetrahydropyridine in a mixture of 5 cm³ of 37% hydrochloric acid and of 5 cm³ of ethanol is heated at 80° C. for 6 hours and then concentrated to dryness under reduced pressure (3 kPa). The residue is taken up with 100 cm³ of ethanol and concentrated to dryness, 4 times. The residue is triturated in 40 cm³ of acetone and isolated by filtration. 0.403 g of 1-[2-(3,6-dihydro-2H-pyridin-1-yl)ethyl]-4-phenyl-1H-pyrazol-3-ol dihydrochloride is thus obtained in the form of a brown powder which melts at 192° C.

$^1$H NMR spectrum (300 MHz, $(CD_3)_2SO$ d6, δ in ppm): 2.29 (very broad d, J=18 Hz: 1H); from 2.40 to 2.60 (mt: 1H); 3.07 (mt: 1H); 3.47 (mt: 1H); 3.55 (mt: 2H); 3.62 (very broad d, J=16.5 Hz: 1H); 3.84 (broad d, J=16.5 Hz: 1H); 4.47 (t, J=6.5 Hz: 2H); 5.72 (broad d, J=10.5 Hz: 1H); 5.93 (very broad d, J=10.5 Hz: 1H); 7.15 (broad t, J=7.5 Hz: 1H); 7.34 (broad t, J=7.5 Hz: 2H); 7.66 (broad d, J=7.5 Hz: 2H); 8.06 (s: 1H); from 10.20 to 10.80 (broad unresolved peak: 1H); 10.88 (unresolved peak: 1H).

IR spectrum (KBr): 3422; 2948; 2688; 2579; 1607; 1526; 1452; 1184; 1023; 768; 699; 667; 670 and 511 cm⁻¹.

The 1-[2-(3-benzyloxy-4-phenylpyrrol-1-yl)ethyl]-1,2,3,6-tetrahydropyridine can be prepared in the following way:

A suspension of 1 g of 1-[(toluene-4-sulfonyl)oxy]-2-(3-benzyloxy-4-phenylpyrazol-1-yl)ethyl, 0.36 cm³ of 1,2,3,6-tetrahydropyridine and 0.88 g of potassium carbonate in 25 cm³ of acetonitrile is stirred for 6 hours at a temperature in the region of 80° C. The mixture is concentrated to dryness under reduced pressure (3 kPa). The residue is taken up with 50 cm³ of water and extracted with 200 cm³ of ethyl acetate. The organic phase is washed with 3 times 25 cm³ of water, and is then dried, filtered and concentrated to dryness under reduced pressure (3 kPa). The oily residue obtained is purified by chromatography on silica gel (particle size 15-35 μm), eluting with a mixture of dichloromethane and methanol (97/3 by volume). After concentration of the fractions under reduced pressure, 0.6 g of 1-[2-(3-benzyloxy-4-phenylpyrrol-1-yl)ethyl]-1,2,3,6-tetrahydropyridine is obtained in the form of a colorless viscous oil, which is used as it is in the following step.

Mass spectrometry (CI): m/z 360 ([M+H]⁺) (base peak).

EXAMPLE 11

1-[2-(7-Azabicyclo[2.2.1]hept-7-yl)ethyl]-4-phenyl-1H-pyrazol-3-ol Dihydrochloride 3 cm³ of 1M hydrochloric acid are added to a solution of 0.6 g of 7-[2-(3-benzyloxy-4-phenylpyrazol-1-yl)ethyl]-7-azabicyclo[2.2.1]heptane in 40 cm³ of ethanol and the mixture is stirred for a quarter of an hour at ambient temperature and then concentrated to dryness under reduced pressure (3 kPa). The residue obtained and 0.078 g of palladium-on-charcoal (at 10%) are suspended in 20 cm³ of ethanol and stirred in an autoclave under a hydrogen pressure of 1 000 kPa, at a temperature of 20° C. for 8 hours. The reaction medium is then filtered over Celite® and concentrated to dryness under reduced pressure (3 kPa). The residue is triturated in 25 cm³ of acetone and isolated by filtration. 0.466 g of 1-[2-(7-azabicyclo[2.2.1]hept-7-yl)ethyl]-4-phenyl-1H-pyrazol-3-ol dihydrochloride is thus obtained in the form of a white powder which melts at 228° C. (with decomposition).

¹H NMR spectrum (300 MHz, (CD₃)₂SO d6, δ in ppm): 1.66 (unresolved peak: 4H); 2.00 (unresolved peak: 4H); 3.43 (mt: 2H); 3.93 (broad s: 2H); 4.43 (broad t, J=6.5 Hz: 2H); 7.15 (broad t, J=7.5 Hz: 1H); 7.35 (broad t, J=7.5 Hz: 2H); 7.65 (broad d, J=7.5 Hz: 2H); 8.08 (s: 1H); from 10.35 to 10.55 (broad unresolved peak: 1H); 10.47 (unresolved peak: 1H).

IR spectrum (KBr): 2988; 2789; 2661; 2537; 1608; 1533; 1449; 1279; 1179; 875; 761; 698; 674 and 510 cm⁻¹.

The 7-[2-(3-benzyloxy-4-phenylpyrazol-1-yl)ethyl]-7-azabicyclo[2.2.1]heptane can be prepared in the following way:

A suspension of 1 g of 1-[(toluene-4-sulfonyl)oxy]-2-(3-benzyloxy-4-phenylpyrazol-1-yl)ethyl, 0.616 g of 7-azabicyclo[2.2.1]heptane hydrochloride and 0.88 g of potassium carbonate in 25 cm³ of acetonitrile is stirred for 5 hours at a temperature in the region of 80° C. The mixture is concentrated to dryness under reduced pressure (3 kPa). The residue is taken up with 30 cm³ of water and extracted with 250 cm³ of ethyl acetate. The organic phase is washed with 3 times 30 cm³ of water, and is then dried, filtered and concentrated to dryness under reduced pressure (3 kPa). The oily residue obtained is purified by chromatography on silica gel (particle size 15-35 μm), eluting with a mixture of dichloromethane and methanol (98/2 by volume). After concentration of the fractions under reduced pressure, 0.6 g of 7-[2-(3-benzyloxy-4-phenylpyrazol-1-yl)ethyl]-7-azabicyclo[2.2.1]heptane is obtained in the form of a colorless viscous oil, which is used as it is in the following step.

Mass spectrum (CI): m/z 374 ([M+H]⁺) (base peak).

EXAMPLE 12

1-[2-(2-Azabicyclo[2.2.2]oct-2-yl)ethyl]-4-phenyl-1H-pyrazol-3-ol Dihydrochloride 2 cm³ of 6M hydrochloric acid is added to a solution of 0.9 g of 2-[2-(3-benzyloxy-4-phenylpyrazol-1-yl)ethyl]-2-azabicyclo[2.2.2]octane in 50 cm³ of ethanol, and the mixture is stirred for a quarter of an hour at ambient temperature and then concentrated to dryness under reduced pressure (3 kPa). The residue obtained and 0.124 g of palladium-on-charcoal (at 10%) are suspended in 20 cm³ of ethanol and stirred in an autoclave under a hydrogen pressure of 1 000 kPa, at a temperature of 20° C. for 8 hours. The reaction medium is then filtered over Celite® and concentrated to dryness under reduced pressure (3 kPa). The residue is triturated in 25 cm³ of acetone and isolated by filtration. 0.56 g of 1-[2-(2-azabicyclo[2.2.2]oct-2-yl)ethyl]-4-phenyl-1H-pyrazol-3-ol dihydrochloride is thus obtained in the form of a beige powder which melts at 171° C. (with decomposition).

¹H NMR spectrum (300 MHz, (CD₃)₂SO d6, δ in ppm): from 1.50 to 1.75 (mt: 6H); 1.90 (very broad s: 1H); from 2.00 to 2.15 (mt: 1H); 2.28 (mt: 1H); 2.86 (very broad dd, J=12 and 4.5 Hz: 1H); from 3.35 to 3.55 (mt: 1H); 3.38 (very broad s: 1H); 3.55 (broad t, J=6.5 Hz: 2H); 4.46 (broad t, J=6.5 Hz: 2H); 7.14 (broad t, J=7.5 Hz: 1H); 7.34 (broad t, J=7.5 Hz: 2H); 7.65 (broad d, J=7.5 Hz: 2H); 8.04 (s: 1H); 10.84 (unresolved peak: 1H).

IR spectrum (KBr): 2949; 2870; 2629; 2184; 1608; 1579; 1510; 1455; 1198; 870; 761; 692; 670 and 510 cm⁻¹.

The 2-[2-(3-benzyloxy-4-phenylpyrazol-1-yl)ethyl]-2-azabicyclo[2.2.2]octane can be prepared in the following way:

A suspension of 1 g of 1-[(toluene-4-sulfonyl)oxy]-2-(3-benzyloxy-4-phenylpyrazol-1-yl)ethyl, 0.563 g of 2-azabicyclo[2.2.2]octane hydrochloride and 0.88 g of potassium carbonate in 25 cm³ of acetonitrile is stirred for 8 hours at a temperature in the region of 80° C. The mixture is concentrated to dryness under reduced pressure (3 kPa). The residue is taken up with 30 cm³ of water and extracted with 200 cm³ of ethyl acetate. The organic phase is washed with twice 30 cm³ of water, and is then dried, filtered and concentrated to dryness under reduced pressure (3 kPa). The oily residue obtained is purified by chromatography on silica gel (particle size 15-35 μm), eluting with a mixture of dichloromethane and methanol (95/5 by volume). After concentration of the fractions under reduced pressure, 0.92 g of 2-[2-(3-benzyloxy-4-phenylpyrazol-1-yl)ethyl]-2-azabicyclo[2.2.2]octane is obtained in the form of a colorless viscous oil, which is used as it is in the following step.

Mass spectrum (CI): m/z 388 ([M+H]⁺) (base peak).

The 2-azabicyclo[2.2.2]octane hydrochloride can be obtained according to the method described by M. Yokota et al., Eur. J. Med. Chem. Chim. Ther., 1997, 32 (5), 377-384.

EXAMPLE 13

1-[2-(2-Azabicyclo[2.2.1]hept-2-yl)ethyl]-4-phenyl-1H-pyrazol-3-ol Dihydrochloride 1.6 cm³ of 6M hydrochloric acid are added to a solution of 0.7 g of 2-[2-(3-benzyloxy-4-phenylpyrazol-1-yl)ethyl]-2- azabicyclo[2.2.1]heptane in 50 cm³ of ethanol, and the mixture is stirred for a quarter of an hour at ambient temperature and then concentrated to dryness under reduced pressure (3 kPa). The residue obtained and 0.10 g of palladium-on-charcoal (at 10%) are suspended in 20 cm³ of ethanol and stirred in an autoclave under a hydrogen pressure of 1 000 kPa, at a temperature of 20° C. for 8 hours. The reaction medium is then filtered over Celite® and concentrated to dryness under reduced pressure (3 kPa). The residue is triturated in 40 cm³ of acetone and isolated by filtration. 0.565 g of 1-[2-(2-azabicyclo[2.2.1]hept-2-yl)ethyl]-4-phenyl-1H-pyrazol-3-ol dihydrochloride is thus obtained in the form of a beige powder which melts at 173° C. (with decomposition).

$^1$H NMR spectrum (400 MHz, $(CD_3)_2SO$ d6 with addition of a few drops of $CD_3COOD$ d4, at a temperature of 363 K, δ in ppm): from 1.45 to 1.55 (mt: 1H); from 1.65 to 1.80 (mt: 3H); from 1.95 to 2.05 (mt: 2H); 2.65 (mt: 1H); from 3.10 to 3.25 (broad unresolved peak: 2H); 3.48 (mt: 1H); 3.59 (mt: 1H); 4.04 (mt: 1H); 4.34 (broad t, J=6.5 Hz: 2H); 7.15 (broad t, J=7.5 Hz: 1H); 7.32 (broad t, J=7.5 Hz: 2H); 7.62 (broad d, J=7.5 Hz: 2H); 7.90 (s: 1H).

IR spectrum (KBr): 2955; 2827; 2601; 2554; 1607; 1528; 1454; 1177; 1010; 767; 699; 672 and 515 cm$^{-1}$.

The 2-[2-(3-benzyloxy-4-phenylpyrazol-1-yl)ethyl]-2-azabicyclo[2.2.1]heptane can be prepared in the following way:

A suspension of 1 g of 1-[(toluene-4-sulfonyl)oxy]-2-(3-benzyloxy-4-phenylpyrazol-1-yl)ethyl, 0.51 g of 2-azabicyclo[2.2.1]heptane hydrochloride and 0.88 g of potassium carbonate in 25 cm³ of acetonitrile is stirred for 8 hours at a temperature in the region of 80° C. The mixture is concentrated to dryness under reduced pressure (3 kPa). The residue is taken up with 30 cm³ of water and extracted with 200 cm³ of ethyl acetate. The organic phase is washed with two times 30 cm³ of water, and is then dried, filtered and concentrated to dryness under reduced pressure (3 kPa). The oily residue obtained is purified by chromatography on silica gel (particle size 15-35 μm), eluting with a mixture of dichloromethane and methanol (95/5 by volume). After concentration of the fractions under reduced pressure, 0.75 g of 2-[2-(3-benzyloxy-4-phenylpyrazol-1-yl)-ethyl]-2-azabicyclo[2.2.1]heptane is obtained in the form of a colorless viscous oil, which is used as it is in the following step.

Mass spectrum (EI): m/z 373 (M$^{+}$), m/z 110 (base peak).

The 2-azabicyclo[2.2.1]heptane hydrochloride can be obtained according to the method described by J. R. Malpass et al., J.C.S., Perkin Trans. 1 1977, 8, 874-884.

EXAMPLE 14

1-[2-Dimethylaminoethyl]-4-phenyl-1H-pyrazol-3-ol Dihydrochloride

The process is carried out as in example 2, but with 0.10 g of [2-(3-benzyloxy-4-phenylpyrazol-1-yl)ethyl]-dimethylamine dihydrochloride and 0.012 g of palladium-on-charcoal (at 10%). 0.049 g of 1-[2-dimethylamino-ethyl]-4-phenyl-1H-pyrazol-3-ol dihydrochloride is thus obtained in the form of a beige powder which melts at around 135° C. (with decomposition).

$^1$H NMR spectrum (300 MHz, $(CD_3)_2SO$ d6, δ in ppm): 2.81 (d, J=5 Hz: 6H); 3.51 (mt: 2H); 4.38 (t, J=6.5 Hz: 2H); 7.16 (broad t, J=7.5 Hz: 1H); 7.35 (broad t, J=7.5 Hz: 2H); 7.65 (broad d, J=7.5 Hz: 2H); 8.05 (s: 1H); 10.27 (unresolved peak: 1H); from 10.30 to 10.70 (very broad unresolved peak: 1H).

IR spectrum (KBr): 3311; 2985; 2558; 2463; 1629; 1582; 1508; 1467; 1409; 1190; 985; 760; 687 and 673 cm$^{-1}$. The [2-(3-benzyloxy-4-phenylpyrazol-1-yl)ethyl]di-methylamine dihydrochloride can be prepared in the following way:

0.154 g of sodium hydride (at 75% by mass in liquid petroleum jelly) is added gradually, under an argon atmosphere and at ambient temperature, to a solution of 0.25 g of 3-benzyloxy-4-phenylpyrazole in 3 cm³ of anhydrous dimethylformamide, followed, after disappearance of the foams, by 0.5 g of (2-bromoethyl)-dimethylamine hydrobromide. After stirring for 2 hours at ambient temperature, water is slowly added and the mixture is extracted with ethyl acetate. The organic phase is dried over magnesium sulfate, filtered and concentrated to dryness under reduced pressure (3 kPa). The oily residue obtained is purified by chromatography on silica gel, eluting with a mixture of dichloromethane, methanol and aqueous ammonia at 28% (90/8/2 by volume). After concentration of the fractions under reduced pressure, 0.21 g of an oil is obtained, which is dissolved in ethyl ether, has 1 cm³ of an approximately 3M hydrochloric ether solution added to it, and is returned to dryness. The residue is triturated in acetone and then isolated by filtration. 0.1 g of [2-(3-benzyloxy-4-phenylpyrazol-1-yl)ethyl]-dimethylamine dihydrochloride is thus obtained in the form of white crystals which melt at 105° C.

$^1$H NMR spectrum (300 MHz, $(CD_3)_2SO$ d6, δ in ppm): 2.82 (d, J=5 Hz: 6H); 3.57 (mt: 2H); 4.34 (t, J=6.5 Hz: 2H); 5.36 (s: 2H); 7.18 (broad t, J=7.5 Hz: 1H); from 7.30 to 7.50 (mt: 5H); 7.52 (broad d, J=7.5 Hz: 2H); 7.65 (broad d, J=7.5 Hz: 2H); 8.17 (s: 1H); 9.68 (unresolved peak: 1H).

The (2-bromoethyl)dimethylamine hydrobromide can be obtained according to the method described by L. H. Amundsen et al., J. Am. Chem. Soc. 1941, 63, 305-307.

EXAMPLE 15

1-[3-Dimethylaminopropyl]-4-phenyl-1H-pyrazol-3-ol Dihydrochloride

The process is carried out as in example 2, but with 0.274 g of [3-(3-benzyloxy-4-phenylpyrazol-1-yl)-propyl]dimethylamine dihydrochloride and 0.04 g of palladium-on-charcoal (at 10%). 0.209 g of 1-[3-dimethylaminopropyl]-4-phenyl-1H-pyrazol-3-ol dihydro-chloride is thus obtained in the form of a beige powder which melts at around 208° C. (with decomposition).

$^1$H NMR spectrum (300 MHz, $(CD_3)_2SO$ d6, δ in ppm): 2.20 (mt: 2H); 3.5 (d, J=5 Hz: 6H); 3.07 (mt: 2H); 4.04 (t, J=6.5 Hz: 2H); 7.13 (broad t, J=7.5 Hz: 1H); 7.33 (broad t, J=7.5 Hz: 2H); 7.66 (broad d, J=7.5 Hz: 2H); 7.99 (s: 1H); 10.82 (unresolved peak: 1H). IR spectrum (KBr): 3078; 2954; 2591; 2470; 1603; 1476; 1369; 1268; 1188; 881; 763; 700; 570 and 494 cm$^{-1}$.

The [3-(3-benzyloxy-4-phenylpyrazol-1-yl)propyl]di-methylamine dihydrochloride can be prepared in the following way:

3.6 cm³ of 1N sodium hydroxide solution are added to a suspension of 0.38 g of [3-(3-benzyloxy-4-phenylpyrazol-1-yl)propyl]dimethylamine oxalate in 10 cm³ of water and the mixture is stirred for a quarter of an hour and then extracted with 3 times 25 cm³ of ethyl acetate. The pooled organic phases are dried over magnesium sulfate, and then concentrated to dryness under reduced pressure (3 kPa). The residue obtained is dissolved in 25 cm³ of ethanol, an excess of an approximately 3M hydrochloric ether solution is added, and the mixture is returned to dryness. 0.274 g of [3-(3-benzyloxy-4-phenylpyrazol-1-yl)propyl]dimethylamine dihydrochloride is thus obtained in the form of a pasty white solid used as it is in the following step.

The [3-(3-benzyloxy-4-phenylpyrazol-1-yl)propyl]di-methylamine oxalate can be prepared in the following way:

0.106 g of sodium hydride (at 75% by mass in liquid petroleum jelly) is added gradually, under an argon atmosphere and at ambient temperature, to a solution of 0.25 g of 3-benzyloxy-4-phenylpyrazole in 15 cm$^3$ of anhydrous dimethylformamide. After stirring for three quarters of an hour at a temperature in the region of 50° C., 0.316 g of (3-chloropropyl)dimethylamine hydrochloride is added in small portions and the mixture is then stirred for 16 hours at ambient temperature. The mixture is run into 150 cm$^3$ of water and extracted with 3 times 150 cm$^3$ of ethyl acetate. The pooled organic phases are washed with 50 cm$^3$ of water, and are then dried over anhydrous magnesium sulfate, filtered and concentrated to dryness under reduced pressure (3 kPa). The oily residue obtained (0.8 g) is dissolved in 10 cm$^3$ of ethyl ether and a solution of 0.09 g of oxalic acid in 5 cm$^3$ of ethyl ether is added. The white precipitate formed is filtered and then dried under vacuum (70 Pa) at ambient temperature. 0.395 g of [3-(3-benzyloxy-4-phenylpyrazol-1-yl)propyl]dimethylamine oxalate is thus obtained in the form of a white solid used as it is in the following step.

$^1$H NMR spectrum (300 MHz, (CD$_3$)$_2$SO d6, δ in ppm): 2.15 (mt: 2H); 30 (s: 6H); 2.98 (mt: 2H); 4.08 (t, J=6.5 Hz: 2H); 5.33 (s: 2H); 7.16 (broad t, J=7.5 Hz: 1H); from 7.30 to 7.45 (mt: 3H); 7.43 (broad t, J=7.5 Hz: 2H); 7.51 (broad d, J=7.5 Hz: 2H); 7.65 (broad d, J=7.5 Hz: 2H); 8.09 (s: 1H).

EXAMPLE 16

1-[2-((2S,6R)-2,6-Dimethylpiperidin-1-yl)ethyl]-4-phenyl-1H-pyrazol-3-ol Dihydrochloride The process is carried out as in example 2, but with 0.123 g of (2S,6R)-1-[2-(3-benzyloxy-4-phenylpyrazol-1-yl) ethyl]-2,6-dimethylpiperidine dihydrochloride and 0.014 g of palladium-on-charcoal (at 10%). 0.075 g of 1-[2-((2S,6R)-2,6-dimethylpiperidin-1-yl)ethyl]-4-phenyl-1H-pyrazol-3-ol dihydrochloride is thus obtained in the form of a beige powder which melts at around 206° C. (with decomposition).

$^1$H NMR spectrum (400 MHz, (CD$_3$)$_2$SO d6, at a temperature of 403K, δ in ppm): 1.36 (d, J=6.5 Hz: 6H); 1.57 (mt: 1H); from 1.65 to 1.90 (mt: 5H); 3.28 (unresolved peak: 2H); 3.49 (unresolved peak: 2H); 4.36 (broad t, J=6.5 Hz: 2H); 7.15 (tt, J=7.5 and 1.5 Hz: 1H); 7.33 (broad t, J=7.5 Hz: 2H); 7.66 (broad d, J=7.5 Hz: 2H); 8.00 (s: 1H).

IR spectrum (KBr): 3428; 3058; 2978; 2942; 2657; 2571; 1606; 1580; 1521; 1452; 1388; 1173; 997; 914; 766; 699; 671 and 511 cm$^{-1}$.

The (2S,6R)-1-[2-(3-benzyloxy-4-phenylpyrazol-1-yl)-ethyl]-2,6-dimethylpiperidine dihydrochloride can be prepared in the following way:

0.5 cm$^3$ of an approximately 3M hydrochloric ether solution is added to a solution of 0.117 g of (2S,6R)-1-[2-(3-benzyloxy-4-phenylpyrazol-1-yl)ethyl]-2,6-dimethylpiperidine in 25 cm$^3$ of ethanol, which is then brought back to dryness. 0.123 g of (2S,6R)-1-[2-(3-benzyloxy-4-phenylpyrazol-1-yl)ethyl]-2,6-dimethyl-piperidine dihydrochloride is thus obtained in the form of a colorless paste used as it is in the following step.

The (2S,6R)-1-[2-(3-benzyloxy-4-phenylpyrazol-1-yl)-ethyl]-2,6-dimethylpiperidine can be prepared in the following way:

0.211 g of sodium hydride (at 75% by mass in liquid petroleum jelly) is added gradually, under an argon atmosphere and at ambient temperature, to a solution of 0.25 g of 3-benzyloxy-4-phenylpyrazole in 20 cm$^3$ of anhydrous dimethylformamide. After stirring for three quarters of an hour at a temperature in the region of 50° C., 0.636 g of (2S,6R)-1-(2-chloroethyl)-2,6-dimethylpiperidine hydrochloride is added in small portions, and the mixture is then stirred for 16 hours at ambient temperature. The mixture is run into 150 cm$^3$ of water and extracted with twice 150 cm$^3$ of ethyl acetate. The pooled organic phases are washed with 50 cm$^3$ of water, and are then dried over anhydrous magnesium sulfate, filtered and concentrated to dryness under reduced pressure (3 kPa). The oily residue obtained is dissolved in 25 cm$^3$ of ethyl ether and a solution of 0.09 g of oxalic acid in 25 cm$^3$ of ethyl ether is added. The pasty product formed is washed with 3 times 25 cm$^3$ of ethyl ether, and is then taken up with 25 cm$^3$ of water, 4 cm$^3$ of 1N sodium hydroxide solution are added, and the mixture is stirred for a quarter of an hour and then extracted with two times 25 cm$^3$ of ethyl acetate. The pooled organic phases are dried over magnesium sulfate, and then concentrated to dryness under reduced pressure (3 kPa). The oily residue obtained is purified by chromatography on silica gel, eluting with a mixture of ethyl acetate and methanol (80/20 by volume). After concentration of the fractions under reduced pressure, 0.117 g of (2S,6R)-1-[2-(3-benzyloxy-4-phenylpyrazol-1-yl)ethyl]-2,6-dimethyl-piperidine is obtained in the form of a colorless oil used as it is in the following step.

$^1$H NMR spectrum (300 MHz, (CD$_3$)$_2$SO d6, δ in ppm): 1.08 (d, J=6.5 Hz: 6H); 1.17 (broad double t, J=12 and 3 Hz: 2H); 1.28 (mt: 1H); 1.53 (broad d, J=12 Hz: 2H); 1.62 (mt: 1H); 2.48 (mt: 2H); 2.95 (t, J=6.5 Hz: 2H); 3.98 (t, J=6.5 Hz: 2H); 5.32 (s: 2H); 7.15 (tt, J=7.5 and 1.5 Hz: 1H); from 7.30 to 7.45 (mt: 1H); 7.34 (broad t, J=7.5 Hz: 2H); 7.42 (broad t, J=7.5 Hz: 2H); 7.52 (broad d, J=7.5 Hz: 2H); 7.66 (broad d, J=7.5 Hz: 2H); 8.10 (s: 1H).

The (2S,6R)-1-(2-chloroethyl)-2,6-dimethylpiperidine-amine hydrochloride can be obtained according to the method described by R. Dahlbom et al., Acta Pharmaceutica Suecica 1969, 6 (3), 413-418.

EXAMPLE 17

1-[2-Diethylaminoethyl]-4-phenyl-1H-pyrazol-3-ol Dihydrochloride

The process is carried out as in example 2, but with 0.31 g of [2-(3-benzyloxy-4-phenylpyrazol-1-yl)ethyl]diethylamine dihydrochloride and 0.04 g of palladium-on-charcoal (at 10%). 0.139 g of 1-[2-diethylaminoethyl]-4-phenyl-1H-pyrazol-3-ol dihydrochloride is thus obtained in the form of a white powder which melts at around 174° C. (with decomposition).

$^1$H NMR spectrum (300 MHz, (CD$_3$)$_2$SO d6, δ in ppm): 1.23 (t, J=7 Hz: 6H); 3.12 (very broad q, J=7 Hz: 4H); 3.46 (very broad t, J=6.5 Hz: 2H); 4.40 (broad t, J=6.5 Hz: 2H); 7.14 (broad t, J=7.5 Hz: 1H); 7.33 (broad t, J=7.5 Hz: 2H); 7.65 (broad d, J=7.5 Hz: 2H); 8.07 (s: 1H); 10.46 (unresolved peak: 1H); from 10.60 to 10.85 (broad unresolved peak: 1H).

IR spectrum (KBr): 3065; 2974; 2589; 2484; 1609; 1530; 1454; 1179; 1012; 765; 693; 677 and 508 cm$^{-1}$.

The [2-(3-benzyloxy-4-phenylpyrazol-1-yl)ethyl]diethylamine dihydrochloride can be obtained in the following way:

The process is carried out as in example 15, but with 0.31 g of [2-(3-benzyloxy-4-phenylpyrazol-1-yl)-ethyl]diethylamine oxalate. 0.31 g of [2-(3-benzyloxy-4-phenylpyrazol-1-yl)ethyl]diethylamine dihydrochloride is thus obtained in the form of a colorless gum used as it is in the following step.

The [2-(3-benzyloxy-4-phenylpyrazol-1-yl)ethyl]diethylamine oxalate can be obtained in the following way:

The process is carried out as in example 15, but with 0.211 g of sodium hydride (at 75% by mass in liquid petroleum jelly) and 0.516 g of (2-chloroethyl)diethyl-amine hydrochloride. 0.376 g of [2-(3-benzyloxy-4-phenylpyrazol-1-yl)ethyl]diethylamine oxalate is thus obtained in the form of a white powder which melts at 133° C.

$^1$H NMR spectrum (300 MHz, $(CD_3)_2SO$ d6, δ in ppm): 1.12 (t, J=7 Hz: 6H); 2.98 (broad q, J=7 Hz: 4H); 3.35 (very broad t, J=6.5 Hz: 2H); 4.31 (broad t, J=6.5 Hz: 2H); 5.35 (s: 2H); 7.17 (broad t, J=7.5 Hz: 1H); 7.36 (mt: 3H); 7.43 (broad t, J=7.5 Hz: 2H); 7.51 (broad d, J=7.5 Hz: 2H); 7.65 (broad d, J=7.5 Hz: 2H); 8.14 (s: 1H).

EXAMPLE 18

1-(2-Diisopropylaminoethyl)-4-phenyl-1H-pyrazol-3-ol Dihydrochloride

The process is carried out as in example 2, but with 0.21 g of [2-(3-benzyloxy-4-phenylpyrazol-1-yl)ethyl]-diisopropylamine dihydrochloride and 0.025 g of palladium-on-charcoal (at 10%). 0.122 g of 1-[2-diiso-propylaminoethyl]-4-phenyl-1H-pyrazol-3-ol dihydrochloride is thus obtained in the form of a beige powder which melts at around 220° C. (with decomposition).

$^1$H NMR spectrum (300 MHz, $(CD_3)_2SO$ d6, δ in ppm): 1.32 (broad d, J=7 Hz: 6H); 1.34 (broad d, J=7 Hz: 6H); 3.47 (unresolved peak: 2H); 3.71 (mt: 2H); 4.40 (broad t, J=6.5 Hz: 2H); 7.14 (broad t, J=7.5 Hz: 1H); 7.33 (broad t, J=7.5 Hz: 2H); 7.65 (broad d, J=7.5 Hz: 2H); 8.12 (s: 1H); 9.96 (unresolved peak: 1H); 10.49 (broad s: 1H).

IR spectrum (KBr): 2984; 2654; 2507; 2469; 1607; 1580; 1531; 1453; 1193; 759; 693; 673 and 511 cm$^{-1}$.

The [2-(3-benzyloxy-4-phenylpyrazol-1-yl)ethyl]diisopropylamine dihydrochloride can be obtained in the following way:

The process is carried out as in example 15, but with 0.31 g of [2-(3-benzyloxy-4-phenylpyrazol-1-yl)ethyl]-diisopropylamine oxalate. 0.21 g of [2-(3-benzyloxy-4-phenylpyrazol-1-yl)ethyl]diisopropylamine dihydro-chloride is thus obtained in the form of a beige semi-solid used as it is in the following step.

The [2-(3-benzyloxy-4-phenylpyrazol-1-yl)ethyl]diisopropylamine oxalate can be obtained in the following way:

The process is carried out as in example 15, but with 0.211 g of sodium hydride (at 75% by mass in liquid petroleum jelly) and 0.6 g of (2-chloroethyl)diisopropylamine hydrochloride. 0.312 g of [2-(3-benzyloxy-4-phenylpyrazol-1-yl)ethyl]diethylamine oxalate is thus obtained in the form of a white powder which melts at 134° C.

$^1$H NMR spectrum (300 MHz, $(CD_3)_2SO$ d6 with addition of a few drops of $CD_3COOD$ d4, δ in ppm): 1.21 (d, J=6 Hz: 12H); 3.39 (broad t, J=6.5 Hz: 2H); 3.57 (mt: 2H); 4.30 (t, J=6.5 Hz: 2H); 5.35 (s: 2H); 7.17 (broad t, J=7.5 Hz: 1H); 7.35 (mt: 3H); 7.41 (broad t, J=7.5 Hz: 2H); 7.49 (broad d, J=7.5 Hz: 2H); 7.65 (broad d, J=7.5 Hz: 2H); 8.10 (s: 1H).

EXAMPLE 19

4-Phenyl-1-(2-pyrrolidin-1-ylethyl)-1H-pyrazol-3-ol dihydrochloride

The process is carried out as in example 2, but with 0.285 g of 3-benzyloxy-4-phenyl-1-(2-pyrrolidin-1-ylethyl)-1H-pyrazole dihydrochloride and 0.037 g of palladium-on-charcoal (at 10%). 0.101 g of 4-phenyl-1-(2-pyrrolidin-1-ylethyl)-1H-pyrazol-3-ol dihydro-chloride is thus obtained in the form of a beige powder which melts at around 173° C. (with decomposition).

$^1$H NMR spectrum (300 MHz, $(CD_3)_2SO$ d6, δ in ppm): from 1.80 to 2.10 (mt: 4H); from 2.90 to 3.10 (unresolved peak: 2H); from 3.45 to 3.65 (unresolved peak: 4H); 4.34 (broad t, J=6.5 Hz: 2H); 7.14 (broad t, J=7.5 Hz: 1H); 7.33 (broad t, J=7.5 Hz: 2H); 7.65 (broad d, J=7.5 Hz: 2H); 8.02 (s: 1H); from 10.30 to 10.60 (broad unresolved peak: 1H); 10.43 (unresolved peak: 1H).

IR spectrum (KBr): 3416; 3054; 2973; 2670; 2585; 2476; 2405; 1608; 1581; 1527; 1453; 1247; 1175; 1011; 768; 702; 673 and 514 cm$^{-1}$.

The 3-benzyloxy-4-phenyl-1-(2-pyrrolidin-1-ylethyl)-1H-pyrazole dihydrochloride can be obtained in the following way:

The process is carried out as in example 15, but with 0.34 g of 3-benzyloxy-4-phenyl-1-(2-pyrrolidin-1-ylethyl)-1H-pyrazole oxalate. 0.285 g of 3-benzyloxy-4-phenyl-1-(2-pyrrolidin-1-ylethyl)-1H-pyrazole dihydrochloride is thus obtained in the form of a beige gum used as it is in the following step.

The 3-benzyloxy-4-phenyl-1-(2-pyrrolidin-1-ylethyl)-1H-pyrazole oxalate can be obtained in the following way:

The process is carried out as in example 15, but with 0.211 g of sodium hydride (at 75% by mass in liquid petroleum jelly) and 0.51 g of 1-(2-chloroethyl)-pyrrolidine hydrochloride. 0.354 g of 3-benzyloxy-4-phenyl-1-(2-pyrrolidin-1-ylethyl)-1H-pyrazole oxalate is thus obtained in the form of a white powder which melts at 144° C.

$^1$H NMR spectrum (300 MHz, $(CD_3)_2SO$ d6, δ in ppm): 1.87 (mt: 4H); 3.10 (mt: 4H); 3.46 (mt: 2H); 4.33 (t, J=6.5 Hz: 2H); 5.35 (s: 2H); 7.18 (broad t, J=7.5 Hz: 1H); 7.36 (mt: 3H); 7.43 (broad t, J=7.5 Hz: 2H); 7.52 (broad d, J=7.5 Hz: 2H); 7.66 (broad d, J=7.5 Hz: 2H); 8.13 (s: 1H).

EXAMPLE 20

3-(3-Methoxy-4-phenylpyrazol-1-yl)-1-azabicyclo[2.2.2]-octane hydrochloride 1.94 g of potassium tert-butoxide are added gradually, under an argon atmosphere and at ambient temperature, to a solution of 1.2 g of 3-methoxy-4-phenylpyrazole in 20 cm$^3$ of anhydrous dimethylformamide. After stirring for 1.5 hours at ambient temperature, a solution of 2.8 g of 3-[(methanesulfonyl)oxy]-1-azabicyclo[2.2.2]-octane in 20 cm$^3$ of anhydrous dimethylformamide is added dropwise, and the mixture is then heated for 16 hours at a temperature in the region of 100° C. The mixture is cooled to ambient temperature and is then concentrated under reduced pressure (3 kPa). The residue is taken up with 30 cm$^3$ of water and extracted with 250 cm$^3$ of ethyl acetate. The organic phase is washed with 3 times 30 cm$^3$ of water, and dried, filtered and concentrated to dryness under reduced pressure (3 kPa). The oily residue obtained is purified by chromatography on silica gel, eluting with a mixture of ethyl acetate and methanol (90/10, then 75/25 by volume). After concentration of the fractions under reduced pressure, 0.36 g of an oil is obtained, which is dissolved in 15 cm$^3$ of acetone, and 5 cm$^3$ of an approximately 1M hydrochloric ether solution are added. The precipitate which has appeared is triturated overnight and then isolated by filtration. 0.308 g of 3-(3-methoxy-4-phenylpyrazol-1-yl)-1-azabicyclo[2.2.2]octane hydrochloride is thus obtained in the form of a hygroscopic beige powder which melts at around 207° C. (with decomposition).

¹H NMR spectrum (300 MHz, (CD₃)₂SO d6, δ in ppm): from 1.65 to 2.05 (mt: 4H); 2.42 (mt: 1H); 3.28 (mt: 3H); from 3.35 to 3.55 (mt: 1H); 3.80 (mt: 2H); 3.97 (s: 3H); 4.75 (mt: 1H); 7.18 (broad t, J=7.5 Hz: 1H); 7.36 (broad t, J=7.5 Hz: 2H); 7.65 (broad d, J=7.5 Hz: 2H); 8.30 (s: 1H); 10.76 (unresolved peak: 1H).

IR spectrum (KBr): 3430; 2939; 2907; 2666; 2584; 1607; 1580; 1570; 1518; 1454; 1409; 1049; 1028; 764; 698; 623 and 513 cm⁻¹.

EXAMPLE 21

1-[2-(3-Difluoromethoxy-4-phenylpyrazol-1-yl)ethyl]-piperidine hydrochloride The process is carried out as in example 1, but with 0.25 g of 3-difluoromethoxy-4-phenyl-1H-pyrazole, 0.303 g of sodium hydride (at 75% by mass in liquid petroleum jelly) and 0.6 g of 1-(2-chloroethyl)-piperidine hydrochloride, and then eluting with a mixture of dichloromethane and methanol (95/5 by volume). 0.175 g of 1-[2-(3-difluoromethoxy-4-phenyl-pyrazol-1-yl)ethyl]piperidine hydrochloride is thus obtained in the form of a white solid which melts at around 174° C. (with decomposition).

¹H NMR spectrum (300 MHz, (CD₃)₂SO d6, δ in ppm): 1.40 (unresolved peak: 1H); from 1.60 to 1.90 (mt: 5H); 2.94 (unresolved peak: 2H); 3.47 (very broad d, J=12 Hz: 2H); 3.54 (unresolved peak: 2H); 4.55 (broad t, J=6.5 Hz: 2H); 7.29 (tt, J=7.5 and 2.5 Hz: 1H); 7.41 (t, J=72 Hz: 1H); 7.44 (broad t, J=7.5 Hz: 2H); 7.59 (broad d, J=7.5 Hz: 2H); 8.30 (s: 1H); from 10.00 to 10.20 (unresolved peak: 1H).

IR spectrum (KBr): 3100; 2931; 2644; 2543; 1609; 1581; 1507; 1482; 1456; 1364; 1181; 1125; 1100; 1076; 761; 694 and 513 cm⁻¹.

The 3-difluoromethoxy-4-phenyl-1H-pyrazole can be prepared in the following way:

A suspension of 2.55 g of 1-(3-hydroxy-4-phenylpyrazol-1-yl)ethanone, 1.75 g of potassium carbonate and 1.82 g of methyl 2-chloro-2,2-difluoroacetate in 40 cm³ of dimethylformamide is stirred, under an argon atmosphere, at ambient temperature for 16 hours and then at a temperature of 65° C. for 8 hours. After cooling, 10 cm³ of a 10N sodium hydroxide solution are added and the mixture is stirred for 1 hour at ambient temperature, and then concentrated under reduced pressure (3 kPa). The residue is extracted with 200 cm³ of ethyl acetate. The organic phase is washed with 3 times 25 cm³ of water, dried and concentrated under reduced pressure (3 kPa). The oily residue obtained is purified by chromatography on silica gel, eluting with a mixture of dichloromethane and methanol (99/1 by volume). After concentration of the fractions under reduced pressure, 0.8 g of 3-difluoromethoxy-4-phenyl-1H-pyrazole is obtained in the form of a yellow solid which melts at 125° C. Mass spectrum (EI): m/z 210 (M⁺·) (base peak), m/z 160 [M–CF₂]⁺·.

EXAMPLE 22

4-Phenyl-1-(2-piperidin-1-ylethyl)-1H-pyrazol-3-ylamine dihydrochloride 10 cm³ of 1N hydrochloric ether solution is added, in excess, to a solution of 0.2 g of 4-phenyl-1-(2-piperidin-1-ylethyl)-1H-pyrazol-3-ylamine in 10 cm³ of methanol, and the mixture is concentrated to dryness under reduced pressure (3 kPa). The residue provides, after trituration in ethyl ether, 0.244 g of 4-phenyl-1-(2-piperidin-1-ylethyl)-1H-pyrazol-3-ylamine dihydrochloride in the form of white crystals which melt at around 120° C.

¹H NMR spectrum (300 MHz, (CD₃)₂SO d6, δ in ppm): from 1.25 to 1.55 (mt: 1H); from 1.60 to 1.90 (mt: 5H); 2.95 (unresolved peak: 2H); 3.44 (unresolved peak: 2H); 4.53 (t, J=6.5 Hz: 2H); 7.27 (broad t, J=7.5 Hz: 1H); 7.42 (broad t, J=7.5 Hz: 2H); 7.56 (broad d, J=7.5 Hz: 2H); 8.07 (s: 1H); 10.46 (unresolved peak: 1H).

IR spectrum (KBr): 3277; 2945; 2630; 2545; 1612; 1540; 1451; 1099; 1005; 768; 707; 572 and 559 cm⁻¹.

The 4-phenyl-1-(2-piperidin-1-ylethyl)-1H-pyrazol-3-ylamine can be prepared in the following way:

A suspension of 1.59 g of 4-phenyl-1H-pyrazol-3-ylamine, 2.2 g of 1-(2-chloroethyl)piperidine hydrochloride, 4 g of potassium carbonate and 1.66 g of potassium iodide in 50 cm³ of 2-butanone is stirred at the boiling temperature of the reaction medium for 22 hours. After cooling, the mixture is brought to dryness under reduced pressure (3 kPa). The residue is taken up with 40 cm³ of 0.5N sodium hydroxide solution and extracted with 50 cm³ of ethyl acetate. The organic phase is dried over magnesium sulfate, filtered and concentrated to dryness under reduced pressure (3 kPa). The yellow oily residue is purified by chromatography on basic alumina, eluting successively with a mixture of ethyl acetate and dichloromethane (50/50 by volume) and then with pure ethyl acetate. 0.2 g of 4-phenyl-1-(2-piperidin-1-ylethyl)-1H-pyrazol-3-ylamine is thus obtained in the form of a white solid which melts at 96° C. and has an Rf of 0.4 (ethyl acetate, aluminum oxide plate reference 105731, Merck).

¹H NMR spectrum (300 MHz, (CD₃)₂SO d6, δ in ppm): 1.40 (mt: 2H); 1.49 (mt: 4H); 2.39 (broad t, J=5 Hz: 4H); 2.64 (t, J=6.5 Hz: 2H); 3.98 (t, J=6.5 Hz: 2H); 4.63 (s: 2H); 7.15 (tt, J=7.5 and 1.5 Hz: 1H); 7.34 (broad t, J=7.5 Hz: 2H); 7.49 (broad d, J=7.5 Hz: 2H); 7.74 (s: 1H).

The 4-phenyl-1H-pyrazol-3-ylamine can be prepared according to the method described by S. A. Lang, Jr. et al., J. Heterocyclic Chem. 1977, 14, 65-69.

EXAMPLE 23

4-Phenyl-1-(2-piperidin-1-ylethyl)-1H-pyrazol-3-ylamine dihydrochloride 2 cm³ of a 1M lithium aluminum hydride solution are added gradually, at ambient temperature and under an argon atmosphere, to a solution of 0.25 g of N-[4-phenyl-1-(2-piperidin-1-ylethyl)-1H-pyrazol-3-yl]-formamide in 10 cm³ of anhydrous tetrahydrofuran. After stirring for 66 hours at ambient temperature, 1 cm³ of 1N sodium hydroxide solution is added gradually and the mixture is extracted with 20 cm³ of ethyl acetate. After removal of the gel by filtration, the organic phase is concentrated to dryness under reduced pressure (3 kPa). The oily residue obtained is purified by chromatography on basic alumina, eluting with a mixture of dichloromethane and ethyl acetate (80/20 by volume). After concentration of the fractions under reduced pressure, a colorless oil is obtained, which is dissolved in 10 cm³ of ethyl ether, and 1 cm³ of an approximately 6N solution of hydrochloric dioxane is added, and the mixture is then concentrated to dryness under reduced pressure (3 kPa). The residue is triturated in acetone and isolated by filtration. 0.045 g of 4-phenyl-1-(2-piperidin-1-ylethyl)-1H-pyrazol-3-ylamine dihydrochloride is thus obtained in the form of a white solid which melts at around 165° C. (with decomposition).

¹H NMR spectrum (300 MHz, (CD₃)₂SO d6, δ in ppm): from 1.25 to 1.50 (unresolved peak: 1H); from 1.60 to 1.90

(mt: 5H); 1.6 (s: 3H); 2.94 (unresolved peak: 2H); from 3.40 to 3.65 (mt: 4H); 4.42 (t, J=6.5 Hz: 2H); 7.20 (broad t, J=7.5 Hz: 1H); 7.37 (broad t, J=7.5 Hz: 2H); 7.47 (broad d, J=7.5 Hz: 2H); 7.89 (s: 1H); 9.93 (unresolved peak: 1H).

IR spectrum (KBr): 3289; 2943; 2600; 2534; 2481; 1627; 1530; 1446; 1342; 1189; 850; 770; 706 and 499 cm$^{-1}$.

The N-[4-phenyl-1-(2-piperidin-1-ylethyl)-1H-pyrazol-3-yl]formamide can be prepared in the following way:

A solution of 0.24 g of 4-phenyl-1-(2-piperidin-1-ylethyl)-1H-pyrazol-3-ylamine in 10 cm$^3$ of ethyl formate is stirred at the boiling temperature of the reaction medium for 23 hours. After cooling, the mixture is concentrated to dryness under reduced pressure (3 kPa). 0.31 g of N-[4-phenyl-1-(2-piperidin-1-ylethyl)-1H-pyrazol-3-yl]formamide is thus obtained in the form of a colorless lacquer, which is used as it is in the following step.

$^1$H NMR spectrum (400 MHz, (CD$_3$)$_2$SO d6, at a temperature of 373 K, δ in ppm): 1.42 (mt: 2H); 1.52 (mt: 4H); 2.45 (t, J=5 Hz: 4H); 3.6 (t, J=6.5 Hz: 2H); 4.17 (t, J=6.5 Hz: 2H); 7.24 (broad t, J=7.5 Hz: 1H); 7.38 (broad t, J=7.5 Hz: 2H); 7.49 (broad d, J=7.5 Hz: 2H); 7.96 (s: 1H); 8.30 (broad d, J=5 Hz: 1H); 9.49 (unresolved peak: 1H).

IR spectrum (KBr): 34434; 3218; 2955; 2799; 1683; 1631; 1607; 1325; 1289; 765; 698 and 592 cm$^{-1}$.

EXAMPLE 24

N-[4-Phenyl-1-(2-piperidin-1-ylethyl)-1H-pyrazol-3-yl]-acetamide oxalate 0.1 cm$^3$ of acetic anhydride is added to a solution of 0.27 g of 4-phenyl-1-(2-piperidin-1-ylethyl)-1H-pyrazol-3-ylamine in 5 cm$^3$ of chloroform, and the mixture is then stirred at ambient temperature for 100 hours. After the mixture has been concentrated to dryness under reduced pressure (3 kPa), 15 cm$^3$ of a saturated sodium hydrogen carbonate solution are added to the residue, which is extracted with 20 cm$^3$ of ethyl acetate. The organic phase is dried over magnesium sulfate, filtered and concentrated to dryness under reduced pressure (3 kPa). The oily residue obtained is dissolved in 10 cm$^3$ of acetone and 0.1 g of oxalic acid is added. The solution obtained is concentrated to dryness under reduced pressure (3 kPa) and the residue is triturated in ethyl ether and isolated by filtration. 0.05 g of N-[4-phenyl-1-(2-piperidin-1-ylethyl)-1H-pyrazol-3-yl]acetamide oxalate is thus obtained in the form of a hygroscopic white solid.

$^1$H NMR spectrum (300 MHz, (CD$_3$)$_2$SO d6, δ in ppm): 1.52 (mt: 2H); 1.70 (mt: 4H); 2.01 (broad s: 3H); 3.01 (unresolved peak: 4H); 3.36 (broad t, J=6.5 Hz: 2H); 4.44 (broad t, J=6.5 Hz: 2H); 7.25 (broad t, J=7.5 Hz: 1H); 7.38 (broad t, J=7.5 Hz: 2H); 7.47 (broad d, J=7.5 Hz: 2H); 8.11 (broad s: 1H); 9.66 (unresolved peak: 1H).

IR spectrum (KBr): 3258; 3026; 2952; 2683; 2540; 1725; 1640; 1525; 1447; 1373; 1202; 1008; 765 and 700 cm$^{-1}$.

EXAMPLE 25

N-[4-Phenyl-1-(2-piperidin-1-ylethyl)-1H-pyrazol-3-yl]-methanesulfonamide 0.06 cm$^3$ of methanesulfonyl chloride is added to a solution of 0.18 g of 4-phenyl-1-(2-piperidin-1-ylethyl)-1H-pyrazol-3-ylamine in 5 cm$^3$ of chloroform, and the mixture is then stirred at ambient temperature for 22 hours. 0.04 cm$^3$ of methanesulfonyl chloride is added to the mixture and the stirring is continued at ambient temperature for 3 hours. 15 cm$^3$ of a saturated sodium hydrogen carbonate solution are added to the mixture, which is extracted with 25 cm$^3$ of ethyl acetate. The organic phase is dried over magnesium sulfate, filtered and concentrated to dryness under reduced pressure (3 kPa). The oily residue obtained is purified by chromatography on basic alumina, eluting successively with pure ethyl acetate and then with a mixture of ethyl acetate and methanol (30/1 by volume). After concentration of the fractions under reduced pressure, a colorless residue is obtained, which is crystallized by trituration from ethyl ether and isolated by filtration. 0.05 g of N-[4-phenyl-1-(2-piperidin-1-ylethyl)-1H-pyrazol-3-yl]-methanesulfonamide is thus obtained in the form of a white solid which melts at 121° C.

$^1$H NMR spectrum (300 MHz, (CD$_3$)$_2$SO d6, δ in ppm): from 1.40 to 1.55 (mt: 6H); 2.41 (broad t, J=5 Hz: 4H); 3.1 (t, J=6.5 Hz: 2H); 3.11 (s: 3H); 4.18 (t, J=6.5 Hz: 2H); 7.23 (broad t, J=7.5 Hz: 1H); 7.38 (broad t, J=7.5 Hz: 2H); 7.69 (broad d, J=7.5 Hz: 2H); 8.06 (s: 1H); from 9.00 to 9.70 (very broad unresolved peak: 1H).

IR spectrum (KBr): 3105; 2928; 1610; 1440; 1321; 1149; 976; 765; 699; 524 and 518 cm$^{-1}$.

EXAMPLE 26

1-(2-Dimethylaminopropyl)-4-phenyl-1H-pyrazol-3-ol dihydrochloride 1 cm$^3$ of a 4N hydrochloric solution in dioxane is added gradually, at a temperature in the region of 20° C., to a solution of 0.42 g of {2-[3-(cyclohex-2-enyloxy)-4-phenylpyrazol-1-yl]-1-methylethyl}dimethylamine in 5 cm$^3$ of methanol, with stirring. After stirring for 15 hours at a temperature in the region of 20° C., the reaction mixture is concentrated to dryness under reduced pressure (2.7 kPa) and dried at 40° C. under reduced pressure (2.7 kPa) so as to give 0.37 g of 1-(2-dimethylaminopropyl)-4-phenyl-1H-pyrazol-3-ol dihydrochloride in the form of a white solid which melts at 189° C. Mass spectrum (CI): m/z 246 (MH$^+$) base peak.

The {2-[3-(cyclohex-2-enyloxy)-4-phenylpyrazol-1-yl]-1-methylethyl}dimethylamine can be prepared in the following way:

A solution of 1 g of 3-(cyclohex-2-enyloxy)-4-phenyl-1H-pyrazole in 5 cm$^3$ of dimethylformamide is added to a suspension, which is stirred under an argon atmosphere, of 1.3 g of sodium hydride (at 75% in liquid petroleum jelly) in 5 cm$^3$ of dimethylformamide. After stirring for 15 minutes at a temperature in the region of 20° C., and then for 30 minutes at 50° C., the reaction medium is cooled to a temperature in the region of 20° C., and 1.3 g of (2-chloro-1-methylethyl)dimethylamine hydrochloride are added with stirring, and the mixture is then brought to 50° C. for 15 hours. After the addition of a further 0.14 g of sodium hydride (at 75% in liquid petroleum jelly) and a further 0.7 g of (2-chloro-1-methylethyl)dimethylamine hydrochloride, the reaction is continued for 15 hours at 50° C., and the reaction medium is then cooled to a temperature in the region of 20° C. and concentrated to dryness under reduced pressure (2.7 kPa). The residue obtained is taken up in 100 cm$^3$ of water; the resulting aqueous phase is extracted with 3 times 30 cm$^3$ of dichloromethane, and the organic phase is dried over magnesium sulfate and concentrated to dryness under reduced pressure (2.7 kPa). 1.2 g of a brown oil is obtained, which is purified by flash chromatography on silica under an argon pressure (50 kPa) [eluent: dichloromethane/methanol (95/5 by volume)]. After concentration of the fractions to dryness under reduced pressure (2.7 kPa), 0.42 g of {2-[3-(cyclohex-2-enyloxy)-4-phenylpyrazol-1-yl]-1-methylethyl}dimethylamine is obtained in the form of an oil [TLC: eluent: dichloromethane/methanol (95/5 by volume), Rf=0.13]. Mass spectrum (EI): m/z 325 (M$^{+\cdot}$), m/z 72 (C$_4$H$_{10}$N$^{+\cdot}$).

The 3-(cyclohex-2-enyloxy)-4-phenyl-1H-pyrazole can be prepared in the following way:

2.02 g of 1-(3-hydroxy-4-phenylpyrazol-1-yl)ethanone, 1.27 cm$^3$ of 3-bromocyclohexene and 1.52 g of potassium carbonate are added to 20 cm$^3$ of methyl ethyl ketone with stirring at a temperature in the region of 20° C. After heating for 3 hours at the reflux of the solvent, the reaction medium is cooled to a temperature in the region of 20° C. and concentrated to dryness under reduced pressure (2.7 kPa). The residue obtained is taken up in a mixture of 20 cm$^3$ of tetrahydrofuran and 20 cm$^3$ of methanol, and 2 cm$^3$ of 5N sodium hydroxide are then added thereto with stirring. After stirring for 30 minutes at a temperature in the region of 20° C., the reaction medium is concentrated to dryness under reduced pressure (2.7 kPa), which results in a residue which is solubilized in 100 cm$^3$ of ethyl acetate. The organic solution is washed with two times 20 cm$^3$ of water and with 20 cm$^3$ of water saturated with sodium chloride, dried over magnesium sulfate, filtered, and evaporated to dryness under reduced pressure (2.7 kPa). The solid obtained is taken up with 5 cm$^3$ of ethyl acetate under hot conditions with stirring; 40 cm$^3$ of diisopropyl ether are added to the solution, which is brought to the reflux of the solvent for 15 minutes and then cooled to a temperature in the region of 20° C. A first crystallization crop is filtered off, washed with 10 cm$^3$ of diisopropyl ether and 10 cm$^3$ of pentane, and dried under reduced pressure (2.7 kPa) to give 1.07 g of 3-(cyclohex-2-enyloxy)-4-phenyl-1H-pyrazole in the form of a white powder. The crystallization filtrate is evaporated to dryness under reduced pressure (2.7 kPa) and taken up with 20 cm$^3$ of diisopropyl ether, and 20 cm$^3$ of pentane are added; a second crystallization crop is filtered off and dried under reduced pressure (2.7 kPa), to give 0.33 g of a batch which is identical to the preceding one [TLC: eluent: cyclohexane/ethyl acetate (70/30 by volume), Rf=0.23]. Mass spectrum (EI): m/z 240 (M$^{+\cdot}$), m/z 160 [(M–C$_6$H$_8$)$^{+\cdot}$].

EXAMPLE 27

1-(1-Methylpiperidin-3-ylmethyl)-4-phenyl-1H-pyrazol-3-ol 0.86 g of 3-(3-benzyloxy-4-phenylpyrazol-1-ylmethyl)-1-methylpiperidine, 0.1 g of palladium-on-charcoal at 10%, 10 cm$^3$ of cyclohexene and 20 cm$^3$ of ethanol are added to 20 cm$^3$ of ethanol at a temperature in the region of 20° C. After 15 hours at 50° C., 0.1 g of palladium-on-charcoal at 10% and 10 cm$^3$ of cyclohexene are added to the reaction medium; the mixture is brought to the reflux of the solvent for 1 hour, and a further 15 cm$^3$ of cyclohexene are then added and the reaction is continued at the reflux of the solvent for 5 hours. The catalyst is filtered off over supercel, and the solution is evaporated to dryness under reduced pressure (2.7 kPa) to give 0.48 g of a solid which is triturated in 10 cm$^3$ of a mixture of diisopropyl ether and pentane. After filtration, 0.3 g of a solid is obtained, which is used again in reaction with 10 cm$^3$ of ethanol, 10 cm$^3$ of cyclohexene and 0.1 g of palladium-on-charcoal at 10% with stirring and at the reflux of the solvent for 15 hours. The catalyst is filtered off over supercel, and the filtrate is evaporated to dryness under reduced pressure (2.7 kPa) to give 0.3 g of a solid which is purified by flash chromatography on silica under an argon pressure (50 kPa) [eluent: dichloromethane/methanol/38% aqueous ammonia solution (88/10/2 by volume)]. After concentration of the fractions under reduced pressure (2.7 kPa), 0.15 g of a yellowish solid is obtained, which is taken up in 70 cm$^3$ of methanol at a temperature in the region of 20° C. 1 cm$^3$ of 4N hydrochloric acid in dioxane is added to the solution, which is stirred for 15 minutes at a temperature in the region of 20° C. and is then evaporated to dryness under reduced pressure (2.7 kPa) to give 0.19 g of a foam which is triturated in diisopropyl ether and filtered. The deliquescent solid is taken up with 1 cm$^3$ of 1N sodium hydroxide, and the aqueous phase is washed with dichloromethane, partially evaporated under reduced pressure (2.7 kPa), adjusted to pH 8 by adding 0.1N hydrochloric acid, and extracting with dichloromethane. The organic phase is dried over magnesium sulfate, filtered and evaporated under reduced pressure (2.7 kPa) to give 0.15 g of 1-(1-methylpiperidin-3-ylmethyl)-4-phenyl-1H-pyrazol-3-ol in the form of a cream foam which melts at 132° C. Mass spectrum (ES): m/z 272 (MH$^+$).

The 3-(3-benzyloxy-4-phenylpyrazol-1-ylmethyl)-1-methylpiperidine can be prepared in the following way:

0.4 g of sodium hydride (at 75% in liquid petroleum jelly) is added gradually, at a temperature in the region of 20° C., to a solution of 1 g of 3-benzyloxy-4-phenyl-1H-pyrazole in 10 cm$^3$ of dimethylformamide under an argon atmosphere and with stirring, and the mixture is then brought to 50° C. for 10 minutes. After the addition of 1.5 g of 3-chloromethyl-1-methylpiperidine hydrochloride, the reaction medium is heated at 80° C. for 15 hours, and is then cooled to a temperature in the region of 20° C. and poured into 100 cm$^3$ of water. The mixture is extracted with dichloromethane; the organic phase is dried over magnesium sulfate, filtered and evaporated to dryness under reduced pressure (2.7 kPa) to give 1.6 g of a brown oil which is purified by flash chromatography on silica under an argon pressure (50 kPa) [eluent: dichloromethane/methanol (95/5 by volume)]. After concentration of the fractions to dryness under reduced pressure (2.7 kPa), 0.86 g of 3-(3-benzyloxy-4-phenyl-pyrazol-1-ylmethyl)-1-methylpiperidine is obtained in the form of a yellow oil [TLC: eluent: dichloromethane/methanol/38% aqueous ammonia solution (88/10/2 by volume), Rf=0.41]. Mass spectrum (EI): m/z 361 (M$^{+\cdot}$), m/z 270 [(M–C$_7$H$_7$)$^{+\cdot}$].

EXAMPLE 28

5-Methyl-4-phenyl-1-(2-piperidin-1-ylethyl)-1H-pyrazol-3-ol dihydrochloride 1.5 cm$^3$ of a 4N hydrochloric solution in dioxane are added gradually, with stirring, at a temperature in the region of 20° C., to a solution of 0.3 g of 1-{2-[3-(cyclohex-2-enyloxy)-5-methyl-4-phenylpyrazol-1-yl]-ethyl}piperidine in 10 cm$^3$ of methanol. After stirring for 15 hours at a temperature in the region of 20° C., the reaction mixture is concentrated to dryness under reduced pressure (2.7 kPa). The residue is triturated in diisopropyl ether, filtered, and dried under reduced pressure (2.7 kPa) at 40° C. for 2 hours to give 0.19 g of 5-methyl-4-phenyl-1-(2-piperidin-1-ylethyl)-1H-pyrazol-3-ol dihydrochloride in the form of a cream solid which melts at 222° C. Mass spectrum (CI): m/z 286 (MH$^+$).

The 1-{2-[3-(cyclohex-2-enyloxy)-5-methyl-4-phenyl-pyrazol-1-yl]ethyl}piperidine can be prepared in the following way:

0.2 g of sodium hydride at 75% in liquid petroleum jelly is added gradually, at a temperature in the region of 20° C., to a solution of 0.46 g of 3-(cyclohex-2-enyloxy)-5-methyl-4-phenyl-1H-pyrazole in 15 cm$^3$ of dimethylformamide with stirring and under an argon atmosphere. After heating for 5 minutes at 50° C., 0.67 g of 1-(2-chloroethyl)piperidine hydrochloride is added to the reaction medium, and the solution is then heated at 80° C. for 15 hours. The reaction medium is poured into 100 cm³ of water; the aqueous phase is extracted with dichloromethane, which is dried over magnesium sulfate and concentrated to dryness under reduced pressure (2.7 kPa). The resulting brown oil (0.8 g) is purified by flash chromatography on silica under an argon pressure (50 kPa) [eluent: dichloro-methane/methanol (95/5 by volume)]. After concentration of the fractions to dryness under reduced pressure (2.7 kPa), 0.3 g of 3-(cyclohex-2-en-1-yloxy)-5-methyl-4-phenyl-1-(2-piperidin-1-ylethyl)-1H-pyrazole is obtained in the form of a yellow oil [TLC: eluent: dichloromethane/methanol (90/10 by volume), Rf=0.27]. Mass spectrum (CI): m/z 366 (MH⁺).

The 3-(cyclohex-2-enyloxy)-5-methyl-4-phenyl-1H-pyrazole can be prepared in the following way:

0.54 cm³ of 5N sodium hydroxide is added gradually, at a temperature in the region of 20° C., to a solution, with stirring, of 0.8 g of 1-[3-(cyclohex-2-enyloxy)-5-methyl-4-phenylpyrazol-1-yl]ethanone in a mixture of 20 cm³ of methanol and 20 cm³ of tetrahydrofuran. After stirring for 6 hours at a temperature in the region of 20° C., the reaction mixture is concentrated to dryness under reduced pressure (2.7 kPa), and the residue is taken up with 100 cm³ of dichloromethane and 10 cm³ of water; the organic phase is separated by settling out, dried over magnesium sulfate, filtered and concentrated to dryness under reduced pressure (2.7 kPa) to give 0.46 g of 3-(cyclohex-2-enyloxy)-5-methyl-4-phenyl-1H-pyrazole in the form of a yellow gum [TLC: eluent: cyclohexane/ethyl acetate (70/30 by volume), Rf=0.19]. Mass spectrum (EI): m/z (254 M⁺·), m/z 174 [(M−C₆H₈)⁺·].

The 1-[3-(cyclohex-2-enyloxy)-5-methyl-4-phenylpyrazol-1-yl]ethanone can be prepared in the following way:

2 g of 1-(3-hydroxy-5-methyl-4-phenylpyrazol-1-yl)ethanone, 1.3 g of potassium carbonate and 1.06 cm³ of 3-bromocyclohexene are added to 100 cm³ of methyl ethyl ketone at 20° C. with stirring. After heating at the reflux of the solvent for 5 hours, the reaction medium is cooled to a temperature in the region of 20° C. and then concentrated to dryness under reduced pressure (2.7 kPa). The residue is taken up with 100 cm³ of water and 100 cm³ of dichloromethane; the organic phase is separated by settling out, dried over magnesium sulfate, filtered and concentrated to dryness under reduced pressure (2.7 kPa). The resulting brown oil (2.7 g) is purified by flash chromatography on silica [eluent: cyclohexane/ethyl acetate (70/30 by volume)]. After concentration of the fractions to dryness under reduced pressure (2.7 kPa), 0.8 g of 1-[3-(cyclohex-2-enyloxy)-5-methyl-4-phenylpyrazol-1-yl] ethanone is obtained in the form of a yellow oil [TLC: eluent: cyclohexane/ethyl acetate (70/30 by volume), Rf=0.74]. Mass spectrum (EI): m/z 296 (M⁺·), m/z 174 [(216−C₂H₂O)⁺·].

The 1-(3-hydroxy-5-methyl-4-phenylpyrazol-1-yl)ethanone can be prepared in the following way:

0.85 cm³ of acetic anhydride is added to a solution of 1.74 g of 5-methyl-4-phenyl-1H-pyrazol-3-ol (CAS No.: 64754-67-2) in 17 cm³ of pyridine with stirring and which has been brought to 100° C. After heating at this temperature for 30 minutes, the reaction medium is cooled to a temperature in the region of 20° C. and is then poured into 100 cm³ of a mixture of ice and water. The solution is extracted with 2 times 50 cm³ of ethyl acetate; the organic phases are pooled, washed with twice 100 cm³ of water, dried over magnesium sulfate, filtered and evaporated to dryness under reduced pressure (2.7 kPa); 2 g of 1-(3-hydroxy-5-methyl-4-phenylpyrazol-1-yl)ethanone are obtained in the form of an orange-yellow oil. Mass spectrum (EI): m/z 216 (M⁺·), m/z 174 [(M−C₂H₂O)⁺·].

EXAMPLE 29

4-(3-Aminophenyl)-1-(2-dimethylaminoethyl)-1H-pyrazol-3-ol trihydrochloride

A solution of 500 mg of {2-[3-benzyloxy-4-(3-nitrophenyl)pyrazol-1-yl]ethyl}dimethylamine in 15 cm³ of methanol is added to a mixture of 860 mg of ammonium formate and of 50 mg of palladium hydroxide at 10% in 15 cm³ of methanol, and this mixture is heated for 3 hours at the reflux of the solvent with stirring. The reaction medium is then filtered over supercel, and the filtrate is evaporated under reduced pressure (2.7 kPa). The reaction crude is taken up with dichloromethane and the resulting mixture is washed successively with a saturated aqueous hydrogen carbonate solution, water and a saturated aqueous sodium chloride solution. The aqueous phases are pooled and evaporated under reduced pressure (2.7 kPa). The residue obtained is taken up with methanol and the suspension is filtered. After evaporation of the filtrate under reduced pressure (2.7 kPa), the residual solid is triturated in 3N hydrochloric ethanol. The precipitate formed is filtered off and dried under vacuum (2.7 kPa) to give 110 mg of 4-(3-aminophenyl)-1-(2-dimethylaminoethyl)-1H-pyrazol-3-ol trihydrochloride in the form of a beige solid.

IR spectrum (KBr): 3432; 2839; 2689; 2586; 1627; 1603; 1523; 1462; 1178; 786 and 696 cm⁻¹.

¹H NMR spectrum (300 MHz, (CD₃)₂SO d6, δ in ppm): 2.80 (s: 6H); 3.45 (t, J=6.5 Hz: 2H); 4.41 (t, J=6.5 Hz: 2H); 7.10 (broad d, J=8 Hz: 1H); 7.42 (t, J=8 Hz: 1H); 7.58 (broad d, J=8 Hz: 1H); 7.67 (broad s: 1H); 8.10 (s: 1H); from 9.50 to 10.40 (very broad unresolved peak: 1H); 10.50 (unresolved peak: 1H); 10.73 (unresolved peak: 1H).

The {2-[3-benzyloxy-4-(3-nitrophenyl)pyrazol-1-yl]ethyl}dimethylamine can be prepared in the following way:

A solution of 3.45 g of 3-benzyloxy-4-(3-nitrophenyl)-1H-pyrazole in 50 cm³ of dimethylformamide is added to a suspension of 1.13 g of sodium hydride (at 75% in liquid petroleum jelly) in 50 cm³ of dimethylformamide under an argon atmosphere and with stirring. After heating at 50° C. for 30 minutes, the mixture is stirred for 1 h at a temperature in the region of 20° C. and is then cooled in an ice bath and a solution of 4.5 g of (2-bromoethyl)dimethylamine hydrobromide in 50 cm³ of dimethylformamide is added. The reaction mixture is stirred for 15 h at a temperature in the region of 20° C., and 1.5 h at 50° C., and is then cooled to a temperature in the region of 20° C. and poured into 400 cm³ of water. The aqueous phase is extracted twice with ethyl acetate. The organic phases are pooled, washed successively with water and a saturated aqueous sodium chloride solution, dried over magnesium sulfate, filtered and evaporated under reduced pressure (2.7 kPa) to give an orange-colored oil which is purified by flash chromatography on silica under an argon pressure (50 kPa) [eluent: ethyl acetate, then ethyl acetate/methanol (90/10 by volume)]. After concentration of the fractions under reduced pressure, 1.7 g of {2-[3-benzyloxy-4-(3-nitrophenyl)pyrazol-1-yl]ethyl}dimethylamine are obtained in the form of an orange-colored oil. Mass spectrum (EI): m/z 366 (M⁺·), m/z 91 (C₇H₇⁺), m/z 71 (C₄H₉N⁺·), m/z 58 (C₃H₈N⁺).

The 3-benzyloxy-4-(3-nitrophenyl)-1H-pyrazole can be prepared in the following way:

2.75 g of potassium carbonate and 2.2 cm³ of benzyl bromide are added to a suspension of 4.1 g of 1-[3-hydroxy-4-(3-nitrophenyl)pyrazol-1-yl]ethanone in 50 cm³ of methyl ethyl ketone with stirring. The mixture is heated at the reflux of the solvent for 2.5 h, cooled to a temperature in the region of 20° C., and filtered. The filtrate is evaporated under reduced pressure (2.7 kPa) and the residue is taken up with 25 cm³ of tetrahydrofuran and 25 cm³ of methanol and 1 cm³ of 10N sodium hydroxide is added thereto. After stirring for 30 min at a temperature in the region of 20° C., the reaction medium is evaporated under reduced pressure (2.7 kPa). The reaction crude is taken up in dichloromethane. The organic phase is washed successively with water and a saturated aqueous sodium chloride solution, dried over magnesium sulfate, filtered and evaporated under reduced pressure (2.7 kPa) to give an oil which is triturated in diisopropyl ether. The precipitate formed is filtered and dried under vacuum (2.7 kPa) to give 3.47 g of 3-benzyloxy-4-(3-nitrophenyl)-1H-pyrazole in the form of a yellow solid.

$^1$H NMR spectrum (300 MHz, $(CD_3)_2SO$ d6, δ in ppm): 5.40 (s: 2H); 7.36 (broad t, J=7.5 Hz: 1H); 7.44 (broad t, J=7.5 Hz: 2H); 7.55 (broad d, J=7.5 Hz: 2H); 7.64 (t, J=8 Hz: 1H); 8.00 (dd, J=8 and 2 Hz: 1H); 8.13 (broad d, J=8 Hz: 1H); 8.33 (s: 1H); 8.62 (t, J=2 Hz: 1H); from 12.00 to 12.80 (very broad unresolved peak: 1H).

The 1-[3-hydroxy-4-(3-nitrophenyl)pyrazol-1-yl]ethanone can be prepared in the following way:

A solution of 3.8 g of dimethylammonium 4-(3-nitrophenyl)-1H-pyrazol-3-olate in 40 cm³ of pyridine, under an argon atmosphere and with stirring, is heated to 90° C. and 1.5 cm³ of acetic anhydride are then added dropwise. After heating for 1 h at 90° C., the reaction medium is cooled to a temperature in the region of 20° C. and is poured into 100 cm³ of ice-cold water. The precipitate formed is filtered, washed 3 times with water and dried under vacuum (2.7 kPa) to give 4.33 g of a solid which is used again in reaction with 40 cm³ of pyridine and 0.39 cm³ of acetic anhydride according to the protocol stated above. 4.1 g of 1-[3-hydroxy-4-(3-nitrophenyl)pyrazol-1-yl]ethanone are obtained in the form of a pale yellow solid. IR spectrum (KBr): 3118; 3082; 2669; 1730; 1604; 1520; 1390; 1349; 1256; 1223; 1101; 748 and 719 cm$^{-1}$.

The dimethylammonium 4-(3-nitrophenyl)-1H-pyrazol-3-olate can be prepared in the following way:

A solution, with stirring, of 9.3 g of benzyl ester of 3-dimethylamino-2-(3-nitrophenyl)acrylic acid and 1.4 cm³ of hydrazine monohydrate in 100 cm³ of ethanol is heated for 3 h at the reflux of the solvent, and then cooled in an ice bath. The solid formed is filtered off, washed with water, and dried under vacuum (2.7 kPa) to give 4.44 g of dimethylammonium 4-(3-nitrophenyl)-1H-pyrazol-3-olate in the form of an orange-colored solid.

IR spectrum (KBr): 3346; 3199; 3071; 2855; 2685; 2386; 1583; 1538; 1469; 1350; 934; 766; 747 and 681 cm$^{-1}$.

The benzyl ester of 3-dimethylamino-2-(3-nitrophenyl)acrylic acid can be prepared in the following way:

11.5 cm³ of C-tert-butoxy-N,N,N',N'-tetramethylmethanediamine is added to a solution of 10 g of benzyl ester of 2-(3-nitrophenyl)acrylic acid in 100 cm³ of tetrahydrofuran and the mixture is heated for 15 h at the reflux of the solvent. After cooling to a temperature in the region of 20° C., the reaction mixture is evaporated to dryness under reduced pressure (2.7 kPa). The residue is taken up with ethyl acetate and the organic solution is washed 3 times with water and then with a saturated aqueous sodium chloride solution, dried over magnesium sulfate, filtered and evaporated under reduced pressure (2.7 kPa). The brown oil obtained is purified by flash chromatography on silica under an argon pressure (50 kPa) [eluent: cyclohexane/ethyl acetate (70/30 by volume)]. After concentration of the fractions under reduced pressure, 9.3 g of benzyl ester of 3-dimethylamino-2-(3-nitrophenyl)acrylic acid are obtained in the form of an orange-colored oil. Mass spectrum (EI): m/z 326 (M$^{+\cdot}$), m/z 235 [(M−C$_7$H$_7$)$^+$], m/z 91 (C$_7$H$_7^+$).

EXAMPLE 30

N-{3-[3-Hydroxy-1-(2-dimethylaminoethyl)-1H-pyrazol-4-yl]phenyl}acetamide dihydrochloride 1.8 cm³ of 3N hydrochloric diethyl ether are added to a solution of 400 mg of N-{3-[3-benzyloxy-1-(2-dimethylaminoethyl)-1H-pyrazol-4-yl]phenyl}acetamide in 20 cm³ of ethanol. After stirring for 15 min at a temperature in the region of 20° C., the solution is evaporated to dryness under reduced pressure (2.7 kPa). The residue is taken up in 20 cm³ of ethanol. The solution obtained is introduced into an autoclave, and 50 mg of palladium-on-charcoal at 10% are added, and it is then placed under hydrogen (5 bar). After stirring for 2 h at a temperature in the region of 20° C., the reaction medium is filtered over supercel and the filtrate is evaporated. The yellow oil obtained (440 mg) is dissolved in 20 cm³ of ethanol and used again in reaction with 50 mg of palladium-on-charcoal at 10%, under hydrogen (5 bar), at 40° C. and with stirring for 4 h. The reaction medium is then filtered over supercel, the filtrate is evaporated, and the residue is triturated in diisopropyl ether. The precipitate formed is filtered, and dried under vacuum (2.7 kPa) to give 289 mg of N-{3-[3-hydroxy-1-(2-dimethylaminoethyl)-1H-pyrazol-4-yl]phenyl}acetamide dihydrochloride in the form of a pale yellow solid.

IR spectrum (KBr): 3242; 3130; 2967; 2573; 2464; 1678; 1614; 1588; 1525; 1462; 1258; 1187; 787 and 690 cm$^{-1}$.

$^1$H NMR spectrum (300 MHz, $(CD_3)_2SO$ d6, δ in ppm): 2.05 (s: 3H); 2.80 (broad s: 6H); 3.48 (broad t, J=6.5 Hz: 2H); 4.35 (broad t, J=6.5 Hz: 2H); 7.23 (t, J=7.5 Hz: 1H); 7.31 (broad d, J=7.5 Hz: 1H); 7.38 (broad d, J=7.5 Hz: 1H); 7.89 (broad s: 1H); 7.95 (s: 1H); from 9.60 to 9.85 (broad unresolved peak: 1H); 9.91 (broad s: 1H); 10.45 (broad s: 1H).

The N-{3-[3-benzyloxy-1-(2-dimethylaminoethyl)-1H-pyrazol-4-yl]phenyl}acetamide can be prepared in the following way:

0.116 cm³ of acetyl chloride is added to a solution of 500 mg of 3-[3-benzyloxy-1-(2-dimethylaminoethyl)-1H-pyrazol-4-yl]phenylamine and 0.418 cm³ of triethylamine in 20 cm³ of dichloromethane under an argon atmosphere and with stirring, while maintaining the temperature of the medium at 5° C. After stirring for 15 h at a temperature in the region of 20° C., a further 0.1 cm³ of triethylamine and 0.1 cm³ of acetyl chloride are added to the reaction mixture and the reaction is continued for 2 h. The reaction medium is then washed successively twice with water and a saturated aqueous sodium chloride solution, dried over magnesium sulfate, filtered and evaporated under reduced pressure (2.7 kPa) to give 540 mg of N-{3-[3-benzyloxy-1-(2-dimethylaminoethyl)-1H-pyrazol-4-yl]phenyl}acetamide in the form of a yellow oil.

IR spectrum (CCl$_4$): 3444; 3305; 2945; 2822; 2773; 1670; 1614; 1588; 1549; 1502; 1452; 1423; 1357; 1177; 1018; 695 and 537 cm$^{-1}$.

The 3-[3-benzyloxy-1-(2-dimethylaminoethyl)-1H-pyrazol-4-yl]phenylamine can be prepared in the following way:

A solution of 1.1 g of {2-[3-benzyloxy-4-(3-nitrophenyl)pyrazol-1-yl]ethyl}dimethylamine in 15 cm³ of ethanol is added to a mixture, with stirring, of 840 mg of iron powder, 200 mg of ammonium chloride in 15 cm³ of ethanol and 15 cm³ of water, heated at the reflux of the solvent. The stirring is continued for 3 h at the reflux of the solvent and then for 15 h at a temperature in the region of 20° C. The reaction mixture is filtered and the filtrate is evaporated. The residue is taken up with a mixture of ethyl acetate, water and 1N sodium hydroxide. The organic phase is separated by settling out, washed successively with water and a saturated aqueous sodium chloride solution, dried over magnesium sulfate, filtered and evaporated under reduced pressure (2.7 kPa) to give 1 g of 3-[3-benzyloxy-1-(2-dimethylaminoethyl)-1H-pyrazol-4-yl]phenylamine in the form of an orange-colored oil. Mass spectrum (EI): m/z 336 (M$^{+\cdot}$), m/z 265 [(M–C$_7$H$_7$)$^+$], m/z 91 (C$_7$H$_7$$^+$), m/z 71 (C$_4$H$_9$N$^{+\cdot}$), m/z 58 (C$_3$H$_8$N$^+$).

EXAMPLE 31

4-(4-Aminophenyl)-1-(2-dimethylaminoethyl)-1H-pyrazol-3-ol dihydrochloride 1.2 cm$^3$ of 3N hydrochloric diethyl ether are added to a solution of 250 mg of {2-[3-benzyloxy-4-(4-nitro-phenyl)pyrazol-1-yl]ethyl}dimethylamine in 20 cm$^3$ of ethanol. After stirring for 20 minutes at a temperature in the region of 20° C., the solution is evaporated to dryness under reduced pressure (2.7 kPa). The residue is taken up with 20 cm$^3$ of ethanol. The solution obtained is introduced into an autoclave and 36 mg of palladium-on-charcoal at 10% are added, and it is then placed under hydrogen (7 bar). After stirring for 5 h at 40° C., the reaction medium is filtered over supercel, the filtrate is evaporated and the residue is triturated in diisopropyl ether. The precipitate formed is filtered, and dried under vacuum (2.7 kPa) to give 169 mg of 4-(4-aminophenyl)-1-(2-dimethylaminoethyl)-1H-pyrazol-3-ol dihydrochloride in the form of a yellow solid.

IR spectrum (KBr): 3372; 3296; 3205; 3025; 1627; 1592; 1522; 1514; 1451; 1280; 1177; 828; 612 and 525 cm$^{-1}$.

$^1$H NMR spectrum (300 MHz, (CD$_3$)$_2$SO d6, δ in ppm): 2.75 (s: 6H); 3.42 (mt: 2H); 4.27 (t, J=6 Hz: 2H); from 4.70 to 5.30 (broad unresolved peak: 2H); 6.55 (d, J=8.5 Hz: 2H); 7.31 (d, J=8.5 Hz: 2H); 7.75 (s: 1H); 10.08 (unresolved peak: 1H).

The {2-[3-benzyloxy-4-(4-nitrophenyl)pyrazol-1-yl]-ethyl}dimethylamine can be prepared in the following way:

A solution of 3 g of 3-benzyloxy-4-(4-nitrophenyl)-1H-pyrazole in 50 cm$^3$ of dimethylformamide is added to a suspension of 980 mg of sodium hydride (at 75% in liquid petroleum jelly) in 50 cm$^3$ of dimethylformamide under an argon atmosphere and with stirring. After heating for 30 min at 50° C., the mixture is stirred for 1 h at a temperature in the region of 20° C. and is then cooled in an ice bath and a solution of 4.7 g of (2-bromoethyl)dimethylamine hydrobromide in 50 cm$^3$ of dimethylformamide is added. The reaction medium is stirred for 15 h at a temperature in the region of 20° C. and is then poured into 400 cm$^3$ of water. The aqueous phase is extracted twice with ethyl acetate. The organic phases are pooled, washed successively with water twice and a saturated aqueous sodium chloride solution, dried over magnesium sulfate, filtered and evaporated under reduced pressure (2.7 kPa) to give an orange-colored oil which is purified by flash chromatography on silica under an argon pressure (50 kPa) [eluent: ethyl acetate, then ethyl acetate/methanol (90/10 by volume)]. After concentration of the fractions under reduced pressure, 1.2 g {2-[3-benzyloxy-4-(4-nitrophenyl)pyrazol-1-yl]-ethyl}dimethylamine are obtained in the form of a brown oil. Mass spectrum (EI): m/z 366 (M$^{+\cdot}$), m/z 91 (C$_7$H$_7$$^+$), m/z 71 (C$_4$H$_9$N$^{+\cdot}$), m/z 58 (C$_3$H$_8$N$^+$).

The 3-benzyloxy-4-(4-nitrophenyl)-1H-pyrazole can be prepared in the following way:

3 g of potassium carbonate and 2.2 cm$^3$ of benzyl bromide are added to a suspension of 4.5 g of 1-[3-hydroxy-4-(4-nitrophenyl)pyrazol-1-yl]ethanone in 50 cm$^3$ of methyl ethyl ketone with stirring. The mixture is heated at the reflux of the solvent for 2.5 h, cooled to a temperature in the region of 20° C., and filtered. The filtrate is evaporated under reduced pressure (2.7 kPa) and the residue is taken up with 25 cm$^3$ of tetrahydrofuran and 25 cm$^3$ of methanol, and 2 cm$^3$ of 10N sodium hydroxide are then added. After stirring for 30 min at a temperature in the region of 20° C., the reaction medium is evaporated under reduced pressure (2.7 kPa). The reaction crude is taken up in dichloromethane. The organic phase is washed successively with water and a saturated aqueous sodium chloride solution, dried over magnesium sulfate, filtered and evaporated under reduced pressure (2.7 kPa) to give an oil which is triturated in diisopropyl ether. The precipitate formed is filtered and dried under vacuum (2.7 kPa) to give 3 g of 3-benzyloxy-4-(4-nitrophenyl)-1H-pyrazole in the form of an ochre solid.

$^1$H NMR spectrum (300 MHz, (CD$_3$)$_2$SO d6, δ in ppm): 5.41 (s: 2H); from 7.30 to 7.60 (mt: 5H); 7.97 (d, J=9 Hz: 2H); 8.23 (d, J=9 Hz: 2H); 8.36 (s: 1H); 12.49 (unresolved peak: 1H).

The 1-[3-hydroxy-4-(4-nitrophenyl)pyrazol-1-yl]-ethanone can be prepared in the following way:

A solution of 4.85 g of dimethylammonium 4-(4-nitrophenyl)-1H-pyrazol-3-olate in 40 cm$^3$ of pyridine, under an argon atmosphere and with stirring, is heated to 90° C. and 2 cm$^3$ of acetic anhydride are then added dropwise. After heating for 1 h at 90° C., the reaction medium is cooled to a temperature in the region of 20° C. and is poured into 100 cm$^3$ of ice-cold water. The precipitate formed is filtered, washed three times with water, and dried under vacuum (2.7 kPa) to give 4.5 g of 1-[3-hydroxy-4-(4-nitrophenyl)pyrazol-1-yl]ethanone in the form of a yellow solid.

IR spectrum (KBr): 3370; 3128; 2980; 2587; 1721; 1615; 1600; 1509; 1341; 1224; 1111; 855; 757 and 643 cm$^{-1}$.

The dimethylammonium 4-(4-nitrophenyl)-1H-pyrazol-3-olate can be prepared in the following way:

A solution, with stirring, of 10.7 g of methyl ester of 3-dimethylamino-2-(4-nitrophenyl)acrylic acid and of 2.1 cm$^3$ of hydrazine monohydrate in 120 cm$^3$ of ethanol is heated for 3 h at the reflux of the solvent, and cooled in an ice bath. The solid formed is filtered, rinsed with diisopropyl ether, and dried under vacuum (2.7 kPa) to give 5 g of dimethylammonium 4-(4-nitro-phenyl)-1H-pyrazol-3-olate in the form of an orange-colored solid.

IR spectrum (KBr): 3188; 3089; 2909; 2728; 2423; 1603; 1589; 1567; 1538; 1501; 1345; 1330; 1212; 1112; 923; 880; 761 and 581 cm$^{-1}$.

The methyl ester of 3-dimethylamino-2-(4-nitrophenyl)acrylic acid can be prepared in the following way:

16.6 cm$^3$ of C-tert-butoxy-N,N,N',N'-tetramethylmethanediamine are added to a solution of 10.5 g of methyl ester of 2-(4-nitrophenyl)acrylic acid in 100 cm$^3$ of tetrahydrofuran, and the mixture is heated for 2.5 h at the reflux of the solvent. After stirring for 15 h at a temperature in the region of 20° C., the reaction mixture is evaporated to dryness under reduced pressure (2.7 kPa). The residue is taken up with ethyl acetate and the organic solution is washed with three times water, and then dried over magnesium sulfate, filtered and evaporated under reduced pressure (2.7 kPa) to give 10.7 g of methyl ester of 3-dimethylamino-2-(4-nitrophenyl)acrylic acid in the form of a brown oil.

IR spectrum (CCl$_4$): 2949; 1693; 1603; 1519; 1433; 1344; 1219; 1095; 1048 and 855 cm$^{-1}$.

EXAMPLE 32

1-(2-Dimethylaminoethyl)-4-(4'-fluorobiphenyl-3-yl)-1H-pyrazol-3-ol dihydrochloride 1.2 cm$^3$ of 3N hydrochloric diethyl ether are added to a solution of 300 mg of {2-[3-benzyloxy-4-(4'-fluoro-biphenyl-3-yl)pyrazol-1-yl]ethyl}dimethylamine in 20 cm$^3$ of ethanol. After stirring for 30 min at a temperature in the region of 20° C., the solution is evaporated to dryness under reduced pressure (2.7 kPa). The residue is taken up with 20 cm$^3$ of ethanol. The solution obtained is introduced into an autoclave and 14 mg of palladium-on-charcoal at 10% are added, and it is then placed under hydrogen (7 bar). After stirring for 5 h at 30° C., the reaction medium is filtered over supercel, and the filtrate is evaporated. Diisopropyl ether is added to the residue, resulting in a suspension, which is heated at the reflux of the solvent and filtered under hot conditions. The resulting solid is dried under vacuum (2.7 kPa) to give 84 mg of 1-(2-dimethylaminoethyl)-4-(4'-fluorobiphenyl-3-yl)-1H-pyrazol-3-ol dihydrochloride in the form of a white powder.

IR spectrum (KBr): 3049; 2962; 2682; 2355; 1608; 1514; 1460; 1221; 1184; 1162; 843; 804; 703 and 560 cm$^{-1}$.

$^1$H NMR spectrum (300 MHz, (CD$_3$)$_2$SO d6, δ in ppm): 2.76 (broad s: 6H); 3.45 (mt: 2H); 4.32 (broad t, J=6 Hz: 2H); 7.32 (t, J=8.5 Hz: 2H); from 7.35 to 7.50 (mt: 2H); 7.66 (mt: 1H); 7.70 (dd, J=9 and 6 Hz: 2H); 7.90 (broad s: 1H); 8.14 (s: 1H); 9.76 (unresolved peak: 1H); 10.50 (broad s: 1H).

The {2-[3-benzyloxy-4-(4'-fluorobiphenyl-3-yl)pyrazol-1-yl]ethyl}dimethylamine can be prepared in the following way:

860 mg of 4-fluorophenylboronic acid, 1.3 g of potassium phosphate and 330 mg of bis(triphenyl-phosphine)palladium chloride are added to a stirred solution of 620 mg of {2-[3-benzyloxy-4-(3-bromophenyl)pyrazol-1-yl]ethyl}dimethylamine in 25 cm$^3$ of toluene under an argon atmosphere. After heating at the reflux of the solvent for 15 h, the reaction medium is cooled to a temperature in the region of 20° C., ethyl acetate and water are added, and the mixture is filtered over supercel. The filtrate is separated by settling out and the organic phase is then washed successively with 0.5N sodium hydroxide, water and a saturated aqueous sodium chloride solution; it is dried over magnesium sulfate, filtered and evaporated under reduced pressure (2.7 kPa). The brown oil obtained (1.3 g) is purified by flash chromatography on alumina CRB1 under an argon pressure (50 kPa) [eluent: cyclohexane/ethyl acetate (80/20 by volume)]. After concentration of the fractions under reduced pressure, 300 mg of {2-[3-benzyloxy-4-(4'-fluorobiphenyl-3-yl)-pyrazol-1-yl]ethyl}dimethylamine are obtained in the form of a yellow oil.

IR spectrum (CCl$_4$): 2823; 2773; 1610; 1571; 1515; 1462; 1358; 1235; 1158; 1014; 837; 696 and 559 cm$^{-1}$.

The {2-[3-benzyloxy-4-(3-bromophenyl)pyrazol-1-yl]ethyl}dimethylamine can be prepared in the following way:

A solution of 7.67 g of 3-benzyloxy-4-(3-bromophenyl)-1H-pyrazole in 70 cm$^3$ of dimethylformamide is added to a suspension of 2.25 g of sodium hydride (at 75% in liquid petroleum jelly) in 70 cm$^3$ of dimethylformamide under an argon atmosphere and with stirring. After heating for 30 min at 50° C., the mixture is stirred for 1 h at a temperature in the region of 20° C. and is then cooled in an ice bath and a solution of 10.85 g of (2-bromoethyl)dimethylamine hydrobromide in 100 cm$^3$ of dimethylformamide is added. The reaction medium is stirred for 15 h at a temperature in the region of 20° C., and for 3 h at 50° C., and is then cooled to a temperature in the region of 20° C. and poured into 500 cm$^3$ of water. The aqueous phase is extracted twice with ethyl acetate. The organic phases are pooled, washed successively with water twice and a saturated aqueous sodium chloride solution, dried over magnesium sulfate, filtered and evaporated under reduced pressure (2.7 kPa) to give an orange-colored oil which is purified by flash chromatography on silica under an argon pressure (50 kPa) [eluent: ethyl acetate, ethyl acetate/methanol (90/10 by volume)]. After concentration of the fractions under reduced pressure, 2.4 g of {2-[3-benzyloxy-4-(3-bromophenyl)pyrazol-1-yl]ethyl}dimethylamine are obtained in the form of an orange-colored oil.

Mass spectrum (CI): m/z 400 (MH$^+$), m/z 322 [(M−Br+2H)$^+$].

The 3-benzyloxy-4-(3-bromophenyl)-1H-pyrazole can be prepared in the following way:

2.6 g of potassium carbonate and 2.05 cm$^3$ of benzyl bromide are added to a suspension of 4.4 g of 1-[3-benzyloxy-4-(3-bromophenyl)pyrazol-1-yl]ethanone in 50 cm$^3$ of methyl ethyl ketone with stirring. The mixture is heated at the reflux of the solvent for 2.5 h, cooled to a temperature in the region of 20° C., and filtered. The filtrate is evaporated under reduced pressure (2.7 kPa), and the residue is taken up with 25 cm$^3$ of tetrahydrofuran and 25 cm$^3$ of methanol, and 1 cm$^3$ of 10N sodium hydroxide is then added. After stirring for 30 min at a temperature in the region of 20° C., the reaction medium is evaporated under reduced pressure (2.7 kPa). The reaction crude is taken up in dichloromethane. The organic phase is washed successively with water twice and a saturated aqueous sodium chloride solution, dried over magnesium sulfate, filtered and evaporated under reduced pressure (2.7 kPa) to give an oil which is purified by flash chromatography on silica under an argon pressure (50 kPa) [eluent: cyclohexane/ethyl acetate (80/20 by volume)]. After concentration of the fractions under reduced pressure, 3.3 g of 3-benzyloxy-4-(3-bromophenyl)-1H-pyrazole are obtained in the form of a cream solid.

$^1$H NMR spectrum (300 MHz, (CD$_3$)$_2$SO d6, δ in ppm): 5.35 (s: 2H); from 7.25 to 7.40 (mt: 3H); 7.42 (broad t, J=7.5 Hz: 2H); 7.51 (broad d, J=7.5 Hz: 2H); 7.71 (dt, J=7.5 and 2 Hz: 1H); 7.93 (broad s: 1H); 8.18 (s: 1H); 12.25 (unresolved peak: 1H).

The 1-[4-(3-bromophenyl)-3-hydroxypyrazol-1-yl]ethanone can be prepared in the following way:

A solution of 4.3 g of 4-(3-bromophenyl)-1H-pyrazol-3-ol in 40 cm$^3$ of pyridine, under an argon atmosphere and with stirring, is heated to 90° C. and 1.6 cm$^3$ of acetic anhydride are then added dropwise. After heating for 1 h at 90° C., the reaction medium is cooled to a temperature in the region of 20° C. and is poured into 100 cm$^3$ of ice-cold water. The precipitate formed is filtered, washed three times with water and dried under vacuum (2.7 kPa) to give 4.42 g of 1-[4-(3-bromophenyl)-3-hydroxypyrazol-1-yl]ethanone in the form of a cream solid.

IR spectrum (KBr): 3125; 2687; 2577; 1729; 1616; 1529; 1391; 1318; 1256; 1219; 945; 791; 715 and 629 cm$^{-1}$.

The 4-(3-bromophenyl)-1H-pyrazol-3-ol can be prepared in the following way:

A solution, with stirring, of 12.22 g of methyl ester of 2-(3-bromophenyl)-3-dimethylaminoacrylic acid and of 2.1 cm$^3$ of hydrazine monohydrate in 100 cm$^3$ of ethanol is heated at the reflux of the solvent for 3 h. The reaction mixture is evaporated to dryness under reduced pressure (2.7 kPa) and the residue is triturated in diisopropyl ether. The solid formed is filtered and is dried under vacuum (2.7 kPa) to give 5.1 g of dimethylammonium 4-(3-bromophenyl)-1H-pyrazol-3-olate in the form of a cream solid. The filtrate is evaporated under reduced pressure (2.7 kPa), the residue is triturated in diisopropyl ether, and the solid formed is filtered and dried under vacuum (2.7 kPa), resulting in 4.3 g of 4-(3-bromophenyl)-1H-pyrazol-3-ol in the form of a cream solid.

IR spectrum (KBr): 3099; 2768; 2668; 1620; 1590; 1410; 1241; 1081; 787; 712 and 689 cm$^{-1}$.

The methyl ester of 2-(3-bromophenyl)-3-dimethylaminoacrylic acid can be prepared in the following way:

14.4 cm$^3$ of C-tert-butoxy-N,N,N',N'-tetramethylmethanediamine are added to a solution of 10.5 g of methyl ester of 2-(3-bromophenyl)acrylic acid in 100 cm$^3$ of tetrahydrofuran and the mixture is heated at the reflux of the solvent for 2.5 h. After stirring for 15 h at a temperature in the region of 20° C., the reaction mixture is evaporated to dryness under reduced pressure (2.7 kPa). The residue is taken up with ethyl acetate, and the organic solution is washed with 3 times water, and then dried over magnesium sulfate, filtered and evaporated under reduced pressure (2.7 kPa) to give 12.22 g of methyl ester of 2-(3-bromophenyl)-3-dimethylaminoacrylic acid in the form of a yellow oil.

IR spectrum (CCl$_4$): 2947; 2813; 1691; 1603; 1432; 1285; 1221; 1098 and 694 cm$^{-1}$.

EXAMPLE 33

4-Biphenyl-3-yl-1-(2-dimethylaminoethyl)-1H-pyrazol-3-ol dihydrochloride 1 cm$^3$ of 3N hydrochloric diethyl ether is added to a solution of 121 mg of {2-[3-benzyloxy-4-biphenyl-3-ylpyrazol-1-yl]ethyl}dimethylamine in 20 cm$^3$ of ethanol. After stirring for 30 min at a temperature in the region of 20° C., the solution is evaporated to dryness under reduced pressure (2.7 kPa). The residue is taken up with 20 cm$^3$ of ethanol. The solution obtained is introduced into an autoclave, 11 mg of palladium-on-charcoal at 10% are added, and it is then placed under hydrogen (7 bar). After stirring for 5 h at 30° C., the reaction medium is filtered over supercel, and the filtrate is evaporated. Diisopropyl ether is added to the residue, resulting in a suspension which is heated at the reflux of the solvent and filtered under hot conditions. The resulting solid is dried under vacuum (2.7 kPa) to give 69 mg of 4-biphenyl-3-yl-1-(2-dimethylaminoethyl)-1H-pyrazol-3-ol dihydrochloride in the form of a white powder.

IR spectrum (KBr): 3054; 2959; 2685; 2299; 1606; 1522; 1457; 1298; 1182; 760; 698 and 671 cm$^{-1}$.

$^1$H NMR spectrum (300 MHz, (CD$_3$)$_2$SO d6, δ in ppm): 2.79 (unresolved peak: 6H); 3.43 (unresolved peak: 2H); 4.31 (unresolved peak: 2H); from 7.25 to 7.55 (mt: 5H); 7.68 (mt: 3H); 7.94 (broad s: 1H); 8.15 (s: 1H); from 9.45 to 9.65 (broad unresolved peak: 1H); 10.49 (broad s: 1H).

The {2-[3-benzyloxy-4-biphenyl-3-ylpyrazol-1-yl]ethyl}-dimethylamine can be prepared in the following way:

503 mg of phenylboronic acid, 891 mg of potassium phosphate and 217 mg of bis(triphenylphosphine)-palladium chloride are added to a stirred solution of 550 mg of {2-[3-benzyloxy-4-(3-bromophenyl)pyrazol-1-yl]ethyl}dimethylamine in 25 cm$^3$ of toluene under an argon atmosphere. After heating at the reflux of the solvent for 15 h, 168 mg of phenylboronic acid, 297 mg of potassium phosphate and 148 mg of bis(triphenyl-phosphine)palladium chloride are added to the reaction medium and the reaction is continued at the same temperature for 15 h. The mixture is then cooled to a temperature in the region of 20° C., ethyl acetate and water are added, and it is filtered over supercel. The filtrate is separated by settling out, and the organic phase is then washed successively with 0.5N sodium hydroxide, water and a saturated aqueous sodium chloride solution; it is dried over magnesium sulfate, filtered and evaporated under reduced pressure (2.7 kPa). The brown oil obtained (1.2 g) is purified by flash chromatography on alumina CTB1 under an argon pressure (50 kPa) [eluent: cyclohexane/ethyl acetate (80/20 by volume)]. After concentration of the fractions under reduced pressure, 300 mg of an orange-colored oil are obtained, which is again used in a reaction for 15 h with 25 cm$^3$ of toluene, 503 mg of phenylboronic acid, 891 mg of potassium phosphate and 217 mg of bis(triphenylphosphine) palladium chloride according to the protocol described above. A brown oil is obtained (800 mg), which is purified by flash chromatography on alumina CTB1 under an argon pressure (50 kPa) [eluent: cyclohexane/ethyl acetate (80/20 by volume)]. After concentration of the fractions under reduced pressure (2.7 kPa), 120 mg of {2-[3-benzyloxy-4-biphenyl-3-yl-pyrazol-1-yl]ethyl}dimethylamine are obtained in the form of a yellow oil.

IR spectrum (CCl$_4$): 3065; 3033; 2823; 2774; 1609; 1579; 1505; 1450; 1240 and 699 cm$^{-1}$.

EXAMPLE 34

1-(2-Dimethylaminoethyl)-4-(4'-fluorobiphenyl-4-yl)-1H-pyrazol-3-ol dihydrochloride 0.06 cm$^3$ of 12N hydrochloric acid is added to a solution of 200 mg of {2-[3-benzyloxy-4-(4'-fluorobiphenyl-4-yl)pyrazol-1-yl]ethyl}dimethylamine in 20 cm$^3$ of ethanol. The mixture is introduced into an autoclave, 28 mg of palladium-on-charcoal at 10% are added, and it is then placed under hydrogen (5 bar). After stirring for 4 h at 40° C., the reaction medium is filtered over supercel and the filtrate is evaporated. The residue is triturated in diisopropyl ether. The solid obtained, dissolved in 20 cm$^3$ of ethanol, is used again in a reaction in an autoclave with 10 mg of palladium-on-charcoal at 10% and under hydrogen (7 bar). After stirring for 5 h at 35° C., the reaction mixture is filtered over supercel and the filtrate is evaporated. The residue is triturated in diisopropyl ether, filtered and dried under vacuum (2.7 kPa) to give 77 mg of 1-(2-dimethylaminoethyl)-4-(4'-fluorobiphenyl-4-yl)-1H-pyrazol-3-ol dihydrochloride in the form of a beige solid.

IR spectrum (KBr): 2964; 2676; 2468; 1611; 1585; 1528; 1514; 1493; 1460; 1234; 1161; 826; 810 and 511 cm$^{-1}$.

$^1$H NMR spectrum (300 MHz, (CD$_3$)$_2$SO d6, δ in ppm): 2.79 (broad s: 6H); 3.48 (unresolved peak: 2H); 4.36 (broad t, J=6.5 Hz: 2H); 7.30 (broad t, J=9 Hz: 2H); 7.65 (broad d, J=8 Hz: 2H); from 7.70 to 7.80 (mt: 4H); 8.09 (s: 1H); 9.92 (unresolved peak: 1H); 10.52 (broad s: 1H).

The {2-[3-benzyloxy-4-(4'-fluorobiphenyl-4-yl)pyrazol-1-yl]ethyl}dimethylamine can be prepared in the following way:

770 mg of 4-fluorophenylboronic acid, 1.19 g of potassium phosphate and 290 mg of bis(triphenylphosphine)palladium chloride are added to a stirred solution of 500 mg of {2-[3-benzyloxy-4-(4-bromophenyl)pyrazol-1-yl]ethyl}dimethylamine in 25 cm$^3$ of toluene under an argon atmosphere. After heating at the reflux of the solvent for 15 h, the reaction mixture is cooled to a temperature in the region of 20° C., ethyl acetate and water are added, and it is filtered over supercel. The filtrate is separated by settling out, and the organic phase is then washed successively with 0.5N sodium hydroxide, water and a saturated aqueous sodium chloride solution; it is dried over magnesium sulfate, filtered and evaporated under reduced pressure (2.7 kPa). The brown oil obtained (800 mg) is purified by flash chromatography on alumina CTB1 under an argon pressure (50 kPa) [eluent: cyclohexane/ethyl acetate (80/20 by volume)]. After concentration of the fractions under reduced pressure (2.7 kPa), 220 mg of {2-[3-benzyloxy-4-(4'-fluoro-biphenyl-4-yl)pyrazol-1-yl]ethyl}dimethylamine are obtained in the form of a yellow oil.

Mass spectrum (EI): m/z 415 (M$^{+\cdot}$), m/z 344 [(M−C$_4$H$_9$N)$^+$], m/z 91 (C$_7$H$_7^+$), m/z 58 (C$_3$H$_8$N$^+$).

The {2-[3-benzyloxy-4-(4-bromophenyl)pyrazol-1-yl]ethyl}dimethylamine can be prepared in the following way:

A solution of 5.2 g of 3-benzyloxy-4-(4-bromophenyl)-1H-pyrazole in 50 cm$^3$ of dimethylformamide is added to a suspension of 1.36 g of sodium hydride (at 75% in liquid petroleum jelly) in 50 cm$^3$ of dimethylformamide under an argon atmosphere and with stirring. After heating at 50° C. for 30 min, the mixture is stirred for 1 h at a temperature in the region of 20° C., and is then cooled in an ice bath and a solution of 5.5 g of (2-bromoethyl)dimethylamine in 50 cm$^3$ of dimethylformamide is added. The reaction medium is stirred for 15 h at a temperature in the region of 20° C., and is then cooled to a temperature in the region of 20° C. and poured into 400 cm$^3$ of water. The aqueous phase is extracted twice with ethyl acetate. The organic phases are pooled, washed successively with water twice and a saturated aqueous sodium chloride solution, dried over magnesium sulfate, filtered and evaporated under reduced pressure (2.7 kPa) to give a brown oil which is purified by flash chromatography on silica under an argon pressure (50 kPa) [eluent: ethyl acetate, ethyl acetate/methanol (90/10 by volume)]. After concentration of the fractions under reduced pressure, 2.3 g of {2-[3-benzyloxy-4-(4-bromophenyl)pyrazol-1-yl]ethyl}dimethylamine are obtained in the form of a yellow oil.

Mass spectrum (EI): m/z 399 (M$^{+\cdot}$), m/z 328 [(M−C$_4$H$_9$N)$^+$], m/z 91 (C$_7$H$_7^{+\cdot}$), m/z 58 (C$_3$H$_8$N$^+$).

The 3-benzyloxy-4-(4-bromophenyl)-1H-pyrazole can be prepared in the following way:

3.88 g of potassium carbonate and 3.1 cm$^3$ of benzyl bromide are added to a suspension of 6.58 g de 1-[3-benzyloxy-4-(4-bromophenyl)pyrazol-1-yl]ethanone in 70 cm$^3$ of methyl ethyl ketone with stirring. The mixture is heated at the reflux of the solvent for 2.5 h, cooled to a temperature in the region of 20° C., and filtered. The filtrate is evaporated under reduced pressure (2.7 kPa), and the residue is taken up with 50 cm$^3$ of tetrahydrofuran and 50 cm$^3$ of methanol and 1.5 cm$^3$ of 10N sodium hydroxide are then added. After stirring for 30 min at a temperature in the region of 20° C., the reaction medium is evaporated under reduced pressure (2.7 kPa). The reaction crude is taken up in dichloromethane. The organic phase is washed successively with two times water and a saturated aqueous sodium chloride solution, dried over magnesium sulfate, filtered and evaporated under reduced pressure (2.7 kPa). The solid obtained is triturated in diisopropyl ether, filtered and dried under vacuum (2.7 kPa) to give 2.9 g of 3-benzyloxy-4-(4-bromo-phenyl)-1H-pyrazole in the form of a beige solid. The filtrate is evaporated under reduced pressure (2.7 kPa) and the residue is taken up with dichloromethane. The organic solution is washed with water and a saturated aqueous sodium chloride solution, dried over magnesium sulfate, filtered and evaporated under reduced pressure (2.7 kPa). The resulting solid is triturated in diisopropyl ether, filtered and dried under vacuum (2.7 kPa) to give a further 2.3 g of 3-benzyloxy-4-(4-bromophenyl)-1H-pyrazole in the form of a beige solid.

$^1$H NMR spectrum (400 MHz, (CD$_3$)$_2$SO d6, δ in ppm): 5.35 (s: 2H); 7.35 (broad t, J=7.5 Hz: 1H); 7.42 (broad t, J=7.5 Hz: 2H); 7.50 (broad d, J=7.5 Hz: 2H); 7.51 (broad d, J=8.5 Hz: 2H); 7.65 (broad d, J=8.5 Hz: 2H); 8.09 (s: 1H).

The 1-[4-(4-bromophenyl)-3-hydroxypyrazol-1-yl]ethanone can be prepared in the following way:

A solution of 6 g of 4-(4-bromophenyl)-1H-pyrazol-3-ol in 50 cm$^3$ of pyridine, under an argon atmosphere and with stirring, is heated to 90° C., and 2.25 cm$^3$ of acetic anhydride are then added dropwise. After heating at 90° C. for 1 h, the reaction medium is cooled to a temperature in the region of 20° C. and poured into 150 cm$^3$ of ice-cold water. The precipitate formed is filtered, washed three times with water and dried under vacuum (2.7 kPa) to give 6.6 g of 1-[4-(4-bromophenyl)-3-hydroxypyrazol-1-yl]ethanone in the form of a white solid.

IR spectrum (KBr): 3132; 2968; 2696; 2653; 1714; 1621; 1533; 1417; 1392; 1328; 1279; 1231; 1008; 949; 822; 645 and 508 cm$^{-1}$.

The 4-(4-bromophenyl)-1H-pyrazol-3-ol can be prepared in the following way:

A solution, with stirring, of 11.5 g of ethyl ester of 2-(4-bromophenyl)-3-dimethylaminoacrylic acid and of 1.9 cm$^3$ of hydrazine monohydrate in 100 cm$^3$ of ethanol is heated at the reflux of the solvent for 3 h. The reaction mixture is evaporated to dryness under reduced pressure (2.7 kPa) and the residue is triturated in diisopropyl ether. The solid formed is filtered and is dried under vacuum (2.7 kPa) to give 6 g of 4-(4-bromophenyl)-1H-pyrazol-3-ol in the form of a white solid.

IR spectrum (KBr): 3299; 3123; 2958; 2674; 1606; 1579; 1517; 1488; 1399; 1163; 1080; 1008; 824 and 509 cm$^{-1}$.

The ethyl ester of 2-(4-bromophenyl)-3-dimethylaminoacrylic acid can be prepared in the following way:

13.5 cm$^3$ of C-tert-butoxy-N,N,N',N'-tetramethylmethanediamine are added to a solution of 10 g of ethyl ester of 2-(4-bromophenyl)acrylic acid in 100 cm$^3$ of tetrahydrofuran and the mixture is heated at the reflux of the solvent for 3 h. After stirring for 15 h at a temperature in the region of 20° C., the reaction mixture is evaporated to dryness under reduced pressure (2.7 kPa). The residue is taken up with ethyl acetate, and the organic solution is washed 3 times with water and then dried over magnesium sulfate, filtered and evaporated under reduced pressure (2.7 kPa) to give 11.3 g of ethyl ester of 2-(4-bromophenyl)-3-dimethylaminoacrylic acid in the form of a yellow oil.

Mass spectrum (CI): m/z 298 (MH$^+$).

EXAMPLE 35

1-(2-Piperidin-1-ylethyl)-4-pyridin-2-yl-1H-pyrazol-3-ol dihydrochloride 10 cm$^3$ of 4N hydrochloric dioxane are added to a solution of 1.6 g of 2-[3-(cyclohex-2-enyloxy)-1-(2-piperidin-1-ylethyl)-1H-pyrazol-4-yl]pyridine in 20 cm$^3$ of dioxane. After stirring for 15 h at a temperature in the region of 20° C., the suspension is filtered, and the solid is rinsed once with dioxane and then three times with diisopropyl ether, and is dried under vacuum (2.7 kPa) to give 55 mg of 1-(2-piperidin-1-ylethyl)-4-pyridin-2-yl-1H-pyrazol-3-ol dihydrochloride in the form of a white powder.

IR spectrum (KBr): 3037; 2943; 2644; 2541; 1633; 1606; 1577; 1454; 1179; 782 and 685 cm$^{-1}$.

$^1$H NMR spectrum (300 MHz, (CD$_3$)$_2$SO d6, δ in ppm): 1.40 (mt: 1H); from 1.60 to 1.90 (mt: 5H); 2.95 (mt: 2H); from 3.35 to 3.55 (mt: 4H); 4.57 (t, J=6.5 Hz: 2H); 7.58 (mt: 1H); 8.15 (broad d, J=7 Hz: 1H); 8.31 (broad t, J=7 Hz: 1H); 8.61 (broad d, J=5 Hz: 1H); 8.69 (broad s: 1H); 10.64 (unresolved peak: 1H).

The 2-[3-(cyclohex-2-enyloxy)-1-(2-piperidin-1-yl-ethyl)-1H-pyrazol-4-yl]pyridine can be prepared in the following way:

A suspension of 1.5 g of 2-[3-(cyclohex-2-enyloxy)-1H-pyrazol-4-yl]pyridine in 20 cm$^3$ of dimethylformamide is added to a suspension of 500 mg of sodium hydride (at 75% in liquid petroleum jelly) in 15 cm$^3$ of dimethylformamide under an argon atmosphere and with stirring. After heating at 50° C. for 30 min, the mixture is stirred for 30 min at a temperature in the region of 20° C., and a solution of 1.6 g of 1-(2-chloroethyl)-piperidine hydrochloride is then added. The reaction medium is stirred for 15 h at a temperature in the region of 20° C. and is then poured into water. The aqueous phase is extracted twice with ethyl acetate. The organic phases are pooled, washed successively with water and a saturated aqueous sodium chloride solution, dried over magnesium sulfate, filtered and evaporated under reduced pressure (2.7 kPa) to give a yellow oil which is purified by flash chromatography on alumina CTB1 under an argon pressure (50 kPa) [eluent: cyclohexane/ethyl acetate (90/10 by volume)]. After concentration of the fractions under reduced pressure, 1.6 g of 2-[3-(cyclohex-2-enyloxy)-1-(2-piperidin-1-ylethyl)-1H-pyrazol-4-yl]pyridine are obtained in the form of a pale yellow oil.

Mass spectrum (EI): m/z 352 (M$^{+\cdot}$), m/z 271 [(M−C$_6$H$_9$)$^+$], m/z 111 (C$_7$H$_{13}$N$^{+\cdot}$), m/z 98 (C$_6$H$_{12}$N$^+$).

The 2-[3-(cyclohex-2-enyloxy)-1H-pyrazol-4-yl]pyridine can be prepared in the following way:

5.4 g of potassium carbonate and 4.6 cm$^3$ of 3-bromocyclohexene are added to a suspension of 7.1 g of 1-(3-hydroxy-4-pyridin-2-ylpyrazol-1-yl)ethanone in 70 cm$^3$ of methyl ethyl ketone with stirring. The mixture is heated at the reflux of the solvent for 4 h, cooled to a temperature in the region of 20° C., and evaporated under reduced pressure (2.7 kPa). The residue is taken up with 50 cm$^3$ of tetrahydrofuran and 50 cm$^3$ of methanol, and 7 cm$^3$ of 5N sodium hydroxide are then added along with water until complete solubilization of the medium. After stirring for 15 h at a temperature in the region of 20° C., the reaction medium is evaporated under reduced pressure (2.7 kPa). The reaction crude is taken up with ethyl acetate and water. The insoluble solid is filtered off and dried under reduced pressure (2.7 kPa) to give 5.3 g of 2-[3-(cyclohex-2-enyloxy)-1H-pyrazol-4-yl]pyridine in the form of a white powder.

IR spectrum (KBr): 3180; 2928; 2723; 1602; 1533; 1497; 1463; 1288; 1065; 786 and 700 cm$^{-1}$.

The 1-(3-hydroxy-4-pyridin-2-ylpyrazol-1-yl)ethanone can be prepared in the following way:

A solution, stirred and under an argon atmosphere, of 7.3 g of 4-pyridin-2-yl-1H-pyrazol-3-ol hydrochloride in 70 cm$^3$ of pyridine is heated to 100° C., and 3.75 cm$^3$ of acetic anhydride are then added dropwise. After heating at 100° C. for 1.5 h, the reaction medium is cooled to a temperature in the region of 20° C. and is poured into 150 cm$^3$ of ice-cold water. The precipitate formed is filtered, washed three times with water and dried under vacuum (2.7 kPa) to give 7.1 g of 1-(3-hydroxy-4-pyridin-2-ylpyrazol-1-yl)ethanone in the form of a pale yellow solid.

IR spectrum (KBr): 3157; 2396; 1719; 1608; 1391; 1274; 1223; 1000; 929; 790 and 618 cm$^{-1}$.

The 4-pyridin-2-yl-1H-pyrazol-3-ol hydrochloride can be prepared in the following way:

A solution, with stirring, of 18 g of ethyl ester of 3-dimethylamino-2-pyridin-2-ylacrylic acid and of 3.95 cm$^3$ of hydrazine monohydrate in 120 cm$^3$ of ethanol is heated at the reflux of the solvent for 3 h. The reaction mixture is concentrated under reduced pressure (2.7 kPa), 3N hydrochloric ethanol is added, and the mixture is cooled in an ice bath. The solid formed is filtered, and is dried under vacuum (2.7 kPa) to give 11.3 g of 4-pyridin-2-yl-1H-pyrazol-3-ol hydrochloride in the form of a yellow solid.

IR spectrum (KBr): 3166; 1644; 1620; 1587; 1551; 1430; 1209; 1159; 907; 774 and 518 cm$^{-1}$.

The ethyl ester of 3-dimethylamino-2-pyridin-2-yl-acrylic acid can be prepared in the following way:

20 cm$^3$ of C-tert-butoxy-N,N,N',N'-tetramethyl-methanediamine are added to a solution of 13 g of ethyl ester of 2-pyridin-2-ylacrylic acid in 100 cm$^3$ of tetrahydrofuran, heating is carried out at the reflux of the solvent for 15 h, and the reaction mixture is then cooled to a temperature in the region of 20° C. and evaporated to dryness under reduced pressure (2.7 kPa). The resulting brown oil is purified by flash chromatography on silica under an argon pressure (50 kPa) [eluent: cyclohexane/ethyl acetate (90/10 by volume)]. After concentration of the fractions under reduced pressure, 18 g of ethyl ester of 3-dimethylamino-2-pyridin-2-ylacrylic acid are obtained in the form of an orange-colored oil.

IR spectrum (CCl$_4$): 2980; 2929; 1686; 1619; 1602; 1297; 1271; 1219; 1096 and 1085 cm$^{-1}$.

EXAMPLE 36

1-(2-Piperidin-1-ylethyl)-4-pyridin-4-yl-1H-pyrazol-3-ol dihydrochloride monohydrate 7 cm$^3$ of 12N hydrochloric acid are added to a stirred solution of 720 mg of 4-[3-benzyloxy-1-(2-piperidin-1-ylethyl)-1H-pyrazol-4-yl]pyridine in 7 cm$^3$ of ethanol. After 7 h at the reflux of the solvent, and then 15 h at a temperature in the region of 20° C., the reaction medium is evaporated under reduced pressure (2.7 kPa). The residue is taken up with ethanol, and the mixture is then evaporated to dryness under reduced pressure (2.7 kPa). The operation is repeated twice, ethanol is then added to the solid and the mixture is heated at the reflux of the solvent. After cooling of the solution in an ice bath, the crystals formed are filtered off and dried under vacuum (2.7 kPa) to give 300 mg of 1-(2-piperidin-1-ylethyl)-4-pyridin-4-yl-1H-pyrazol-3-ol dihydrochloride monhoydrate in the form of a white solid.

IR spectrum (KBr): 3495; 3414; 3197; 2934; 2652; 2545; 1637; 1599; 1540; 1513; 1206; 813 and 523 cm$^{-1}$.

$^1$H NMR spectrum (300 MHz, (CD$_3$)$_2$SO d6, δ in ppm): from 1.30 to 1.60 (very broad unresolved peak: 1H); from 1.60 to 1.90 (mt: 5H); from 2.85 to 3.05 (unresolved peak: 2H); from 3.30 to 3.45 (mt: 2H); 3.49 (t, J=6.5 Hz: 2H); 4.54 (t, J=6.5 Hz: 2H); 8.12 (broad d, J=7 Hz: 2H); 8.67 (s: 1H); 8.69 (broad d, J=7 Hz: 2H); 11.75 (unresolved peak: 1H).

The 4-[3-benzyloxy-1-(2-piperidin-1-ylethyl)-1H-pyrazol-4-yl]pyridine can be prepared in the following way:

A solution of 720 mg of 4-(3-benzyloxy-1H-pyrazol-4-yl) pyridine in 20 cm$^3$ of dimethylformamide is added to a suspension of 230 mg of sodium hydride (at 75% in liquid petroleum jelly) in 10 cm$^3$ of dimethylformamide under an argon atmosphere and with stirring. After heating at 50° C. for 30 min, the mixture is stirred for 30 min at a temperature in the region of 20° C., and a solution of 740 mg of 1-(2-chloroethyl)piperidine hydrochloride is then added. The reaction medium is stirred for 15 h at a temperature in the region of 20° C. and is then poured into water. The aqueous phase is extracted twice with ethyl acetate. The organic phases are pooled, washed successively with water and a saturated aqueous sodium chloride solution, dried over magnesium sulfate, filtered and evaporated under reduced pressure (2.7 kPa) to give an orange-colored oil which is purified by flash chromatography on alumina CTB1 under an argon pressure (50 kPa) [eluent: cyclohexane/ethyl acetate (90/10, then 80/20 by volume)]. After concentration of the fractions under reduced pressure, 720 mg of 4-[3-benzyloxy-1-(2-piperidin-1-ylethyl)-1H-pyrazol-4-yl]pyridine are obtained in the form of a pale yellow oil.

IR spectrum (CH$_2$Cl$_2$): 2940; 1604; 1573; 1513; 1453; 1363; 1172; 992; 815; 676 and 534 cm$^{-1}$.

The 4-(3-benzyloxy-1H-pyrazol-4-yl)pyridine can be prepared in the following way:

1.8 g of potassium carbonate and 1.55 cm$^3$ of benzyl bromide are added to a suspension of 2.4 g of 1-(3-hydroxy-4-pyridin-4-ylpyrazol-1-yl)ethanone in 25 cm$^3$ of methyl ethyl ketone with stirring. The mixture is heated at the reflux of the solvent for 3 h, cooled to a temperature in the region of 20° C., and filtered. The filtrate is evaporated under reduced pressure (2.7 kPa). The resulting brown oil is purified by flash chromatography on silica under an argon pressure (50 kPa) [eluent: ethyl acetate/cyclohexane (80/20 by volume)]. After concentration of the fractions under reduced pressure, 720 mg of 4-(3-benzyloxy-1H-pyrazol-4-yl)pyridine are obtained in the form of a white solid.

$^1$H NMR spectrum (300 MHz, (CD$_3$)$_2$SO d6, δ in ppm): 5.27 (s: 2H); 7.36 (tt, J=7.5 and 1.5 Hz: 1H); 7.44 (tt, J=7.5 and 1.5 Hz: 2H); 7.52 (broad d, J=7.5 Hz: 2H); 7.66 (dd, J=5 and 2 Hz: 2H); 8.33 (s: 1H); 8.47 (dd, J=5 and 2 Hz: 2H); from 12.25 to 12.50 (unresolved peak: 1H).

The 1-(3-hydroxy-4-pyridin-4-ylpyrazol-1-yl)ethanone can be prepared in the following way:

A suspension of 2.5 g of 4-pyridin-4-yl-1H-pyrazol-3-ol hydrochloride in 25 cm$^3$ of pyridine, with stirring and under an argon atmosphere, is heated to 100° C., and 1.25 cm$^3$ of acetic anhydride are then added dropwise. After heating at 100° C. for 2 h, the reaction medium is cooled in an ice bath. The solid formed is filtered off, washed with water and then with heptane, and dried under vacuum (2.7 kPa) to give 1-(3-hydroxy-4-pyridin-4-ylpyrazol-1-yl)ethanone, which is used directly in the following step.

The 4-pyridin-4-yl-1H-pyrazol-3-ol hydrochloride can be prepared in the following way:

A solution, with stirring, of 12.46 g of ethyl ester of 3-dimethylamino-2-pyridin-4-ylacrylic acid and of 2.75 cm$^3$ of hydrazine monohydrate in 80 cm$^3$ of ethanol is heated at the reflux of the solvent for 3 h. The reaction mixture is cooled in an ice bath, and the solid formed is filtered off and taken up with water. The suspension is adjusted to pH 6 with 1N hydrochloric acid and is then filtered. The solid obtained is washed with water and is dried under vacuum (2.7 kPa) to give 5.1 g of 4-pyridin-4-yl-1H-pyrazol-3-ol hydrochloride in the form of a yellow solid.

IR spectrum (KBr): 3355; 2464; 2059; 1965; 1637; 1575; 1527; 1207; 1193; 1075; 1022; 914; 838 and 519 cm$^{-1}$.

The ethyl ester of 3-dimethylamino-2-pyridin-4-yl-acrylic acid can be prepared in the following way:

24 cm$^3$ of C-tert-butoxy-N,N,N',N'-tetramethylmethanediamine are added to a solution of 15 cm$^3$ of ethyl ester of 2-pyridin-4-ylacrylic acid in 100 cm$^3$ of tetrahydrofuran and heating is carried out at the reflux of the solvent for 15 h, and the reaction mixture is then evaporated to dryness under reduced pressure (2.7 kPa). The residue is taken up with ethyl acetate, and the organic solution is washed twice with water and a saturated aqueous sodium chloride solution, dried over magnesium sulfate, filtered and evaporated under reduced pressure (2.7 kPa). The brown oil obtained is purified by flash chromatography on silica under an argon pressure (50 kPa) [eluent: cyclohexane/ethyl acetate (90/10 by volume)]. After concentration of the fractions under reduced pressure, 12.46 g of ethyl ester of 2-pyridin-4-ylacrylic acid are obtained in the form of an orange-colored oil.

IR spectrum (CCl$_4$): 2981; 1690; 1596; 1280; 1218; 1095 and 1051 cm$^{-1}$.

EXAMPLE 37

4-(4-Fluorophenyl)-1-(2-piperidin-1-ylethyl)-1H-pyrazol-3-ol 0.5 g of 3-benzyloxy-4-(4-fluorophenyl)-1-(2-piperidin-1-ylethyl)-1H-pyrazole hydrochloride is introduced into an autoclave with 12.8 mg of palladium-on-charcoal (at 10%) and 25 cm$^3$ of ethanol. The device is placed under a hydrogen pressure of 500 kPa at a temperature of 25° C. for 5 hours. After cooling to a temperature in the region of 20° C., the reaction medium is filtered over supercel; the filtrate is washed with 3 times 100 cm$^3$ of ethanol, and concentrated to dryness under reduced pressure (2 kPa). The residue obtained is purified by chromatography, under a nitrogen pressure of 50 kPa, on a column of silica gel (particle size 20-45µ; diameter 1 cm; height 25 cm), eluting with a mixture of dichloromethane and of a 2N solution of ammoniacal methanol (93/7 by volume). Concentration is performed under reduced pressure (2 kPa); 160 mg of 4-(4-fluoro-phenyl)-1-(2-piperidin-1-ylethyl)-1H-pyrazol-3-ol are obtained in the form of a white solid.

$^1$H NMR spectrum (300 MHz, (CD$_3$)$_2$SO d6, δ in ppm): from 1.30 to 1.55 (mt: 6H); 2.40 (broad t, J=5.5 Hz: 4H); 2.65 (t, J=7 Hz: 2H); 4.00 (t, J=7 Hz: 2H); 7.15 (t, J=9 Hz: 2H); 7.65 (dd, J=9 and 5.5 Hz: 2H); 7.91 (s: 1H); 10.32 (broad s: 1H). Mass spectrum (EI): m/z 289 (M$^{+\cdot}$), m/z 98 (base peak).

The 3-benzyloxy-4-(4-fluorophenyl)-1-(2-piperidin-1-ylethyl)-1H-pyrazole can be prepared in the following way:

A suspension of 0.80 g of 3-benzyloxy-4-bromo-1-(2-piperidin-1-ylethyl)-1H-pyrazole, 1.12 g of 4-fluorophenylboronic acid, 0.20 g of dichloro-bis(triphenylphosphine)palladium and 1.88 g of potassium phosphate in 30 cm$^3$ of 1,2-dimethoxyethane is stirred, under an argon atmosphere, at the boiling temperature of the reaction medium, for 14 hours. After cooling, 30 cm$^3$ of a saturated sodium hydrogen carbonate solution are added to the mixture, which is extracted with 30 cm$^3$ of ethyl acetate. The organic phase is dried over magnesium sulfate, filtered and concentrated to dryness under reduced pressure (3 kPa). The residue is purified by chromatography on silica gel, eluting with a mixture of ethyl acetate and methanol (30/1 by volume). After concentration of the fractions under reduced pressure, 0.57 g of a yellowish oil is obtained, which is used as it is in the following step. 0.57 g of 3-benzyloxy-4-(4-fluorophenyl)-1-(2-piperidin-1-ylethyl)-1H-pyrazole is taken up with 5 cm$^3$ of diethyl ether and 0.5 cm$^3$ of a 4N solution of hydrochloric acid in diethyl ether. The precipitate formed is filtered over dried. 0.5 g of 3-benzyloxy-4-(4-fluorophenyl)-1-(2-piperidin-1-ylethyl)-1H-pyrazole is obtained. $^1$H NMR spectrum (300 MHz, (CD$_3$)$_2$SO d6, δ in ppm): from 1.25 to 1.50 (mt: 1H); from 1.60 to 1.85 (mt: 5H); 2.91 (mt: 2H); 3.44 (very broad d, J=12.5 Hz: 2H); 3.52 (mt: 2H); 4.47 (broad t, J=6.5 Hz: 2H); 5.34 (s: 2H); 7.72 (t, J=9 Hz: 2H); from 7.30 to 7.45 (mt: 3H); 7.51 (broad d, J=7.5 Hz: 2H); 7.68 (dd, J=9 and 6 Hz: 2H); 8.16 (s: 1H); from 9.70 to 10.00 (unresolved peak: 1H).

The 3-benzyloxy-4-bromo-1-(2-piperidin-1-ylethyl)-1H-pyrazole can be prepared in the following way:

5.6 g of sodium hydride (at 75% by mass in liquid petroleum jelly) and 25 cm$^3$ of anhydrous dimethylformamide are added gradually, at a temperature in the region of 5° C., to a solution of 8 g of 3-benzyloxy-4-bromo-1H-pyrazole hydrochloride in 100 cm³ of anhydrous dimethylformamide. After stirring for 1 hour at ambient temperature, 6.93 g of 1-(2-chloro-ethyl)piperidine hydrochloride and 30 cm³ of anhydrous dimethylformamide are added in small portions. After stirring for 21 hours at ambient temperature, the excess sodium hydride is destroyed by slowly adding water, and the reaction medium is then run into 1 dm³ of water and extracted with 2 times 200 cm³ of ethyl acetate. The pooled organic phases are dried over magnesium sulfate, filtered and concentrated to dryness under reduced pressure (3 kPa). The oily residue obtained is taken up with 20 cm³ of acetone and run into a solution of 3.6 g of oxalic acid in 30 cm³ of acetone. The solid formed is triturated and then isolated by filtration and dried at ambient temperature, to give 11.3 g of 3-benzyloxy-4-bromo-1-(2-piperidin-1-ylethyl)-1H-pyrazole oxalate. 50 cm³ of a saturated sodium hydrogen carbonate solution are added to 5 g of this oxalate and the mixture is extracted with 2×100 cm³ of ethyl acetate. The pooled organic phases are dried over magnesium sulfate, filtered and concentrated to dryness under reduced pressure (3 kPa). 3.84 g of 3-benzyloxy-4-bromo-1-(2-piperidin-1-ylethyl)-1H-pyrazole are thus obtained in the form of a light oil.

$^1$H NMR spectrum (300 MHz, $(CD_3)_2SO$ d6, δ in ppm): from 1.25 to 1.55 (mt: 6H); 2.35 (broad t, J=5 Hz: 4H); 2.61 (t, J=6.5 Hz: 2H); 4.04 (t, J=6.5 Hz: 2H); 5.20 (s: 2H); from 7.30 to 7.50 (mt: 5H); 7.81 (s: 1H).

The 3-benzyloxy-4-bromo-1H-pyrazole hydrochloride can be prepared in the following way:

A solution of 2.6 cm³ of bromine in 50 cm³ of dichloromethane is added dropwise, over 0.5 hour, to a suspension of 8.76 g of 3-benzyloxy-1H-pyrazole and 11 g of sodium carbonate in 100 cm³ of dichloromethane, which has been cooled and kept at around 5° C. with stirring. After stirring for 0.5 hour at this temperature, 20 cm³ of 0.1N sodium thiosulfate solution is added to the mixture, which is stirred for a further 1 hour at around 5° C., and then 100 cm³ of dichloromethane are added and the mixture is separated by settling out. The organic phase is extracted again with 50 cm³ of water and the organic phases are pooled and dried over magnesium sulfate, filtered and concentrated to dryness under reduced pressure (3 kPa). The oily residue obtained is taken up with 10 cm³ of 6N hydrochloric dioxane and the solid formed is triturated in ethyl ether and isolated by filtration. 12.5 g of 3-benzyloxy-4-bromo-1H-pyrazole are thus obtained in the form of a white solid which melts at around 80° C. (with decomposition).

Mass spectrum (EI): m/z 252 (M$^{+\cdot}$), m/z 91 (base peak).

$^1$H NMR spectrum (300 MHz, $(CD_3)_2SO$ d6, δ in ppm): 5.22 (s: 2H); from 7.30 to 7.50 (mt: 5H); 7.81 (s: 1H); from 11.80 to 12.70 (very broad unresolved peak: 1H).

The 3-benzyloxy-1H-pyrazole can be prepared in the following way:

50 cm³ of a saturated sodium hydrogen carbonate solution are added to 10.6 g of 3-benzyloxy-1H-pyrazole hydrochloride and the mixture is extracted with 2×150 cm³ of dichloromethane. The pooled organic phases are dried over magnesium sulfate, filtered and concentrated to dryness under reduced pressure (3 kPa) to give 8.76 g of 3-benzyloxy-1H-pyrazole in the form of an oil, which is used as it is in the following step.

The 3-benzyloxy-1H-pyrazole hydrochloride can be prepared in the following way:

A suspension of 11 g of 1-(3-hydroxypyrazol-1-yl)-ethanone, 12.5 g of potassium carbonate and 11.3 cm³ (16.25 g) of benzyl bromide in 250 cm³ of 2-butanone is stirred at the boiling temperature of the mixture for 1.25 hours. The insoluble inorganic material is then removed by filtration and the filtrate is concentrated to dryness under reduced pressure (3 kPa). The oily residue obtained is dissolved in a mixture of 150 cm³ of tetrahydrofuran and 100 cm³ of methanol, and 4 cm³ of a 10M sodium hydroxide solution are then added thereto.

After stirring for 0.65 hour at ambient temperature, the mixture is concentrated to dryness under reduced pressure (3 kPa). The pasty residue obtained is taken up with 250 cm³ of ethyl acetate and washed with 2 times 10 cm³ of brine. The organic phase is dried over magnesium sulfate, filtered and concentrated under reduced pressure (3 kPa). 100 cm³ of 1N hydrochloric ether are added to the residue and the solid formed is triturated and then isolated by filtration. The solid is solubilized in 250 cm³ of isopropanol at around 60° C., and the mixture is then partially concentrated until the first crystals appear, 5 cm³ isopropyl acetate are added, and the mixture is cooled to around 0° C. After filtration and drying, 10.6 g of 3-benzyloxy-1H-pyrazole hydrochloride are obtained in the form of salmon-pink crystals which melt at 100° C.

$^1$H NMR spectrum (300 MHz, $(CD_3)_2SO$ d6, δ in ppm): 5.16 (s: 2H); 5.75 (d, J=3 Hz: 1H); from 7.30 to 7.50 (mt: 5H); 7.57 (d, J=3 Hz: 1H).

The 1-(3-hydroxypyrazol-1-yl)ethanone can be prepared in the following way:

A solution of 9.5 cm³ of acetic anhydride in 18 cm³ of pyridine is added slowly, over 0.33 hours, to a solution of 8.4 g of 1H-pyrazol-3-ol (No. CAS 60456-92-0) in 38 cm³ of pyridine preheated to 95° C., and this temperature is then maintained for 1 hour. The mixture is then concentrated under reduced pressure (3 kPa). 100 cm³ of ethyl ether are added to the residual suspension, which is triturated to finish off the crystallization. After filtration and drying, 11 g of 1-(3-hydroxypyrazol-1-yl)ethanone are obtained in the form of whitish crystals which sublimate at around 215° C.

$^1$H NMR spectrum (300 MHz, $(CD_3)_2SO$ d6, δ in ppm): 2.50 (s: 3H); 6.02 (d, J=3 Hz: 1H); 8.15 (d, J=3 Hz: 1H); from 10.80 to 11.20 (unresolved peak: 1H).

EXAMPLE 38

4-(4-Trifluoromethoxyphenyl)-1-(2-piperidin-1-ylethyl)-1H-pyrazol-3-ol dihydrochloride 600 mg of 3-benzyloxy-4-(4-trifluoromethoxyphenyl)-1-(2-piperidin-1-ylethyl)-1H-pyrazole in 4.5 cm³ of ethanol and 4.5 cm³ of 12N hydrochloric acid are brought to reflux at a temperature in the region of 100° C. for 7 hours. After cooling to a temperature in the region of 20° C., the reaction medium is concentrated to dryness under reduced pressure (2 kPa); the residue is precipitated from a mixture of diisopropyl ether and acetone. 464 mg of 4-(4-trifluoromethoxyphenyl)-1-(2-piperidin-1-ylethyl)-1H-pyrazol-3-ol dihydrochloride are obtained in the form of a white powder.

IR spectrum (KBr): 3428; 2951; 2642; 2538; 1615; 1591; 1533; 1456; 1275; 1219; 1159; 1012; 856 and 806 cm$^{-1}$.

$^1$H NMR spectrum (300 MHz, $(CD_3)_2SO$ d6, δ in ppm): 1.41 (mt: 1H); from 1.60 to 1.85 (mt: 5H); 2.94 (unresolved peak: 2H); 3.46 (mt: 4H); 4.41 (mt: 2H); 7.34 (broad d, J=8 Hz: 2H); 7.76 (d, J=8 Hz: 2H); 8.09 (s: 1H). 10.04 (broad unresolved peak: 1H); 10.62 (broad s: 1H).

The 3-benzyloxy-4-(4-trifluoromethoxyphenyl)-1-(2-piperidin-1-ylethyl)-1H-pyrazole can be prepared in the following way:

560 mg of 3-benzyloxy-4-(4-trifluoromethoxyphenyl)-1H-pyrazole in 15 cm³ of anhydrous dimethylformamide are cooled, with stirring, to a temperature in the region of −5° C. and under an inert atmosphere; 140 mg of sodium hydride (at 75% in liquid petroleum jelly) are added portionwise to the reaction medium and the temperature is allowed to return to approximately 20° C. 431 mg of 1-(2-chloroethyl)piperidine hydrochloride are then added and the stirring is maintained at this temperature for 15 hours. The reaction medium is taken up with 300 cm$^3$ of ice-cold water and 300 cm$^3$ of ethyl acetate. The organic phase is separated by settling out, washed with 200 cm$^3$ of water and concentrated to dryness under reduced pressure (2 kPa). The residue is purified on an FC50SI-HP silica cartridge, eluting with a mixture of dichloromethane and methanol (95/5 by volume). The product obtained is again purified on an FC50SI-HP silica cartridge, eluting with a mixture of dichloromethane and methanol (98/2 by volume). 600 mg of 3-benzyloxy-4-(4-trifluoromethoxyphenyl)-1-(2-piperidin-1-ylethyl)-1H-pyrazole are obtained in the form of a colorless oil. Mass spectrum (CI): m/z 446 ([M+H]$^+$) (base peak).

The 3-benzyloxy-4-(4-trifluoromethoxyphenyl)-1H-pyrazole can be prepared in the following way:

1.07 g of 1-(toluene-4-sulfonyl)-3-benzyloxy-4-(4-trifluoromethoxyphenyl)-1H-pyrazole, 5 cm$^3$ of a 1N solution of n-tetrabutylammonium fluoride in tetrahydrofuran and 50 cm$^3$ of tetrahydrofuran are heated, with stirring, at the reflux of the solvent for 15 hours. The reaction medium is cooled to a temperature in the region of 20° C., and taken up with 300 cm$^3$ of ethyl acetate and 100 cm$^3$ of water. The organic phase is separated by settling out, dried over anhydrous magnesium sulfate, filtered and concentrated to dryness under reduced pressure (2 kPa). The residue obtained is purified on an FC50SI-HP silica cartridge, eluting with dichloromethane. 560 mg of 3-benzyloxy-4-(4-trifluoromethoxyphenyl)-1H-pyrazole are obtained in the form of a powder. Mass spectrum (EI): m/z 334 (M$^{+\cdot}$), m/z 91 (base peak).

The 3-benzyloxy-1-(toluene-4-sulfonyl)-4-(4-trifluoromethoxyphenyl)-1H-pyrazole can be prepared in the following way:

2.04 g of 4-trifluoromethoxyphenylboronic acid, 4.96 cm$^3$ of a 2N aqueous potassium carbonate solution and 496 mg of tetrakis(triphenylphosphine)palladium are added to a solution of 1.5 g of 3-benzyloxy-4-iodo-1-(toluene-4-sulfonyl)-1H-pyrazole in a mixture of 40 cm$^3$ of toluene and ethanol (4/1 by volume) in a three-necked flask. The three-necked flask containing the reaction medium is placed in a bath preheated to a temperature in the region of 120° C.; the stirring is continued for 90 minutes at this temperature. The mixture is then cooled to a temperature in the region of 20° C., and filtered over supercel. The filtrate is taken up with 300 cm$^3$ of ethyl acetate and 100 cm$^3$ of water. The organic phase is separated by settling out and concentrated to dryness under reduced pressure (2 kPa). The residue obtained is purified on an FC50SI-HP silica cartridge, eluting with a mixture of cyclohexane and ethyl acetate (90/10 by volume). 1.07 g of 3-benzyloxy-1-(toluene-4-sulfonyl)-4-(4-trifluoromethoxyphenyl)-1H-pyrazole are obtained in the form of a yellow powder. Mass spectrum (CI): m/z 489 ([M+H]$^+$), m/z 335 (base peak).

The 3-benzyloxy-4-iodo-1-(toluene-4-sulfonyl)-1H-pyrazole can be prepared in the following way:

5 g of 3-benzyloxy-4-(4-iodophenyl)-1H-pyrazole in 110 cm$^3$ of dimethylformamide are cooled while stirring, under an inert atmosphere, to a temperature in the region of −5° C. 587 mg of sodium hydride (at 75% in liquid petroleum jelly) are added portionwise and the mixture is allowed to return to a temperature in the region of 20° C. 4.4 g of para-toluenesulfonyl chloride are then added and the stirring is maintained at this temperature for 15 hours. The reaction medium is taken up with 300 cm$^3$ of ice-cold water and 500 cm$^3$ of ethyl acetate. The organic phase is separated by settling out, washed with 300 cm$^3$ of water and 300 cm$^3$ of a saturated aqueous sodium chloride solution, dried over anhydrous magnesium sulfate, filtered and concentrated to dryness under reduced pressure (2 kPa). The residue is crystallized from diisopropyl ether. 7.24 g of 3-benzyloxy-4-iodo-1-(toluene-4-sulfonyl)-1H-pyrazole are obtained in the form of a powder. Mass spectrum (EI): m/z 454 (M$^{+\cdot}$), m/z 299, m/z 91 (base peak).

The 3-benzyloxy-4-iodo-1H-pyrazole can be prepared in the following way:

A suspension of 0.32 g of 3-benzyloxy-1H-pyrazole, 0.3 g of sodium acetate and 0.65 g of iodine in 50 cm$^3$ of chloroform is stirred at ambient temperature for 26 hours. 50 cm$^3$ of a 0.5N sodium thiosulfate solution are then added to the mixture, which is stirred until decoloration is observed and separated by settling out. The aqueous phase is extracted again with 25 cm$^3$ of chloroform. The pooled organic phases are dried over magnesium sulfate, filtered and concentrated under reduced pressure (3 kPa). The residue obtained is purified by chromatography on silica gel, eluting with a mixture of cyclohexane and ethyl acetate (80/20 by volume). After concentration of the fractions under reduced pressure, a colorless oil is obtained which crystallizes rapidly and provides 0.4 g of 3-benzyloxy-4-iodo-1H-pyrazole in the form of a white solid having an Rf of 0.6 [mixture of cyclohexane and ethyl acetate (50/50 by volume), plate of silica gel 60 F254 reference 105719, Merck]. Mass spectrum (EI): m/z 300 (M+.) (base peak).

$^1$H NMR spectrum (300 MHz, (CD$_3$)$_2$SO d6, δ in ppm): 5.22 (s: 2H); from 7.30 to 7.50 (mt: 5H); 7.74 (s: 1H); from 12.20 to 12.60 (broad unresolved peak: 1H).

EXAMPLE 39

4-Phenyl-1-(2-piperidin-1-ylpropyl)-1H-pyrazol-3-ol dihydrochloride 2 cm$^3$ of a 4N solution of hydrochloric acid in dioxane are added, at a temperature in the region of 20° C., to a mixture of 150 mg of 1-{2-[3-(cyclohex-2-enyloxy)-4-phenylpyrazol-1-yl]-1-methylethyl}piperidine in 5 cm$^3$ of anhydrous methanol. The reaction medium is stirred at this temperature for 20 hours, concentrated to dryness under reduced pressure (2 kPa), and taken up with 20 cm$^3$ of dichloromethane. The solution is concentrated to dryness under reduced pressure (2 kPa). The residue is precipitated with 20 cm$^3$ of diisopropyl ether. 110 mg of 4-phenyl-1-(2-piperidin-1-ylpropyl)-1H-pyrazol-3-ol dihydrochloride are obtained in the form of a yellow solid.

IR spectrum (KBr): 3431; 2949; 2651; 2521; 1606; 1580; 1527; 1451; 1175; 1121; 1012; 765; 698 and 672 cm$^{-1}$.

$^1$H NMR spectrum (300 MHz, (CD3)2SO d6, δ in ppm): 1.24 (d, J=6.5 Hz: 3H); 1.44 (mt: 1H); from 1.65 to 1.95 (mt: 5H); 2.95 (mt: 1H); 3.10 (mt: 1H); from 3.35 to 3.55 (mt: 2H); 3.71 (mt: 1H); 4.21 (dd, J=14.5 and 7.5 Hz: 1H); 4.43 (dd, J=14.5 and 5.5 Hz: 1H); 7.15 (broad t, J=7.5 Hz: 1H); 7.34 (broad t, J=7.5 Hz: 2H); 7.66 (broad d, J=7.5 Hz: 2H); 8.01 (s: 1H); 9.51 (unresolved peak: 1H); 10.51 (s: 1H).

The 1-{2-[3-(cyclohex-2-enyloxy)-4-phenylpyrazol-1-yl]-1-methylethyl}piperidine can be prepared in the following way:

A mixture of 0.5 g of methanesulfonic acid 2-[3-(cyclohex-2-enyloxy)-4-phenylpyrazol-1-yl]-1-methylethyl ester, 0.4 cm$^3$ of piperidine and 1.0 g of potassium carbonate in 20 cm$^3$ of dimethylformamide is heated while stirring at a temperature in the region of 80° C. for 6 hours and then for 15 hours at a temperature in the region of 20° C. The reaction medium is taken up with 100 cm³ of water and 100 cm³ of ethyl acetate. The organic phase is separated by settling out, washed with 2 times 100 cm³ of water and 100 cm³ of a saturated aqueous sodium chloride solution, dried over anhydrous magnesium sulfate, filtered and concentrated to dryness under reduced pressure (2 kPa). The residue is purified by chromatography, under a nitrogen pressure of 50 kPa, on a column of silica gel (particle size 20-45µ; diameter 2 cm; height 40 cm), eluting with a mixture of cyclohexane and ethyl acetate (80/20 by volume). After concentration of the fractions under reduced pressure (2 kPa), 150 mg of 1-{2-[3-(cyclohex-2-enyloxy)-4-phenylpyrazol-1-yl]-1-methylethyl}piperidine are obtained in the form of a yellow oil. Mass spectrum (EI): m/z 365 (M$^{+\cdot}$), m/z 112 (base peak).

The methanesulfonic acid 2-[3-(cyclohex-2-enyloxy)-4-phenylpyrazol-1-yl]-1-methylethyl ester can be prepared in the following way:

1 cm³ of methanesulfonyl chloride and 2.59 cm³ of triethylamine are added to a stirred solution of 550 mg of 1-[3-(cyclohex-2-enyloxy)-4-phenylpyrazol-1-yl]-propan-2-ol in 30 cm³ of dichloromethane, at a temperature in the region of 20° C. The reaction medium is stirred for 7 hours at a temperature in the region of 20° C., and taken up with 50 cm³ of distilled water and 50 cm³ of ethyl acetate. The organic phase is separated by settling out, dried over anhydrous magnesium sulfate, filtered and concentrated to dryness under reduced pressure (2 kPa). The residue is purified by chromatography, under a nitrogen pressure of 50 kPa, on a column of silica gel (particle size 20-45µ; diameter 4 cm; height 60 cm), eluting with a mixture of cyclohexane and ethyl acetate (80/20 by volume). After concentration of the fractions under reduced pressure (2 kPa), 300 mg of methanesulfonic acid 2-[3-(cyclohex-2-enyloxy)-4-phenylpyrazol-1-yl]-1-methylethyl ester are obtained in the form of a colorless oil. Mass spectrum (EI): m/z 376 (M$^{+\cdot}$), m/z 296 (base peak).

The 1-[3-(cyclohex-2-enyloxy)-4-phenylpyrazol-1-yl]-propan-2-ol can be prepared in the following way:

2.4 g of 3-(cyclohex-2-enyloxy)-4-phenyl-1H-pyrazole are dissolved in 25 cm³ of anhydrous dimethylformamide under an inert atmosphere and with stirring. 2.24 g of potassium tert-butoxide, followed by 0.7 cm³ of methyloxirane are added at a temperature in the region of 20° C. The reaction medium is heated at a temperature in the region of 60° C. for 1 hour. A further 0.7 cm³ of methyloxirane is then added and the mixture is heated for 1 hour at a temperature in the region of 60° C. The mixture is cooled to a temperature in the region of 20° C., and taken up with 200 cm³ of water and 200 cm³ of ethyl acetate. The organic phase is separated by settling out, washed with 3 times 200 cm³ of water and 200 cm³ of a saturated aqueous sodium chloride solution, dried over anhydrous magnesium sulfate, filtered and concentrated to dryness under reduced pressure (2 kPa). The residue is purified by chromatography, under a nitrogen pressure of 50 kPa, on a column of silica gel (particle size 20-45µ; diameter 4 cm; height 50 cm), eluting with a mixture of cyclohexane and ethyl acetate (80/20 by volume). After concentration of the fractions under reduced pressure (2 kPa), 450 mg of 1-[3-(cyclohex-2-enyloxy)-4-phenylpyrazol-1-yl]propan-2-ol are obtained in the form of a colorless oil. Mass spectrum (EI): m/z 298 (M$^{+\cdot}$), m/z 218, m/z 173 (base peak)

EXAMPLE 40

3-(4-Phenylpyrazol-1-ylmethyl)-1-aza-bicyclo[2.2.2]-octane dihydrochloride

A solution of 0.4 g of 3-(pyrazol-1-ylmethyl)-1-azabicyclo[2.2.2]octane in 5 cm³ of dimethylformamide is added to a mixture of 0.4 g of sodium hydride (at 75% in liquid petroleum jelly) and of 10 cm³ of dimethyl-formamide. The reaction medium is heated at a temperature in the region of 50° C. for approximately 1 hour, and the solution is then cooled to a temperature in the region of 20° C. 1.75 g of 3-chloro-methylquinuclidine are added slowly, and the reaction medium is heated at a temperature in the region of 50° C. for 16 hours and then cooled to a temperature in the region of 20° C. The mixture is taken up with 100 cm³ of water and 100 cm³ of ethyl acetate. The organic phase is separated by settling out, washed with 2 times 100 cm³ of water and 100 cm³ of a saturated aqueous sodium chloride solution, and then concentrated to dryness under reduced pressure (2 kPa). The residue is purified by chromatography, under a nitrogen pressure of 50 kPa, on a column of alumina CTB1 (diameter 3 cm; height 40 cm), eluting with ethyl acetate and then with a mixture of ethyl acetate and methanol (98/2, 95/5 then 90/10 by volume), collecting fractions of 60 cm³. Fractions 14 to 20 are concentrated under reduced pressure. The residue obtained is purified a second time by chromatography, under a nitrogen pressure (50 kPa), on a column of alumina CTB1 (diameter 3 cm; height 40 cm), eluting with ethyl acetate and then with a mixture of ethyl acetate and methanol (98/2, 95/5 then 90/10 by volume), collecting fractions of 60 cm³. Fractions 14 to 20 are concentrated under reduced pressure. 150 mg of 3-(4-phenylpyrazol-1-ylmethyl)-1-azabicyclo[2.2.2]octane are obtained. The dihydrochloride is prepared with 1.2 cm³ of a 4.7N solution of hydrochloric acid in isopropyl ether and 5 cm³ of ethanol. 230 mg of 3-(4-phenylpyrazol-1-yl-methyl)-1-azabicyclo[2.2.2]octane dihydrochloride are obtained.

$^1$H NMR spectrum (300 MHz, (CD3)2SO d6, δ in ppm): from 1.65 to 1.95 (mt: 4H); from 2.00 to 2.15 (mt: 1H); 2.62 (mt: 1H); 2.97 (broad dd, J=13 and 7 Hz: 1H); from 3.10 to 3.40 (mt: 5H); 4.25 (dd, J=13 and 8 Hz: 1H); 4.32 (dd, J=13 and 8 Hz: 1H); 7.21 (broad t, J=7.5 Hz: 1H); 7.38 (t, J=7.5 Hz: 2H); 7.59 (broad d, J=7.5 Hz: 2H); 7.94 (s: 1H); 8.25 (s: 1H); 10.44 (unresolved peak: 1H). Mass spectrum (EI): m/z 267 (M$^{+\cdot}$) (base peak), m/z 183, m/z 123.

The 4-phenyl-1H-pyrazole can be prepared in the following way:

1.044 g of 4-phenyl-1-(toluene-4-sulfonyl)-1H-pyrazole, 7 cm³ of a 1N solution of n-tetrabutylammonium fluoride in tetrahydrofuran and 35 cm³ of tetrahydrofuran are heated at a temperature in the region of 70° C. for 6 hours. A further 3.5 cm³ of a 1N solution of n-tetrabutylammonium fluoride in tetrahydrofuran are added and heating is continued for 15 hours at this temperature. The reaction medium is cooled to a temperature in the region of 20° C., concentrated to dryness under reduced pressure (2 kPa) and then taken up with 100 cm³ of ethyl acetate and 100 cm³ of water. The organic phase is separated by settling out, washed with 100 cm³ of water and 100 cm³ of a saturated aqueous sodium chloride solution, dried over anhydrous magnesium sulfate, filtered and concentrated to dryness under reduced pressure (2 kPa) The residue obtained is taken up with 20 cm³ of dichloromethane. The precipitate is filtered off and dried. 0.4 g of 4-phenyl-1H-pyrazole is obtained in the form of a white powder. Mass spectrum (EI): m/z 144 (M$^{+\cdot}$) (base peak).

The 4-phenyl-1-(toluene-4-sulfonyl)-1H-pyrazole can be prepared in the following way:

11.72 g of phenylboronic acid are added to a stirred solution of 8.7 g of 4-iodo-1-(toluene-4-sulfonyl)-1H-pyrazole in 200 cm³ of 1,2-dimethoxyethane under an inert atmosphere. The reaction medium is heated to 110° C. and then 20.63 g of finely ground tribasic potassium phosphate and 2.18 g of bis(triphenyl-phosphine)palladium chloride are added; the mixture is heated at the reflux of the solvent for 3 hours and then cooled to a temperature in the region of 20° C. and then filtered over supercel. The filtrate is taken up with 250 cm³ of ethyl acetate and washed with 8 times 100 cm³ of water and 100 cm³ of a saturated aqueous sodium chloride solution. The organic phase is separated by settling out, dried over anhydrous magnesium sulfate, filtered and concentrated to dryness under reduced pressure (2 kPa). The residue is purified by chromatography, under a nitrogen pressure of 50 kPa, on a column of silica gel (particle size 20-45µ; diameter 6 cm; height 45 cm), eluting with a mixture of cyclohexane and ethyl acetate (70/30 by volume), collecting fractions of 20 cm³. Fractions 6 to 12 are concentrated under reduced pressure. 4.04 g of 4-phenyl-1-(toluene-4-sulfonyl)-1H-pyrazole are obtained in the form of white crystals. Mass spectrum (EI): m/z 298 ($M^{+\cdot}$) (base peak), m/z 234, m/z 91.

The 4-iodo-1-(toluene-4-sulfonyl)-1H-pyrazole can be prepared in the following way:

A stirred solution of 10 g of 4-iodo-1H-pyrazole in 300 cm³ of dimethylformamide, under an inert atmosphere, is cooled to a temperature in the region of −3° C. 1.8 g of sodium hydride (at 75% in liquid petroleum jelly) are added over 5 minutes and the temperature is allowed to return to approximately 20° C. 13.9 g of para-toluenesulfonyl chloride are then added and the stirring is maintained for 3 hours at this temperature. The reaction medium is taken up with 100 g of ice and then 700 cm³ of water and 700 cm³ of ethyl acetate. The organic phase is separated by settling out, washed with 9 times 300 cm³ of water and 2 times 100 cm³ of an aqueous sodium chloride solution, dried over anhydrous magnesium sulfate, filtered and then concentrated under reduced pressure (2 kPa). The residue is recrystallized from 1 000 cm³ of diisopropyl ether. 10.9 g of 4-iodo-1-(toluene-4-sulfonyl)-1H-pyrazole are obtained in the form of white crystals. Mass spectrum (EI): m/z 348 ($M^{+\cdot}$), m/z 284, m/z 91 (base peak).

EXAMPLE 41

4-(5-Chlorothiophen-2-yl)-1-(2-piperidin-1-ylethyl)-1H-pyrazol-3-ol hydrochloride The product is prepared according to the procedure described for the preparation of 4-(4-trifluoro-methoxyphenyl)-1-(2-piperidin-1-ylethyl)-1H-pyrazol-3-ol, using 400 mg of 3-benzyloxy-4-(5-chlorothiophen-2-yl)-1-(2-piperidin-1-ylethyl)-1H-pyrazole, 3.3 cm³ of 12N hydrochloric acid and 3.3 cm³ of ethanol. The medium is taken up with diisopropyl ether and filtered over sintered glass. The filtrate is precipitated from ethanol. 160 mg of the expected product are obtained in the form of a powder.

¹H NMR spectrum (300 MHz, (CD₃)₂SO d6, δ in ppm): from 1.25 to 1.50 (mt: 1H); from 1.60 to 1.90 (mt: 5H); from 2.80 to 3.00 (unresolved peak: 2H); from 3.35 to 3.50 (mt: 4H); 4.40 (broad t, J=6.5 Hz: 2H); 7.00 (d, J=5.5 Hz: 1H); 7.03 (d, J=5.5 Hz: 1H); 7.97 (s: 1H); from 10.00 to 10.30 (unresolved peak: 1H); 10.78 (broad s: 1H). Mass spectrum (CI): m/z 312 ([M+H]⁺) (base peak).

The 3-benzyloxy-4-(5-chlorothiophen-2-yl)-1-(2-piperidin-1-ylethyl)-1H-pyrazole can be prepared in the following way:

The product is prepared according to the procedure described for the preparation of 3-benzyloxy-4-(4-trifluoromethoxyphenyl)-1-(2-piperidin-1-ylethyl)-1H-pyrazole, using 345 mg of 3-benzyloxy-4-(5-chlorothiophen-2-yl)-1H-pyrazole, 100 mg of sodium hydride at 75% in liquid petroleum jelly, 305 mg of 1-(2-chloroethyl)piperidine and 10 cm³ of anhydrous dimethylformamide. After purification on an FC50SI-HP silica cartridge, eluting with a mixture of dichloromethane and methanol (95/5 by volume), 400 mg of the expected product are obtained in the form of an orange-colored oil. Mass spectrum (CI): m/z 402 ([M+H]⁺) (base peak).

The 3-benzyloxy-4-(5-chlorothiophen-2-yl)-1H-pyrazole can be prepared in the following way:

The product is prepared according to the procedure described for the preparation of 3-benzyloxy-4-(4-trifluoromethoxyphenyl)-1H-pyrazole, using 740 mg of 3-benzyloxy-4-(5-chlorothiophen-2-yl)-1-(toluene-4-sulfonyl)-1H-pyrazole, 3.8 cm³ of a 1N solution of n-tetrabutylammonium fluoride in tetrahydrofuran and 38 cm³ of tetrahydrofuran. After purification on an FC50SI-HP silica cartridge, eluting with a mixture of dichloromethane and methanol (95/5 by volume), 345 mg of the expected product are obtained in the form of an ecru-colored powder. Mass spectrum (EI): m/z 290 ($M^{+\cdot}$), m/z 91 (base peak)

The 3-benzyloxy-4-(5-chlorothiophen-2-yl)-1-(toluene-4-sulfonyl)-1H-pyrazole can be prepared in the following way:

589 mg of 2-bromo-5-chlorothiophene, 32.5 mg of tris(trifuryl)phosphine and 34.7 mg of tris(di-benzylideneacetone)dipalladium are added, with stirring and under an inert atmosphere, to a solution of 1.8 g of 3-benzyloxy-1-(toluene-4-sulfonyl)-4-tributyl-stannanyl-1H-pyrazole in 20 cm³ of dioxane. The reaction medium is heated at a temperature in the region of 100° C. for 15 hours. The mixture is then cooled to a temperature in the region of 20° C., and filtered over supercel. The filtrate is concentrated to dryness under reduced pressure (2 kPa), and taken up with cyclohexane; the insoluble material is filtered off over sintered glass, and the filtrate is concentrated to dryness under reduced pressure (2 kPa); the residue obtained is purified on an FC50SI-HP silica cartridge, eluting with a mixture of cyclohexane and ethyl acetate (90/10 by volume). 200 mg of 3-benzyloxy-4-(5-chlorothiophen-2-yl)-1-(toluene-4-sulfonyl)-1H-pyrazole are obtained in the form of a yellow powder. Mass spectrum (EI): m/z 444 ($M^{+\cdot}$), m/z 289 and m/z 91 (base peak).

The 3-benzyloxy-1-(toluene-4-sulfonyl)-4-tributyl-stannanyl-1H-pyrazole can be prepared in the following way:

325 mg of triphenylphosphine, 5.9 cm³ of 1,1,1,2,2,2-hexabutyldistannane and 141.3 mg of palladium diacetate are added, with stirring and under an inert atmosphere, to a solution of 4.4 g of 3-benzyloxy-4-iodo-1-(toluene-4-sulfonyl)-1H-pyrazole in 45 cm³ of dimethylformamide. The reaction medium is heated at a temperature in the region of 80° C. for 1 hour. The mixture is then cooled to a temperature in the region of 20° C., and filtered over supercel. The filtrate is taken up with 200 cm³ of water and 100 cm³ of ethyl acetate. The organic phase is separated by settling out, washed with 3 times 100 cm³ of water, dried over anhydrous magnesium sulfate, filtered and concentrated to dryness under reduced pressure (2 kPa). The residue is purified by chromatography, under a nitrogen pressure of 50 kPa, on a column of silica gel (particle size 20-45µ; diameter 2 cm; height 40 cm), eluting with a mixture of cyclohexane and ethyl acetate (95/5 by volume). 4.5 g of 3-benzyloxy-1-(toluene-4-sulfonyl)-4-tributylstannanyl-1H-pyrazole are obtained in the form of a yellow oil. Mass spectrum (EI): m/z 618 ($M^{+\cdot}$), m/z 561 (base peak).

EXAMPLE 42

4-(3-Methoxyphenyl)-1-(2-piperidin-1-ylethyl)-1H-pyrazol-3-ol hydrochloride

The product is prepared according to the procedure described for the preparation of 4-(4-trifluorometh-oxyphenyl)-1-(2-piperidin-1-ylethyl)-1H-pyrazol-3-ol, using 760 mg of 3-benzyloxy-4-(3-methoxyphenyl)-1-(2-piperidin-1-ylethyl)-1H-pyrazole, 6.5 cm³ of 12N hydrochloric acid and 6.5 cm³ of ethanol. The medium is concentrated to dryness under reduced pressure (2 kPa); the residue is precipitated from ethanol. 232 mg of the expected product are obtained in the form of a powder.

$^1$H NMR spectrum (300 MHz, $(CD_3)_2SO$ d6, δ in ppm): from 1.25 to 1.50 (unresolved peak: 1H); from 1.60 to 1.90 (mt: 5H); from 2.80 to 3.05 (unresolved peak: 2H); from 3.35 to 3.55 (unresolved peak: 4H); 3.78 (s: 3H); 4.38 (mt: 2H); 6.72 (ddd, J=7-6 and 3 Hz: 1H); from 7.15 to 7.30 (mt: 3H); 8.05 (s: 1H); from 9.80 to 10.10 (broad unresolved peak: 1H); 10.45 (unresolved peak: 1H). Mass spectrum (EI): m/z 301 (M$^{+\cdot}$), m/z 98 (base peak).

The 3-benzyloxy-4-(3-methoxyphenyl)-1-(2-piperidin-1-ylethyl)-1H-pyrazole can be prepared in the following way:

The product is prepared according to the procedure described for the preparation of 3-benzyloxy-4-(4-trifluoromethoxyphenyl)-1-(2-piperidin-1-ylethyl)-1H-pyrazole, using 590 mg of 3-benzyloxy-4-(3-methoxyphenyl)-1H-pyrazole, 176 mg of sodium hydride (at 75% in liquid petroleum jelly), 542 mg of 1-(2-chloroethyl)piperidine and 10 cm³ of anhydrous dimethylformamide. After purification on an FC50SI-HP silica cartridge, eluting with a mixture of dichloromethane and methanol (98/2 by volume), 760 mg of the expected product are obtained in the form of a colorless oil. Mass spectrum (EI): m/z 391 (M$^{+\cdot}$), m/z 98 (base peak).

The 3-benzyloxy-4-(3-methoxyphenyl)-1H-pyrazole can be prepared in the following way:

The product is prepared according to the procedure described for the preparation of 3-benzyloxy-4-(4-trifluoromethoxyphenyl)-1H-pyrazole, using 1.32 g of 3-benzyloxy-4-(3-methoxyphenyl)-1-(toluene-4-sulfonyl)-1H-pyrazole, 6.94 cm³ of a 1N solution of n-tetrabutylammonium fluoride in tetrahydrofuran and 80 cm³ of tetrahydrofuran. After purification by precipitation from diethyl ether and purification on an FC50SI-HP silica cartridge, eluting with a mixture of dichloromethane and methanol (95/5 by volume), 590 mg of the expected product are obtained. Mass spectrum (EI): m/z 280 (M$^{+\cdot}$), m/z 91 (base peak).

The 3-benzyloxy-4-(3-methoxyphenyl)-1-(toluene-4-sulfonyl)-1H-pyrazole can be prepared in the following way:

The product is prepared according to the procedure described for the preparation of 3-benzyloxy-1-(toluene-4-sulfonyl)-4-(4-trifluoromethoxyphenyl)-1H-pyrazole, using 1.5 g of 3-benzyloxy-4-iodo-1-(toluene-4-sulfonyl)-1H-pyrazole, 1.5 g of 3-methoxyphenyl-boronic acid, 496 mg of tetrakis(triphenylphosphine)-palladium, and 496 cm³ of a 2N aqueous solution of potassium carbonate in a mixture of 30 cm³ of toluene and ethanol (4/1 by volume). After purification on an FC50SI-HP silica cartridge, eluting with a mixture of cyclohexane and ethyl acetate (90/10 by volume), 1.13 g of the expected product are obtained in the form of pale yellow crystals. Mass spectrum (EI): m/z 434 (M$^{+\cdot}$), m/z 279 and m/z 91 (base peak).

EXAMPLE 43

4-(2-Methoxyphenyl)-1-(2-piperidin-1-ylethyl)-1H-pyrazol-3-ol hydrochloride

The product is prepared according to the procedure described for the preparation of 4-(4-trifluoromethoxy-phenyl)-1-(2-piperidin-1-ylethyl)-1H-pyrazol-3-ol, using 450 mg of 3-benzyloxy-4-(2-methoxyphenyl)-1-(2-piperidin-1-ylethyl)-1H-pyrazole, 3.8 cm³ of 12N hydrochloric acid and 3.8 cm³ of ethanol. The medium is concentrated to dryness under reduced pressure (2 kPa); the residue is precipitated from acetonitrile. 380 mg of the expected product are obtained in the form of a yellow powder.

$^1$H NMR spectrum (300 MHz, $(CD_3)_2SO$ d6, δ in ppm): from 1.25 to 1.50 (mt: 1H); from 1.60 to 1.90 (mt: 5H); 2.94 (mt: 2H); from 3.30 to 3.60 (mt: 4H); 3.86 (s: 3H); 4.44 (t, J=6.5 Hz: 2H); 6.95 (double doublet of triplet, J=7.5 and 1 Hz: 1H); 7.05 (broad d, J=7.5 Hz: 1H); 7.17 (double doublet of triplet, J=7.5 and 1.5 Hz: 1H); 7.91 (dd, J=7.5 and 1.5 Hz: 1H); 8.03 (s: 1H); from 10.10 to 10.30 (unresolved peak: 1H); from 10.20 to 10.45 (broad unresolved peak: 1H).

Mass spectrum (CI): m/z 302 ([M+H]$^+$) (base peak).

The 3-benzyloxy-4-(2-methoxyphenyl)-1-(2-piperidin-1-ylethyl)-1H-pyrazole can be prepared in the following way:

The product is prepared according to the procedure described for the preparation of 3-benzyloxy-4-(4-trifluoromethoxyphenyl)-1-(2-piperidin-1-ylethyl)-1H-pyrazole, using 382 mg of 3-benzyloxy-4-(2-methoxy-phenyl)-1H-pyrazole, 114 mg of sodium hydride at 75% in liquid petroleum jelly, 351 mg of 1-(2-chloroethyl)-piperidine and 11 cm³ of anhydrous dimethylformamide. After purification on an FC50SI-HP silica cartridge, eluting with a mixture of dichloromethane and methanol (95/5 by volume), 450 mg of the expected product are obtained in the form of a pale yellow oil. Mass spectrum (EI): m/z 391 (M$^{+\cdot}$), m/z 98 (base peak).

The 3-benzyloxy-4-(2-methoxyphenyl)-1H-pyrazole can be prepared in the following way:

The product is prepared according to the procedure described for the preparation of 3-benzyloxy-4-(4-trifluoromethoxyphenyl)-1H-pyrazole, using 720 mg of 3-benzyloxy-4-(2-methoxyphenyl)-1-(toluene-4-sulfonyl)-1H-pyrazole, 3.5 cm³ of an N solution of n-tetrabutyl-ammonium fluoride in tetrahydrofuran and 50 cm³ of tetrahydrofuran. After purification on an FC50SI-HP silica cartridge, eluting with a mixture of dichloromethane and methanol (95/5 by volume), 382 mg of the expected product are obtained in the form of a pinkish beige solid. Mass spectrum (EI): m/z 280 (M+.), m/z 91 (base peak).

The 3-benzyloxy-4-(2-methoxyphenyl)-1-(toluene-4-sulfonyl)-1H-pyrazole can be prepared in the following way:

The product is prepared according to the procedure described for the preparation of 3-benzyloxy-1-(toluene-4-sulfonyl)-4-(4-trifluoromethoxyphenyl)-1H-pyrazole, using 1 g of 3-benzyloxy-4-iodo-1-(toluene-4-sulfonyl)-1H-pyrazole, 1 g of 2-methoxyphenylboronic acid, 330 mg of tetrakis (triphenylphosphine)palladium, and 3.3 cm³ of a 2N aqueous solution of potassium carbonate in a mixture of 15 cm³ of toluene and ethanol (4/1 by volume). After purification on an FC50SI-HP silica cartridge, eluting with a mixture of cyclohexane and ethyl acetate (80/20 by volume), 720 mg of the expected product are obtained in the form of a beige powder. Mass spectrum (CI): m/z 435 ([M+H]+) and m/z 281 (base peak).

EXAMPLE 44

4-(3-Hydroxyphenyl)-1-(2-piperidin-1-ylethyl)-1H-pyrazol-3-ol hydrochloride

A stirred solution of 516 mg of 4-(3-methoxyphenyl)-1-(2-piperidin-1-ylethyl)-1H-pyrazol-3-ol hydrochloride in 13 cm³ of dichloromethane, under an inert atmosphere, is cooled to a temperature in the region of −78° C. 4.38 cm³ of boron tribromide are added and the stirring is continued for 15 hours at a temperature in the region of 20° C. The solution is taken up with methanol and is then concentrated to dryness under reduced pressure (2 kPa). The residue is taken up with 20 cm³ of water and 20 cm³ of dichloromethane. The organic phase is separated by settling out; the aqueous phase is washed with a saturated aqueous sodium bicarbonate solution until a pH of 8-8.4 is obtained (pH meter), and then taken up with dichloromethane. The organic phase is separated by settling out, and concentrated to dryness under reduced pressure (2 kPa). The white powder obtained is taken up with 0.4 cm³ of 12N hydrochloric acid and 5 cm³ of dioxane. The mixture is stirred for 10 minutes and is then concentrated to dryness under reduced pressure (2 kPa). 198 mg of 4-(3-hydroxyphenyl)-1-(2-piperidin-1-ylethyl)-1H-pyrazol-3-ol hydrochloride are obtained in the form of an ecru-colored powder.

$^1$H NMR spectrum (300 MHz, $(CD_3)_2SO$ d6, δ in ppm): from 1.25 to 1.50 (mt: 1H); from 1.60 to 1.90 (mt: 5H); 2.94 (mt: 2H); from 3.30 to 3.55 (mt: 4H); 4.40 (t, J=6.5 Hz: 2H); 6.55 (ddd, J=8-3 and 1.5 Hz: 1H); from 7.00 to 7.15 (mt: 3H); 8.06 (s: 1H); from 9.10 to 9.40 (broad unresolved peak: 1H); from 9.90 to 10.10 (unresolved peak: 1H); from 10.30 to 10.45 (unresolved peak: 1H). Mass spectrum (EI): m/z 287 (M+.), m/z 98 (base peak).

EXAMPLE 45

4-(4-Hydroxyphenyl)-1-(2-piperidin-1-ylethyl)-1H-pyrazol-3-ol hydrochloride 200 mg of 4-(4-methoxyphenyl)-1-(2-piperidin-1-ylethyl)-1H-pyrazol-3-ol hydrochloride are brought to pH 7 (Lyphan paper) with a 1N aqueous sodium hydroxide solution. The organic phase is extracted with dichloromethane and concentrated to dryness under reduced pressure (2 kPa). The residue is taken up with 5 cm³ of dichloromethane. The stirred solution is cooled to a temperature in the region of −78° C. 1.7 cm³ of boron tribromide are added and the stirring is continued for 15 hours at a temperature in the region of 20° C. The solution is taken up with 20 cm³ of ice-cold water and 10 cm³ of dichloromethane. The organic phase is separated by settling out; the aqueous phase is washed with dichloromethane and then with a saturated aqueous sodium bicarbonate solution until a pH of 8-8.4 (pH meter) is obtained, and then taken up with dichloromethane. The organic phase is separated by settling out, and concentrated to dryness under reduced pressure (2 kPa). The white powder obtained is taken up with 300 µl of 12N hydrochloric acid and 5 cm³ of dioxane. The mixture is stirred for 10 minutes and then concentrated to dryness under reduced pressure (2 kPa). 101 mg of 4-(4-hydroxyphenyl)-1-(2-piperidin-1-ylethyl)-1H-pyrazol-3-ol hydrochloride are obtained in the form of an ecru-colored powder.

$^1$H NMR spectrum (300 MHz, $(CD_3)_2SO$ d6, δ in ppm): from 1.25 to 1.50 (mt: 1H); from 1.60 to 1.90 (mt: 5H); 2.92 (mt: 2H); from 3.30 to 3.50 (mt: 4H); 4.38 (t, J=6.5 Hz: 2H); 6.75 (broad d, J=8.5 Hz: 2H); 7.45 (broad d, J=8.5 Hz: 2H); 7.85 (s: 1H); from 9.10 to 9.35 (broad unresolved peak: 1H); from 10.00 to 10.20 (unresolved peak: 1H); from 10.15 to 10.30 (unresolved peak: 1H).

Mass spectrum (EI): m/z 287 (M+.), m/z 98 (base peak).

EXAMPLE 46

4-(4-Methoxyphenyl)-1-(2-piperidin-1-ylethyl)-1H-pyrazol-3-ol dihydrochloride 7 cm³ of 1N hydrochloric diethyl ether are added to a solution of 640 mg of 1-{2-[3-benzyloxy-4-(4-methoxyphenyl)pyrazol-1-yl]ethyl}piperidine in 20 cm³ of ethanol. After stirring for 30 min at a temperature in the region of 20° C., the solution is evaporated to dryness under reduced pressure (2.7 kPa). The residue is taken up with 20 cm³ of ethanol. The solution obtained is introduced into an autoclave, and 87 mg of palladium-on-charcoal at 10% are added, and it is then placed under hydrogen (8 bar). After stirring for 8 h at a temperature in the region of 30° C., the reaction medium is filtered over supercel and the filtrate is evaporated. Diisopropyl ether is added to the residue, resulting in a suspension, which is heated at the reflux of the solvent and filtered under hot conditions. The resulting solid is dried under vacuum (2.7 kPa) to give 400 mg of 4-(4-methoxyphenyl)-1-(2-piperidin-1-ylethyl)-1H-pyrazol-3-ol dihydrochloride in the form of a white powder.

IR spectrum (KBr): 3052; 2933; 2655; 2559; 1578; 1569; 1518; 1501; 1453; 1248; 1170; 1020; 837; 810; 652 and 528 cm$^{-1}$.

$^1$H NMR spectrum (300 MHz, $(CD_3)_2SO$ d6, δ in ppm): from 1.30 to 1.50 (mt: 1H); from 1.60 to 1.90 (mt: 5H); from 2.80 to 3.05 (mt: 2H); 3.46 (mt: 4H); 3.76 (s: 3H); 4.37 (broad t, J=6 Hz: 2H); 6.93 (d, J=8.5 Hz: 2H); 7.57 (d, J=8.5 Hz: 2H); 7.92 (broad s: 1H); from 9.75 to 9.95 (broad unresolved peak: 1H); 10.32 (broad s: 1H).

The 1-{2-[3-benzyloxy-4-(4-methoxyphenyl)pyrazol-1-yl]ethyl}piperidine can be prepared in the following way:

2 g of 4-methoxyphenylboronic acid, 2.85 g of potassium phosphate and 750 mg of bis(triphenylphosphine)palladium chloride are added to a stirred solution of 1.2 g of 1-[2-(3-benzyloxy-4-bromopyrazol-1-yl)ethyl]piperidine in 60 cm³ of 1,2-dimethoxyethane under an argon atmosphere. After heating for 15 h at the reflux of the solvent, the reaction medium is evaporated under reduced pressure (2.7 kPa). Ethyl acetate and water are added to the residue, which is filtered over supercel. The filtrate is separated by settling out, and the organic phase is washed successively with water, a saturated aqueous hydrogen carbonate solution, and a saturated aqueous sodium chloride solution; it is dried over magnesium sulfate, filtered and evaporated under reduced pressure (2.7 kPa). The brown oil obtained (3.6 g) is purified by flash chromatography on alumina CTB1 under an argon pressure (50 kPa) [eluent: cyclohexane/ethyl acetate (90/10 by volume)]. After concentration of the fractions under reduced pressure (2.7 kPa), 700 mg of 1-{2-[3-benzyloxy-4-(4-methoxyphenyl)pyrazol-1-yl]ethyl}piperidine are obtained in the form of a yellow oil.

Mass spectrum (EI): m/z 391 (M$^+$·), m/z 280 [(M−$C_7H_{13}N)^+$·], m/z 111 $(C_7H_{13}N^+·)$, m/z 98 $(C_6H_{12}N^+)$, m/z 91 $(C_7H_7^+)$.

EXAMPLE 47

4-(3-Fluorophenyl)-1-(2-piperidin-1-ylethyl)-1H-pyrazol-3-ol dihydrochloride 3.5 cm³ of 12N hydrochloric acid are added to a stirred solution of 400 mg of 1-{2-[3-benzyloxy-4-(3-fluorophenyl)pyrazol-1-yl]ethyl}piperidine in 3.5 cm³ of ethanol. After 7 h at the reflux of the solvent, and then 15 h at a temperature in the region of 20° C., the reaction medium is evaporated to dryness under reduced pressure (2.7 kPa). The residue is dried under vacuum (2.7 kPa) at 45° C. for 1 h, and is triturated in diisopropyl ether. The precipitate formed is filtered and dried under vacuum (2.7 kPa) to give 350 mg of 4-(3-fluorophenyl)-1-(2-piperidin-1-ylethyl)-1H-pyrazol-3-ol dihydrochloride in the form of a white solid.

IR spectrum (KBr): 2951; 2647; 2540; 1619; 1586; 1530; 1456; 1267; 1178; 882; 785; 687 and 523 cm$^{-1}$.

¹H NMR spectrum (300 MHz, (CD₃)₂SO d6 with the addition of a few drops of CD₃COOD d4, δ in ppm): 1.42 (mt: 1H); from 1.60 to 1.90 (mt: 5H); 2.95 (mt: 2H); from 3.40 to 3.55 (mt: 2H); 3.50 (t, J=6.5 Hz: 2H); 4.39 (t, J=6.5 Hz: 2H); 6.95 (tdd, J=7.5-3 and 1 Hz: 1H); from 7.30 to 7.50 (mt: 3H); 8.09 (s: 1H).

The 1-{2-[3-benzyloxy-4-(3-fluorophenyl)pyrazol-1-yl]-ethyl}piperidine can be prepared in the following way:

1.15 g of 3-fluorophenylboronic acid, 4.1 cm³ of a 2N aqueous potassium carbonate solution and 475 mg of tetrakis (triphenylphosphine)palladium are added to a stirred solution, under an argon atmosphere, of 1 g of 1-[2-(3-benzyloxy-4-bromopyrazol-1-yl)ethyl]piperidine in a mixture of 20 cm³ of toluene and of 5 cm³ of ethanol. After heating at the reflux of the solvent for 3 h and at a temperature in the region of 20° C. for 15 h, ethyl acetate and water are added to the reaction medium, which is filtered over supercel. The filtrate is separated by settling out, and the organic phase is then washed successively with 2 times water and a saturated aqueous sodium chloride solution; it is dried over magnesium sulfate, filtered and evaporated under reduced pressure (2.7 kPa). The brown oil obtained (2.1 g) is purified by flash chromatography on silica under an argon pressure (50 kPa) [eluent: ethyl acetate]. After concentration of the fractions under reduced pressure, 400 mg of 1-{2-[3-benzyloxy-4-(3-fluorophenyl)pyrazol-1-yl]ethyl}piperidine are obtained in the form of a yellow oil.

IR spectrum (CCl₄): 2939; 2854; 2802; 1617; 1586; 1509; 1463; 1432; 1359; 1272; 1187; 1169; 1160; 1043; 883; 695 and 687 cm⁻¹.

EXAMPLE 48

1-(2-Piperidin-1-ylethyl)-4-(3-trifluoromethylphenyl)-1H-pyrazol-3-ol dihydrochloride 5 cm³ of 12N hydrochloric acid are added to a stirred solution of 470 mg of 1-{2-[3-benzyloxy-4-(3-trifluoro-methylphenyl)pyrazol-1-yl]ethyl}piperidine in 5 cm³ of ethanol. After 7 h at the reflux of the solvent, and then 15 h at a temperature in the region of 20° C., the reaction medium is evaporated to dryness under reduced pressure (2.7 kPa). The residue is dried under vacuum (2.7 kPa) at 45° C. for 1 h, and is then triturated in diisopropyl ether. The precipitate formed is filtered and dried under vacuum (2.7 kPa) to give 350 mg of 1-(2-piperidin-1-ylethyl)-4-(3-trifluoromethylphenyl)-1H-pyrazol-3-ol dihydrochloride in the form of a pale yellow solid.

IR spectrum (KBr): 2955; 2629; 2533; 1619; 1533; 1325; 1188; 1170; 1117; 1076; 800; 696 and 688 cm⁻¹.

¹H NMR spectrum (300 MHz, (CD₃)₂SO d6, δ in ppm): 1.40 (mt: 1H); from 1.60 to 1.90 (mt: 5H); 2.94 (mt: 2H); from 3.30 to 3.55 (mt: 4H); 4.43 (t, J=6.5 Hz: 2H); 7.50 (broad d, J=7.5 Hz: 1H); 7.59 (t, J=7.5 Hz: 1H); 7.95 (broad d, J=7.5 Hz: 1H); 8.01 (broad s: 1H); 8.22 (s: 1H); 10.24 (unresolved peak: 1H); from 10.60 to 10.90 (broad unresolved peak: 1H).

The 1-{2-[3-benzyloxy-4-(3-trifluoromethylphenyl)-pyrazol-1-yl]ethyl}piperidine can be prepared in the following way:

1.58 g of 3-trifluoromethylphenylboronic acid, 4.1 cm³ of a 2N aqueous potassium carbonate solution and 475 mg of tetrakis(triphenylphosphine)palladium are added to a stirred solution, under an argon atmosphere, of 1 g of 1-[2-(3-benzyloxy-4-bromopyrazol-1-yl)ethyl]piperidine in a mixture of 20 cm³ of toluene and of 5 cm³ of ethanol. After heating at the reflux of the solvent for 3 h, the reaction medium is evaporated under reduced pressure (2.7 kPa). Ethyl acetate and water are added to the residue, which is filtered over supercel. The filtrate is separated by settling out, and the organic phase is then washed successively with 2 times water and a saturated aqueous sodium chloride solution; it is dried over magnesium sulfate, filtered and evaporated under reduced pressure (2.7 kPa). The brown oil obtained (3 g) is purified by flash chromatography on silica under an argon pressure (50 kPa) [eluent: ethyl acetate/methanol (95/5 by volume)]. After concentration of the fractions under reduced pressure (2.7 kPa), a residue is obtained which is taken up with ethyl acetate. The solution is treated with carbon black, filtered and evaporated under reduced pressure (2.7 kPa) to give 470 mg of 1-{2-[3-benzyloxy-4-(3-trifluoromethylphenyl)pyrazol-1-yl]ethyl}piperidine in the form of an orange-colored oil.

¹H NMR spectrum (300 MHz, (CD₃)₂SO d6, δ in ppm): from 1.30 to 1.55 (mt: 6H); 2.40 (unresolved peak: 4H); 2.70 (unresolved peak: 2H); 4.10 (unresolved peak: 2H); 5.34 (s: 2H); from 7.30 to 7.55 (mt: 6H); 7.58 (t, J=7.5 Hz: 1H); 7.92 (broad d, J=7.5 Hz: 1H); 8.03 (broad s: 1H); 8.25 (s: 1H).

EXAMPLE 49

1-(2-Piperidin-1-ylethyl)-4-pyridin-3-yl-1H-pyrazol-3-ol dihydrochloride 7 cm³ of 12N hydrochloric acid are added to a stirred solution of 720 mg of 3-[3-benzyloxy-1-(2-piperidin-1-yl-ethyl)-1H-pyrazol-4-yl]pyridine in 7 cm³ of ethanol. After 7 h at the reflux of the solvent, and then 15 h at a temperature in the region of 20° C., the reaction medium is evaporated to dryness under reduced pressure (2.7 kPa). The residue is taken up with ethanol, and the mixture is then evaporated to dryness under vacuum (2.7 kPa). The operation is repeated twice, and the solid is then dried under vacuum (2.7 kPa) at 45° C. for 1 h, and is triturated in acetone. The precipitate formed is filtered off and dried under vacuum (2.7 kPa) to give 190 mg of 1-(2-piperidin-1-ylethyl)-4-pyridin-3-yl-1H-pyrazol-3-ol dihydrochloride in the form of a white solid.

IR spectrum (KBr): 2970; 2434; 2931; 1601; 1551; 1460; 1307; 1178; 825; 691 and 624 cm⁻¹.

¹H NMR spectrum (300 MHz, (CD₃)₂SO d6, δ in ppm): 1.40 (mt: 1H); from 1.60 to 1.90 (mt: 5H); 2.94 (mt: 3H); from 3.25 to 3.65 (mt: 3H); 4.50 (t, J=6.5 Hz: 2H); 7.88 (broad dd, J=8 and 5 Hz: 1H); 8.39 (s: 1H); 8.55 (broad d, J=8 Hz: 1H); 8.60 (broad d, J=5 Hz: 1H); 9.02 (broad d, J=1.5 Hz: 1H); 10.60 (unresolved peak: 1H); 11.20 (unresolved peak: 1H).

The 3-[3-benzyloxy-1-(2-piperidin-1-ylethyl)-1H-pyrazol-4-yl]pyridine can be prepared in the following way:

580 mg of 3-diethylboranylpyridine, 690 mg of sodium carbonate dissolved in 20 cm³ of water, and 390 mg of tetrakis (triphenylphosphine)palladium are added to a stirred solution of 950 mg of 1-[2-(3-benzyloxy-4-bromopyrazol-1-yl)ethyl] piperidine in 100 cm³ of dioxane and under an argon atmosphere. After heating at the reflux of the solvent for 3 h, the reaction medium is cooled to a temperature in the region of 20° C., ethyl acetate and water are added, and the mixture is filtered over supercel. The filtrate is separated by settling out, and the organic phase is then washed with water and a saturated aqueous sodium chloride solution; it is dried over magnesium sulfate, filtered and evaporated under reduced pressure (2.7 kPa). The brown oil obtained (2 g) is purified by flash chromatography on alumina CTB1 under an argon pressure (50 kPa) [eluent: cyclohexane/ethyl acetate (97/3 by volume), then ethyl acetate]. After concentration of the fractions under reduced pressure (2.7 kPa), a residue is obtained which is purified by flash chromatography on silica under an argon pressure (50 kPa) [eluent: ethyl acetate/methanol (90/

10 by volume)]. After concentration of the fractions under reduced pressure (2.7 kPa), 220 mg of 3-[3-benzyloxy-1-(2-piperidin-1-ylethyl)-1H-pyrazol-4-yl]pyridine are obtained in the form of a yellow oil.

IR spectrum (CCl$_4$): 2940; 2854; 2801; 1599; 1575; 1505; 1453; 1362; 1167; 1020; 708 and 702 cm$^{-1}$.

EXAMPLE 50

4-(4-Chlorophenyl)-1-(2-piperidin-1-ylethyl)-1H-pyrazol-3-ol dihydrochloride 3.5 cm$^3$ of 12N hydrochloric acid are added to a stirred solution of 470 mg of 1-{2-[3-benzyloxy-4-(4-chlorophenyl)pyrazol-1-yl]ethyl}piperidine in 3.5 cm$^3$ of ethanol. After 7 h at the reflux of the solvent, and then 15 h at a temperature in the region of 20° C., the reaction mixture is evaporated to dryness under reduced pressure (2.7 kPa). The residue is dried under vacuum (2.7 kPa) at 45° C. for 2 h, and is then triturated in diisopropyl ether. The precipitate formed is filtered and dried under vacuum (2.7 kPa) to give 430 mg of 4-(4-chlorophenyl)-1-(2-piperidin-1-ylethyl)-1H-pyrazol-3-ol dihydrochloride in the form of a white solid.

IR spectrum (KBr): 2952; 2640; 2534; 1607; 1578; 1552; 1521; 1455; 1191; 1093; 1011; 830; 818 and 516 cm$^{-1}$.

$^1$H NMR spectrum (300 MHz, (CD$_3$)$_2$SO d6, δ in ppm): 1.39 (mt: 1H); from 1.60 to 1.85 (mt: 5H); 2.92 (mt: 2H); from 3.35 to 3.45 (mt: 2H); 3.46 (broad t, J=6.5 Hz: 2H); 4.42 (t, J=6.5 Hz: 2H); 7.39 (dmt, J=8.5 Hz: 2H); 7.67 (dmt, J=8.5 Hz: 2H); 8.08 (s: 1H); 10.39 (unresolved peak: 1H).

The 1-{2-[3-benzyloxy-4-(4-chlorophenyl)pyrazol-1-yl]ethyl}piperidine can be prepared in the following way:

A solution of 440 mg of 3-benzyloxy-4-(4-chlorophenyl)-1H-pyrazole in 20 cm$^3$ of dimethylformamide is added to a suspension of 132 mg of sodium hydride (at 75% in liquid petroleum jelly) in 15 cm$^3$ of dimethylformamide under an argon atmosphere and with stirring. After heating at 50° C. for 30 min, the mixture is stirred for 30 min at a temperature in the region of 20° C., and 400 mg of 1-(2-chloroethyl)piperidine hydrochloride are then added. The reaction medium is stirred for 15 h at a temperature in the region of 20° C., and is then poured into water. The aqueous phase is extracted twice with ethyl acetate. The organic phases are pooled, washed successively with water and a saturated aqueous sodium chloride solution, dried over magnesium sulfate, filtered and evaporated under reduced pressure (2.7 kPa) to give a pale yellow oil, which is purified by flash chromatography on alumina CTB1 under an argon pressure (50 kPa) [eluent: cyclohexane/ethyl acetate (95/5, then 90/10 by volume)]. After concentration of the fractions under reduced pressure, 470 mg of 1-{2-[3-benzyloxy-4-(4-chlorophenyl)pyrazol-1-yl]ethyl}piperidine are obtained in the form of a pale yellow oil.

IR spectrum (CCl$_4$): 2938; 1574; 1509; 1482; 1452; 1358; 1171; 1094; 1037; 1014; 834; 695 and 511 cm$^{-1}$.

The 3-benzyloxy-4-(4-chlorophenyl)-1H-pyrazole can be prepared in the following way:

2 cm$^3$ of 1N solution of tetrabutylammonium fluoride in tetrahydrofuran are added to a stirred solution, under an argon atmosphere, of 800 mg of 3-benzyloxy-4-(4-chlorophenyl)-1-(toluene-4-sulfonyl)-1H-pyrazole in 20 cm$^3$ of tetrahydrofuran. After heating at the reflux of the solvent for 2 h, 0.5 cm$^3$ of 1N solution of tetrabutylammonium fluoride in tetrahydrofuran is added to the reaction medium, which is maintained at 60° C. for 15 h. A further 0.5 cm$^3$ of 1N solution of tetrabutylammonium fluoride in tetrahydrofuran is added to the solution, which is heated at the reflux of the solvent for a further 2 h. The reaction medium is then cooled to a temperature in the region of 20° C. and evaporated under reduced pressure (2.7 kPa). Ethyl acetate is added to the residue, and the organic phase is washed successively with two times water and a saturated aqueous sodium chloride solution; it is dried over magnesium sulfate, filtered and evaporated under reduced pressure (2.7 kPa). The resulting yellow solid is purified by flash chromatography on silica under an argon pressure (50 kPa) [eluent: cyclohexane/ethyl acetate (80/20 by volume), then ethyl acetate]. After concentration of the fractions under reduced pressure (2.7 kPa), 440 mg of 3-benzyloxy-4-(4-chlorophenyl)-1H-pyrazole are obtained in the form of a white solid. Mass spectrum (EI): m/z 284 (M$^+$·), m/z 206 [(M−C$_6$H$_6$)$^+$·], m/z 91 (C$_7$H$_7^+$).

The 3-benzyloxy-4-(4-chlorophenyl)-1-(toluene-4-sulfonyl)-1H-pyrazole can be prepared in the following way:

1.15 g of 4-chlorophenylboronic acid, 3.6 cm$^3$ of a 2N aqueous potassium carbonate solution and 360 mg of tetrakis(triphenylphosphine)palladium are added to a stirred solution, under an argon atmosphere, of 1.1 g of 3-benzyloxy-4-iodo-1-(toluene-4-sulfonyl)-1H-pyrazole in 20 cm$^3$ of toluene to which 5 cm$^3$ of ethanol have been added. After heating at the reflux of the solvent for 15 h, the reaction medium is evaporated under reduced pressure (2.7 kPa). Ethyl acetate, water and carbon black are added to the residue, which is filtered over supercel. The filtrate is separated by settling out, and the organic phase is then washed successively with two times water and a saturated aqueous sodium chloride solution; it is dried over magnesium sulfate, filtered and evaporated under reduced pressure (2.7 kPa). The brown oil obtained (2.6 g) is purified by flash chromatography on silica under an argon pressure (50 kPa) [eluent: cyclohexane/ethyl acetate (90/10 by volume)]. After concentration of the fractions under reduced pressure (2.7 kPa), 800 mg of 3-benzyloxy-4-(4-chlorophenyl)-1-(toluene-4-sulfonyl)-1H-pyrazole are obtained in the form of an orange-colored solid. Mass spectrum (CI): m/z 456 (MNH$_4^+$), m/z 439 (MH$^+$).

EXAMPLE 51

4-(3-Chlorophenyl)-1-(2-piperidin-1-ylethyl)-1H-pyrazol-3-ol dihydrochloride 5 cm$^3$ of 12N hydrochloric acid are added to a stirred solution of 550 mg of 1-{2-[3-benzyloxy-4-(3-chlorophenyl)pyrazol-1-yl]ethyl}piperidine in 5 cm$^3$ of ethanol. After 7 h at the reflux of the solvent, and then 15 h at a temperature in the region of 20° C., the reaction medium is evaporated to dryness under reduced pressure (2.7 kPa). The residue is dried under vacuum (2.7 kPa) at 45° C. for 2 h, and is then triturated in diisopropyl ether. The precipitate formed is filtered and dried under vacuum (2.7 kPa) to give 460 mg of 4-(3-chlorophenyl)-1-(2-piperidin-1-ylethyl)-1H-pyrazol-3-ol dihydrochloride in the form of a white solid.

IR spectrum (KBr): 2951; 2637; 2436; 1394; 1603; 1565; 1521; 1454; 1180; 778 and 689 cm$^{-1}$.

$^1$H NMR spectrum (300 MHz, (CD$_3$)$_2$SO d6, δ in ppm): 1.40 (mt: 1H); from 1.60 to 1.90 (mt: 5H); 2.95 (mt: 2H); from 3.35 to 3.55 (mt: 4H); 4.40 (t, J=6.5 Hz: 2H); 7.20 (dmt, J=8 Hz: 1H); 7.37 (t, J=8 Hz: 1H); 7.62 (broad d, J=8 Hz: 1H); 7.73 (t, J=2 Hz: 1H); 8.14 (s: 1H); 9.90 (unresolved peak: 1H); 10.69 (unresolved peak: 1H).

The 1-{2-[3-benzyloxy-4-(3-chlorophenyl)pyrazol-1-yl]ethyl}piperidine can be prepared in the following way:

A solution of 500 mg of 3-benzyloxy-4-(3-chlorophenyl)-1H-pyrazole in 20 cm$^3$ of dimethylformamide is added to a suspension of 142 mg of sodium hydride (at 75% in liquid petroleum jelly) in 15 cm$^3$ of dimethylformamide under an argon atmosphere and with stirring. After heating at 50° C. for 30 min, the mixture is stirred for 30 min at a temperature in the region of 20° C., and a solution of 500 mg of 1-(2-chloroethyl)piperidine hydrochloride is then added. The reaction medium is stirred at a temperature in the region of 20° C. for 15 h, and is then poured into water. The aqueous phase is extracted twice with ethyl acetate. The organic phases are pooled, washed successively with water and a saturated aqueous sodium chloride solution, dried over magnesium sulfate, filtered and evaporated under reduced pressure (2.7 kPa) to give a yellow oil which is purified by flash chromatography on alumina CTB1 under an argon pressure (50 kPa) [eluent: cyclohexane/ethyl acetate (95/5 by volume)]. After concentration of the fractions under reduced pressure, 550 mg of 1-{2-[3-benzyloxy-4-(3-chlorophenyl)pyrazol-1-yl]ethyl}piperidine are obtained in the form of a yellow oil.

IR spectrum (CCl$_4$): 2938; 2853; 1603; 1574; 1507; 1452; 1357; 1260; 1174; 1046; 997; 695 and 687 cm$^{-1}$.

The 3-benzyloxy-4-(3-chlorophenyl)-1H-pyrazole can be prepared in the following way:

4.6 cm$^3$ of a 1N solution of tetrabutylammonium fluoride in tetrahydrofuran are added to a stirred solution, under an argon atmosphere, of 810 mg of 3-benzyloxy-4-(3-chlorophenyl)-1-(toluene-4-sulfonyl)-1H-pyrazole in 20 cm$^3$ of tetrahydrofuran. After heating at the reflux of the solvent for 15 h, the reaction medium is evaporated under reduced pressure (2.7 kPa) and ethyl acetate is added to the residue. The organic phase is washed successively with two times water and a saturated aqueous sodium chloride solution; it is dried over magnesium sulfate, filtered and evaporated under reduced pressure (2.7 kPa). The resulting oil (0.7 g) is purified by flash chromatography on silica under an argon pressure (50 kPa) [eluent: cyclohexane/ethyl acetate (70/30 by volume)]. After concentration of the fractions under reduced pressure (2.7 kPa), 500 mg of 3-benzyloxy-4-(3-chlorophenyl)-1H-pyrazole are obtained in the form of a white solid.

IR spectrum (KBr): 3148; 2957; 1601; 1505; 1446; 1422; 1355; 1237; 1229; 1046; 785; 729; 682 and 597 cm$^{-1}$.

The 3-benzyloxy-4-(3-chlorophenyl)-1-(toluene-4-sulfonyl)-1H-pyrazole can be prepared in the following way:

1.03 g of 3-chlorophenylboronic acid, 3.3 cm$^3$ of a 2N aqueous potassium carbonate solution and 380 mg of tetrakis(triphenylphosphine)palladium are added to a stirred solution, under an argon atmosphere, of 1 g of 3-benzyloxy-4-iodo-1-(toluene-4-sulfonyl)-1H-pyrazole in 20 cm$^3$ of toluene to which 5 cm$^3$ of ethanol have been added. After heating at the reflux of the solvent for 2.5 h, the reaction medium is evaporated under reduced pressure (2.7 kPa). Ethyl acetate, water and carbon black are added to the residue, which is filtered over supercel. The filtrate is separated by settling out, and the organic phase is then washed successively with two times water and a saturated aqueous sodium chloride solution; it is dried over magnesium sulfate, filtered and evaporated under reduced pressure (2.7 kPa). The orange-colored oil obtained (2 g) is purified by flash chromatography on silica under an argon pressure (50 kPa) [eluent: cyclohexane/ethyl acetate (97/3 by volume)]. After concentration of the fractions under reduced pressure (2.7 kPa), 810 mg of 3-benzyloxy-4-(3-chlorophenyl)-1-(toluene-4-sulfonyl)-1H-pyrazole are obtained in the form of a yellow solid.

IR spectrum (KBr): 3098; 1604; 1508; 1372; 1357; 1189; 1180; 1094; 991; 790; 672; 586; 554 and 536 cm$^{-1}$.

EXAMPLE 52

4-(2-Fluorophenyl)-1-(2-piperidin-1-ylethyl)-1H-pyrazol-3-ol dihydrochloride 7 cm$^3$ of 12N hydrochloric acid are added to a stirred solution of 800 mg of 1-{2-[3-benzyloxy-4-(2-fluorophenyl) pyrazol-1-yl]ethyl}piperidine in 10 cm$^3$ of ethanol. After 7 h at the reflux of the solvent, and then 15 h at a temperature in the region of 20° C., the reaction medium is evaporated to dryness under reduced pressure (2.7 kPa). The crude is taken up with ethanol, and the mixture is then evaporated to dryness under reduced pressure (2.7 kPa); the operation is repeated twice. The residue is triturated in diisopropyl ether, and the precipitate formed is filtered off, and is then dissolved under hot conditions in ethanol. The crystals which have appeared after cooling of the solution in an ice bath are filtered and dried under vacuum (2.7 kPa) to give 470 mg of 4-(2-fluorophenyl)-1-(2-piperidin-1-ylethyl)-1H-pyrazol-3-ol dihydrochloride in the form of a white solid.

IR spectrum (KBr): 2947; 2621; 2540; 1620; 1538; 1463; 1231; 1186; 1093; 970; 761 and 656 cm$^{-1}$.

$^1$H NMR spectrum (300 MHz, (CD$_3$)$_2$SO d6, δ in ppm): 1.41 (mt: 1H); from 1.60 to 1.90 (mt: 5H); 2.94 (mt: 2H); from 3.35 to 3.55 (mt: 4H); 4.46 (broad t, J=6.5 Hz: 2H); from 7.15 to 7.30 (mt: 3H); from 7.90 to 8.05 (mt: 2H); 10.15 (unresolved peak: 1H); 10.65 (broad s: 1H).

The 1-{2-[3-benzyloxy-4-(2-fluorophenyl)pyrazol-1-yl]ethyl}piperidine can be prepared in the following way:

A solution of 650 mg of 3-benzyloxy-4-(2-fluorophenyl)-1H-pyrazole in 20 cm$^3$ of dimethylformamide is added to a suspension of 200 mg of sodium hydride (at 75% in liquid petroleum jelly) in 10 cm$^3$ of dimethylformamide under an argon atmosphere and with stirring. After heating at 50° C. for 30 min, the mixture is stirred at a temperature in the region of 20° C. for 30 min, and 625 mg of 1-(2-chloroethyl)piperidine hydrochloride are added. The reaction medium is stirred for 15 h at a temperature in the region of 20° C., and is then poured into 100 cm$^3$ of water. The aqueous phase is extracted twice with ethyl acetate. The organic phases are pooled, washed successively with two times water and a saturated aqueous sodium chloride solution, dried over magnesium sulfate, filtered and evaporated under reduced pressure (2.7 kPa) to give a yellow oil (1.1 g), which is purified by flash chromatography on alumina CTB1 under an argon pressure (50 kPa) [eluent: cyclohexane/ethyl acetate (95/5 by volume)]. After concentration of the fractions under reduced pressure, 800 mg of 1-{2-[3-benzyloxy-4-(2-fluorophenyl) pyrazol-1-yl]ethyl}piperidine are obtained in the form of a yellow oil.

IR spectrum (CCl$_4$): 2938; 2855; 2801; 1572; 1512; 1486; 1358; 1175; 1044; 1027 and 696 cm$^{-1}$.

The 3-benzyloxy-4-(2-fluorophenyl)-1H-pyrazole can be prepared in the following way:

7.4 cm$^3$ of a 1N solution of tetrabutylammonium fluoride in tetrahydrofuran are added to a stirred solution, under an argon atmosphere, of 1.25 g of 3-benzyloxy-4-(2-fluorophenyl)-1-(toluene-4-sulfonyl)-1H-pyrazole in 30 cm$^3$ of tetrahydrofuran. After heating at the reflux of the solvent for 15 h, the reaction medium is evaporated under reduced pressure (2.7 kPa) and ethyl acetate is added to the residue. The organic phase is washed successively with two times water and a saturated aqueous sodium chloride solution; it is dried over magnesium sulfate, filtered and evaporated under reduced pressure (2.7 kPa). The resulting oil (0.92 g) is purified by flash chromatography on silica under an argon pressure (50 kPa) [eluent: cyclohexane/ethyl acetate (70/30 by volume)]. After concentration of the fractions under reduced pressure (2.7 kPa), 650 mg of 3-benzyloxy-4-(2-fluorophenyl)-1H-pyrazole are obtained in the form of a white solid.

IR spectrum (KBr): 3161; 2954; 2691; 1572; 1474; 1440; 1353; 1264; 1045; 1036; 1027; 759; 729 and 654 cm$^{-1}$.

The 3-benzyloxy-4-(2-fluorophenyl)-1-(toluene-4-sulfonyl)-1H-pyrazole can be prepared in the following way:

1.4 g of 2-fluorophenylboronic acid, 5 cm³ of a 2N aqueous potassium carbonate solution and 500 mg of tetrakis(triphenylphosphine)palladium are added to a stirred solution, under an argon atmosphere, of 1.5 g of 3-benzyloxy-4-iodo-1-(toluene-4-sulfonyl)-1H-pyrazole in a mixture of 20 cm³ of toluene and of 5 cm³ of ethanol. After heating at the reflux of the solvent for 3 h, the reaction medium is cooled to a temperature in the region of 20° C. and evaporated under reduced pressure (2.7 kPa). Ethyl acetate, water and carbon black are added to the residue, which is filtered over supercel. The filtrate is separated by settling out, and the organic phase is then washed successively with two times water and a saturated aqueous sodium chloride solution; it is dried over magnesium sulfate, filtered and evaporated under reduced pressure (2.7 kPa). The orange-colored oil obtained (2 g) is purified by flash chromatography on silica under an argon pressure (50 kPa) [eluent: cyclohexane/ethyl acetate (95/5 by volume)]. After concentration of the fractions under reduced pressure (2.7 kPa), 1.25 g of 3-benzyloxy-4-(2-fluorophenyl)-1-(toluene-4-sulfonyl)-1H-pyrazole are obtained in the form of an orange-colored oil. Mass spectrum (EI): m/z 422 (M$^{+\cdot}$), m/z 267 [(M–C$_7$H$_7$O2S)$^+$], m/z 91 (C$_7$H$_7^+$).

EXAMPLE 53

4-(2-Chlorophenyl)-1-(2-piperidin-1-ylethyl)-1H-pyrazol-3-ol hydrochloride 5 cm³ of 12N hydrochloric acid are added to a stirred solution of 570 mg of 1-{2-[3-benzyloxy-4-(2-chlorophenyl)pyrazol-1-yl]ethyl}piperidine in 7 cm³ of ethanol. After 7 h at the reflux of the solvent, and then 15 h at a temperature in the region of 20° C., the reaction medium is evaporated to dryness under reduced pressure (2.7 kPa). The residue is taken up with ethanol, and the mixture is then evaporated to dryness under vacuum (2.7 kPa). The operation is repeated twice, and the lacquer obtained is then dried under vacuum (2.7 kPa) at 45° C. for 30 min, and is then dissolved under hot conditions in ethanol. The crystals formed after cooling of the solution in an ice bath are filtered and dried under vacuum (2.7 kPa) to give 380 mg of 4-(2-chlorophenyl)-1-(2-piperidin-1-ylethyl)-1H-pyrazol-3-ol hydrochloride in the form of a white solid.

IR spectrum (KBr): 3097; 2939; 2674; 2545; 1579; 1517; 1439; 1224; 1171; 935; 758 and 653 cm$^{-1}$.

$^1$H NMR spectrum (200 MHz, (CD$_3$)$_2$SO d6 with the addition of a few drops of CD$_3$COOD d4, at a temperature of 363 K, δ in ppm): 1.60 (mt: 2H); 1.81 (mt: 4H); 3.20 (unresolved peak: 4H); 3.49 (broad t, J=6.5 Hz: 2H); 4.42 (broad t, J=6.5 Hz: 2H); 7.26 (broad t, J=7.5 Hz: 1H); 7.35 (broad t, J=7.5 Hz: 1H); 7.48 (broad d, J=7.5 Hz: 1H); 7.66 (broad d, J=7.5 Hz: 1H); 7.93 (broad s: 1H).

The 1-{2-[3-benzyloxy-4-(2-chlorophenyl)pyrazol-1-yl]ethyl}piperidine can be prepared in the following way:

A solution of 500 mg of 3-benzyloxy-4-(2-chlorophenyl)-1H-pyrazole in 20 cm³ of dimethylformamide is added to a suspension of 140 mg of sodium hydride (at 75% in liquid petroleum jelly) in 10 cm³ of dimethylformamide under an argon atmosphere and with stirring. After heating at 50° C. for 30 min, the mixture is stirred at a temperature in the region of 20° C. for 30 min, and 453 mg of 1-(2-chloroethyl)piperidine hydrochloride are then added. The reaction medium is stirred at a temperature in the region of 20° C. for 15 h, and is then poured into 100 cm³ of water. The aqueous phase is extracted twice with ethyl acetate. The organic phases are pooled, washed successively with two times water and a saturated aqueous sodium chloride solution, dried over magnesium sulfate, filtered and evaporated under reduced pressure (2.7 kPa) to give a yellow oil (0.8 g), which is purified by flash chromatography on alumina CTB1 under an argon pressure (50 kPa) [eluent: cyclohexane/ethyl acetate (95/5 by volume)]. After concentration of the fractions under reduced pressure, 570 mg of 1-{2-[3-benzyloxy-4-(2-chlorophenyl)pyrazol-1-yl]ethyl}piperidine are obtained in the form of a colorless oil.

IR spectrum (CCl$_4$): 2938; 2853; 2801; 1573; 1506; 1456; 1450; 1357; 1174; 1125; 1036; 1025; 716 and 695 cm$^{-1}$.

The 3-benzyloxy-4-(2-chlorophenyl)-1H-pyrazole can be prepared in the following way:

6.9 cm³ of a 1N solution of tetrabutylammonium fluoride in tetrahydrofuran are added to a stirred solution, under an argon atmosphere, of 1.2 g of 3-benzyloxy-4-(2-chlorophenyl)-1-(toluene-4-sulfonyl)-1H-pyrazole in 30 cm³ of tetrahydrofuran. After heating at the reflux of the solvent for 15 h, the reaction medium is evaporated under reduced pressure (2.7 kPa) and ethyl acetate is added to the residue. The organic phase is washed successively with two times water and a saturated aqueous sodium chloride solution; it is dried over magnesium sulfate, filtered and evaporated under reduced pressure (2.7 kPa). The resulting oil is triturated in pentane. The precipitate formed is filtered off and dried under reduced pressure to give 500 mg of 3-benzyloxy-4-(2-chlorophenyl)-1H-pyrazole in the form of a yellow solid. Mass spectrum (EI): m/z 284 (M$^{+\cdot}$), m/z 249 [(M–Cl)$^+$], m/z 91 (C$_7$H$_7^+$).

The 3-benzyloxy-4-(2-chlorophenyl)-1-(toluene-4-sulfonyl)-1H-pyrazole can be prepared in the following way:

1.55 g of 2-chlorophenylboronic acid, 5 cm³ of a 2N aqueous potassium carbonate solution and 500 mg of tetrakis(triphenylphosphine)palladium are added to a stirred solution, under an argon atmosphere, of 1.5 g of 3-benzyloxy-4-iodo-1-(toluene-4-sulfonyl)-1H-pyrazole in 20 cm³ of toluene to which 5 cm³ of ethanol have been added. After heating at the reflux of the solvent for 5 h, the reaction medium is evaporated under reduced pressure (2.7 kPa). Ethyl acetate, water and carbon black are added to the residue, which is filtered over supercel. The filtrate is separated by settling out, and the organic phase is washed successively with two times water and a saturated aqueous sodium chloride solution; it is dried over magnesium sulfate, filtered and evaporated under reduced pressure (2.7 kPa). The orange-colored oil obtained is purified by flash chromatography on silica under an argon pressure (50 kPa) [eluent: cyclohexane/ethyl acetate (95/5 by volume)]. After concentration of the fractions under reduced pressure (2.7 kPa), 1.2 g of 3-benzyloxy-4-(2-chlorophenyl)-1-(toluene-4-sulfonyl)-1H-pyrazole are obtained in the form of an orange-colored oil. Mass spectrum (EI): m/z 438 (M$^{+\cdot}$), m/z 283 [(M–C$_7$H$_7$SO2)$^+$], m/z 91 (C$_7$H$_7^+$).

EXAMPLE 54

1-(1-Azabicyclo[2.2.2]oct-3-yl)-4-(4-chlorophenyl)-1H-pyrazol-3-ol dihydrochloride 2.5 cm³ of 12N hydrochloric acid are added to a stirred solution of 220 mg of 3-[3-benzyloxy-4-(4-chlorophenyl)pyrazol-1-yl]-1-azabicyclo[2.2.2]octane in 5 cm³ of ethanol. After 7 h at the reflux of the solvent, and then 15 h at a temperature in the region of 20° C., the reaction medium is evaporated to dryness under reduced pressure (2.7 kPa). The residue is taken up with ethanol, and the mixture is then evaporated to dryness under vacuum (2.7 kPa). The operation is repeated twice, and the foam obtained is then triturated in diisopropyl ether. The precipitate formed is filtered off and dried under vacuum (2.7 kPa) to give 170 mg of 1-(1-azabicyclo[2.2.2]oct-3-yl)-4-(4-chlorophenyl)-1H-pyrazol-3-ol dihydrochloride in the form of a white solid.

IR spectrum (KBr): 3052; 2926; 2793; 2559; 1606; 1576; 1520; 1486; 1454; 1195; 1167; 1090; 1010; 827; 626 and 515 cm$^{-1}$.

$^1$H NMR spectrum (300 MHz, (CD$_3$)$_2$SO d6, δ in ppm): from 1.65 to 2.05 (mt: 4H); 2.42 (mt: 1H); from 3.15 to 3.50 (mt: 4H); from 3.70 to 3.85 (mt: 2H); 4.67 (mt: 1H); 7.40 (broad d, J=8 Hz: 2H); 7.71 (broad d, J=8 Hz: 2H); 8.35 (s: 1H); from 10.50 to 10.70 (broad unresolved peak: 1H); 10.73 (unresolved peak: 1H).

The 3-[3-benzyloxy-4-(4-chlorophenyl)pyrazol-1-yl]-1-azabicyclo[2.2.2]octane can be prepared in the following way:

500 mg of potassium tert-butoxide, followed by a solution of 660 mg of toluene-4-sulfonic acid 1-aza-bicyclo[2.2.2]oct-3-yl ester in 20 cm$^3$ of dimethyl-formamide, are added to a stirred solution, under an argon atmosphere, of 500 mg of 3-benzyloxy-4-(4-chloro-phenyl)-1H-pyrazole in 20 cm$^3$ of dimethylformamide. After heating at 110° C. for 15 h, the reaction medium is poured into 100 cm$^3$ of water and the mixture is extracted twice with ethyl acetate. The organic phases are washed successively with two times water and a saturated aqueous sodium chloride solution, dried over magnesium sulfate, filtered and evaporated under reduced pressure (2.7 kPa). The orange-colored oil (650 mg) obtained is purified by flash chromatography on silica under an argon pressure (50 kPa) [eluent: ethyl acetate, then dichloromethane/methanol (80/20 by volume)]. After concentration of the fractions under reduced pressure (2.7 kPa), 220 mg of 3-[3-benzyloxy-4-(4-chlorophenyl)pyrazol-1-yl]-1-azabicyclo[2.2.2]octane are obtained in the form of a pale yellow oil.

IR spectrum (CCl$_4$): 3035; 2941; 2873; 1605; 1574; 1508; 1481; 1454; 1165; 1095; 1014; 834; 695 and 513 cm$^{-1}$.

EXAMPLE 55

1-(1-Azabicyclo[2.2.2]oct-3-yl)-4-(3-chlorophenyl)-1H-pyrazol-3-ol hydrochloride 3 cm$^3$ of 12N hydrochloric acid are added to a stirred solution of 270 mg of 3-[3-benzyloxy-4-(3-chlorophenyl) pyrazol-1-yl]-1-azabicyclo[2.2.2]octane in 6 cm$^3$ of ethanol. After 7 h at the reflux of the solvent, the reaction medium is evaporated to dryness under reduced pressure (2.7 kPa). The residue is taken up with ethanol, and the mixture is then evaporated to dryness under vacuum (2.7 kPa). The operation is repeated twice, and the foam obtained is then triturated in diisopropyl ether. The precipitate formed is filtered off and dried under vacuum (2.7 kPa) to give 180 mg of 1-(1-azabicyclo[2.2.2]oct-3-yl)-4-(3-chlorophenyl)-1H-pyrazol-3-ol hydrochloride in the form of a white solid.

IR spectrum (KBr): 2931; 2801; 2660; 2557; 1599; 1563; 1517; 1459; 1425; 1165; 1095; 950; 891; 840; 788; 685; 627 and 440 cm$^{-1}$.

$^1$H NMR spectrum (300 MHz, (CD$_3$)$_2$SO d6, δ in ppm): from 1.65 to 2.05 (mt: 4H); 2.43 (mt: 1H); from 3.15 to 3.45 (mt: 4H); from 3.70 to 3.85 (mt: 2H); 4.67 (mt: 1H); 7.20 (ddd, J=8-2 and 1 Hz: 1H); 7.38 (t, J=8 Hz: 1H); 7.67 (broad d, J=8 Hz: 1H); 7.75 (t, J=2 Hz: 1H); 8.31 (s: 1H); from 10.30 to 10.60 (broad unresolved peak: 1H); 10.68 (broad s: 1H).

The 3-[3-benzyloxy-4-(3-chlorophenyl)pyrazol-1-yl]-1-azabicyclo[2.2.2]octane can be prepared in the following way:

560 mg of potassium tert-butoxide, followed by a solution of 740 mg of toluene-4-sulfonic acid 1-azabicyclo[2.2.2]oct-3-yl ester in 20 cm$^3$ of dimethyl-formamide, are added to a stirred solution, under an argon atmosphere, of 570 mg of 3-benzyloxy-4-(3-chloro-phenyl)-1H-pyrazole in 20 cm$^3$ of dimethylformamide. After heating at 110° C. for 15 h, the reaction medium is poured into 100 cm$^3$ of water and the mixture is extracted twice with ethyl acetate. The organic phases are washed successively with two times water and a saturated aqueous sodium chloride solution, dried over magnesium sulfate, filtered and evaporated under reduced pressure (2.7 kPa). The orange-colored oil (800 mg) obtained is purified by flash chromatography on silica under an argon pressure (50 kPa) [eluent: ethyl acetate/methanol (90/10 by volume), then dichloromethane/methanol (80/20 by volume)]. After concentration of the fractions under reduced pressure (2.7 kPa), 270 mg of 3-[3-benzyloxy-4-(3-chlorophenyl)pyrazol-1-yl]-1-azabicyclo[2.2.2]octane are obtained in the form of a pale yellow oil.

IR spectrum (CCl$_4$): 3034; 1602; 1574; 1507; 1454; 1356; 1176; 1097; 1048; 695 and 687 cm$^{-1}$.

EXAMPLE 56

1-(1-Azabicyclo[2.2.2]oct-3-yl)-4-(3-fluorophenyl)-1H-pyrazol-3-ol hydrochloride 2 cm$^3$ of 12N hydrochloric acid are added to a stirred solution of 85 mg of 3-[3-benzyloxy-4-(3-fluorophenyl)-pyrazol-1-yl]-1-azabicyclo[2.2.2]octane in 4 cm$^3$ of ethanol. After 7 h at the reflux of the solvent, and then 15 h at a temperature in the region of 20° C., the reaction medium is evaporated to dryness under reduced pressure (2.7 kPa). The residue is taken up with ethanol, and the mixture is then evaporated to dryness under vacuum (2.7 kPa). The operation is repeated twice, and the foam obtained is then triturated in diisopropyl ether. The precipitate formed is filtered off and dried under vacuum (2.7 kPa) to give 63 mg of 1-(1-azabicyclo[2.2.2]oct-3-yl)-4-(3-fluorophenyl)-1H-pyrazol-3-ol hydrochloride in the form of a beige solid.

IR spectrum (KBr): 2932; 2765; 2663; 2577; 1617; 1586; 1521; 1457; 1436; 1265; 1180; 1165; 876; 783; 666; 625 and 521 cm$^{-1}$.

$^1$H NMR spectrum (300 MHz, (CD$_3$)$_2$SO d6, δ in ppm): from 1.65 to 2.05 (mt: 4H); 2.43 (mt: 1H); from 3.10 to 3.50 (mt: 4H); 3.78 (broad d, J=7 Hz: 2H); 4.67 (mt: 1H); 6.96 (broad double doublet of a triplet, J=8 and 2.5 Hz: 1H); from 7.25 to 7.55 (mt: 3H); 8.28 (s: 1H); 10.12 (unresolved peak: 1H); 10.65 (s: 1H).

The 3-[3-benzyloxy-4-(3-fluorophenyl)pyrazol-1-yl]-1-azabicyclo[2.2.2]octane can be prepared in the following way:

260 mg of potassium tert-butoxide, followed by a solution of 400 mg of toluene-4-sulfonic acid 1-azabicyclo[2.2.2]oct-3-yl ester in 20 cm$^3$ of dimethylformamide, are added to a stirred solution, under an argon atmosphere, of 250 mg of 3-benzyloxy-4-(3-fluorophenyl)-1H-pyrazole in 20 cm$^3$ of dimethylformamide. After heating at 110° C. for 15 h, the reaction medium is poured into 100 cm$^3$ of water, and the mixture is extracted twice with ethyl acetate. The organic phases are washed successively with two times water and a saturated aqueous sodium chloride solution, dried over magnesium sulfate, filtered and evaporated under reduced pressure (2.7 kPa). The orange-colored oil (345 mg) obtained is purified by flash chromatography on silica under an argon pressure (50 kPa) [eluent: cyclohexane/ethyl acetate (90/10 by volume), then dichloromethane/methanol (80/20 by volume)]. After concentration of the fractions under reduced pressure (2.7 kPa), 270 mg of 3-[3-benzyloxy-4-(3-fluorophenyl)pyrazol-1-yl]-1-azabicyclo[2.2.2]octane are obtained in the form of a pale yellow oil.

$^1$H NMR spectrum (300 MHz, $(CD_3)_2SO$ d6, δ in ppm): 0.80 (mt: 1H); 1.53 (mt: 1H); 1.67 (mt: 2H); 2.09 (mt: 1H); from 2.60 to 2.80 (mt: 3H); 2.98 (mt: 1H); 3.21 (ddd, J=14-10 and 1.5 Hz: 1H); 3.37 (broad dd, J=14 and 5.5 Hz: 1H); 4.25 (mt: 1H); 5.35 (s: 2H); 6.95 (broad double doublet of a triplet, J=8 and 2.5 Hz: 1H); from 7.25 to 7.55 (mt: 8H); 8.31 (s: 1H).

EXAMPLE 57

1-(1-Methylpyrrolidin-3-yl)-4-phenyl-1H-pyrazol-3-ol hydrochloride

A few drops of methanol are added to a mixture of 165 mg of 1-(1-methylpyrrolidin-3-yl)-4-phenyl-1H-pyrazol-3-ol in 2 cm$^3$ of ethyl acetate, in order to solubilize the medium, which is cooled to 0° C. before the addition of 5 cm$^3$ of 3M solution of hydrochloric acid in ethyl acetate. The reaction medium is stirred for 5 min at 0° C., left to return to a temperature in the region of 20° C., and then stirred again at this temperature for 20 min before being concentrated under reduced pressure (2.7 kPa). The crude product is dried on a vane pump (10$^{-3}$ kPa) to give 160 mg of 1-(1-methyl-pyrolidin-3-yl)-4-phenyl-1H-pyrazol-3-ol hydrochloride in the form of a very hygroscopic solid. LCMS (electrospray): m/z 244 (MH$^+$).

$^1$H NMR spectrum (300 MHz, $(CD_3)_2SO$ d6 at 80° C., δ in ppm): from 2.30 to 2.65 (m: 2H); 2.91 (s: 3H); from 3.10 to 4.00 (m: 4H); 5.03 (m: 1H); 7.14 (t, J=7.5 Hz: 1H); 7.32 (t, J=7.5 Hz: 2H); 7.65 (t, J=7.5 Hz: 2H); 8.00 (s: 1H).

The 1-(1-methylpyrrolidin-3-yl)-4-phenyl-1H-pyrazol-3-ol can be prepared in the following way:

7.55 cm$^3$ of a 4M aqueous hydrochloric acid solution are added to a solution of 505 mg of 3-benzyloxy-1-(1-methylpyrrolidin-3-yl)-4-phenyl-1H-pyrazole in 3.53 cm$^3$ of ethanol. The reaction medium is stirred at reflux for 8 h and is then concentrated under reduced pressure (2.7 kPa). The violet oil obtained is taken up three times with diethyl ether, evaporated to dryness under reduced pressure (2.7 kPa), taken up three times with isopropanol and concentrated under reduced pressure and, finally, taken up three times with dichloromethane to give a congealed oil which, after drying on a vane pump (10$^{-3}$ kPa), gives 524 mg of a solid. The residue is purified by chromatography on a column of 30 g of silica (irregular 15-40 μm Merck) [eluent: dichloromethane/methanol/39% ammonium hydroxide (95/5/0.4 by volume); flow rate: 8 cm$^3$/min; detection: 250 nm]. After concentration of the fractions under reduced pressure, 279 mg of 1-(1-methylpyrrolidin-3-yl)-4-phenyl-1H-pyrazol-3-ol are obtained in the form of a colorless amorphous solid. LCMS (electrospray): m/z 334 (MH$^+$).

The 3-benzyloxy-1-(1-methylpyrrolidin-3-yl)-4-phenyl-1H-pyrazole can be obtained in the following way:

123 mg of sodium hydride (at 50% in oil) are added to a solution of 428 mg of 3-benzyloxy-4-phenyl-1H-pyrazole in 8.5 cm$^3$ of dimethylformamide, stirred under a nitrogen atmosphere and at 0° C. After stirring at a temperature in the region of 20° C. for 30 min, a solution of 398 mg of methanesulfonic acid (1-methylpyrrolidin-3-yl)ester in 5.6 cm$^3$ of dimethylformamide is added. The reaction medium is stirred for 1 h at 80° C. and then poured into a water/ethyl acetate mixture. After stirring for 5 min, the medium is separated by settling out and the aqueous phase is extracted three times with ethyl acetate. The organic phases are pooled, washed with a saturated aqueous sodium chloride solution, dried over magnesium sulfate, filtered through an Iena filter and evaporated under reduced pressure (2.7 kPa) to give 657 mg of an oil which is purified by chromatography on a column of 30 g of silica (irregular 15-40 μm Merck) [eluent: dichloromethane/methanol (97/3 by volume); flow rate: 8 cm$^3$/min; detection: 250 nm]. After concentration of the fractions under reduced pressure, 511 mg of 3-benzyloxy-1-(1-methylpyrrolidin-3-yl)-4-phenyl-1H-pyrazole are obtained in the form of a colorless amorphous solid. LCMS (electrospray): 334 (MH$^+$).

The methanesulfonic acid (1-methylpyrrolidin-3-yl) ester can be prepared in the following way:

A solution of 0.33 cm$^3$ of methanesulfonyl chloride in 7.07 cm$^3$ of dichloromethane is added dropwise to a stirred solution of 0.39 cm$^3$ of 1-methyl-3-hydroxypyrrolidine and 0.62 cm$^3$ of triethylamine in 7.7 cm$^3$ of dichloromethane under a nitrogen atmosphere, at −10° C. The reaction medium is stirred at −10° C. for 5 min and then at a temperature in the region of 20° C. for 2 h, before being concentrated to dryness under reduced pressure (2.7 kPa). The residue obtained is taken up with water and ethyl acetate. The solution is stirred for 5 min and is then separated by settling out. The aqueous phase is extracted three times with ethyl acetate. The organic phases are pooled, washed successively with a 5% aqueous sodium bicarbonate solution and a saturated aqueous sodium chloride solution, dried over magnesium sulfate, filtered and evaporated under reduced pressure (2.7 kPa) to give 399 mg of methanesulfonic acid (1-methylpyrrolidin-3-yl)ester in the form of a colorless oil. LCMS (electrospray): m/z 180 (MH$^+$), m/z 84 [MH$^+$−(SO$_2$CH$_3$)].

EXAMPLE 58

1-[2-(1-Methylpyrrolidin-2-yl)ethyl]-4-phenyl-1H-pyrazol-3-ol dihydrochloride

A suspension of 200 mg of 3-benzyloxy-1-[2-(1-methylpyrrolidin-2-yl)ethyl]-4-phenyl-1H-pyrazole and of the tip of a spatula of palladium-on-charcoal at 10% in 6 cm$^3$ of ethanol is hydrogenated at a temperature in the region of 20° C. under an atmosphere of 1600 mbar for 3 h 30 min. The reaction medium is taken up with a dichloromethane/methanol mixture and filtered over Clarcel®. The filtrate is concentrated to dryness under reduced pressure (2.7 kPa) to give 120 mg of 1-[2-(1-methylpyrrolidin-2-yl)ethyl]-4-phenyl-1H-pyrazol-3-ol in the form of a crystallized product. A second batch of 100 mg of 1-[2-(1-methylpyrrolidin-2-yl)ethyl]-4-phenyl-1H-pyrazol-3-ol is prepared according to the same process, but using 140 mg of 3-benzyloxy-1-[2-(1-methylpyrrolidin-2-yl)ethyl]-4-phenyl-1H-pyrazole.

A solution of 160 mg of 1-[2-(1-methylpyrrolidin-2-yl)ethyl]-4-phenyl-1H-pyrazol-3-ol in 5 cm$^3$ of methanol is acidified (pH 1) with a solution of hydrochloric acid in methanol. The reaction medium is stirred for 10 min at a temperature in the region of 20° C., and is then concentrated under reduced pressure (2.7 kPa) and placed in a freezer overnight. The residue is taken up with acetonitrile, spin-filtered, and then washed with acetonitrile before being dried under vacuum to give 160 mg of 1-[2-(1-methylpyrrolidin-2-yl)ethyl]-4-phenyl-1H-pyrazol-3-ol dihydrochloride in the form of a hygroscopic amorphous white powder. LCMS (electrospray): m/z 272 (MH$^+$).

$^1$H NMR spectrum (400 MHz, $(CD_3)_2SO$ d6, δ in ppm): 1.65 (m: 1H); 1.92 (m: 2H); 2.09 (m: 1H); 2.21 (m: 1H); 2.41 (m: 1H); 2.77 (d, J=5.0 Hz: 3H); 3.01 (m: 1H); 3.15 (m: 1H);

3.52 (m: 1H); 4.04 (dt, J=14.0 and 6.5 Hz: 1H); 4.07 (dt, J=14.0 and 6.5 Hz: 1H); 7.11 (t, J=7.5 Hz: 1H); 7.31 (t, J=7.5 Hz: 2H); 7.63 (t, J=7.5 Hz: 2H); 7.98 (s: 1H); 10.70 (s: 1H).

The 3-benzyloxy-1-[2-(1-methylpyrrolidin-2-yl)ethyl]-4-phenyl-1H-pyrazole can be prepared in the following way:

82 mg of sodium hydride (at 50% in oil) are added, in three portions, to a solution of 425 mg of 3-benzyloxy-4-phenyl-1H-pyrazole in 2.5 cm³ of dimethylformamide. Once no more gas is being given off, the reaction medium is stirred at a temperature in the region of 20° C. for a further 15 minutes before the addition of a solution of 250 mg of 1-methyl-2-(2-chloroethyl)-pyrrolidine in 0.5 cm³ of dimethylformamide. The reaction medium is stirred at a temperature in the region of 20° C. for 1 h, and then at 50° C. for 3 h, before being poured into water. The solution is extracted with ethyl acetate. The organic phase is washed with a saturated aqueous sodium chloride solution, dried over magnesium sulfate, filtered and evaporated under reduced pressure (2.7 kPa) to give 580 mg of a crude product which is purified by chromatography on 25 g of silica gel [eluent: dichloromethane then dichloromethane/methanol (90/10 by volume)]. After concentration of the fractions under reduced pressure, 200 mg of 3-benzyloxy-1-[2-(1-methylpyrrolidin-2-yl)ethyl]-4-phenyl-1H-pyrazole are obtained in the form of an amorphous white powder, along with 240 mg of a mixture consisting of 3-benzyloxy-1-[2-(1-methylpyrrolidin-2-yl)ethyl]-4-phenyl-1H-pyrazole and of 3-benzyloxy-4-phenyl-1H-pyrazole. The mixture is again purified by chromatography on 10 g of silica gel [eluent: dichloromethane/methanol (50/50 then 90/10 by volume)] to give 90 mg of 3-benzyloxy-4-phenyl-1H-pyrazole and 140 mg of 3-benzyloxy-1-[2-(1-methylpyrrolidin-2-yl)-ethyl]-4-phenyl-1H-pyrazole, having the same appearance as the previous batch. LCMS (electrospray): m/z 362 (MH⁺).

The 1-methyl-2-(2-chloroethyl)pyrrolidine can be prepared in the following way:

A solution of 330 mg of 1-methyl-2-(2-chloroethyl)-pyrrolidine hydrochloride and of 5 cm³ of 1N sodium hydroxide in 20 cm³ of dichloromethane is stirred at a temperature in the region of 20° C. for 1 h. The reaction medium is extracted with dichloromethane. The organic phase is washed with a saturated aqueous sodium chloride solution, dried over magnesium sulfate, filtered and concentrated under reduced pressure (2.7 kPa) to give 255 mg of 1-methyl-2-(2-chloroethyl) pyrrolidine, which are immediately used in a reaction.

EXAMPLE 59

1-(Pyrrolidin-3-yl)-4-phenyl-1H-pyrazol-3-ol dihydrochloride

A suspension of 608 mg of 3-benzyloxy-4-phenyl-1-(pyrrolidin-3-yl)-1H-pyrazole dihydrochloride and 60 mg of palladium-on-charcoal at 10% in 18 cm³ of ethanol is hydrogenated at a temperature in the region of 20° C. under an atmosphere of 1300 mbar for 3 h. The reaction medium is diluted with methanol, filtered over hyflosupercel and rinsed with methanol. The filtrate is evaporated under reduced pressure (2.7 kPa) to give 365 mg of a white powder. This reaction crude is recrystallized from 20 cm³ of ethanol at reflux. The solution obtained is allowed to return to a temperature in the region of 20° C., and is then immersed in an ice bath. The crystals obtained are filtered under cold conditions through an Iena filter, rinsed successively with ethanol and then ethyl ether and dried under vacuum (13 kPa) to give 185 mg of 1-(pyrrolidin-3-yl)-4-phenyl-1H-pyrazol-3-ol dihydrochloride in the form of a white powder. LCMS (electrospray): m/z 230 (MH⁺).

¹H NMR spectrum (400 MHz, (CD₃)₂SO d6, δ in ppm): 2.32 (m: 2H); 3.37 (m, in water: 2H); 3.45 (dd, J=12.5 and 5.0 Hz: 1H); 3.60 (dd, J=12.5 and 7.0 Hz: 1H); 4.91 (m: 1H); 7.13 (t, J=7.5 Hz: 1H); 7.32 (t, J=7.5 Hz: 2H), 7.66 (t, J=7.5 Hz: 2H); 8.11 (s: 1H); 9.44 (s: 2H); 10.40 (s: 1H).

The 3-benzyloxy-4-phenyl-1-(pyrrolidin-3-yl)-1H-pyrazole dihydrochloride can be prepared in the following way:

6 cm³ of a 3M solution of hydrochloric acid in ethyl acetate are added dropwise to a solution of 569 mg of 3-benzyloxy-1-(1-tert-butoxycarbonylpyrrolidin-3-yl)-4-phenyl-1H-pyrazole in 6 cm³ of ethyl acetate stirred at 0° C. The reaction medium is stirred at a temperature in the region of 20° C. for 2 h, before being concentrated under reduced pressure to give 608 mg of 3-benzyloxy-4-phenyl-1-(pyrrolidin-3-yl)-1H-pyrazole dihydrochloride, in the form of a white powder, which are used immediately.

The 3-benzyloxy-1-(1-tert-butoxycarbonylpyrrolidin-3-yl)-4-phenyl-1H-pyrazole can be prepared in the following way:

129 mg of sodium hydride (at 50% in oil) are added to a solution of 450 mg of 3-benzyloxy-4-phenyl-1H-pyrazole in 9 cm³ of dimethylformamide, stirred under a nitrogen atmosphere at 0° C. After stirring at a temperature in the region of 20° C. for 30 min, 621 mg of methanesulfonic acid (1-tert-butoxycarbonylpyrrolidin-3-yl)ester are added. The reaction medium is stirred for 1 h at 80° C. and then poured into a water/ethyl acetate mixture. After stirring for 5 min, the medium is separated by settling out and the aqueous phase is extracted three times with ethyl acetate. The organic phases are pooled, washed with a saturated aqueous sodium chloride solution, dried over magnesium sulfate, filtered through an Iena filter, rinsed with ethyl acetate and evaporated under reduced pressure (2.7 kPa) to give 998 mg of an oil which is purified by chromatography on a column of 70 g of silica (irregular 15-40 µm Merck) [eluent: dichloromethane/methanol (98/2 by volume); flow rate: 15 cm³/min; detection: 250 nm]. After concentration of the fractions under reduced pressure, 956 mg of a product are obtained, which is again purified by chromatography on a column of 90 g of silica (irregular 15-40 µm Merck) [eluent: dichloromethane/ethyl acetate (98/2 by volume); flow rate: 15 cm³/min; detection: 250 nm]. After concentration of the fractions under reduced pressure, 575 mg of 3-benzyloxy-1-(1-tert-butoxycarbonyl-pyrrolidin-3-yl)-4-phenyl-1H-pyrazole are recovered in the form of a colorless foam. LCMS (electrospray): m/z 420 (MH⁺), m/z 364 [MH⁺–tBu], m/z 320 [MH⁺–Boc]

The methanesulfonic acid (1-tert-butoxycarbonyl-pyrrolidin-3-yl)ester can be prepared in the following way:

A solution of 0.33 cm³ of methanesulfonyl chloride in 3.2 cm³ of dichloromethane is added dropwise to a solution of 710 mg of 1-tert-butoxycarbonyl-3-hydroxypyrrolidine and 0.62 cm³ of triethylamine in 14.2 cm³ of dichloromethane, stirred under a nitrogen atmosphere at –10° C. The reaction medium is stirred at –10° C. for 5 min, and then at a temperature in the region of 20° C. for 2 h, before being concentrated to dryness under reduced pressure (2.7 kPa). The residue obtained is taken up with water and ethyl acetate. The solution is stirred for 5 min and is then separated by settling out. The aqueous phase is extracted three times with ethyl acetate. The organic phases are pooled, washed successively with an aqueous solution of sodium bicarbonate at 5% and of sodium chloride, dried over magnesium sulfate, filtered and evaporated under reduced pressure (2.7 kPa) to give 938 mg of methanesulfonic acid (1-tert-butoxycarbonylpyrrolidin-3-yl)

ester in the form of a pale yellow oil. LCMS (electrospray): m/z 266 (MH⁺), m/z 210 [MH⁺–tBu].

The 1-tert-butoxycarbonyl-3-hydroxypyrrolidine can be prepared in the following way:

A solution of 2.78 cm³ of triethylamine and 3.27 g of di-tert-butyl dicarbonate is added to 0.848 cm³ of 3-hydroxy-pyrrolidine in a mixture of 30 cm³ of tetrahydrofuran and 9.6 cm³ of water. The reaction medium is stirred at a temperature in the region of 20° C. for 3 h, and is then concentrated to dryness under reduced pressure (2.7 kPa). The residue obtained is taken up with water and ethyl acetate. The solution is stirred for 5 min, and is then separated by settling out. The aqueous phase is extracted three times with ethyl acetate. The organic phases are pooled, dried over magnesium sulfate, filtered through an Iena filter and then concentrated to dryness under reduced pressure (2.7 kPa) to give 1.823 g of 1-tert-butoxycarbonyl-3-hydroxypyrrolidine in the form of colorless crystals. m/z 188 (MH⁺), m/z 132 [MH⁺–tBu]

EXAMPLE 60

1-[(1-Methylpyrrolidin-2-(S)-yl)methyl]-4-phenyl-1H-pyrazol-3-ol 3.75 cm³ of a 4M hydrochloric acid solution are added to a solution of 263 mg of 3-benzyloxy-1-[(1-methylpyrrolidin-2-(S)-yl)methyl]-4-phenyl-1H-pyrazole in 2 cm³ of ethanol. The reaction medium is stirred at reflux for 7 h and is then concentrated under reduced pressure. The violet oil obtained is taken up three times with 10 cm³ of isopropanol and then evaporated to dryness under reduced pressure, to give 259 mg of violet resin. This resin is dissolved in a mixture of 0.6 cm³ of ethanol and 3 cm³ of 1,4-dioxane. After the addition of 0.665 cm³ of a 4M solution of hydrogen chloride in 1,4-dioxane and stirring at ambient temperature, the medium is concentrated under reduced pressure at 40° C. The residue is dissolved in 10 cm³ of water and the solution obtained is washed with dichloromethane (3×1 cm³) and then brought to pH 9-10 by adding sodium carbonate. After extraction with dichloromethane, the organic phases are pooled and then dried over magnesium sulfate, filtered and concentrated under reduced pressure at 35° C. The pale pink solid obtained (124 mg) is recrystallized under hot conditions from ethanol, so as to give 73 mg of 1-[(1-methylpyrrolidin-2-(S)-yl)methyl]-4-phenyl-1H-pyrazol-3-ol in the form of a white solid. LCMS (electrospray): m/z 258 (MH⁺).
¹H NMR spectrum (400 MHz, DMSO d6, δ in ppm): 1.63 (m: 1H); 1.76 (m: 2H); 1.95 (m: 1H); 2.30 (partially masked m: 1H); 2.34 (s: 3H); 2.82 (m: 1H); 3.14 (m: 1H); 3.90 (dd, J=7-14 Hz: 1H); 4.11 (dd, J=6-14 Hz: 1H); 7.18 (bt, J=8 Hz: 1H); 7.35 (bt, J=8 Hz: 2H); 7.57 (s: 1H); 7.70 (bd, J=8 Hz: 2H).

The 3-benzyloxy-1-[(1-methylpyrrolidin-2-(S)-yl)-methyl]-4-phenyl-1H-pyrazole can be prepared in the following way:

136 mg of sodium hydride (at 50% in oil) are added to a solution of 283 mg of 3-benzyloxy-4-phenyl-1H-pyrazole in 6 cm³ of dimethylformamide, stirred under a nitrogen atmosphere at ambient temperature. After stirring at ambient temperature for 30 min, a solution of 250 mg of 1-methyl-2-(S)-chloromethylpyrrolidine hydrochloride in 6 cm³ of dimethylformamide is added. The reaction medium is stirred at 80° C. for 1 h, and is then cooled to ambient temperature and hydrolyzed. After extraction with ethyl acetate, the organic phases are pooled, washed with a saturated aqueous sodium bicarbonate solution, dried over magnesium sulfate, filtered and concentrated under reduced pressure at 35° C. to give 554 mg of a yellow oil. After purification by chromatography under a column of 30 g of silica (irregular 15-40 µm Merck) [eluent: dichloromethane/methanol (98/2); flow rate: 15 cm³/min] and concentration of the fractions under reduced pressure, 263 mg of 3-benzyloxy-1-[(1-methylpyrrolidin-2-(S)-yl)methyl]-4-phenyl-1H-pyrazole are obtained. LCMS (electrospray): m/z 348 (MH⁺).

The 1-methyl-2-(S)-chloromethylpyrrolidine hydro-chloride can be prepared in the following way:

388 µl of thionyl chloride are added slowly to a solution of 250 mg of (S)-(–)-1-methyl-2-pyrrolidine methanol in 2 cm³ of dichloromethane cooled in a bath of ice-cold water. The solution obtained is heated at reflux for 3 hours and then stirred at ambient temperature for 18 hours. After evaporation under reduced pressure at 35° C., the brown residue obtained is dissolved in ethanol and then concentrated to dryness under reduced pressure. The dry extract obtained is dissolved in 1 cm³ of ethanol and then precipitated by gradually adding 6 cm³ of ethyl ether. The suspension obtained is cooled using a bath of ice-cold water and the solid is filtered off and then washed with ethyl ether. After drying under vacuum, 258 mg of 1-methyl-2-(S)chloromethylpyrrolidine hydrochloride are obtained in the form of a very hygroscopic ochre solid. Mass spectrum (EI): m/z 133 (M⁺·).

EXAMPLE 61

4-Phenyl-1-pyrrolidin-3-ylmethyl-1H-pyrazol-3-ol hydrochloride 163.5 mg of 1-(1-benzylpyrrolidin-3-ylmethyl)-4-phenyl-1H-pyrazol-3-ol hydrochloride in 5 cm³ of methanol, 139.4 mg of ammonium formate and 10 mg of palladium-on-charcoal at 10% are added to a reactor for a microwave oven equipped with a magnetic stirrer. The tube is sealed and placed in a microwave device for 60 seconds at a temperature of 100° C. under a pressure of 10.5 bar. The reaction medium is filtered through Acodisc GHP Polypro (PALL) and then rinsed with methanol. The filtrate is concentrated to dryness under reduced pressure, to give a gum which is solidified with ethanol. 40 mg of a white powder are thus obtained. The operation is repeated with the above ethanolic filtrate to give, after combining the two batches, 52 mg of a white powder. The final ethanolic filtrate is again concentrated to dryness, and the residue obtained is taken up with 10 cm³ of water. The solution is chilled and then lyophilized overnight. The various batches are combined, to give 80 mg of 4-phenyl-1-pyrrolidin-3-ylmethyl-1H-pyrazol-3-ol hydrochloride in the form of a white powder. ¹H NMR spectrum (300 MHz, (CD₃)₂SO d6, δ in ppm): 1.66 (m, 1H); 1.99 (m, 1H); 2.73 (m, 1H); 2.92 (m, 1H); from 3.02 to 3.25 (m, 2H); 4.01 (d, J=7.0 Hz, 2H); 7.12 (broad t, J=7.5 Hz, 1H); 7.32 (broad t, J=7.5 Hz, 2H); 7.65 (broad d, J=7.5 Hz, 2H); 7.99 (s, 1H); 8.36 (broad s, 1H); from 6.70 to 8.70 (very very broad m, 1H). Mass spectrum (EI): m/z 244⁺ (M+H)⁺.

The 1-(1-benzylpyrrolidin-3-ylmethyl)-4-phenyl-1H-pyrazol-3-ol hydrochloride can be prepared in the following way:

A suspension of 937 mg of 3-benzyloxy-1-(1-benzylpyr-rolidin-3-ylmethyl)-4-phenyl-1H-pyrazole hydrochloride and 93 mg of palladium-on-charcoal at 10% in 9.4 cm³ of ethanol is hydrogenated at a temperature in the region of 20° C. under an atmosphere of 1500 mbar for 16 h. The reaction medium is filtered through hyflosupercel and rinsed with ethanol. After concentration of the filtrate to dryness, 350 mg of a beige gum are obtained, which gum is recrystallized from ethanol. After filtration through an iena funnel, rinsing with ethyl ether and then drying in an industrial vacuum oven, 178 mg of 1-(1-benzylpyrrolidin-3-ylmethyl)-4-phenyl-1H-pyrrazol-3-ol hydrochloride are obtained. Mass spectrum (EI): m/z 334$^+$ [(M+H)$^+$–HCl].

The 3-benzyloxy-1-(1-benzylpyrrolidin-3-ylmethyl)-4-phenyl-1H-pyrazole hydrochloride can be prepared in the following way:

129 mg of sodium hydride (at 50% in oil) are added, in a single step, to a solution of 450 mg of 3-benzyloxy-4-phenyl-1H-pyrazole in 9 cm$^3$ of anhydrous dimethylformamide stirred under an argon atmosphere at 0° C. After stirring for 30 min at a temperature in the region of 20° C., a solution of 630 mg of methanesulfonic acid (1-benzylpyrrolidin-3-ylmethyl) ester in 9 cm$^3$ of anhydrous dimethylformamide is added. The reaction medium is stirred for 4 h at 80° C. and then plunged into a water/ethyl acetate mixture. After stirring for 5 min, the medium is separated by settling out and the aqueous phase is extracted three times with ethyl acetate. The organic phases are combined, washed twice with water and then once with a saturated aqueous sodium chloride solution, dried over magnesium sulfate, and filtered through an iena funnel. The magnesium sulfate is rinsed with ethyl acetate. The combined organic phases are evaporated under reduced pressure and the residue obtained is dried overnight on a vane pump, to give 939 mg of a pale yellow oil which is purified by chromatography on a column of 90 g of silica (Merck irregular silica 15-40 μm) [eluent: dichloromethane/methanol (98/2 by volume); flow rate: 10 cm$^3$/min; detection: 250 nm]. After concentration of the fractions under reduced pressure, 586 mg of 83%-pure 3-benzyloxy-1-(1-benzylpyrrolidin-3-ylmethyl)-4-phenyl-1H-pyrazole are obtained in the form of a foam. This is taken up with water (pH=1) and then ethyl acetate is added thereto. After stirring for 5 min, the medium is separated by settling out and the aqueous phase is extracted with ethyl acetate. The organic phases are brought to pH=9 with an ammonium hydroxide solution, extracted three times with ethyl acetate, combined, dried over magnesium sulfate, filtered, rinsed, and then concentrated to dryness under reduced pressure, to give 497 mg of 3-benzyloxy-1-(1-benzylpyrrolidin-3-ylmethyl)-4-phenyl-1H-pyrazole in the form of a free base. The product is taken up with 5 cm$^3$ of ethyl acetate. The medium is cooled to 0° C., before the addition of 5 cm$^3$ of a 3M hydrochloric acid solution in ethyl acetate. The solution is concentrated to dryness under reduced pressure, to give a brown oil. Attempts to crystallize the crude residue obtained were carried out in vain (ethyl acetate, ethanol, methanol, diethyl ether or hexane). 940 mg of 3-benzyloxy-1-(1-benzylpyrrolidin-3-ylmethyl]-4-phenyl-1H-pyrazole hydrochloride are thus recovered. Mass spectrum (EI): m/z 424$^+$ (M+H)$^+$.

The methanesulfonic acid (1-benzylpyrrolidin-3-ylmethyl)ester can be prepared in the following way:

A solution of 0.455 cm$^3$ of methanesulfonic chloride in 9.7 cm$^3$ of anhydrous dichloromethane is added dropwise to a solution of 1 g of (1-benzylpyrrolidin-3-yl)methanol and 0.844 cm$^3$ of triethylamine in 20 cm$^3$ of dichloromethane, stirred under an argon atmosphere at 0° C. The reaction medium is stirred for 5 min at 0° C. and then for 2 h at a temperature close to 20° C., before being concentrated to dryness under reduced pressure. The residue obtained is taken up with water and ethyl acetate. The solution is stirred for 5 min and is then separated by settling out. The aqueous phase is extracted three times with ethyl acetate. The organic phases are combined, washed successively with an aqueous 5% sodium bicarbonate solution and with a saturated aqueous sodium chloride solution, dried over magnesium sulfate, filtered, and evaporated under reduced pressure, to give 1.2 g of methanesulfonic acid (1-benzylpyrrolidin-3-ylmethyl)ester. Mass spectrum (EI): m/z 270$^+$ (M+H)$^+$.

The (1-benzylpyrrolidin-3-yl)methanol can be prepared in the following way:

17.1 cm$^3$ of a 1M lithium aluminum hydride solution in tetrahydrofuran are added to a solution of 2 g of 1-benzyl-5-oxopyrrolidine-3-carboxylic acid methyl ester in 40 cm$^3$ of tetrahydrofuran, stirred at 0° C. under a nitrogen atmosphere. After stirring for 15 min at 0° C., the reaction medium is allowed to return to a temperature in the region of 20° C. and is stirred for 4 h. A mixture consisting of 0.65 cm$^3$ of water and of 6.5 cm$^3$ of tetrahydrofuran is added dropwise to the reaction medium. 0.65 cm$^3$ of a 15% aqueous sodium hydroxide solution and 1.95 cm$^3$ of water are then successively added. The medium is stirred at a temperature in the region of 20° C. until the formation of a filterable solid, to which two spatulas of magnesium sulfate are added. After filtration through an iena funnel, rinsing and concentrating to dryness under reduced pressure, 1.72 g of (1-benzylpyrrolidin-3-yl) methanol are obtained in the form of a colorless oil. Mass spectrum (EI): m/z 192$^+$ (M+H)$^+$.

EXAMPLE 62

1-((2R)-1-methylpyrrolidin-2-ylmethyl)-4-phenyl-1H-pyrazol-3-ol 2.89 cm$^3$ of 6N hydrochloric acid are added to a solution of 211 mg of 3-benzyloxy-1-((2R)-1-methylpyrrolidin-2-ylmethyl)-4-phenyl-1H-pyrazole in 1.5 cm$^3$ of ethanol. The reaction medium is stirred for 5 h 30 min at 110° C. before being concentrated to dryness under reduced pressure. The residue is taken up with isopropanol and is concentrated to dryness, to give 136 mg of a foam which is crystallized from a minimum amount of ethanol under hot conditions. After chilling overnight, no crystallization is apparent. The residue is taken up with 5 cm$^3$ of water and extracted three times with 1 cm$^3$ of dichloromethane, brought to pH 9-10 with solid sodium carbonate. The aqueous phase is again extracted three times with dichloromethane. The organic phases are combined, dried over magnesium sulfate, filtered and concentrated to dryness under reduced pressure, to give 100 mg of a product which is recrystallized from a minimum amount of ethanol. After leaving the product overnight in a refrigerator, filtering and drying, 58 mg of 1-((2R)-1-methylpyrrolidin-2-ylmethyl)-4-phenyl-1H-pyrazol-3-ol are obtained in the form of a white solid. $^1$H NMR spectrum (400 MHz, (CD$_3$)$_2$SO d6 with a drop of AcOH d4, δ in ppm): from 1.62 to 2.00 (m, 4H); 2.42 (s, 3H); 3.02 (m, 1H); 3.21 (m, 2H); 3.96 (dd, J=7.0 and 14.0 Hz, 1H); 4.13 (dd, J=5.5 and 14.0 Hz, 1H); 7.13 (broad t, J=7.5 Hz, 1H); 7.33 (broad t, J=7.5 Hz, 2H); 7.65 (broad d, J=7.5 Hz, 2H); 7.97 (s, 1H). Mass spectrum (EI): 258(+)= (M+H)(+).

The 3-benzyloxy-1-((2R)-1-methylpyrrolidin-2-ylmethyl)-4-phenyl-1H-pyrazole can be prepared in the following way:

A solution of 400 mg of 3-benzyloxy-4-phenyl-((2R)-pyrrolidin-2-ylmethyl)-1H-pyrazole hydrochloride, 297 mg of potassium carbonate and 0.101 cm$^3$ of methyl iodide in 4 cm$^3$ of dimethylformamide is stirred overnight at a temperature in the region of 20° C. The medium is diluted with water and then extracted with ethyl acetate. The organic phase is dried over magnesium sulfate, filtered, and concentrated to dryness under reduced pressure, to give a reaction crude which is purified by chromatography on silica gel (eluent: dichloromethane containing 3% of methanol). After concentration of the fractions to dryness, 215 mg of 3-benzyloxy-1-((2R)-1-methylpyrrolidin-2-ylmethyl)-4-phenyl-1H-pyrazole are obtained.

The 3-benzyloxy-4-phenyl-1-((2R)-pyrrolidin-2-yl-methyl)-1H-pyrazole hydrochloride can be prepared in the following way:

3.17 cm$^3$ of a 4N hydrochloric acid solution in dioxane are added to a solution of 500 mg of 3-benzyloxy-1-((2R)-1-tert-butoxycarbonylpyrrolidin-2-ylmethyl)-4-phenyl-1H-pyrazole in 5 cm$^3$ of dioxane. The reaction medium is stirred overnight at a temperature in the region of 20° C. and is then concentrated to dryness under reduced pressure, to give 400 mg of 3-benzyloxy-4-phenyl-1-((2R)-pyrrolidin-2-ylmethyl)-1H-pyrazole hydrochloride in the form of a white solid. Mass spectrum (EI): m/z 334$^+$ (M+H)$^+$, m/z 667$^+$ (2M+H)$^+$.

The 3-benzyloxy-4-phenyl-1-((2R)-1-tert-butoxycarbonyl-pyrrolidin-2-ylmethyl)-1H-pyrazole can be prepared in the following way:

A solution of 251 mg of 3-benzyloxy-4-phenyl-1H-pyrazole and 72 mg of sodium hydride (50% in oil) in 5 cm$^3$ of dimethylformamide is stirred for 1 h before adding a solution of 364 mg of methanesulfonic acid ((2R)-1-tert-butoxycarbonylpyrrolidin-2-ylmethyl)ester in 5 cm$^3$ of dimethylformamide. The reaction medium is stirred at 80° C. for 3 h and is then poured into water. After extraction with ethyl acetate, the organic phase is washed three times with a saturated aqueous sodium chloride solution, dried over magnesium sulfate, filtered, and then concentrated to dryness, to give 440 mg of a crude product which is purified by chromatography on silica gel (eluent: 80/20 heptane/ethyl acetate). After concentration of the fractions to dryness, 202 mg of 3-benzyloxy-4-phenyl-1-((2R)-1-tert-butoxycarbonylpyrrolidin-2-ylmethyl)-1H-pyrazole are obtained. Mass spectrum (EI): m/z 456$^+$ (M+Na)$^+$, m/z 434$^+$ (M+H)$^+$, m/z 334$^+$ [(M+H)$^+$–CO$_2$tBu+H]. The methanesulfonic acid ((2R)-1-tert-butoxycarbonyl-pyrrolidin-2-ylmethyl)ester can be prepared in the following way:

A solution of 1.2 cm$^3$ of methanesulfonyl chloride in 20 cm$^3$ of dichloromethane is added dropwise to a solution of 3 g of (2R)-1-tert-butoxycarbonyl-2-hydroxymethylpyrrolidine and 2.27 cm$^3$ of triethylamine in 65 cm$^3$ of dichloromethane, stirred under a nitrogen atmosphere at −10° C. The reaction medium is allowed to return to 20° C., before concentrating to dryness under reduced pressure. The residue obtained is taken up with water, and extracted twice with 20 cm$^3$ of ethyl acetate. The combined organic phases are washed three times with 20 cm$^3$ of a 5% aqueous sodium bicarbonate solution, dried over magnesium sulfate, filtered, and concentrated to dryness under reduced pressure, to give 3.75 g of a mixture of methanesulfonic acid ((2R)-1-tert-butoxycarbonylpyrrolidin-2-ylmethyl)ester and of (2R)-1-tert-butoxycarbonyl-2-hydroxymethylpyrrolidine. The mixture is again reacted under the same conditions as above, but with 0.3 eq of triethylamine and 0.3 eq of methanesulfonyl chloride. After a similar treatment, 3.63 g of methanesulfonic acid ((2R)-1-tert-butoxycarbonylpyrrolidin-2-ylmethyl)ester are obtained in the form of a colorless liquid. Mass spectrum (EI) m/z 280$^+$ (M+H)$^+$.

EXAMPLE 63

4-Phenyl-1-(piperidin-3-yl)-1H-pyrazol-3-ol hydrochloride

A suspension of 130 mg of 3-benzyloxy-4-phenyl-1-(piperidin-3-yl)-1H-pyrazole hydrochloride and 13 mg of palladium-on-charcoal at 10% in 4 cm$^3$ of ethanol is hydrogenated at a temperature in the region of 20° C. under an atmosphere of 1500 mbar for 3 h. The reaction medium is taken up with a mixture of 15 cm$^3$ of 80/20 by volume dichloromethane/methanol, spin-filtered through Clarcel, and then washed twice with 10 cm$^3$ of an 80/20 by volume dichloromethane/methanol mixture. After concentration to dryness, the crystalline product is taken up with 5 cm$^3$ of ethyl acetate, spin-filtered, and taken up twice with 0.5 cm$^3$ of ethyl acetate, to give 70 mg of 4-phenyl-1-(piperidin-3-yl)-1H-pyrazol-3-ol hydrochloride in the form of a crystalline product.

$^1$H NMR spectrum (300 MHz, (CD$_3$)$_2$SO d6, δ in ppm): from 1.72 to 2.22 (m, 4H); 2.86 (m, 1H); from 3.10 to 3.57 (partially masked m, 3H); 4.36 (m, 1H); 7.14 (broad t, J=7.5 Hz, 1H); 7.33 (broad t, J=7.5 Hz, 2H); 7.68 (broad d, J=7.5H, 2H); 8.07 (s, 1H); 9.18 (broad m, 2H); 10.4 (broad s, 1H). Mass spectrum (EI): m/z 244$^+$ (M+H)$^+$.

The 3-benzyloxy-4-phenyl-1-(piperidin-3-yl)-1H-pyrazole hydrochloride can be prepared in the following way:

2 cm$^3$ of a 4N hydrochloric acid solution in ethyl acetate are added to a solution of 230 mg of 3-benzyloxy-1-(1-tert-butoxycarbonylpiperidin-3-yl)-4-phenyl-1H-pyrazole in 2 cm$^3$ of ethyl acetate, cooled by means of an ice bath. The reaction medium is allowed to return to a temperature in the region of 20° C. and is then stirred for 2 h 30 min before concentration of the ethyl acetate. The residue is taken up three times with 2 cm$^3$ of diethyl ether and the insoluble material is filtered off, to give 150 mg of 3-benzyloxy-4-phenyl-1-(piperidin-3-yl)-1H-pyrazole hydrochloride. Mass spectrum (EI): m/z 334$^+$ (M+H)$^+$, m/z 36$^+$/38$^+$ HCl$^+$.

The 3-benzyloxy-1-(1-tert-butoxycarbonylpiperidin-3-yl)-4-phenyl-1H-pyrazole can be prepared in the following way:

153 mg of sodium hydride (at 50% in oil) are added, in three portions, to a solution of 725 mg of 3-benzyloxy-4-phenyl-1H-pyrazole in 7 cm$^3$ of anhydrous dimethylformamide, stirred under a nitrogen atmosphere. After stirring for 45 min at a temperature in the region of 20° C., a solution of 890 mg of methanesulfonic acid (1-tert-butoxycarbonylpiperidin-3-yl)ester in 4.5 cm$^3$ of anhydrous dimethylformamide is added. The reaction medium is stirred for 3 h at 80° C. and is then, after cooling, poured into water. The aqueous phase is extracted four times with 50 cm$^3$ of ethyl acetate. The combined organic phases are washed with a saturated aqueous sodium chloride solution, dried over magnesium sulfate, filtered, and then concentrated to dryness under reduced pressure. The product obtained is taken up with dichloromethane, which, after spin-filtering, gives 380 mg of 3-benzyloxy-4-phenyl-1H-pyrazole in the form of a beige solid. The filtrate, after concentration to dryness, is purified by chromatography on a column of 70 g of silica (Merck, eluent: 95/5 by volume dichloromethane/ethyl acetate). After concentration of the fractions under reduced pressure, 280 mg of 3-benzyloxy-1-(1-tert-butoxycarbonyl-piperidin-3-yl)-4-phenyl-1H-pyrazole are obtained with a purity of 70%. These 280 mg are again purified by chromatography on a column of 30 g of silica (Merck, eluent: 70/30 by volume dichloromethane/heptane). After concentration of the fractions under reduced pressure, 230 mg of 3-benzyloxy-1-(1-tert-butoxycarbonyl-piperidin-3-yl)-4-phenyl-1H-pyrazole are obtained. $^1$H NMR spectrum (300 MHz, (CD$_3$)$_2$SO d6, δ in ppm): 1.20 (m, 1H); 1.41 (s, 9H); from 1.45 to 2.16 (m, 3H); 2.93 (m, 1H); from 3.00 to 3.40 (broad m, 1H); 3.79 (m, 1H); from 3.98 to 4.16 (m, 2H); 5.31 (broad s, 2H); 7.15 (broad t, J=7.5 Hz, 1H); from 7.30 to 7.45 (m, 5H); 7.51 (broad d, J=7.5 Hz, 2H); 7.65 (broad d, J=7.5 Hz, 2H); 8.14 (s, 1H).

The methanesulfonic acid (1-tert-butoxycarbonyl-piperidin-3-yl)ester can be prepared in the following way:

A solution of 0.305 cm³ of methanesulfonyl chloride is added dropwise to a solution of 750 mg of 1-tert-butoxycarbonyl-3-hydroxypiperidine and 0.570 cm³ of triethylamine in 7 cm³ of dichloromethane, stirred under a nitrogen atmosphere at −10° C. The reaction medium is allowed to return to a temperature in the region of 20° C. and is stirred for 3 h, before concentrating to dryness under reduced pressure. The residue obtained is taken up with ethyl acetate. The organic phase is successively washed with a 5% aqueous sodium bicarbonate solution and then a saturated aqueous sodium chloride solution, dried over magnesium sulfate, filtered, and concentrated to dryness under reduced pressure, to give 0.9 g of methanesulfonic acid (1-tert-butoxycarbonylpiperidin-3-yl)ester in the form of a colorless oil. Mass spectrum (EI): m/z 280⁺ (M+H)⁺, m/z 224⁺ [(M+H)⁺−tBu+H].

EXAMPLE 64

1-(1-Methylpiperidin-2-ylmethyl)-4-phenyl-1H-pyrazol-3-ol hydrochloride

A solution of 610 mg of 3-benzyloxy-1-(1-methylpiperidin-2-ylmethyl)-4-phenyl-1H-pyrazole in 12 cm³ of ethyl acetate and 6 cm³ of a 4M hydrochloric solution in ethyl acetate is stirred for 15 min at a temperature in the region of 20° C. After concentration to dryness under reduced pressure, 669 mg of 3-benzyloxy-1-(1-methylpiperidin-2-ylmethyl)-4-phenyl-1H-pyrazole hydrochloride are obtained, which product is immediately reacted again. A suspension of 669 mg of the preceding hydrochloride and 66 mg of palladium-on-charcoal at 10% in 15 cm³ of ethanol is hydrogenated at a temperature in the region of 20° C. under an atmosphere of 1500 mbar for 3 h. The reaction medium is taken up with a mixture of 25 cm³ of 80/20 dichloromethane/methanol and then spin-filtered through Clarcel. After concentration to dryness, the product obtained is dissolved in 20 cm³ of water and then lyophilized, to give 500 mg of 1-(1-methylpiperidin-2-ylmethyl)-4-phenyl-1H-pyrazol-3-ol hydrochloride. ¹H NMR spectrum (300 MHz, (CD₃)₂SO d6 at 353K, δ in ppm): from 1.37 to 1.87 (m, 6H); 2.86 (broad m, 4H); from 3.32 to 3.60 (very broad m, 2H); 4.24 (broad m, 1H); 4.50 (broad m, 1H); 7.16 (broad t, J=7.5 Hz, 1H); 7.34 (broad t, J=7.5 Hz, 2H); 7.67 (broad d, J=7.5 Hz, 2H); 7.97 (s, 1H); from 10.0 to 10.6 (very broad m, 2H). Mass spectrum (EI): m/z 272⁺ (M+H)⁺, m/z 36⁺/38⁺ HCl⁺.

EXAMPLE 65

1-(1-methylazepan-3-yl)-4-phenyl-1H-pyrazol-3-ol hydrochloride

The 1-(1-methylazepan-3-yl)-4-phenyl-1H-pyrazol-3-ol hydrochloride can be prepared according to the same method used for preparing the 1-(1-methylpiperidin-2-ylmethyl)-4-phenyl-1H-pyrazol-3-ol hydrochloride, but using 470 mg of 3-benzyloxy-1-(1-methylazepan-3-yl)-4-phenyl-1H-pyrazole, 10 cm³ of ethyl acetate, 5 cm³ of a 4M hydrochloric acid solution in ethyl acetate, and then 51 mg of palladium-on-charcoal at 10% and 15 cm³ of ethanol. According to the same treatment conditions, 400 mg of 1-(1-methylazepan-3-yl)-4-phenyl-1H-pyrazol-3-ol hydrochloride are thus obtained. ¹H NMR spectrum (400 MHz, (CD₃)₂SO d6 at 343K, δ in ppm): from 1.62 to 2.32 (m, 6H); 2.86 (broad s, 3H); from 2.92 to 3.76 (partially masked m, 4H); from 4.62 to 4.92 (very broad m, 1H); 7.15 (broad t, J=7.5 Hz, 1H); 7.33 (broad t, J=7.5 Hz, 2H); 7.65 (broad d, J=7.5 Hz, 2H); 7.93 (broad s, 1H); from 9.85 to 10.3 (broad m, 1H); from 10.7 to 11.4 (very broad m, 1H). Mass spectrum (EI): m/z 272⁺ (M+H)⁺.

The 3-benzyloxy-1-(1-methylpiperidin-2-ylmethyl)-4-phenyl-1H-pyrazole and 3-benzyloxy-1-(1-methylazepan-3-yl)-4-phenyl-1H-pyrazole can be prepared in the following way:

426 mg of sodium hydride (at 50% in oil) are added, in three portions, to a solution of 2 g of 3-benzyloxy-4-phenyl-1H-pyrazole in 20 cm³ of anhydrous dimethyl-formamide, stirred under a nitrogen atmosphere. After stirring for 30 min at a temperature in the region of 20° C., 1.3 g of a 75/25 mixture of 1-methyl-2-chloromethylpiperidine and of methanesulfonic acid (1-methylpiperidin-2-ylmethyl)ester are added dropwise. The reaction medium is stirred for 3 h at 80° C. and then, after cooling, is poured into a water/ice mixture. The aqueous phase is extracted with ethyl acetate. The organic phase is washed with a saturated aqueous sodium chloride solution, dried over magnesium sulfate, filtered, and then concentrated to dryness under reduced pressure. The product is purified by two successive chromatographies on a column of 119 g of silica (Merck, eluent: 97/3 by volume dichloromethane/methanol). After concentration of the fractions under reduced pressure, 460 mg of 3-benzyloxy-1-(1-methylazepan-3-yl)-4-phenyl-1H-pyrazole and 650 mg of 3-benzyloxy-1-(1-methylpiperidin-2-ylmethyl)-4-phenyl-1H-pyrazole are obtained.

3-Benzyloxy-1-(1-methylpiperidin-2-ylmethyl)-4-phenyl-1H-pyrazole. ¹H NMR spectrum (400 MHz, (CD₃)₂SO d6, δ in ppm): from 1.12 to 1.65 (m, 6H); 2.06 (m, 1H); 2.29 (s, 3H); 2.34 (m, 1H); 2.77 (m, 1H); 3.86 (dd, J=7.5 and 14.0 Hz, 1H); 4.25 (dd, J=5.5 and 14.0 Hz, 1H); 5.30 (s, 2H); 7.14 (broad t, J=7.5 Hz, 1H); from 7.30 to 7.44 (m, 5H); 7.50 (broad d, J=7.5 Hz, 2H); 7.64 (broad d, J=7.5 Hz, 2H); 8.06 (s, 1H).

3-Benzyloxy-1-(1-methylazepan-3-yl)-4-phenyl-1H-pyrazole. ¹H NMR spectrum (400 MHz, (CD₃)₂SO d6, δ in ppm): from 1.56 to 1.82 (m, 4H); from 1.96 to 2.08 (m, 2H); 2.33 (s, 3H); from 2.50 to 2.93 (partially masked m, 4H); 4.26 (m, 1H); 5.30 (s, 2H); 7.13 (broad t, J=7.5 Hz, 1H); from 7.28 to 7.45 (m, 5H); 7.51 (broad d, J=7.5 Hz, 2H); 7.65 (broad d, J=7.5 Hz, 2H); 8.11 (s, 1H).

The mixture of 2-chloromethyl-1-methylpiperidin and of methanesulfonic acid (1-methylpiperidin-2-ylmethyl)ester can be prepared in the following way:

A solution of 0.815 cm³ of methanesulfonyl chloride is added dropwise to a solution of 1.31 cm³ of (1-methyl-piperidin-2-yl)methanol and 1.53 cm³ of triethylamine in 26 cm³ of dichloromethane, stirred under a nitrogen atmosphere at −10° C. The reaction medium is allowed to return to a temperature in the region of 20° C. and is stirred for 3 h before concentration to dryness under reduced pressure. The residue obtained is taken up with ethyl acetate. The organic phase is successively washed with a 5% aqueous sodium bicarbonate solution and then a saturated aqueous sodium chloride solution, dried over magnesium sulfate, filtered, and concentrated to dryness under reduced pressure, to give 1.3 g of a 75/25 mixture of 2-chloromethyl-1-methylpiperidin and of methanesulfonic acid (1-methylpiperidin-2-ylmethyl)ester. Mass spectrum (EI): m/z 148⁺ (M+H)⁺, m/z 208⁺ (M+H)⁺.

EXAMPLE 66

4-Phenyl-1-(2-piperidin-1-ylethyl)-1H-pyrazol-3-ol hydrochloride

The procedure is carried out as in example 38, but with 0.75 g of 3-benzyloxy-4-phenyl-1(2-piperidin-1-ylethyl)-1H- pyrazol oxalate, 5.9 cm³ of 12N hydrochloric acid and 5.9 cm³ of ethanol. The mixture is heated for 4 hours at a temperature close to 100° C. After cooling to a temperature close to 20° C., the reaction medium is taken up with ethanol, and concentrated to dryness under reduced pressure (2 kPa); the residue is precipitated from a mixture of diisopropyl ether and ethanol. 0.357 g of 4-phenyl-1-(2-piperidin-1-ylethyl)-1H-pyrazol-3-ol hydrochloride is obtained in the form of a white solid. ¹H NMR spectrum (300 MHz)—δ in ppm in DMSO-d6: 1.40 (m, 1H); from 1.63 to 1.87 (m, 5H); 2.92 (m, 2H); from 3.36 to 3.52 (m, 4H); 4.43 (t, J=6.5 Hz, 2H); 7.14 (tt, J=1.5 and 7.5 Hz, 1H); 7.33 (broad t, J=7.5 Hz, 2H); 7.64 (broad d, J=7.5 Hz, 2H); 8.05 (s, 1H); from 10.35 to 10.72 (broad m, 2H).

IR spectrum (KBr): 2939; 1606; 1581; 1520; 1454; 1444; 1170; 771; 700; 673 and 427 cm⁻¹.

The 3-benzyloxy-4-phenyl-1-(2-piperidin-1-ylethyl)-1H-pyrazole oxalate can be obtained in the following way:

The procedure is carried out as in example 15, but with 0.166 g of sodium hydride (at 75% by mass in liquid petroleum jelly), 0.515 g of 1-(2-chloroethyl)-piperidine hydrochloride and 0.5 g of 3-benzyloxy-4-phenylpyrazole. 0.754 g of 3-benzyloxy-4-phenyl-1-(2-piperidin-1-ylethyl)-1H-pyrazole oxalate is thus obtained in the form of a white powder. IR spectrum (KBr): 2930; 2638; 2542; 1606; 1511; 1454; 1357; 1280; 1181; 763; 721; 697 and 501 cm⁻¹. Mass spectrum (CI): m/z=362 (MH⁺)⁺ base peak.

4-Phenyl-1-(2-piperidin-1-ylethyl)-1H-pyrazole oxalate

The procedure is carried out as in example 15, but with 0.231 g of sodium hydride (at 75% by mass in liquid petroleum jelly), 0.715 g of 1-(2-chloro-ethyl)piperidine hydrochloride and 0.4 g of 4-phenyl-pyrazole. 0.832 g of 4-phenyl-1-(2-piperidin-1-ylethyl)-1H-pyrazole oxalate are thus obtained in the form of white crystals.

¹H NMR spectrum (300 MHz)—δ in ppm—in DMSO-d6: 1.60 (m, 2H); 1.79 (m, 4H); 3.06 (m, 4H); 3.43 (t, J=6.5 Hz, 2H); 4.58 (t, J=6.5 Hz, 2H); 7.32 (broad t, J=7.5 Hz, 1H); 7.48 (broad t, J=7.5 Hz, 2H); 7.69 (broad d, J=7.5 Hz, 2H); 8.06 (s, 1H); 8.33 (s, 1H).

IR spectrum (KBr): 2949; 1679; 1713; 1606; 1460; 1187; 955; 763; 703 and 476 cm⁻¹.

EXAMPLE 67

4-(Thiophen-2-yl)-1-(2-piperidin-1-ylethyl)-1H-pyrazol-3-ol hydrochloride

A suspension of 0.15 g of 4-(5-chlorothiophen-2-yl)-1-(2-piperidin-1-ylethyl)-1H-pyrazol-3-ol hydrochloride and 5 mg of palladium-on-charcoal (at 10%) in 15 cm³ of methanol is stirred in an autoclave under a hydrogen pressure of 3000 kPa, at a temperature of 60° C. for 20 hours. The reaction medium is then filtered through Celite®, rinsed with methanol and concentrated to dryness under reduced pressure (3 kPa). The residue is triturated with diisopropyl ether; after filtration of the solid which has appeared and drying under vacuum (70 Pa) at a temperature of 60° C., 0.1 g of 4-(thiophen-2-yl)-1-(2-piperidin-1-ylethyl)-1H-pyrazol-3-ol hydro-chloride is obtained in the form of a gray powder which melts at around 180° C. (with decomposition). ¹H NMR spectrum (300 MHz)—δ in ppm—in DMSO-d6: 1.40 (m, 1H); from 1.62 to 1.85 (m, 5H); from 2.82 to 3.02 (broad m, 2H); from 3.30 to 3.52 (partially masked m, 4H); 4.40 (broad t, J=6.5 Hz, 2H); 7.02 (m, 1H); 7.19 (m, 1H); 7.32 (m, 1H); 7.93 (broad s, 1H); from 10.1 to 10.65 (broad m, 2H). IR spectrum, KBr: 2952; 2539; 1605; 1545; 1455; 1404; 1175; 969 and 697 cm⁻¹.

EXAMPLE 68

4-(3,4-Dichlorophenyl)-1-(2-piperidin-1-ylethyl)-1H-pyrazol-3-ol hydrochloride The procedure is carried out as in example 38 but with 0.47 g of 3-benzyloxy-4-(3,4-dichlorophenyl-1-(2-piperidin-1-ylethyl)-1H-pyrazole, 3 cm³ of 12N hydrochloric acid and 10 cm³ of ethanol. The mixture is heated for 24 hours at a temperature close to 100° C. After cooling to a temperature close to 20° C., the reaction medium is taken up with three times 30 cm³ of toluene and then three times 30 cm³ of acetone the ethanol, concentrated to dryness under reduced pressure (2 kPa); the residue is precipitated from 30 cm³ of acetone. 0.26 g of 4-(3,4-dichlorophenyl)-1-(2-piperidin-1-ylethyl)-1H-pyrazol-3-ol hydrochloride is obtained in the form of a whitish powder. ¹H NMR spectrum (300 MHz)—δ in ppm—in DMSO-d6: from 1.32 to 1.92 (m, 6H); from 2.85 to 3.60 (m, 6H); 4.36 (broad m, 2H); from 7.55 to 7.68 (m, 2H); 7.90 (d, J=2.0 Hz, 1H); 8.15 (broad s, 1H); from 9.35 to 9.48 (broad m, 1H); 10.8 (broad s, 1H). IR spectrum, KBr: 2945; 2533; 1604; 1525; 1448; 1180; 1028 and 806 cm⁻¹.

3-Benzyloxy-4-(3,4-dichlorophenyl)-1-(2-piperidin-1-ylethyl)-1H-pyrazole

The procedure is carried out as in example 15, but with 0.135 g of sodium hydride (75% by mass in liquid petroleum jelly), 0.519 g of 1-(2-chloroethyl)-piperidine hydrochloride and 0.45 g of 3-benzyloxy-4-(3,4-dichlorophenyl)pyrazole. After heating the reaction medium for 1 hour at 50° C. and then for 16 hours at 20° C., the medium is taken up with 150 cm³ of ethyl acetate and 150 cm³ of water; the organic phase is separated by settling out, washed with twice 100 cm³ of distilled water and 100 cm³ of a saturated aqueous sodium chloride solution, dried over sodium sulfate, filtered, and concentrated to dryness under reduced pressure (3 kPa). 0.6 g of 3-benzyloxy-4-(3,4-dichlorophenyl)-1-(2-piperidin-1-ylethyl)-1H-pyrazole is thus obtained in the form of an orange-yellow oil. ¹H NMR spectrum (400 MHz)—δ in ppm—in DMSO-d6: 1.38 (m, 2H); 1.48 (m, 4H); 2.38 (m, 4H); 2.68 (t, J=6.5 Hz, 2H); 4.07 (t, J=6.5 Hz, 2H); 5.33 (s, 2H); 7.36 (tt, J=1.5 and 7.5 Hz, 1H); 7.41 (broad t, J=7.5 Hz, 2H); 7.51 (d, J=7.5 Hz, 2H); from 7.57 to 7.65 (m, 2H); 7.88 (d, J=2.5 Hz, 1H); 8.21 (m, 1H). Mass spectrum (CI): m/z=430 (MH⁺) base peak.

3-Benzyloxy-4-(3,4-dichlorophenyl)-1H-pyrazole

The procedure is carried out as in example 38, but with 0.3 g of 1-(toluene-4-sulfonyl)-3-benzyloxy-4-(3,4-dichlorophenyl)-1H-pyrazole and 1.6 cm³ of a 1N solution of tetrabutylammonium fluoride in tetrahydrofuran and 15 cm³ of tetrahydrofuran. 0.2 g of 3-benzyloxy-4-(3,4-dichlorophenyl)-1H-pyrazole is thus obtained in the form of an oil which crystallizes. ¹H NMR spectrum (300 MHz)—δ in ppm—in DMSO-d6: 5.35 (s, 2H); from 7.32 to 7.46 (m, 3H); 7.50 (broad d, J=7.5 Hz, 2H); 7.59 (d, J=9.0 Hz, 1H); 7.70 (dd, J=2.5 and 9.0 Hz, 1H); 7.95 (d, J=2.5 Hz, 1H); 8.23 (s, 1H); 12.3 (broad m, 1H). Mass spectrum (EI): m/z=318 (M⁺·), m/z=91 ($C_7H_7^+$) base peak.

3-Benzyloxy-1-(toluene-4-sulfonyl)-4-(3,4-dichloro-phenyl)-1H-pyrazole

The procedure is carried out as in example 38, but with 0.3 g of 1-(toluene-4-sulfonyl)-3-benzyloxy-4-iodo-1H-pyrazole, 2.29 g of 3,4-dichlorophenylboronic acid, 2.547 g of tripotassium phosphate, and 0.421 g of dichlorobis(triphenylphosphine)palladium in 40 cm$^3$ of dimethoxyethane. After purification by chromatography, under a nitrogen pressure of 50 kPa, on a column of silica gel (particle size 20-45μ; diameter 4 cm; height 60 cm), eluting with a mixture of ethyl acetate and of cyclohexane (5/95 then 10/90 by volume), fractions 9 to 12 are combined, and concentrated to dryness under reduced pressure (3 kPa). 0.3 g of 3-benzyloxy-1-(toluene-4-sulfonyl)-4-(3,4-dichloro-phenyl)-1H-pyrazole is thus obtained in the form of a white powder. Mass spectrum (EI): m/z=472 (M$^{+\cdot}$), m/z=317 [(M–C$_7$H$_7$SO$_2$)$^+$], m/z=91 (C$_7$H$_7^+$) base peak.

EXAMPLE 69

4-(4-Bromophenyl)-1-(2-piperidin-1-ylethyl)-1H-pyrazol-3-ol

The procedure is carried out as in example 38, but with 0.32 g of 3-benzyloxy-4-(4-bromophenyl)-1-(2-piperidin-1-ylethyl)-1H-pyrazole, 3 cm$^3$ of 12N hydrochloric acid and 10 cm$^3$ of ethanol. The mixture is heated for 20 minutes at a temperature close to 100° C. After cooling to a temperature close to 20° C., the reaction medium is taken up with 5 times 30 cm$^3$ of acetone. After concentration to dryness under reduced pressure (3 kPa), the residue is triturated with 30 cm$^3$ of diisopropyl ether and then purified by chromatography, under a nitrogen pressure of 50 kPa, on a column of silica gel (particle size: 20-45μ; diameter 2 cm; height 20 cm), eluting with ethyl acetate then a mixture of ethyl acetate and methanol (95/5 then 90/10 then 80/20 by volume). Fractions 10 to 28 are combined, and concentrated to dryness under reduced pressure (3 kPa). 0.11 mg of 4-(4-bromophenyl)-1-(2-piperidin-1-ylethyl)-1H-pyrazol-3-ol is thus obtained in the form of a white powder. $^1$H NMR spectrum (300 MHz)—δ in ppm—in DMSO-d6: from 1.32 to 1.55 (m, 6H); 2.39 (m, 4H); 2.65 (t, J=6.5 Hz, 2H); 4.00 (t, J=6.5 Hz, 2H); 7.50 (broad d, J=8.5 Hz, 2H); 7.62 (broad d, J=8.5 Hz, 2H); 7.96 (s, 1H); from 10.3 to 10.50 (broad m, 1H). IR spectrum, KBr: 2941; 1631; 1601; 1529; 1173; 1007; 824 and 510 cm$^{-1}$.

3-Benzyloxy-4-(4-bromophenyl)-1-(2-piperidin-1-ylethyl)-1H-pyrazole

The procedure is carried out as in example 15, but with 2.77 g of sodium hydride (at 75% by mass in liquid petroleum jelly), 1.063 g of 1-(2-chloroethyl)piperidine hydrochloride and 0.95 g of 3-benzyloxy-4-(4-bromophenyl)pyrazole. After heating the reaction medium for 1 hour at 50° C., the medium is cooled to a temperature close to 20° C., and taken up with 300 cm$^3$ of ethyl acetate and 300 cm$^3$ of water; the organic phase is separated by settling out, dried over magnesium sulfate, filtered, and concentrated to dryness under reduced pressure (3 kPa). The residue is purified by chromatography, under a nitrogen pressure of 50 kPa, on a column of silica gel (particle size 20-45μ; diameter 3 cm; height 40 cm), eluting with a mixture of ethyl acetate and of cyclohexane (5/95 then 10/95 by volume). Fractions 19 to 35 are combined, and concentrated to dryness under reduced pressure (3 kPa). 0.32 g of 3-benzyloxy-4-(4-bromophenyl)-1-(2-piperidin-1-ylethyl)-1H-pyrazole is thus obtained in the form of a colorless oil. $^1$H NMR spectrum (300 MHz)—δ in ppm—in DMSO-d6:
From 1.34 to 1.53 (m, 6H); 2.38 (m, 4H); 2.68 (t, J=6.5 Hz, 2H); 4.07 (t, J=6.5 Hz, 2H); 5.32 (s, 2H); from 7.32 to 7.55 (m, 7H); 7.60 (broad d, J=8.5 Hz, 2H); 8.10 (s, 1H). Mass spectrum (ES): m/z=440 (MH$^+$) base peak.

3-Benzyloxy-4-(4-bromophenyl)-1H-pyrazole

The procedure is carried out as in example 38, but with 1.5 g of 1-(toluene-4-sulfonyl)-3-benzyloxy-4-(4-bromophenyl)-1H-pyrazole and 7.1 cm$^3$ of a 1N solution of tetrabutylammonium fluoride in tetrahydrofuran and 50 cm$^3$ of tetrahydrofuran. 0.93 g of 3-benzyloxy-4-(4-bromophenyl)-1H-pyrazole is thus obtained in the form of a whitish powder. $^1$H NMR spectrum (400 MHz)—δ in ppm—in DMSO-d6: 5.34 (s, 2H); 7.35 (tt, J=1.5 and 7.5 Hz, 1H); 7.41 (broad t, J=7.5 Hz, 2H); from 7.47 to 7.54 (m, 4H); 7.66 (m, 2H); 8.13 (s, 1H); 12.2 (broad m, 1H). Mass spectrum (EI): m/z=328 (M$^{+\cdot}$), m/z=91 (C$_7$H$_7^+$) base peak.

3-Benzyloxy-1-(toluene-4-sulfonyl)-4-(4-bromophenyl)-1H-pyrazole

The procedure is carried out as in example 38, but with 1.817 g of 1-(toluene-4-sulfonyl)-3-benzyloxy-4-iodo-1H-pyrazole, 2.41 g of 4-bromophenylboronic acid, 2.54 g of tripotassium phosphate, and 0.421 g of dichlorobis(triphenylphosphine)palladium in 40 cm$^3$ of dimethoxyethane. After purification by chromatography, under a nitrogen pressure of 50 kPa, on a column of silica gel (particle size 20-45μ; diameter 4 cm; height 60 cm), eluting with a mixture of ethyl acetate and of cyclohexane (5/95 by volume), fractions 15 to 30 are combined, and concentrated to dryness under reduced pressure (3 kPa). 1.5 g of 3-benzyloxy-1-(toluene-4-sulfonyl)-4-(4-bromophenyl)-1H-pyrazole are thus obtained in the form of a yellow oil which crystallizes. $^1$H NMR spectrum (300 MHz)—δ in ppm—in DMSO-d6 for 77% of the mixture: 2.42 (s, 3H); 5.33 (s, 2H); from 7.33 to 7.50 (m, 7H); 7.59 (broad d, J=8.5 Hz, 2H); 7.72 (broad d, J=8.5 Hz, 2H); 7.84 (m, 2H); 8.86 (s, 1H). Mass spectrum (EI): m/z=48 (M$^{+\cdot}$), m/z=327 [(M–C$_7$H$_7$SO$_2$)$^+$], m/z=91 (C$_7$H$_7^+$), base peak.

EXAMPLE 70

4-(1H-Indol-5-yl)-1-(2-piperidin-1-ylethyl)-1H-pyrazol-3-ol

A mixture of 0.5 g of 3-benzyloxy-4-(1H-indol-5-yl)-1-(2-piperidin-1-ylethyl)-1H-pyrazole, 0.5 g of ammonium formate and 0.5 g of palladium-on-charcoal (at 10%) in 50 cm$^3$ of ethanol is stirred for 30 minutes, under an inert atmosphere, at a temperature close to 70° C. The reaction medium is then cooled to a temperature close to 20° C., filtered through Celite®, rinsed with ethanol and concentrated to dryness under reduced pressure (3 kPa). The residue is purified on a cartridge of silica (particle size 20-40 μm), eluting with a mixture of dichloromethane and of a 2N solution of ammoniacal methanol (90/10 by volume). 0.258 g of 4-(1H-indol-5-yl)-1-(2-piperidin-1-ylethyl)-1H-pyrazol-3-ol is obtained in the form of a flaky white solid. $^1$H NMR spectrum (300 MHz)—δ in ppm—in DMSO-d6: from 1.33 to 1.55 (m, 6H); 2.40 (m, 4H); 2.66 (t, J=6.5 Hz, 2H); 4.00 (t, J=6.5 Hz, 2H); 6.39 (broad t, J=2.5 Hz, 1H); from 7.27 to 7.40 (m, 3H); 7.81 (m, 2H); 10.05 (broad s, 1H); 10.95 (broad m, 1H). IR spec-

3-Benzyloxy-4-(1H-indol-5-yl)-1-(2-piperidin-1-ylethyl)-1-H-pyrazole

The procedure is carried out as in example 37, but with 3.39 g of 3-benzyloxy-4-bromo-1-(2-piperidin-1-ylethyl)-1H-pyrazole, 3.14 g of 5-indolylboronic acid, 3.87 g of potassium carbonate, 1.2 g of tetrakis-(triphenyl)phosphine palladium in 70 cm³ of toluene and 20 cm³ of ethanol. After purification twice on a cartridge of silica (particle size 20-40 µm), eluting with a mixture of dichloromethane and of methanol (95/5 by volume), 2.17 g of 3-benzyloxy-4-(1H-indol-5-yl)-1-(2-piperidin-1-ylethyl)-1H-pyrazole is thus obtained in the form of a beige oil which crystallizes. $^1$H NMR spectrum (300 MHz)—δ in ppm—in DMSO-d6: from 1.33 to 1.55 (m, 6H); from 2.32 to 2.50 (broad m, 4H); 2.72 (broad m, 2H); 4.10 (t, J=6.5 Hz, 2H); 5.32 (s, 2H); 6.39 (broad t, J=2.5 Hz, 1H); from 7.29 to 7.46 (m, 6H); 7.52 (broad d, J=8.5 Hz, 2H); 7.81 (broad s, 1H); 7.93 (s, 1H); 11.0 (broad m, 1H).

EXAMPLE 71

4-(5-Bromothiophen-2-yl)-1-(2-piperidin-1-ylethyl)-1H-pyrazol-3-ol

The procedure is carried out as in example 38, but with 0.592 g of 3-benzyloxy-4-(5-bromothiophen-2-yl)-1-(2-piperidin-1-ylethyl)-1H-pyrazole, 3.65 cm³ of 12N hydrochloric acid and 4 cm³ of ethanol. The mixture is heated for 2 hours at a temperature close to 100° C. After cooling to a temperature close to 20° C., the reaction medium is taken up with ethanol, and concentrated to dryness under reduced pressure (2 kPa); the residue is precipitated from diisopropyl ether and then purified on a cartridge of silica (particle size 20-40 µm), eluting with a mixture of dichloromethane and of a 2N ammoniacal methanol solution (90/10 by volume). 0.068 g of 4-(5-bromothiophen-2-yl)-1-(2-piperidin-1-ylethyl)-1H-pyrazole-3-ol is obtained in the form of a yellow powder. $^1$H NMR spectrum (300 MHz)—δ in ppm—in DMSO-d6: from 1.33 to 1.53 (m, 6H); 2.37 (m, 4H); 2.62 (t, J=6.5 Hz, 2H); 3.99 (t, J=6.5 Hz, 2H); 6.93 (d, J=3.5 Hz, 1H); 7.10 (d, J=3.5 Hz, 1H); 7.85 (s, 1H); from 10.45 to 10.75 (very broad m, 1H). IR spectrum, KBr: 2938; 1593; 1536; 1471; 1173; 981; 798; 758 and 496 cm$^{-1}$. Mass spectrum (EI): m/z=355 (M$^+$·), m/z=98 (C$_6$H$_{12}$N$^+$) base peak.

3-Benzyloxy-4-(5-bromothiophen-2-yl)-1-(2-piperidin-1-ylethyl)-1H-pyrazole oxalate The procedure is carried out as in example 15, but with 0.154 g of sodium hydride (75% by mass in liquid petroleum jelly), 0.477 g of 1-(2-chloroethyl)-piperidine hydrochloride and 0.62 g of 3-benzyloxy-4-(5-bromothiophen-2-yl)pyrazole in 13 cm³ of dimethyl-formamide. After stirring for 1 hour at a temperature close to 20° C., the medium is taken up with 50 cm³ of ethyl acetate and 50 cm³ of water; the organic phase is separated by settling out, washed with 3 times 50 cm³ of a saturated aqueous sodium chloride solution, dried over magnesium sulfate, filtered, and concentrated to dryness under reduced pressure (3 kPa). The residue is taken up with 10 cm³ of acetone and 170 mg of oxalic acid in solution in 2 cm³ of acetone. The precipitate is filtered through sintered glass, washed with acetone, dried, and then purified on a cartridge of silica (particle size 20-40 µm), eluting with a mixture of dichloromethane and of methanol (95/5 then 90/10 by volume). 0.716 g of 3-benzyloxy-4-(5-bromothiophen-2-yl)-1-(2-piperidin-1-ylethyl)-1H-pyrazole oxalate is thus obtained in the form of a yellow powder. $^1$H NMR spectrum (300 MHz)—δ in ppm—in DMSO-d6: 1.48 (m, 2H); 1.65 (m, 4H); from 2.86 to 3.00 (broad m, 4H); 3.25 (broad partially masked m, 2H); 4.30 (broad t, J=6.5 Hz, 2H); 5.32 (s, 2H); 7.01 (d, J=3.5 Hz, 1H); 7.15 (d, J=3.5 Hz, 1H); from 7.32 to 7.54 (m, 5H); 8.09 (s, 1H). IR spectrum, KBr: 2948; 2536; 1724; 1641; 1595; 1532; 1498; 1451; 1363; 1173; 1008; 795 and 702 cm$^{-1}$. Mass spectrum (EI): m/z=445 (M$^+$·), m/z=98 (C$_6$H$_{12}$N$^+$) base peak.

3-Benzyloxy-4-(5-bromothiophen-2-yl)pyrazole

The procedure is carried out as in example 38, but with 1.1 g of 1-(toluene-4-sulfonyl)-3-benzyloxy-4-(5-bromothiophen-2-yl)-1H-pyrazole and 5 cm³ of a 1N solution of tetrabutylammonium fluoride in tetrahydrofuran and 40 cm³ of tetrahydrofuran. After purification on a cartridge of silica (particle size 20-40 µm), eluting with a mixture of dichloromethane and acetone (95/5 by volume), 0.624 g of 3-benzyloxy-4-(5-bromothiophen-2-yl)-1H-pyrazole is thus obtained in the form of a yellow solid. IR spectrum, KBr: 3193; 1599; 1503; 1438; 1362; 1238; 1023; 795; 731; 694 and 496 cm$^{-1}$. Mass spectrum (EI): m/z=334 (M$^+$·), m/z=91 (C$_7$H$_7^+$) base peak.

1-(Toluene-4-sulfonyl)-3-benzyloxy-4-(5-bromothiophen-2-yl)-1H-pyrazole

The procedure is carried out as in example 38, but with 1 g of 1-(toluene-4-sulfonyl)-3-benzyloxy-4-iodo-1H-pyrazole, 1.32 g of 5-bromothiophen-2-ylboronic acid, 1.22 g of potassium carbonate and 309 mg of dichlorobis(triphenylphosphine)palladium in 20 cm³ of toluene and 5 cm³ of ethanol. After purification on a cartridge of silica (particle size 20-40 µm), eluting with a mixture of ethyl acetate and of cyclohexane (10/90 by volume), 0.85 g of 1-(toluene-4-sulfonyl)-3-benzyloxy-4-(5-bromothiophen-2-yl)-1H-pyrazole is thus obtained in the form of an orange gum. IR spectrum, CCl$_4$: 1597; 1527; 1494; 1391; 1190; 1179; 1096; 1081; 695; 671; 595 and 540 cm$^{-1}$. Mass spectrum (CI): m/z=489 (M$^+$), m/z=263 (HPPh$_3$) base peak.

EXAMPLE 72

2-[1-(2-Piperidin-1-ylethyl)-1H-pyrazol-4-yl]benzamide 0.373 g of 4-(4-cyanophenyl)-1-(2-piperidin-1-ylethyl)-1H-pyrazole oxalate and 11 cm³ of 0.1N sodium hydroxide in 20 cm³ of dichloromethane are stirred at a temperature close to 20° C. for 15 minutes. The organic phase is separated by settling out, dried over anhydrous magnesium sulfate, filtered, and concentrated to dryness under reduced pressure (3 kPa). The residue is taken up with 11 cm³ of toluene. 0.287 g of potassium trimethylsilanolate is added and the reaction medium is heated at the reflux of the solvent for 6 h 30 min. The mixture is cooled to a temperature close to 20° C., and taken up with 40 cm³ of ethyl acetate and 40 cm³ of water. The organic phase is separated by settling out, washed with water, dried over anhydrous magnesium sulfate, filtered, and concentrated to dryness under reduced pressure (3 kPa). The residue is purified on a cartridge of silica (particle size 20-40 µm), eluting with a mixture of dichloromethane and a 2N ammoniacal methanol solution (95/5 by volume). 0.081 g of 2-[1-(2-piperidin-1-ylethyl)-1H-pyrazol-4-yl]benzamide is obtained in the form of a white solid which melts at 168° C.
$^1$H NMR spectrum (300 MHz)—δ in ppm—in DMSO-d6: from 1.33 to 1.55 (m, 6H); 2.40 (m, 4H); 2.68 (t, J=6.5 Hz, 2H); 4.22 (t, J=6.5 Hz, 2H); from 7.23 to 7.45 (m, 4H); 7.50 (broad d, J=8.5 Hz, 1H); 7.70 (d, J=1.0 Hz, 1H); 7.75 (broad m, 1H); 7.98 (d, J=1.0 Hz, 1H). IR spectrum, KBr: 3380; 3162; 2921; 1646; 1402; 954; 858; 754 and 633 cm$^{-1}$. Mass spectrum (CI): m/z=299 (MH$^+$) base peak.

4-(4-Cyanophenyl)-1-(2-piperidin-1-ylethyl)-1H-pyrazole oxalate

The procedure is carried out as in example 15, but with 0.098 g of sodium hydride (at 75% by mass in liquid petroleum jelly), 0.305 g of 1-(2-chloroethyl)-piperidine hydrochloride and 0.2 g of 4-(4-cyanophenyl)-1H-pyrazole. 0.373 g of 4-(4-cyano-phenyl)-1-(2-piperidin-1-ylethyl)-1H-pyrazole oxalate is thus obtained in the form of a white powder. $^1$H NMR spectrum (300 MHz)—δ in ppm—in DMSO-d6: 1.50 (m, 2H); 1.68 (m, 4H); 2.96 (m, 4H); 3.33 (broad t, J=6.5 Hz, 2H); 4.55 (t, J=6.5 Hz, 2H); 7.45 (m, 1H); 7.73 (m, 2H); 7.89 (m, 1H); 8.06 (d, J=1.0 Hz, 1H); 8.42 (d, J=1.0 Hz, 1H). IR spectrum, KBr: 2949; 2223; 1747; 1641; 1600; 1225; 1207; 990; 952; 764; 705 and 504 cm$^{-1}$. Mass spectrum (CI): m/z=281 (MH$^+$) base peak.

4-(4-Cyanophenyl)-1H-pyrazole

The procedure is carried out as in example 38, but with 0.613 g of 1-(toluene-4-sulfonyl)-4-(4-cyanophenyl)-1H-pyrazole and 3.8 cm$^3$ of a 1N solution of tetrabutyl-ammonium fluoride in tetrahydrofuran and 30 cm$^3$ of tetrahydrofuran. After purification on a cartridge of silica (particle size 20-40 μm), eluting with a mixture of dichloromethane and of acetone (90/10 by volume), 0.202 g of 4-(4-cyanophenyl)-1H-pyrazole is thus obtained in the form of a white solid. $^1$H NMR spectrum (300 MHz)—δ in ppm—in DMSO-d6: 7.43 (m, 1H); from 7.69 to 7.80 (m, 2H); 7.88 (m, 1H); from 8.00 to 8.30 (broad m, 2H); 13.3 (broad m, 1H). IR spectrum, KBr: 3153; 2966; 2218; 1601; 1516; 1347; 1044; 949; 763; 656 and 501 cm$^{-1}$. Mass spectrum (EI): m/z=169 (M$^{+\cdot}$) base peak, m/z=142 [(M−CHN)$^+$], m/z=115 [(m/z=142−CHN)$^+$].

1-(Toluene-4-sulfonyl)-4-(4-cyanophenyl)-1H-pyrazole

The procedure is carried out as in example 41 for the preparation of 3-benzyloxy-4-(5-chlorothiophen-1-yl)-1-(toluene-4-sulfonyl)-1H-pyrazole, but using 0.943 g of 1-(toluene-4-sulfonyl)-4-tributylstannanyl-1H-pyrazole, 0.43 g of 2-cyano-1-iodobenzene, 84 mg of tris(dibenzylideneacetone)palladium and 77 mg of tris(trifuryl)phosphine in 11 cm$^3$ of dioxane. After purification on a cartridge of silica (particle size 20-40 μm), eluting with a mixture of cyclohexane and of ethyl acetate (90/10 then 80/20 then 50/50 by volume), 0.613 g of 1-(toluene-4-sulfonyl)-4-(4-cyanophenyl)-1H-pyrazole is thus obtained in the form of an orange-yellow pasty solid. $^1$H NMR spectrum (400 MHz)—δ in ppm—in DMSO-d6: 2.42 (s, 3H); from 7.50 to 7.58 (m, 3H); 7.78 (dt, J=1.5 and 8.0 Hz, 1H); 7.84 (broad d, J=8.0 Hz, 1H); from 7.93 to 7.98 (m, 3H); 8.38 (d, J=1.0 Hz, 1H); 8.98 (d, J=1.0 Hz, 1H). IR spectrum, KBr: 2225; 1382; 1192; 1176; 1091; 1051; 812; 761; 702; 679; 664; 593 and 541 cm$^{-1}$. Mass spectrum (EI): m/z=323 (M$^{+\cdot}$), m/z=259 [(M−SO$_2$)$^{+\cdot}$], m/z=91 (C$_7$H$_7^+$) base peak.

1-(Toluene-4-sulfonyl)-4-tributylstannanyl-1H-pyrazole

The procedure is carried out as in example 41 for the preparation of 3-benzyloxy-1-(toluene-4-sulfonyl)-4-tributylstannanyl-1H-pyrazole, but using 1.5 g of 1-(toluene-4-sulfonyl)-4-iodo-1H-pyrazole, 2.65 cm$^3$ of 1,1,1,2,2,2-hexabutyldistannane, 58 mg of palladium diacetate and 136 mg of triphenylphosphine in 20 cm$^3$ of DMF. After 2 purifications on a cartridge of silica (particle size 20-40 μm), eluting with cyclohexane and then a mixture of cyclohexane and of ethyl acetate (95/5 by volume), 0.743 g of 1-(toluene-4-sulfonyl)-4-tributylstannanyl-1H-pyrazole is thus obtained in the form of a colorless oil. IR spectrum, CH$_2$Cl$_2$: 2959; 2925; 2873; 2854; 1378; 1175; 1064; 957; 673; 594 and 543 cm$^{-1}$. Mass spectrum (EI): m/z=511 (M$^{+\cdot}$), m/z=455 [(M−C$_4$H$_8$)$^{+\cdot}$] base peak, m/z=399 [(m/z=455−C$_4$H$_8$)$^{+\cdot}$], m/z=343 [(m/z=399−C$_4$H$_8$)$^{+\cdot}$], m/z=91 (C$_7$H$_7^+$).

EXAMPLE 73

4-(2-Hydroxyphenyl)-1-(2-piperidin-1-ylethyl)-1H-pyrazole hydrochloride

A stirred solution of 0.582 g of 4-(2-methoxyphenyl)-1-(2-piperidin-1-ylethyl)-1H-pyrazole oxalate in 12 cm$^3$ of dichloromethane, under an inert atmosphere, is cooled to a temperature close to −78° C. 4.3 cm$^3$ of boron tribromide are added and the stirring is continued for 4 hours at a temperature close to −70° C., and then for 15 hours at a temperature close to 20° C. The reaction medium is taken up with 10 cm$^3$ of water. The organic phase is separated by settling out and then washed with a 1N sodium hydroxide solution until a pH of 8-8.4 (Lyphan paper) is obtained, and taken up with 20 cm$^3$ of water. The organic phase is separated by settling out, dried over anhydrous magnesium sulfate, filtered, and concentrated to dryness under reduced pressure (3 kPa). The residue is precipitated from diisopropyl ether; the precipitate is purified on a cartridge of silica (particle size 20-40 μm), eluting with a mixture of dichloromethane and of methanol (90/10 by volume); the gum obtained is taken up with a 1N hydrochloric diethyl ether solution. 0.172 g of 4-(2-hydroxyphenyl)-1-(2-piperidin-1-ylethyl)-1H-pyrazole hydrochloride is obtained in the form of a pink powder. $^1$H NMR spectrum (300 MHz)—δ in ppm—in DMSO-d6: from 1.30 to 1.82 (broad m, 6H); from 2.38 to 3.62 (very broad m, 6H); from 4.22 to 4.60 (broad m, 2H); 6.82 (dt, J=1.5 and 8.0 Hz, 1H); 6.92 (broad d, J=8.0 Hz, 1H); 7.03 (dt, J=1.5 and 8.0 Hz, 1H); 7.54 (dd, J=1.5 and 8.0 Hz, 1H); 7.98 (broad s, 1H); 8.23 (broad s, 1H); from 9.05 to 9.45 (very broad m, 1H); 9.76 (broad s, 1H). IR spectrum, KBr: 3144; 2938; 2539; 1560; 1461; 1351; 1282; 1238; 1111; 954; 856; 747 and 478 cm$^{-1}$. Mass spectrum (EI): m/z=271 (M$^{+\cdot}$), m/z=98 [C$_6$H$_{12}$N$^+$] base peak.

4-(2-Methoxyphenyl)-1-(2-piperidin-1-ylethyl)-1H-pyrazole oxalate

The procedure is carried out as in example 15, but with 0.22 mg of sodium hydride (at 75% by mass in liquid petroleum jelly), 0.681 g of 1-(2-chloroethyl)-piperidine hydrochloride and 0.46 mg of 4-(2-methoxyphenyl)-1H-pyrazole. 0.582 g of 4-(2-methoxy-phenyl)-1-(2-piperidin-1-ylethyl)-1H-pyrazole oxalate is thus obtained in the form of a white solid. $^1$H NMR spectrum (300 MHz)—δ in ppm—in DMSO-d6 for 50% of the mixture: 1.50 (m, 2H); from 1.62 to 1.75 (broad m, 4H); from 2.88 to 3.09 (m, 4H); 3.15 (t, J=6.5 Hz, 2H); 3.89 (s, 3H); 4.52 (t, J=6.5 Hz, 2H); 6.99 (broad t, J=8.0 Hz, 1H);

7.10 (broad d, J=8.0 Hz, 1H); 7.23 (dt, J=1.5 and 8.0 Hz, 1H); 7.63 (dd, J=1.5 and 8.0 Hz, 1H); 8.01 (broad s, 1H); 8.23 (broad s, 1H). IR spectrum, KBr: 2948; 2537; 1719; 1635; 1493; 1246; 1184; 1028; 952; 756; 721; 704 and 497 cm$^{-1}$. Mass spectrum (CI): m/z=281 (MH$^+$) base peak, m/z=148 (M'H$^+$).

4-(2-Methoxyphenyl)-1H-pyrazole

The procedure is carried out as in example 38, but with 1.08 g of 1-(toluene-4-sulfonyl)-4-(2-methoxyphenyl)-1H-pyrazole and 7.3 cm$^3$ of a 1N solution of tetrabutylammonium fluoride in tetrahydrofuran and 58 cm$^3$ of tetrahydrofuran. After purification on a cartridge of silica (particle size 20-40 μm), eluting with a mixture of dichloromethane and of methanol (90/10 by volume), 0.463 g of 4-(2-methoxyphenyl)-1H-pyrazole is thus obtained in the form of an off-white solid. $^1$H NMR spectrum (300 MHz)—δ in ppm—in DMSO-d6: 3.89 (s, 3H); 6.97 (dt, J=1.5 and 8.5 Hz, 1H); 7.06 (broad d, J=8.5 Hz, 1H); 7.21 (m, 1H); 7.63 (dd, J=1.5 and 8.5 Hz, 1H); from 7.85 to 8.20 (very broad m, 2H); 12.9 (broad m, 1H). IR spectrum, KBr: 3156; 2936; 2832; 1569; 1488; 1466; 1263; 1247; 1148; 1027; 950; 753; 661 and 628 cm$^{-1}$. Mass spectrum (EI): m/z=174 (M$^{+\cdot}$) base peak, m/z=159 [(M−CH$_3$)$^+$], m/z=131 [(m/z=159−CO)$^+$].

1-(Toluene-4-sulfonyl)-4-(2-methoxyphenyl)-1H-pyrazole

The procedure is carried out as in example 38, but with 1.5 g of 1-(toluene-4-sulfonyl)-4-iodo-1H-pyrazole, 1.31 g of 2-methoxyphenylboronic acid, 1.74 g of potassium carbonate and 0.605 g of dichlorobis-(triphenylphosphine)palladium in 30 cm$^3$ of toluene and 7.5 cm$^3$ of ethanol. After purification on a cartridge of silica (particle size 20-40 μm), eluting with a mixture of ethyl acetate and of cyclohexane (20/80 by volume), 1.081 g of 1-(toluene-4-sulfonyl)-4-(2-methoxyphenyl)-1H-pyrazole are thus obtained in the form of an orange gum. $^1$H NMR spectrum (300 MHz)—δ in ppm—in DMSO-d6: 2.41 (s, 3H); 3.92 (s, 3H); 7.01 (dt, J=1.5 and 8.5 Hz, 1H); 7.13 (broad d, J=8.5 Hz, 1H); 7.33 (m, 1H); broad d, J=8.5 Hz, 2H); 7.73 (dd, J=1.5 and 8.5 Hz, 1H); 7.93 (broad d, J=8.5 Hz, 2H); 8.41 (broad s, 1H); 8.72 (broad s, 1H). IR spectrum, KBr: 2835; 1497; 1371; 1177; 1097; 1039; 1023; 950; 753; 681; 598 and 550 cm$^{-1}$. Mass spectrum (EI): m/z=328 (M$^{+\cdot}$) base peak, m/z=264 [(M−SO$_2$)$^+$], m/z=173 [(M−C$_7$H$_7$SO$_2$)$^+$], m/z=91 (C$_7$H$_7^+$).

EXAMPLE 74

4-(1H-Indol-5-yl)-1-(2-piperidin-1-ylethyl)-1H-pyrazole

The procedure is carried out as in example 38, but with 1.22 g of 4-iodo-1-(2-piperidin-1-ylethyl)-1H-pyrazole, 1.93 g of 1H-indol-5-ylboronic acid, 2.547 g of tripotassium phosphate, 0.421 g of dichlorobis-(triphenylphosphine)palladium in 50 cm$^3$ of dimethoxy-ethane. After purification by chromatography, under a nitrogen pressure of 50 kPa, on a column of silica gel (particle size 20-45μ; diameter 3 cm; height 60 cm), eluting with a mixture of ethyl acetate and of methanol (95/5 then 90/10 by volume), fractions 18 to 30 are combined, and concentrated to dryness under reduced pressure (3 kPa). 0.23 g of 4-(1H-indol-5-yl)-1-(2-piperidin-1-ylethyl)-1H-pyrazole is thus obtained in the form of a whitish powder. $^1$H NMR spectrum (300 MHz) —δ in ppm—in DMSO-d6: from 1.34 to 1.56 (m, 6H); 2.41 (m, 4H); 2.72 (t, J=6.5 Hz, 2H); 4.22 (t, J=6.5 Hz, 2H); 6.41 (m, 1H); from 7.27 to 7.40 (m, 3H); 7.71 (m, 1H); 7.80 (d, J=1.0 Hz, 1H); 8.06 (broad s, 1H); 11.0 (broad m, 1H).
IR spectrum, KBr: 2937; 1436; 1363; 1167; 1119; 994; 887; 792; 763; 614 and 430 cm$^{-1}$.
Mass spectrum (EI): m/z=294 (M$^{+\cdot}$), m/z=98 (C$_6$H$_{12}$N$^+$) base peak.

4-Iodo-1-(2-piperidin-1-ylethyl)-1H-pyrazole

The procedure is carried out as in example 15, but with 4.94 g of sodium hydride (at 75% by mass in liquid petroleum jelly), 19 g of 1-(2-chloroethyl)piperidine hydrochloride and 10 g of 4-iodopyrazole. After stirring for 16 hours at a temperature close to 20° C., the reaction medium is taken up with 1000 cm$^3$ of ethyl acetate and 1000 cm$^3$ of water; the organic phase is separated by settling out, washed with 3 times 1000 cm$^3$ of water and 500 cm$^3$ of a saturated aqueous sodium chloride solution, dried over magnesium sulfate, filtered, and concentrated to dryness under reduced pressure (3 kPa). The residue is purified by chromatography, under a nitrogen pressure of 50 kPa, on a column of silica gel (particle size 20-45μ; diameter 6 cm; height 60 cm), eluting with a mixture of ethyl acetate and of cyclohexane (30/70 by volume) and then ethyl acetate. Fractions 16 to 20 are combined, and concentrated to dryness under reduced pressure (3 kPa). 8.2 g of 4-iodo-1-(2-piperidin-1-ylethyl)-1H-pyrazole are thus obtained in the form of a light yellow oil. $^1$H NMR spectrum (300 MHz)—δ in ppm—in DMSO-d6: from 1.34 to 1.52 (m, 6H); 2.36 (m, 4H); 2.64 (t, J=6.5 Hz, 2H); 4.22 (t, J=6.5 Hz, 2H); 7.51 (broad s, 1H); 7.92 (broad s, 1H). Mass spectrum (CI): m/z=306 (MH$^+$) base peak.

EXAMPLE 75

4-(4-Methylphenyl)-1-(2-piperidin-1-ylethyl)-1H-pyrazol-3-ol hydrochloride

The procedure is carried out as in example 38, but with 0.63 g of 3-benzyloxy-4-(4-methylphenyl)-1-(2-piperidin-1-ylethyl)-1H-pyrazole, 4.8 cm$^3$ of 12N hydrochloric acid and 4.8 cm$^3$ of ethanol. The mixture is heated for 4 hours at a temperature close to 100° C. After cooling to a temperature close to 20° C., the reaction medium is taken up with ethanol, and concentrated to dryness under reduced pressure (2 kPa); the residue is precipitated from diisopropyl ether. 0.385 g of 4-(4-methylphenyl)-1-(2-piperidin-1-ylethyl)-1H-pyrazol-3-ol hydrochloride is obtained in the form of a white solid. $^1$H NMR spectrum (300 MHz)—δ in ppm—in DMSO-d6: 1.40 (m, 1H); from 1.63 to 1.87 (m, 5H); 2.30 (s, 3H); from 2.82 to 3.02 (broad m, 2H); from 3.27 to 3.53 (m, 4H); 4.38 (broad t, J=6.5 Hz, 2H); 7.15 (broad d, J=8.5 Hz, 2H); 7.54 (broad d, J=8.5 Hz, 2H); 7.98 (s, 1H); 10.05 (very broad m, 1H); 10.4 (broad m, 1H). IR spectrum, KBr: 2941; 2646; 1597; 1534; 1447; 1179; 1010; 818; 627 and 515 cm$^{-1}$. Mass spectrum (EI): m/z=285 (M$^{+\cdot}$), m/z=98 (C$_6$H$_{12}$N$^+$) base peak.

3-Benzyloxy-4-(4-methylphenyl)-1-(2-piperidin-1-yl-ethyl)-1H-pyrazole oxalate

The procedure is carried out as in example 15, but with 0.123 g of sodium hydride (at 75% by mass in liquid petroleum jelly), 0.38 g of 1-(2-chloroethyl)piperidine hydrochloride and 0.39 g of 3-benzyloxy-4-(4-methyl-phenyl)pyrazole. 0.632 g of 3-benzyloxy-4-(4-methylphenyl)-1-(2-piperidin-1-ylethyl)-1H-pyrazole oxalate is thus obtained in the form of a white powder. IR spectrum, KBr: 2931; 2639; 2543; 1719;

1618; 1580; 1519; 1452; 1279; 1180; 818; 721 and 500 cm$^{-1}$. Mass spectrum (CI): m/z=376 (MH$^+$) base peak.

3-Benzyloxy-4-(4-methylphenyl)-1H-pyrazole

The procedure is carried out as in example 38, but with 0.8 g of 1-(toluene-4-sulfonyl)-3-benzyloxy-4-(4-methylphenyl)-1H-pyrazole and 4 cm$^3$ of a 1N solution of tetrabutylammonium fluoride in tetrahydrofuran and 40 cm$^3$ of tetrahydrofuran. 0.397 g of 3-benzyloxy-4-(4-methylphenyl)-1H-pyrazole is thus obtained in the form of a white powder. IR spectrum, KBr: 3187; 2980; 1586; 1498; 1450; 1380; 1233; 1043; 814; 737; 695 and 514 cm$^{-1}$. Mass spectrum (EI): m/z=264 (M$^{+\cdot}$), m/z=186 [(M–C$_6$H$_6$)$^{+\cdot}$], m/z=91 (C$_7$H$_7^+$) base peak. 3-Benzyloxy-1-(toluene-4-sulfonyl)-4-(4-methylphenyl)-1H-pyrazole The procedure is carried out as in example 38, but with 1 g of 1-(toluene-4-sulfonyl)-3-benzyloxy-4-iodo-1H-pyrazole, 0.898 g of 4-methylphenylboronic acid, 0.913 g of potassium carbonate and 0.331 g of tetrakis(triphenylphosphine)palladium in 13 cm$^3$ of toluene, 3 cm$^3$ of ethanol and 3.3 cm$^3$ of water. 0.817 g of 3-benzyloxy-1-(toluene-4-sulfonyl)-4-(4-methyl-phenyl)-1H-pyrazole is thus obtained in the form of a pinkish-beige cottonwool-like solid. IR spectrum, KBr: 1589; 1485; 1377; 1191; 1179; 1098; 813; 702; 672; 580 and 538 cm$^{-1}$. Mass spectrum (EI): m/z=418 (M$^{+\cdot}$), m/z=263 [(M–C$_7$H$_7$SO$_2$)$^+$], m/z=91 (C$_7$H$_7^+$) base peak.

EXAMPLE 76

1-(1-Azabicyclo[2.2.2]oct-3-yl)-4-(1H-indol-5-yl)-1H-pyrazole

The procedure is carried out as in example 38, but with 1 g of 1-(1-azabicyclo[2.2.2]oct-3-yl)-4-iodo-1H-pyrazole, 0.797 g of 1H-indol-5-ylboronic acid, 1.026 g of potassium carbonate, 0.463 g of dichlorobis-(triphenylphosphine)palladium in 30 cm$^3$ of toluene, 6 cm$^3$ of ethanol and 3 cm$^3$ of water. After purification by chromatography, under a nitrogen pressure of 50 kPa, on an alumina CTB1 column, eluting with ethyl acetate and then a mixture of ethyl acetate and of methanol (95/5 then 90/10 then 80/20 by volume), fractions 97 to 110 are combined, and concentrated to dryness under reduced pressure (3 kPa). The residue is precipitated from a mixture of 5 cm$^3$ of ethyl acetate and 25 cm$^3$ of diisopropyl ether. 0.18 g of 1-(1-azabicyclo[2.2.2]oct-3-yl)-4-(1H-indol-5-yl)-1H-pyrazole is thus obtained in the form of a yellow powder. $^1$H NMR spectrum (300 MHz)—δ in ppm—in DMSO-d6: 1.34 (m, 1H); from 1.53 to 1.75 (m, 3H); 2.13 (m, 1H); from 2.67 to 2.81 (m, 3H); 3.02 (m, 1H); 3.26 (partially masked m, 1H); 3.49 (m, 1H); 4.44 (m, 1H); 6.40 (m, 1H); from 7.29 to 7.41 (m, 3H); 7.75 (broad s, 1H); 7.87 (broad s, 1H); 8.22 (broad s, 1H); 11.0 (broad m, 1H). IR spectrum, KBr: 3113; 2939; 1587; 1454; 1362; 1165; 1058; 976; 881; 792; 729; 619 and 435 cm$^{-1}$. Mass spectrum (ES): m/z=293 (MH$^+$) base peak.

The enantiomers are separated by HPLC on chiralpak AD 20 μm with, as eluent, a mixture of heptane, of ethanol and of butylamine (40/60/0.2 by volume). Two enantiomers, A and B, are obtained, which are purified according to the following protocol: enantiomer A is purified by extraction with ethyl acetate and then solubilized in 100 ml of water. The pH of the solution is adjusted to 10 with 0.1N sodium hydroxide. The organic phase is extracted with 100 ml of ethyl acetate. The aqueous phase is separated by settling out with 2×50 ml of dichloromethane. The organic phase is dried with anhydrous sodium sulfate, filtered, and concentrated to dryness under reduced pressure. The organic phase is controlled by reverse-phase polarity HPLC on a Thermo hypersil Hypurity C18 250*4.6*5 μm column; eluent: 95/5 gradient: acetate buffer/aceto-nitrile for 50 minutes. 42.6 mg of (–)-1-(1-azabicyclo-[2.2.2]oct-3-yl)-4-(1H-indol-5-yl)-1H-pyrazole, enantiomer A are obtained ([α]$^{20}_D$=–37.3° (solvent: dimethyl sulfoxide, concentration: 0.3)).

Enantiomer B is purified by extraction with ethyl acetate and then solubilized in 100 ml of water. The pH of the solution is adjusted to 10 with 0.1N sodium hydroxide. The organic phase is extracted with 100 ml of ethyl acetate. The aqueous phase is separated by settling out with 2×50 ml of dichloromethane. The organic phase is dried with anhydrous sodium sulfate, filtered, and concentrated to dryness under reduced pressure. The organic phase is controlled by reverse-phase polarity HPLC on a Thermo hypersil Hypurity C18 250*4.6*5 μm column; eluent: 95/5 gradient: acetate buffer/acetonitrile for 50 minutes. 56.3 mg of (+)-1-(1-azabicyclo [2.2.2]oct-3-yl)-4-(1H-indol-5-yl)-1H-pyrazole, enantiomer B are obtained ([α]$^{20}_D$=+36.2° (solvent: dimethyl sulfoxide, concentration: 0.42)).

1-(1-Azabicyclo[2.2.2]oct-3-yl)-4-iodo-1H-pyrazole

The procedure is carried out as in example 5, but with 0.48 g of sodium hydride (at 75% by mass in liquid petroleum jelly), 3.079 g of toluene-4-sulfonic acid 1-azabicyclo[2.2.2] oct-3-yl ester and 1.94 g of 4-iodo-pyrazole in 30 cm$^3$ of dimethylformamide. The residue is purified by chromatography, under a nitrogen pressure of 50 kPa, on an alumina CBT1 column, eluting with ethyl acetate and then a mixture of ethyl acetate and of methanol (95/5 then 90/10 by volume). Fractions 29 to 39 are combined, and concentrated to dryness under reduced pressure (3 kPa). The oil obtained is again purified on an alumina CBT1 column, eluting with ethyl acetate. Fractions 11 to 15 are combined, and concentrated to dryness under reduced pressure (3 kPa). 0.33 g of 1-(1-azabicyclo[2.2.2]oct-3-yl)-4-iodo-1H-pyrazole is obtained in the form of an oil which crystallizes. $^1$H NMR spectrum (400 MHz)—δ in ppm—in DMSO-d6: 1.30 (m, 1H); 1.46 (m, 1H); 1.66 (m, 2H); 2.05 (m, 1H); from 2.65 to 2.78 (m, 4H); 2.91 (m, 1H); 3.21 (partially masked m, 1H); 4.44 (m, 1H); 7.58 (broad s, 1H); 8.06 (broad s, 1H). Mass spectrum (EI): m/z=303 (M$^{+\cdot}$), m/z=220 [(M–C$_5$H$_9$N)$^{+\cdot}$], m/z=109 (C$_7$H$_{11}$N$^{+\cdot}$), m/z=97 (C$_6$H$_{11}$N$^{+\cdot}$) base peak.

EXAMPLE 77

1-(1-Azabicyclo[2.2.2]oct-3-yl)-4-(5-chlorothiophen-2-yl)-1H-pyrazol-3-ol hydrochloride, isomer A The procedure is carried out as in example 38, but with 0.13 g of 1-(1-azabicyclo[2.2.2]oct-3-yl)-3-benzyloxy-4-(5-chlorothiophen-2-yl)-1H-pyrazole, isomer A, 10 cm$^3$ of 12N hydrochloric acid and 15 cm$^3$ of ethanol. The mixture is heated for 22 hours at a temperature close to 100° C., and then cooled to a temperature close to 20° C.; the reaction medium is concentrated to dryness under reduced pressure (3 kPa), then taken up with twice 20 cm$^3$ of ethanol and concentrated to dryness under reduced pressure (2 kPa); the residue is precipitated from 20 cm$^3$ of diisopropyl ether. 80 mg of 1-(1-azabicyclo[2.2.2]oct-3-yl)-4-(5-chlorothiophen-2-yl)-1H-pyrazol-3-ol hydrochloride, isomer A, are obtained in the form of a grayish powder. $^1$H NMR spectrum (300 MHz)—δ in ppm—in DMSO-d6: from 1.62 to 1.98 (m, 4H); 2.36 (m, 1H); from 3.07 to 3.55 (partially masked m, 4H); 3.71 (m, 2H); 4.62 (m, 1H); 7.03 (m, 2H); 8.10 (broad s, 1H); 10.75 (broad m, 1H).

IR spectrum, KBr: 1602; 1536; 1459; 1164; 1005; 795 and 502 cm$^{-1}$.

Mass spectrum (ES): m/z=310 (MH$^+$) base peak. $[\alpha]_D$=−14° (solvent: MeOH, concentration 0.1266).

EXAMPLE 78

1-(1-Azabicyclo[2.2.2]oct-3-yl)-4-(5-chlorothiophen-2-yl)-1H-pyrazol-3-ol hydrochloride, isomer B The procedure is carried out as in example 38, but with 0.13 g of 1-(1-azabicyclo[2.2.2]oct-3-yl)-3-benzyloxy-4-(5-chlorothiophen-2-yl)-1H-pyrazole, isomer B, 5 cm$^3$ of 12N hydrochloric acid and 10 cm$^3$ of ethanol. The mixture is heated for 16 hours at a temperature close to 100° C., then cooled to a temperature close to 20° C.; the reaction medium is concentrated to dryness under reduced pressure (3 kPa), then taken up with twice 20 cm$^3$ of toluene and concentrated to dryness under reduced pressure (2 kPa); the residue is taken up with 3 times 20 cm$^3$ of ethanol and concentrated to dryness under reduced pressure (2 kPa). The residue thus obtained is precipitated from 20 cm$^3$ of diisopropyl ether. 100 mg of 1-(1-azabicyclo[2.2.2]oct-3-yl)-4-(5-chlorothiophen-2-yl)-1H-pyrazole-3-ol hydrochloride, isomer B, are obtained in the form of a grayish powder. $^1$H NMR spectrum (300 MHz)—δ in ppm—in DMSO-d6: from 1.62 to 2.00 (m, 4H); 2.38 (m, 1H); from 3.05 to 3.53 (m, 4H); 3.73 (m, 2H); 4.63 (m, 1H); 7.03 (m, 2H); 8.11 (broad s, 1H); 10.75 (broad m, 1H). IR spectrum, KBr: 1601; 1536; 1457; 1163; 1004; 794 and 502 cm$^{-1}$. Mass spectrum (CI): m/z=310 (MH$^+$) base peak. $[\alpha]_D$=−18 (solvent: MeOH, concentration: 0.2168).

1-(1-Azabicyclo[2.2.2]oct-3-yl)-3-benzyloxy-4-(5-chlorothiophen-2-yl)-1H-pyrazole, isomers A And B The procedure is carried out as in example 5, but with 0.495 g of sodium hydride (at 75% by mass in liquid petroleum jelly), 3.178 g of toluene-4-sulfonic acid 1-azabicyclo[2.2.2]oct-3-yl ester and 1.94 g of 3-benzyloxy-4-(5-chlorothiophen-2-yl)pyrazole in 70 cm$^3$ of dimethylformamide. The residue is purified by chromatography, under a nitrogen pressure of 50 kPa, on a column of silica gel (particle size 20-45μ; diameter 3 cm; height 50 cm), eluting with dichloromethane and then a mixture of dichloromethane and of methanol (95/5 then 90/10 then 80/20 by volume). Fractions 52 to 74 are combined, and concentrated to dryness under reduced pressure (3 kPa). The oil obtained is again purified on an alumina CBT1 column, eluting with ethyl acetate and then a mixture of ethyl acetate and of methanol (90/10 by volume). Fractions 22, 32 and 40 to 50 are combined, and concentrated to dryness under reduced pressure (3 kPa). 0.5 g of 1-(1-azabicyclo[2.2.2]-oct-3-yl)-3-benzyloxy-4-(5-chlorothiophen-2-yl)-1H-pyrazole is thus obtained in the form of a green oil which crystallizes, for which the two enantiomers are separated by HPLC. Mass spectrum (EI): m/z=399 (M$^{+\cdot}$), m/z=308 [(M−C$_7$H$_7$)$^+$], m/z=110 (C$_7$H$_{12}$N$^+$), m/z=91 (C$_7$H$_7{}^+$) base peak.

Using 0.45 g of 1-(1-aza-bicyclo[2.2.2]oct-3-yl)-3-benzyloxy-4-(5-chlorothiophen-2-yl)-1H-pyrazole, the enantiomers are separated by HPLC on chiralpak AD 20 μm, eluting with a mixture of 70% heptane/15% ethanol/15% methanol/0.1% triethylamine. 138 mg of 1-(1-azabicyclo[2.2.2]oct-3-yl)-3-benzyloxy-4-(5-chlorothiophen-2-yl)-1H-pyrazole, isomer A ($[\alpha]_D$=+28.20° (solvent: MeOH, concentration: 0.5)) and 129 mg of 1-(1-azabicyclo[2.2.2]oct-3-yl)-3-benzyloxy-4-(5-chlorothiopen-2-yl)-1H-pyrazole, isomer B ($[\alpha]_D$=−24.6° (solvent: MeOH, concentration: 0.5)) are obtained. Mass spectrum (IE): m/z=399 (M$^{+\cdot}$), m/z=308 [(M−C$_7$H$_7$)$^+$], m/z=110 (C$_7$H$_{12}$N$^+$), m/z=91 (C$_7$H$_7{}^+$) base peak.

EXAMPLE 79

1-(1-Azabicyclo[2.2.2]oct-2-ylmethyl)-4-phenyl-1H-pyrazol-3-ol hydrochloride 1.8 cm$^3$ of 6N hydrochloric acid is added to a solution of 0.8 g of 2-(3-benzyloxy-4-phenylpyrazol-1-ylmethyl)-1-azabicyclo[2.2.2]octane in 20 cm$^3$ of ethanol and the mixture is stirred at ambient temperature for 30 minutes and then concentrated to dryness under reduced pressure (3 kPa). The suspension of the residue obtained and of 114 mg of palladium-on-charcoal at 10% in 20 cm$^3$ of ethanol is stirred in an autoclave under a hydrogen pressure of 100 kPa, at a temperature of 20° C. for 8 hours. The reaction medium is then filtered through Celite® and concentrated to dryness under reduced pressure (3 kPa), to give a pasty residue, which is covered with 40 cm$^3$ of acetone and triturated until crystallization is complete. After filtration of the solid that has appeared and drying under vacuum (70 Pa) at a temperature of 60° C., 0.6 g of 1-(1-azabicyclo[2.2.2]oct-2-ylmethyl)-4-phenyl-1H-pyrazol-3-ol hydrochloride is obtained in the form of beige crystals which melt at a temperature above 260° C. $^1$H NMR spectrum (300 MHz)—δ in ppm—in DMSO-d6 (referenced at 2.50 ppm): 1.55 (m, 1H); from 1.71 to 1.95 (m, 5H); 2.08 (m, 1H); from 3.12 to 3.35 (partially masked m, 3H); 3.50 (m, 1H); 3.88 (m, 1H); 4.27 (dd, J=7.5 and 14.0 Hz, 1H); 4.42 (dd, J=7.5 and 14.0 Hz, 1H); 7.12 (broad t, J=7.5 Hz, 1H); 7.32 (broad t, J=7.5 Hz, 2H); 7.63 (broad d, J=7.5 Hz, 2H); 8.01 (s, 1H); 9.80 (broad m, 1H); 10.45 (broad m, 1H). Mass spectrum (EI): m/z=283 (M$^{+\cdot}$), m/z=201 [(M−C$_5$H$_8$N)$^+$], m/z=173 [(M−C$_7$H$_{12}$N)$^{+\cdot}$], m/z=124 (C$_8$H$_{14}$N$^+$) base peak, m/z=82 (C$_5$H$_8$N$^+$), m/z=36 (HCl$^{+\cdot}$).

The 2-(3-benzyloxy-4-phenylpyrazol-1-ylmethyl)-1-azabicyclo[2.2.2]octane can be obtained in the following way:

182 mg of sodium hydride (at 75% by mass in liquid petroleum jelly) are added gradually, under an argon atmosphere and at ambient temperature, to a solution of 0.95 g of 3-benzyloxy-4-phenylpyrazole in 20 cm$^3$ of anhydrous dimethylformamide. After stirring for three-quarters of an hour at a temperature in the region of 50° C., a solution of 1.25 g of 1-azabicyclo[2.2.2]oct-2-ylmethyl methanesulfonate in 20 cm$^3$ of anhydrous dimethylformamide is gradually added, and the mixture is then heated for 24 hours at a temperature in the region of 110° C. The mixture is cooled to ambient temperature, and then 10 cm$^3$ of water are slowly added and the mixture is finally concentrated in a rotary evaporator. 25 cm$^3$ of water are added to the residue obtained, which is extracted with 250 cm$^3$ of ethyl acetate. The organic phase is washed with 3 times 25 cm$^3$ of water, then filtered through a phase-separating filter (Whatman®, reference: 2200 185) and concentrated to dryness under reduced pressure (3 kPa). The oily residue obtained is purified by chromatography on alumina, eluting with dichloromethane. After concentrating the fractions under reduced pressure, 0.8 g of 2-(3-benzyloxy-4-phenylpyrazol-1-ylmethyl)-1-azabicyclo[2.2.2]octane is obtained in the form of an oil which solidifies slowly as an amorphous solid. Mass spectrum (EI): m/z=373 (M$^{+\cdot}$), m/z=282 [(M−C$_7$H$_7$)$^+$], m/z=124 (C$_8$H$_{14}$N$^+$), m/z=91 (C$_7$H$_7{}^+$) base peak, m/z=82 (C$_5$H$_8$N$^+$).

The 1-azabicyclo[2.2.2]oct-2-ylmethyl methanesulfonate can be obtained in the following way:

0.69 cm³ of pyridine followed, dropwise, by 0.66 cm³ of methanesulfonyl chloride are added, at a temperature in the region of 0° C. and under an argon atmosphere, to a solution of 1 g of (1-azabicyclo[2.2.2]oct-2-yl)-methanol in 40 cm³ of dichloromethane. The suspension is stirred for 20 minutes at around 0° C. and then for 18 hours at ambient temperature. 15 cm³ of a saturated potassium carbonate solution are then added to the mixture, which is extracted with 3 times 50 cm³ of ethyl acetate. The combined organic phases are dried over anhydrous magnesium sulfate, filtered, and concentrated to dryness under reduced pressure (3 kPa). The residue obtained is purified by chromatography on alumina, eluting with ethyl acetate. After concentrating the fractions under reduced pressure, 1.1 g of 1-aza-bicyclo[2.2.2]oct-2-ylmethyl methanesulfonate are obtained in the form of a colorless oil. Mass spectrum (EI): m/z=219 ($M^{+\cdot}$), m/z=140 [$(M-SO_2CH_3)^+$], m/z=124 ($C_8H_{14}N^+$) base peak.

The (1-azabicyclo[2.2.2]oct-2-yl)methanol can be obtained according to the method described in patent DE 1938546.

EXAMPLE 80

3-[4-(3,5-Difluorophenyl)pyrazol-1-yl]-1-azabicyclo-[2.2.2]octane hydrochloride 0.173 g of sodium hydride (at 75% by mass in liquid petroleum jelly) is added gradually, under an argon atmosphere and at ambient temperature, to a solution of 0.65 g of 4-(3,5-difluorophenyl)-1H-pyrazole in 30 cm³ of anhydrous dimethylformamide. After stirring for three-quarters of an hour at a temperature in the region of 50° C., a solution of 1.17 g of 3-[(methanesulfonyl)oxy]-1-azabicyclo[2.2.2]octane in 10 cm³ of anhydrous dimethylformamide is added dropwise, and the mixture is then heated for 20 hours at a temperature in the region of 110° C. The mixture is cooled to ambient temperature, 5 cm³ of water are slowly added, and the mixture is concentrated under reduced pressure (3 kPa). The residue is taken up with 20 cm³ of water and extracted with 250 cm³ of ethyl acetate. The organic phase is washed with 4 times 20 cm³ of water, then dried, filtered and concentrated to dryness under reduced pressure (3 kPa). The residue obtained is purified by chromatography on alumina, eluting with a mixture of dichloromethane and of ethyl acetate (70/30 by volume). After concentrating the fractions under reduced pressure, an oil is obtained, which is dissolved in 35 cm³ of acetone and 20 cm³ of 1M hydrochloric ether are added. After stirring for 1 hour at ambient temperature, the solid which has appeared is isolated by filtration and dried under vacuum (70 kPa) at a temperature of 40° C. 0.44 g of 3-[4-(3,5-difluoro-phenyl) pyrazol-1-yl]-1-azabicyclo[2.2.2]octane hydrochloride is thus obtained in the form of hygroscopic white crystals. ¹H NMR spectrum (300 MHz)—δ in ppm—in DMSO-d6 (referenced at 2.50 ppm): 1.71 (m, 2H); 2.00 (m, 2H); 2.42 (m, 1H); from 3.20 to 3.48 (m, 4H); from 3.75 to 3.95 (m, 2H); 4.90 (m, 1H); 7.05 (tt, J=2.5 and 9.5 Hz, 1H); 7.40 (m, 2H); 8.17 (broad s, 1H); 8.60 (broad s, 1H); 10.6 (broad m, 1H). Mass spectrum (EI): m/z=289 ($M^{+\cdot}$) base peak, m/z=206 [$(M-C_5H_9N)^{+\cdot}$], m/z=109 ($C_7H_{11}N^{+\cdot}$), m/z=36 ($HCl^{+\cdot}$).

The 4-(3,5-difluorophenyl)-1H-pyrazole can be obtained in the following way:

15.7 cm³ of a solution of tetrabutylammonium fluoride in tetrahydrofuran at 1M are added, at ambient temperature, to a solution of 2.1 g of 4-(3,5-difluoro-phenyl)-1-(toluene-4-sulfonyl)-1H-pyrazole in 70 cm³ of tetrahydrofuran. The mixture is refluxed for 4.5 hours, and then cooled to ambient temperature and concentrated to dryness under reduced pressure (3 kPa). 50 cm³ of water are added to the residue, which is extracted with 200 cm³ of ethyl acetate. The organic phase is washed with 50 cm³ of water and then with 25 cm³ of brine, and is finally dried over anhydrous magnesium sulfate, filtered, and concentrated to dryness under reduced pressure (3 kPa). The residue is triturated in 40 cm³ of dichloromethane, and then isolated by filtration under vacuum. 0.65 g of 4-(3, 5-difluorophenyl)-1H-pyrazole is thus obtained in the form of white crystals which melt at around 185° C. Mass spectrum (EI): m/z=180 ($M^{+\cdot}$) base peak, m/z=153 [$(M-HCN)^+$], m/z=126 [$(m/z=153-HCN)^{+\cdot}$].

The 4-(3,5-difluorophenyl)-1-(toluene-4-sulfonyl)-1H-pyrazole can be prepared in the following way:

6.31 g of 3,5-difluorophenylboronic acid are added, under an argon atmosphere and at ambient temperature, to a solution of 3.5 g of 4-iodo-1-(toluene-4-sulfonyl)-1H-pyrazole in 100 cm³ of 1,2-dimethoxyethane. The reaction medium is heated at 110° C. and 8.5 g of finely ground tribasic potassium phosphate and 0.91 g of bis(triphenylphosphine)palladium chloride are then added and the refluxing is subsequently maintained for 3.5 hours. The mixture is cooled to ambient temperature, and filtered through Celite®, which is then washed with 500 cm³ of ethyl acetate. The organic phase is washed with 5 times 100 cm³ of water and then with twice 100 cm³ of brine, dried over anhydrous magnesium sulfate, filtered, and concentrated to dryness under reduced pressure (3 kPa). The residue is purified by chromatography on silica, eluting with cyclohexane and then dichloromethane. After concentrating the fractions under reduced pressure, 2.2 g of 4-(3,5-difluoro-phenyl)-1-(toluene-4-sulfonyl)-1H-pyrazole are obtained in the form of a white powder. Mass spectrum (EI): m/z=334 ($M^{+\cdot}$), m/z=270 [$(M-SO_2)^{+\cdot}$], m/z=155 ($C_7H_7SO_2^+$), m/z=91 ($C_7H_7^+$) base peak.

EXAMPLE 81

4-Benzo[b]thiophen-2-yl-1-(2-piperidin-1-ylethyl)-1H-pyrazol-3-ol hydrochloride 8 cm³ of 12N hydrochloric acid are added to a stirred solution of 930 mg of 1-[2-(4-benzo[b]thiophen-2-yl-3-benzyloxypyrazol-1-yl)ethyl]piperidine in 15 cm³ of ethanol. After 7 h at the reflux of the solvent, and then 15 h at a temperature in the region of 20° C., the reaction medium is evaporated to dryness under reduced pressure (2.7 kPa). The residue is, three times, successively dissolved in ethanol and evaporated to dryness under reduced pressure (2.7 kPa) and is then triturated in 20 cm³ of diisopropyl ether. The precipitate formed is filtered off and dried under reduced pressure (2.7 kPa), to give 790 mg of 4-benzo[b]thiophen-2-yl-1-(2-piperidin-1-ylethyl)-1H-pyrazol-3-ol hydrochloride in the form of a pale yellow solid. Mass spectrum (CI): 328(+)=(M+H)(+); presence 36(+)/38(+)=HCl(+). ¹H NMR spectrum (300 MHz)—δ in ppm—in DMSO-d6: 1.42 (m, 1H); from 1.65 to 1.89 (m, 5H); 2.95 (m, 2H); from 3.38 to 3.54 (m, 4H); 4.44 (t, J=6.5 Hz, 2H); from 7.23 to 7.38 (m, 2H); 7.50 (s, 1H); 7.78 (broad d, J=7.5 Hz, 1H); 7.90 (broad d, J=7.5 Hz, 1H); 8.07 (s, 1H); from 10.05 to 10.2 (very broad m, 1H); 10.9 (broad m, 1H).

The 1-[2-(4-benzo[b]thiophen-2-yl-3-benzyloxypyrazol-1-yl)ethyl]piperidine can be prepared in the following way:

860 mg of 4-benzo[b]thiophen-2-yl-3-benzyloxy-1H-pyrazole are added, portionwise, to a suspension of 225 mg of sodium hydride (at 75% in liquid petroleum jelly) in 30 cm³ of dimethylformamide under an argon atmosphere and with stirring. After heating at 50° C. for 30 min, the mixture is stirred for 1 h at a temperature in the region of 20° C., and then 725 mg of 1-(2-chloro-ethyl)piperidine are added, portionwise, thereto. The reaction medium is stirred for 15 h at a temperature in the region of 20° C., and is then poured into 100 cm$^3$ of water. The aqueous phase is extracted twice with ethyl acetate. The organic phases are combined, washed successively with two times water and a saturated aqueous sodium chloride solution, dried over magnesium sulfate, filtered, and evaporated under reduced pressure (2.7 kPa), to give a yellow oil which is purified by flash chromatography on alumina CBT1 under an argon pressure (50 kPa) [eluent: cyclohexane/ethyl acetate (95/5 by volume)]. After concentrating the fractions under reduced pressure, 930 mg of 1-[2-(4-benzo[b]thiophen-2-yl-3-benzyloxypyrazol-1-yl)ethyl]-piperidine are obtained in the form of a pale yellow oil. $^1$H NMR spectrum (300 MHz)—δ in ppm—in DMSO-d6: from 1.34 to 1.54 (m, 6H); 2.40 (m, 4H); 2.69 (t, J=6.5 Hz, 2H); 4.11 (t, J=6.5 Hz, 2H); 5.37 (s, 2H); from 7.23 to 7.48 (m, 6H); 7.56 (broad d, J=8.5 Hz, 2H); 7.73 (broad d, J=7.5 Hz, 1H); 7.90 (broad d, J=7.5 Hz, 1H); 8.10 (s, 1H).

The 4-benzo[b]thiophen-2-yl-3-benzyloxy-1H-pyrazole can be prepared in the following way:

7.6 cm$^3$ of a 1N solution of tetrabutylammonium fluoride in tetrahydrofuran are added to a solution, under an argon atmosphere and with stirring, of 1.4 g of 4-benzo[b]thiophen-2-yl-3-benzyloxy-1-(toluene-4-sulfonyl)-1H-pyrazole in 30 cm$^3$ of tetrahydrofuran. After heating for 15 h at the reflux of the solvent, the reaction medium is evaporated under reduced pressure (2.7 kPa) and ethyl acetate is added to the residue. The organic phase is washed successively with two times water and a saturated aqueous sodium chloride solution; it is dried over magnesium sulfate and evaporated under reduced pressure (2.7 kPa). The pale yellow oil obtained (0.98 g) is purified by flash chromatography on silica under an argon pressure (50 kPa) [eluent: cyclohexane/ethyl acetate (70/30 by volume)]. After concentrating the fractions under reduced pressure (2.7 kPa), 860 mg of 4-benzo[b]thiophen-2-yl-3-benzyloxy-1H-pyrazole are obtained in the form of a white solid. IR spectrum (KBr): 3173; 2950; 1586; 1530; 1501; 1445; 1363; 1304; 1215; 1166; 1022; 818; 745; 736; 727; 693 and 564 cm$^{-1}$.

The 4-benzo[b]thiophen-2-yl-3-benzyloxy-1-(toluene-4-sulfonyl)-1H-pyrazole can be prepared in the following way:

2.4 g of 2-benzothienylboronic acid, 6.6 cm$^3$ of a 2N aqueous potassium carbonate solution and 660 mg of tetrakis(triphenylphosphine)palladium are added to a solution, under an argon atmosphere with stirring, of 2 g of 3-benzyloxy-4-iodo-1-(toluene-4-sulfonyl)-1H-pyrazole in 40 cm$^3$ of toluene to which 10 cm$^3$ of ethanol have been added. After heating for 5 h at the reflux of the solvent and for 16 h at a temperature in the region of 20° C., the reaction medium is evaporated under reduced pressure (2.7 kPa). Ethyl acetate, water and carbon black are added to the residue, which is filtered through supercel. The filtrate is separated by settling out, and the organic phase is then washed successively with two times water and a saturated aqueous sodium chloride solution; it is dried over magnesium sulfate and evaporated under reduced pressure (2.7 kPa). The orange oil obtained (3.8 g) is purified by flash chromatography on silica under an argon pressure (50 kPa) [eluent: cyclohexane/ethyl acetate (90/10 by volume)]. After concentrating the fractions under reduced pressure (2.7 kPa), the resulting cream solid is triturated in diisopropyl ether. After filtration, 1.4 g of 4-benzo[b]thiophen-2-yl-3-benzyloxy-1-(toluene-4-sulfonyl)-1H-pyrazole are obtained in the form of a white solid. Mass spectrum (EI): 460(+)=M(+); 305(+)=M(+)−Ts.

EXAMPLE 82

1-(2-Piperidin-1-ylethyl)-4-thiophen-3-yl-1H-pyrazol-3-ol hydrochloride 6 cm$^3$ of 12N hydrochloric acid are added to a stirred solution of 640 mg of 1-[2-(3-benzyloxy-4-thiophen-3-ylpyrazol-1-yl)ethyl]piperidine in 10 cm$^3$ of ethanol. After 7 h at the reflux of the solvent, and then 15 h at a temperature in the region of 20° C., the reaction medium is evaporated to dryness under reduced pressure (2.7 kPa). The residue is, three times, successively dissolved in ethanol and evaporated to dryness under reduced pressure (2.7 kPa), and it is then triturated in diisopropyl ether. The precipitate formed is filtered off and dried under vacuum (2.7 kPa), to give 470 mg of 1-(2-piperidin-1-ylethyl)-4-thiophen-3-yl-1H-pyrazol-3-ol hydrochloride in the form of a white solid. Mass spectrum (CI): 278 (+)=(M+H) (+); presence 36(+)/38(+)=HCl(+). $^1$H NMR spectrum (300 MHz)—δ in ppm—in DMSO-d6: 1.40 (m, 1H); from 1.64 to 1.88 (m, 5H); 2.93 (m, 2H); from 3.35 to 3.52 (m, 4H); 4.39 (t, J=6.5 Hz, 2H); 7.35 (dd, J=1.0 and 5.0 Hz, 1H); 7.49 (dd, J=1.0 and 3.0 Hz, 1H); 7.55 (dd, J=3.0 and 5.0 Hz, 1H); 7.94 (s, 1H); from 9.85 to 10.05 (very broad m, 1H); 10.4 (broad m, 1H).

The 1-[2-(3-benzyloxy-4-thiophen-3-yl-pyrazol-1-yl)-ethyl]piperidine can be prepared in the following way:

650 mg of 3-benzyloxy-4-thiophen-3-yl-1H-pyrazole are added, portionwise, to a suspension of 200 mg of sodium hydride (at 75% in liquid petroleum jelly) in 30 cm$^3$ of dimethylformamide under an argon atmosphere and with stirring. After heating for 30 min at 50° C., the mixture is stirred for 30 min at a temperature in the region of 20° C., and 654 mg of 1-(2-chloroethyl)piperidine hydrochloride are then added portionwise thereto. The reaction medium is stirred for 15 h at a temperature in the region of 20° C. and is then poured into 100 cm$^3$ of water. The aqueous phase is extracted twice with ethyl acetate. The organic phases are combined, washed successively with two times water and a saturated aqueous sodium chloride solution, dried over magnesium sulfate, filtered, and evaporated under reduced pressure (2.7 kPa), to give an orange oil which is purified by flash chromatography on alumina CTB1 under an argon pressure (50 kPa) [eluent: cyclohexane/ethyl acetate (95/5 by volume)]. After concentrating the fractions under reduced pressure, 640 mg of 1-[2-(3-benzyloxy-4-thiophen-3-yl-pyrazol-1-yl)ethyl]piperidine are obtained in the form of a yellow oil. $^1$H NMR spectrum (300 MHz)—δ in ppm—in DMSO-d6: from 1.32 to 1.54 (m, 6H); 2.38 (m, 4H); 2.67 (t, J=6.5 Hz, 2H); 4.06 (t, J=6.5 Hz, 2H); 5.30 (s, 2H); from 7.30 to 7.55 (m, 8H); 7.98 (s, 1H).

The 3-benzyloxy-4-thiophen-3-yl-1H-pyrazole can be prepared in the following way:

8.5 cm$^3$ of a 1N solution of tetrabutylammonium fluoride in tetrahydrofuran are added to a solution, under an argon atmosphere and with stirring, of 1.35 g of 3-benzyloxy-4-thiophen-3-yl-1-(toluene-4-sulfonyl)-1H-pyrazole in 30 cm$^3$ of tetrahydrofuran. After heating for 15 h at the reflux of the solvent, the reaction medium is evaporated under reduced pressure (2.7 kPa) and ethyl acetate is added to the residue. The organic phase is washed successively with three times water and a saturated aqueous sodium chloride solution; it is dried over magnesium sulfate and evaporated under reduced pressure (2.7 kPa). The residue obtained (0.96 g) is purified by flash chromatography on silica under an argon pressure (50 kPa) [eluent: cyclohexane/ethyl acetate (70/30 by volume)]. After concentrating the fractions under reduced pressure (2.7 kPa), 650 mg of 3-benzyloxy-4-thiophen-3-yl-1H- pyrazole are obtained in the form of a cream solid. Mass spectrum (EI): 256(+)=M(+); 91(+)=C$_7$H$_7$(+).

The 3-benzyloxy-4-thiophen-3-yl-1-(toluene-4-sulfonyl)-1H-pyrazole can be prepared in the following way:

1.7 g of 3-thienylboronic acid, 6.6 cm$^3$ of a 2N aqueous potassium carbonate solution and 660 mg of tetrakis(triphenylphosphine)palladium are added to a solution, under an argon atmosphere and with stirring, of 2 g of 3-benzyloxy-4-iodo-1-(toluene-4-sulfonyl)-1H-pyrazole in 40 cm$^3$ of toluene to which 10 cm$^3$ of ethanol have been added. After heating for 5 h at the reflux of the solvent and for 16 h at a temperature in the region of 20° C., the reaction medium is evaporated under reduced pressure (2.7 kPa). Ethyl acetate, water and carbon black are added to the residue, which is filtered through supercel. The filtrate is separated by settling out, and the organic phase is then washed successively with two times water and a saturated aqueous sodium chloride solution; it is dried over magnesium sulfate and evaporated under reduced pressure (2.7 kPa). The resulting solid is triturated in diisopropyl ether, filtered and crystallized from 10 cm$^3$ of ethanol. 1.35 g of 3-benzyloxy-4-thiophen-3-yl-1-(toluene-4-sulfonyl)-1H-pyrazole are thus obtained in the form of a beige solid. Mass spectrum (EI): 410(+)=M(+); 255(+)=M(+)−Ts.

EXAMPLE 83

4-[3-Hydroxy-1-(2-piperidin-1-ylethyl)-1H-pyrazol-4-yl]benzamide hydrochloride 4 cm$^3$ of 3N hydrochloric diethyl ether are added to a solution of 442 mg of 4-[3-benzyloxy-1-(2-piperidin-1-ylethyl)-1H-pyrazol-4-yl]benzamide in 20 cm$^3$ of ethanol. After stirring for 1 h at a temperature in the region of 20° C., the solution is evaporated to dryness under reduced pressure (2.7 kPa). The residue is taken up with 25 cm$^3$ of ethanol. The solution obtained is introduced into an autoclave, and 52 mg of palladium-on-charcoal at 10% are added thereto, and it is then placed under hydrogen (10 bar). After stirring for 8 h at 22° C., the reaction medium is filtered through supercel, the filtrate is evaporated and the residue is triturated in diisopropyl ether. The resulting solid is filtered off, and dried under vacuum (2.7 kPa), to give 118 mg of 4-[3-hydroxy-1-(2-piperidin-1-ylethyl)-1H-pyrazol-4-yl]benzamide hydrochloride in the form of a cream solid. Mass spectrum (CI): 315 (+)=(M+H) (+). $^1$H NMR spectrum (300 MHz)—δ in ppm—in DMSO-d6: 1.41 (m, 1H); from 1.64 to 1.89 (m, 5H); 2.94 (m, 2H); from 3.25 to 3.53 (m, 4H); 4.41 (t, J=6.5 Hz, 2H); 7.23 (broad m, 1H); 7.73 (broad d, J=8.5 Hz, 2H); from 7.83 to 7.91 (m, 3H); 8.14 (s, 1H); from 9.80 to 9.95 (very broad m, 1H); 10.65 (broad s, 1H).

The 4-[3-benzyloxy-1-(2-piperidin-1-ylethyl)-1H-pyrazol-4-yl]benzamide can be prepared in the following way:

527 mg of 4-(3-benzyloxy-1H-pyrazol-4-yl)benzamide are added, portionwise, to a suspension of 144 mg of sodium hydride (75% in liquid petroleum jelly) in 30 cm$^3$ of dimethylformamide under an atmosphere of argon and with stirring. After heating at 50° C. for 30 min, the mixture is stirred for 30 min at a temperature in the region of 20° C. and then 465 mg of 1-(2-chloroethyl)piperidine hydrochloride are added portionwise thereto. The reaction medium is stirred for 15 h at a temperature in the region of 20° C., and is then poured into 100 cm$^3$ of water. The aqueous phase is extracted twice with ethyl acetate. The organic phases are combined, washed successively with two times water and a saturated aqueous sodium chloride solution, dried over magnesium sulfate, filtered and evaporated under reduced pressure (2.7 kPa). The resulting solid is triturated in diisopropyl ether, filtered and crystallized from acetone. 445 mg of 4-[3-benzyloxy-1-(2-piperidin-1-yl-ethyl)-1H-pyrazol-4-yl]benzamide are thus obtained in the form of a white solid. $^1$H NMR spectrum (300 MHz)—δ in ppm—DMSO-d6: from 1.32 to 1.54 (m, 6H); 2.39 (m, 4H); 2.69 (t, J=6.5 Hz, 2H); 4.09 (t, J=6.5 Hz, 2H); 5.33 (s, 2H); 7.24 (broad m, 1H); from 7.32 to 7.46 (m, 3H); 7.52 (broad d, J=8.5 Hz, 2H); 7.70 (broad d, J=7.5 Hz, 2H); from 7.81 to 7.88 (m, 3H); 8.17 (s, 1H).

The 4-(3-benzyloxy-1H-pyrazol-4-yl)benzamide can be prepared in the following way:

6.5 cm$^3$ of a 1N solution of tetrabutylammonium fluoride in tetrahydrofuran are added to a solution, under an argon atmosphere and with stirring, of 1.1 g of 4-[3-benzyloxy-1-(toluene-4-sulfonyl)-1H-pyrazol-4-yl]benzamide in 30 cm$^3$ of tetrahydrofuran. After heating for 15 h at the reflux of the solvent, the reaction medium is cooled in an ice bath. After filtration and then drying of the resulting crystals under vacuum (2.7 kPa), 527 mg of 4-(3-benzyloxy-1H-pyrazol-4-yl)benzamide are obtained in the form of a white solid. IR spectrum (KBr): 3403; 3176; 1667; 1611; 1576; 1553; 1517; 1485; 1393; 1379; 1226; 1040; 1027 and 739 cm$^{-1}$.

The 4-[3-benzyloxy-1-(toluene-4-sulfonyl)-1H-pyrazol-4-yl]benzamide can be prepared in the following way:

2.72 g of 4-aminocarbonylphenylboronic acid, 8.3 cm$^3$ of a 2N aqueous potassium carbonate solution and 830 mg of tetrakis(triphenylphosphine)palladium are added to a solution, under an argon atmosphere and with stirring, of 2.5 g of 3-benzyloxy-4-iodo-1-(toluene-4-sulfonyl)-1H-pyrazole in 40 cm$^3$ of toluene to which 10 cm$^3$ of ethanol have been added. After heating for 15 h at the reflux of the solvent, the reaction medium is cooled to a temperature in the region of 20° C. and evaporated under reduced pressure (2.7 kPa). Ethyl acetate, water and carbon black are added to the residue, which is filtered through supercel. The filtrate is separated by settling out, and the organic phase is then washed successively with two times water and a saturated aqueous sodium chloride solution; it is dried over magnesium sulfate and evaporated under reduced pressure (2.7 kPa). The yellow oil obtained (3.7 g) is purified by flash chromatography on silica under an argon pressure (50 kPa) [eluent: cyclohexane/ethyl acetate (50/50 then 20/80 by volume)]. After concentrating the fractions under reduced pressure (2.7 kPa), 1.1 g of 4-[3-benzyloxy-1-(toluene-4-sulfonyl)-1H-pyrazol-4-yl]-benzamide are obtained in the form of a white solid. Mass spectrum (EI): 447(+)=M(+); 91(+)=C$_7$H$_7$(+).

EXAMPLE 84

3-[3-Hydroxy-1-(2-piperidin-1-ylethyl)-1H-pyrazol-4-yl]benzamide hydrochloride 4 cm$^3$ of 3N hydrochloric diethyl ether are added to a solution of 690 mg of 3-[3-benzyloxy-1-(2-piperidin-1-ylethyl)-1H-pyrazol-4-yl]benzamide in 20 cm$^3$ of ethanol. After stirring for 45 min at a temperature in the region of 20° C., the solution is evaporated to dryness under reduced pressure (2.7 kPa). The residue is taken up with 25 cm$^3$ of ethanol. The solution obtained is introduced into an autoclave, and 80 mg of palladium-on-charcoal at 10% are added thereto, and it is then placed under hydrogen (10 bar). After stirring for 8 h at 22° C., the reaction medium is filtered through supercel, the filtrate is evaporated and the residue is triturated in diisopropyl ether. The resulting solid is filtered off, and dried under vacuum (2.7 kPa), to give 528 mg of 3-[3-hydroxy-1-(2-piperidin-1-ylethyl)-1H-pyrazol-4-yl]benzamide hydrochloride in the form of a pale yellow solid. Mass spectrum (CI): 315(+)=(M+H)(+). $^1$H NMR spectrum (300 MHz)—δ in ppm—in DMSO-d6: 1.40 (m, 1H); from 1.65 to 1.88 (m, 5H); 2.94 (m, 2H); from 3.41 to 3.54 (m, 4H); 4.42 (t, J=6.5 Hz, 2H); 7.33 (broad m, 1H); 7.42 (t, J=8.0 Hz, 1H); 7.64 (broad d, J=8.0 Hz, 1H); 7.82 (broad d, J=8.0 Hz, 1H); 7.94 (broad m, 1H); 8.10 (s, 1H); 8.14 (broad s, 1H); from 9.90 to 10.05 (very broad m, 1H); 10.55 (broad s, 1H).

The 3-[3-benzyloxy-1-(2-piperidin-1-ylethyl)-1H-pyrazol-4-yl]benzamide can be prepared in the following way:

1.16 g of 3-(3-benzyloxy-1H-pyrazol-4-yl)benzamide are added, portionwise, to a suspension of 315 mg of sodium hydride (75% in liquid petroleum jelly) in 30 cm$^3$ of dimethylformamide under an argon atmosphere and with stirring. After heating for 30 min at 50° C., the mixture is stirred for 30 min at a temperature in the region of 20° C., and 1 g of 1-(2-chloroethyl)piperidine hydrochloride is added portionwise thereto. The reaction medium is stirred for 15 h at a temperature in the region of 20° C. and is then poured into 100 cm$^3$ of water. The aqueous phase is extracted twice with ethyl acetate. The organic phases are combined, washed successively with two times water and a saturated aqueous sodium chloride solution, dried over magnesium sulfate, filtered, and evaporated under reduced pressure (2.7 kPa), to give a yellow oil (1.6 g) which is purified by flash chromatography on silica under an argon pressure (50 kPa) [eluent: dichloromethane then dichloromethane/methanol (98/2, 95/5 then 90/10 by volume)]. After concentrating the fractions under reduced pressure, 700 mg of 3-[3-benzyloxy-1-(2-piperidin-1-ylethyl)-1H-pyrazol-4-yl]benzamide are obtained in the form of a pale yellow oil. $^1$H NMR spectrum (300 MHz)—δ in ppm—in DMSO-d6: from 1.33 to 1.54 (m, 6H); 2.40 (m, 4H); 2.70 (t, J=6.5 Hz, 2H); 4.10 (t, J=6.5 Hz, 2H); 5.33 (s, 2H); from 7.30 to 7.44 (m, 5H); 7.53 (broad d, J=8.5 Hz, 2H); 7.63 (broad d, J=8.0 Hz, 1H); 7.80 (broad d, J=8.0 Hz, 1H); 7.92 (broad m, 1H); 8.11 (s, 1H); 8.15 (broad s, 1H).

The 3-(3-benzyloxy-1H-pyrazol-4-yl)benzamide can be prepared in the following way:

11.8 cm$^3$ of a 1N solution of tetrabutylammonium fluoride in tetrahydrofuran is added to a solution, under an argon atmosphere and with stirring, of 2.1 g of 3-[3-benzyloxy-1-(toluene-4-sulfonyl)-1H-pyrazol-4-yl]benzamide in 40 cm$^3$ of tetrahydrofuran. After heating for 15 h at the reflux of the solvent, the reaction medium is evaporated under reduced pressure (2.7 kPa) and ethyl acetate is added to the residue. The organic phase is washed successively with two times water and a saturated aqueous sodium chloride solution; it is dried over magnesium sulfate and evaporated under reduced pressure (2.7 kPa). The residue is triturated in diisopropyl ether, filtered and dried under vacuum (2.7 kPa), to give 1.16 g of 3-(3-benzyloxy-1H-pyrazol-4-yl)benzamide in the form of a cream solid. IR spectrum (KBr): 3332; 3196; 2975; 1682; 1606; 1581; 1572; 1505; 1447; 1389; 1280; 1232; 1049; 732; 695; 672 and 637 cm$^{-1}$.

The 3-[3-benzyloxy-1-(toluene-4-sulfonyl)-1H-pyrazol-4-yl]benzamide can be prepared in the following way:

2.72 g of 3-aminocarbonylphenylboronic acid, 8.3 cm$^3$ of a 2N aqueous potassium carbonate solution and 830 mg of tetrakis(triphenylphosphine)palladium are added to a solution, under an argon atmosphere and with stirring, of 2.5 g of 3-benzyloxy-4-iodo-1-(toluene-4-sulfonyl)-1H-pyrazole in 40 cm$^3$ of toluene to which 10 cm$^3$ of ethanol have been added. After heating for 15 h at the reflux of the solvent, the reaction medium is cooled in an ice bath. After filtration and then drying of the resulting crystals under vacuum (2.7 kPa), 2.1 g of 3-[3-benzyloxy-1-(toluene-4-sulfonyl)-1H-pyrazol-4-yl]-benzamide are obtained in the form of a white solid. Mass spectrum (EI): 447(+)=M(+); 91(+)=C$_7$H$_7$(+).

EXAMPLE 85

(−)-1-(1-Azabicyclo[2.2.2]oct-3-yl)-4-phenyl-1H-pyrazol-3-ol hydrochloride 15 cm$^3$ of 12N hydrochloric acid are added to a stirred solution of 1.44 g of (+)-3-(3-benzyloxy-4-phenylpyrazol-1-yl)-1-azabicyclo[2.2.2]octane in 20 cm$^3$ of ethanol. After 7 h at the reflux of the solvent, and then 15 h at a temperature in the region of 20° C., the reaction medium is evaporated to dryness under reduced pressure (2.7 kPa). The residue is, three times, successively dissolved in ethanol and evaporated to dryness under reduced pressure (2.7 kPa), and is then triturated in 20 cm$^3$ of diisopropyl ether. The precipitate formed is filtered off and dried under vacuum (2.7 kPa), to give 1.2 g of (−)-1-(1-aza-bicyclo[2.2.2]oct-3-yl)-4-phenyl-1H-pyrazol-3-ol hydrochloride in the form of a white solid. Mass spectrum (EI): 269(+)=M(+); presence 36(+)/38(+)= HCl(+). $^1$H NMR spectrum (300 MHz)—δ in ppm—in DMSO-d6: from 1.69 to 2.04 (m, 4H); 2.43 (m, 1H); from 3.22 to 3.47 (m, 4H); from 3.72 to 3.85 (m, 2H); 4.67 (m, 1H); 7.15 (tt, J=1.5 and 7.5 Hz, 1H); 7.34 (broad t, J=7.5 Hz, 2H); 7.67 (broad d, J=7.5 Hz, 2H); 8.18 (s, 1H); 10.2 (broad m, 1H); 10.4 (broad m, 1H). [α]$^{20}_D$=−17.4+/−0.6° (c 0.5, MeOH).

The (+)-3-(3-benzyloxy-4-phenylpyrazol-1-yl)-1-aza-bicyclo[2.2.2]octane and the (−)-3-(3-benzyloxy-4-phenylpyrazol-1-yl)-1-azabicyclo[2.2.2]octane can be prepared in the following way: an ethanolic solution containing 1.5 g of 3-(3-benzyloxy-4-phenylpyrazol-1-yl)-1-azabicyclo[2.2.2]octane is introduced onto a column, 6 cm in diameter, containing 800 g of Chiralpak AD™ chiral stationary phase. The elution is carried out by means of a mixture of 10% ethanol, 10% methanol, 0.1% triethylamine and 80% heptane. The flow of the mobile phase is 90 ml/min. The dextrorotatory enantiomer is eluted in the first position, the solution is evaporated to dryness under reduced pressure (2.7 kPa), to give 0.66 g of oil.

$^1$H NMR spectrum (300 MHz)—δ in ppm—in DMSO-d6: 1.30 (m, 1H); from 1.50 to 1.71 (m, 3H); 2.08 (m, 1H); from 2.65 to 2.79 (m, 3H); 2.99 (m, 1H); from 3.15 to 3.42 (m, 2H); 4.27 (m, 1H); 5.33 (s, 2H); 7.15 (tt, J=1.5 and 7.5 Hz, 1H); from 7.30 to 7.44 (m, 5H); 7.51 (broad d, J=7.5 Hz, 2H); 7.69 (broad d, J=7.5 Hz, 2H); 8.20 (s, 1H). [α]$^{20}_D$=+27.0+/−0.8° (c 0.5, MeOH). The solution containing the levorotatory enantiomer eluted in the second position is evaporated to dryness under reduced pressure (2.7 kPa), to give 0.65 g of oil.

$^1$H NMR spectrum (300 MHz)—δ in ppm—in DMSO-d6: 1.31 (m, 1H); from 1.50 to 1.72 (m, 3H); 2.09 (m, 1H); from 2.66 to 2.80 (m, 3H); 2.99 (m, 1H); from 3.16 to 3.43 (m, 2H); 4.29 (m, 1H); 5.34 (s, 2H); 7.14 (tt, J=1.5 and 7.5 Hz, 1H); from 7.30 to 7.44 (m, 5H); 7.51 (broad d, J=7.5 Hz, 2H); 7.70 (broad d, J=7.5 Hz, 2H); 8.20 (s, 1H). [α]$^{20}_D$=−27.0+/−0.8° (c 0.5, MeOH).

EXAMPLE 86

(+)-1-(1-Azabicyclo[2.2.2]oct-3-yl)-4-phenyl-1H-pyrazol-3-ol hydrochloride 15 cm$^3$ of 12N hydrochloric acid are added to a stirred solution of 1.44 g of (−)-3-(3-benzyloxy-4-phenylpyrazol-1-yl)-1-azabicyclo[2.2.2]octane in 20 cm$^3$ of ethanol. After 7 h at the reflux of the solvent, and then 15 h at a temperature in the region of 20° C., the reaction medium is evaporated to dryness under reduced pressure (2.7 kPa). The residue is, three times, successively dissolved in ethanol and evaporated to dryness under reduced pressure (2.7 kPa), and is then triturated in 20 cm$^3$ of diisopropyl ether. The precipitate formed is filtered off and dried under vacuum (2.7 kPa), to give 1.2 g of (+)-1-(1-aza-bicyclo[2.2.2]oct-3-yl)-4-phenyl-1H-pyrazol-3-ol hydrochloride in the form of a beige solid. Mass spectrum (EI): 269(+)=M(+); presence 36(+)/38(+)=HCl(+). $^1$H NMR spectrum (300 MHz)—δ in ppm—in DMSO-d6: from 1.70 to 2.03 (m, 4H); 2.43 (m, 1H); from 3.22 to 3.47 (m, 4H); from 3.72 to 3.86 (m, 2H); 4.68 (m, 1H); 7.15 (tt, J=1.5 and 7.5 Hz, 1H); 7.34 (broad t, J=7.5 Hz, 2H); 7.67 (broad d, J=7.5 Hz, 2H); 8.19 (s, 1H); 10.2 (broad m, 1H); from 10.3 to 10.5 (very broad m, 1H). $[α]^{20}_D$=+13.7+/−0.6° (c 0.5, MeOH).

EXAMPLE 87

(−)-1-(1-Azabicyclo[2.2.2]oct-3-ylmethyl)-4-phenyl-1H-pyrazol-1-ol hydrochloride 10 cm$^3$ of 12N hydrochloric acid are added to a stirred solution of 825 mg of (−)-3-(3-benzyloxy-4-phenyl-pyrazol-1-ylmethyl)-1-azabicyclo[2.2.2]octane in 10 cm$^3$ of ethanol. After 7 h at the reflux of the solvent, and then 15 h at a temperature in the region of 20° C., the reaction medium is evaporated to dryness under reduced pressure (2.7 kPa). The residue is, three times, successively dissolved in ethanol and evaporated to dryness under reduced pressure (2.7 kPa), and it is then triturated in diisopropyl ether. The precipitate formed is filtered off and dried under vacuum (2.7 kPa), to give 700 mg of (−)-1-(1-aza-bicyclo[2.2.2]oct-3-ylmethyl)-4-phenyl-1H-pyrazol-1-ol hydrochloride in the form of a white solid. Mass spectrum (EI): 283(+)=M(+). $^1$H NMR spectrum (300 MHz)—δ in ppm—in DMSO-d6: from 1.66 to 1.93 (m, 4H); 2.05 (m, 1H); 2.52 (masked m, 1H); 2.94 (m, 1H); from 3.12 to 3.40 (m, 5H); from 3.98 to 4.12 (m, 2H); 7.13 (tt, J=1.5 and 7.5 Hz, 1H); 7.33 (broad t, J=7.5 Hz, 2H); 7.64 (broad d, J=7.5 Hz, 2H); 7.99 (s, 1H); 10.1 (broad m, 1H). $[α]^{20}_D$=−36.8+/−0.8° (c 0.5, MeOH)

The (−)-3-(3-benzyloxy-4-phenylpyrazol-1-ylmethyl)-1-azabicyclo[2.2.2]octane and the (+)-3-(3-benzyloxy-4-phenylpyrazol-1-ylmethyl)-1-azabicyclo[2.2.2]octane can be prepared in the following way:

A solution of 5 g of 3-benzyloxy-4-phenylpyrazole in 30 cm$^3$ of dimethylformamide is added gradually, under an argon atmosphere and at a temperature in the region of 20° C., to a suspension of 1.9 g of sodium hydride (75% by mass in liquid petroleum jelly) in 50 cm$^3$ of dimethylformamide. After stirring for 1 h at a temperature in the region of 50° C., 5.8 g of 3-chloromethyl-1-azabicyclo[2.2.2]octane hydrochloride are added in small portions, and the mixture is then heated for 15 hours at a temperature in the region of 90° C. The mixture is cooled to a temperature in the region of 20° C. and is then poured into 400 cm$^3$ of water. The aqueous phase is extracted with two times ethyl acetate. The combined organic phases are washed with two times water and brine, and then dried over magnesium sulfate, filtered, and concentrated to dryness under reduced pressure (2.7 kPa). The orange oil obtained is purified by flash chromatography on alumina CTB1 under an argon pressure (50 kPa) [eluent: cyclohexane/ethyl acetate (10/90 by volume), ethyl acetate and then ethyl acetate/methanol (95/5 by volume)]. After concentrating the fractions under reduced pressure, 1.7 g of a pale yellow oil are obtained. An ethanolic solution of this oil is introduced onto a column, 8 cm in diameter, containing 1180 g of Chiracel OD™ chiral stationary phase. The elution is carried out by means of a mixture of 50% ethanol, 0.1% triethylamine and 50% heptane. The flow rate of the mobile phase is 120 ml/min. The levorotatory enantiomer is eluted in the first position, the solution is evaporated to dryness under reduced pressure (2.7 kPa), to give 0.82 g of oil.

$^1$H NMR spectrum (300 MHz)—δ in ppm—in DMSO-d6: from 1.24 to 1.59 (m, 4H); 1.78 (m, 1H); 2.14 (m, 1H); 2.37 (m, 1H); from 2.59 to 2.90 (m, 5H); 3.89 (d, J=8.0 Hz, 2H); 5.31 (s, 2H); 7.14 (tt, J=1.5 and 7.5 Hz, 1H); from 7.30 to 7.44 (m, 5H); 7.50 (broad d, J=8.5 Hz, 2H); 7.64 (broad d, J=8.5 Hz, 2H); 8.09 (s, 1H). $[α]^{20}_D$=−37.8+/−0.8° (c 0.5, MeOH). The solution containing the dextrorotatory enantiomer eluted in the second position is evaporated to dryness under reduced pressure (2.7 kPa), to give 0.74 g of oil.

$^1$H NMR spectrum (300 MHz)—δ in ppm—in DMSO-d6: from 1.24 to 1.60 (m, 4H); 1.78 (m, 1H); 2.14 (m, 1H); 2.36 (m, 1H); from 2.60 to 2.90 (m, 5H); 4.00 (d, J=8.0 Hz, 2H); 5.31 (s, 2H); 7.14 (tt, J=1.5 and 7.5 Hz, 1H); from 7.30 to 7.44 (m, 5H); 7.50 (broad d, J=8.5 Hz, 2H); 7.64 (broad d, J=8.5 Hz, 2H); 8.09 (s, 1H). $[α]^{20}_D$=−39.1+/−0.9° (c 0.5, MeOH).

EXAMPLE 88

(+)-1-(1-Azabicyclo[2.2.2]oct-3-yl-methyl)-4-phenyl-1H-pyrazol-1-ol hydrochloride 10 cm$^3$ of 12N hydrochloric acid are added to a stirred solution of 740 mg of (+)-3-(3-benzyloxy-4-phenyl-pyrazol-1-ylmethyl)-1-aza-bicyclo[2.2.2]octane in 10 cm$^3$ of ethanol. After 7 h at the reflux of the solvent, and then 15 h at a temperature in the region of 20° C., the reaction medium is evaporated to dryness under reduced pressure (2.7 kPa). The residue is, three times, successively dissolved in ethanol and evaporated to dryness under reduced pressure (2.7 kPa), and it is then triturated in diisopropyl ether. The precipitate formed is filtered off and dried under vacuum (2.7 kPa), to give 600 mg of (+)-1-(1-aza-bicyclo[2.2.2]oct-3-ylmethyl)-4-phenyl-1H-pyrazol-1-ol hydrochloride in the form of a white solid. Mass spectrum (EI): 283(+)=M(+). $^1$H NMR spectrum (300 MHz)—δ in ppm—in DMSO-d6: from 1.67 to 1.94 (m, 4H); 2.06 (m, 1H); 2.52 (masked m, 1H); 2.94 (m, 1H); from 3.12 to 3.40 (m, 5H); from 3.99 to 4.12 (m, 2H); 7.13 (tt, J=1.5 and 7.5 Hz, 1H); 7.33 (broad t, J=7.5 Hz, 2H); 7.64 (broad d, J=7.5 Hz, 2H); 7.99 (s, 1H); 10.05 (broad m, 1H). $[α]^{20}_D$=+36.5+/−0.8° (c 0.5, MeOH).

EXAMPLE 89

1-(1-Azabicyclo[2.2.2]oct-3-ylmethyl)-4-(4-chlorophenyl)-1H-pyrazol-3-ol hydrochloride 10 cm$^3$ of 12N hydrochloric acid are added to a stirred solution of 430 mg of 3-[3-benzyloxy-4-(4-chlorophenyl)-pyrazol-1-ylmethyl]-1-azabicyclo[2.2.2]octaneborane in 10 cm$^3$ of ethanol. After 15 h at the reflux of the solvent, the reaction medium is cooled to a temperature in the region of 20° C. and evaporated to dryness under reduced pressure (2.7 kPa). The residue is taken up with water. The resulting solution is brought to a pH in the region of 8 with 1N sodium hydroxide and extracted with ethyl acetate. The organic phase is dried over magnesium sulfate, filtered, and concentrated to dryness under reduced pressure (2.7 kPa). The residual solid is triturated in diisopropyl ether, filtered, and dried under reduced pressure (2.7 kPa), to give 137 mg of 1-(1-azabicyclo[2.2.2]oct-3-ylmethyl)-4-(4-chlorophenyl)-1H-pyrazol-3-ol hydrochloride in the form of a white solid. Mass spectrum (EI): 317(+)/ . . . =M(+)/ . . . (1 Cl). ¹H NMR spectrum (400 MHz)—δ in ppm—in DMSO-d6: from 1.30 to 1.61 (m, 4H); 1.78 (m, 1H); 2.15 (m, 1H); 2.38 (m, 1H); from 2.66 to 2.81 (m, 4H); 2.88 (m, 1H); 3.91 (d, J=8.0 Hz, 2H); 7.37 (broad d, J=8.5 Hz, 2H); 7.67 (broad d, J.=8.5 Hz, 2H); 8.00 (s, 1H); from 10.35 to 10.5 (very broad m, 1H).

The 3-[3-benzyloxy-4-(4-chlorophenyl)pyrazol-1-ylmethyl]-1-azabicyclo[2.2.2]octaneborane can be prepared in the following way:

A solution of 3 g of 3-benzyloxy-4-(4-chlorophenyl)-1H-pyrazole and of 3 g of potassium tert-butoxide in 30 cm³ of dimethylformamide, under an inert atmosphere and with stirring, is heated for 30 min at 50° C., and 3.1 g of 3-chloromethyl-1-azabicyclo[2.2.2]octane hydrochloride are then added thereto. After refluxing for 15 h, the reaction medium is poured into water, and the mixture is extracted with two times ethyl acetate. The organic phases are washed successively with two times water and a saturated aqueous sodium chloride solution, dried over magnesium sulfate, and evaporated under reduced pressure (2.7 kPa). The beige oil (5.3 g) obtained is purified by flash chromatography on alumina CTB1 under an argon pressure (50 kPa) [eluent: cyclohexane/ethyl acetate (20/80 by volume), ethyl acetate then ethyl acetate/methanol (90/10 by volume)]. After concen-trating the fractions under reduced pressure (2.7 kPa), a solid is obtained which is dissolved in 10 cm³ of tetrahydrofuran under an inert atmosphere. 3 cm³ of a 1N solution of borane in tetrahydrofuran are added to the solution, which is being stirred and has been cooled to −60° C. After reaction for 2 h 30 min at −60° C., 15 cm³ of water are added to the reaction medium, the temperature of the mixture is allowed to rise to a temperature in the region of 20° C. and the solution is extracted with ethyl acetate. The organic phase is washed with two times water and a saturated aqueous sodium chloride solution, dried over magnesium sulfate and evaporated under reduced pressure (2.7 kPa), to give an oil (1 g) which is purified by flash chromatography on alumina CTB1 under an argon pressure (50 kPa) [eluent: ethyl acetate, ethyl acetate/methanol (90/10 by volume) then dichloromethane/methanol (80/20 by volume)]. After concentrating the fractions under reduced pressure (2.7 kPa), 430 mg of 3-[3-benzyloxy-4-(4-chlorophenyl)-pyrazol-1-ylmethyl]-1-azabicyclo[2.2.2]octaneborane are obtained in the form of an oil which is used without any other purification for the remainder of the synthesis.

EXAMPLE 90

(−)-1-(1-Azabicyclo[2.2.2]oct-3-yl)-4-(4-chlorophenyl)-1H-pyrazol-3-ol hydrochloride 7 cm³ of 12N hydrochloric acid are added to a stirred solution of 690 mg of (+)-3-[3-benzyloxy-4-(4-chloro-phenyl)pyrazol-1-yl]-1-azabicyclo[2.2.2]octane in 10 cm³ of ethanol. After 7 h at the reflux of the solvent, the reaction medium is cooled to a temperature in the region of 20° C. and evaporated to dryness under reduced pressure (2.7 kPa). The residue is triturated in diiso-propyl ether, filtered, and dried under reduced pressure (2.7 kPa), to give 580 mg of (−)-1-(1-aza-bicyclo[2.2.2]oct-3-yl)-4-(4-chlorophenyl)-1H-pyrazol-3-ol hydrochloride in the form of a beige solid. Mass spectrum (EI): 303(+)/ . . . =M(+)/ . . . (1 Cl). ¹H NMR spectrum (300 MHz)—δ in ppm—in DMSO-d6: from 1.68 to 2.03 (m, 4H); 2.42 (m, 1H); from 3.20 to 3.55 (m, 4H); 3.78 (m, 2H); 4.66 (m, 1H); 4.71 (broad d, J=8.5 Hz, 2H); 7.71 (broad d, J=8.5 Hz, 2H); 8.25 (s, 1H); 10.35 (broad m, 1H); 10.65 (broad m, 1H). $[\alpha]^{20}_D$=19.4+/−0.7° (c 0.5, MeOH).

The (+)-3-[3-benzyloxy-4-(4-chlorophenyl)pyrazol-1-yl]-1-azabicyclo[2.2.2]octane and the (−)-3-[3-benzyloxy-4-(4-chlorophenyl)pyrazol-1-yl]-1-azabicyclo[2.2.2]octane can be prepared in the following way:

An ethanolic solution containing 0.29 g of (+/−)-3-[3-benzyloxy-4-(4-chlorophenyl)pyrazol-1-yl]-1-azabicyclo-[2.2.2]octane is introduced onto a column, 8 cm in diameter, containing 1180 g of Chiralpak AD™ chiral stationary phase. The elution is carried out by means of a mixture of heptane, of ethanol, of methanol and of triethylamine (80/10/10/0.1 by volume), the flow rate of the mobile phase being 120 ml/min. The dextro-rotatory enantiomer is eluted in the first position, the solution is evaporated to dryness under reduced pressure (2.7 kPa), so as to obtain 0.69 g of (+)-3-[3-benzyloxy-4-(4-chlorophenyl)pyrazol-1-yl]-1-azabicyclo-[2.2.2]octane in the form of an oil.

Mass spectrum (EI): 393(+)/ . . . =M(+)/ . . . (1 Cl); 91(+)= $C_7H_7$. $[\alpha]^{20}_D$=+25.4+/−0.8° (c 0.5, MeOH). The solution containing the levorotatory enantiomer eluted in the second position is evaporated to dryness under reduced pressure (2.7 kPa) so as to obtain 0.69 g of (−)-3-[3-benzyloxy-4-(4-chlorophenyl)pyrazol-1-yl]-1-azabicyclo-[2.2.2]octane in the form of an oil.

Mass spectrum (EI): 393(+)/ . . . =M(+)/ . . . (1 Cl); 91(+)= $C_7H_7$(+). Optical rotation: $[\alpha]^{20}_D$=−26.2+/−0.8° (c 0.5, MeOH).

EXAMPLE 91

(+)-1-(1-Azabicyclo[2.2.2]oct-3-yl)-4-(4-chlorophenyl)-1H-pyrazol-3-ol hydrochloride 7 cm³ of 12N hydrochloric acid are added to a stirred solution of 690 mg of (−)-3-[3-benzyloxy-4-(4-chloro-phenyl)pyrazol-1-yl]-1-azabicyclo[2.2.2]octane in 10 cm³ of ethanol. After 7 h at the reflux of the solvent, the reaction medium is cooled to a temperature in the region of 20° C. and evaporated to dryness under reduced pressure (2.7 kPa). The residue is triturated in diisopropyl ether, filtered and dried under reduced pressure (2.7 kPa), to give 580 mg of (+)-1-(1-aza-bicyclo[2.2.2]oct-3-yl)-4-(4-chlorophenyl)-1H-pyrazol-3-ol hydrochloride in the form of a beige solid. Mass spectrum (EI): 303(+)/ . . . =M(+)/ . . . (1 Cl). ¹H NMR spectrum (300 MHz)—δ in ppm—in DMSO-d6: from 1.67 to 2.02 (m, 4H); 2.42 (m, 1H); from 3.22 to 3.50 (m, 4H); 3.79 (m, 2H); 4.66 (m, 1H); 7.41 (broad d, J=8.5 Hz, 2H); 7.71 (broad d, J=8.5 Hz, 2H); 8.25 (s, 1H); from 10.2 to 10.3 (very broad m, 1H); 10.65 (broad m, 1H). $[\alpha]^{20}_D$=+17.7+/−0.6° (c 0.5, MeOH).

EXAMPLE 92

(−)-1-(1-Azabicyclo[2.2.2]oct-3-yl)-4-(4-fluorophenyl)-1H-pyrazol-3-ol hydrochloride 5 cm³ of 12N hydrochloric acid are added to a stirred solution of 135 mg of (+)-3-[3-benzyloxy-4-(4-fluoro-phenyl)pyrazol-1-yl]-1-azabicyclo[2.2.2]octane in 5 cm³ of ethanol. After 7 h at the reflux of the solvent, the reaction medium is cooled to a temperature in the region of 20° C. and evaporated to dryness under reduced pressure (2.7 kPa). The residue is triturated in diisopropyl ether, filtered and dried under reduced pressure (2.7 kPa), to give 91 mg of (−)-1-(1-azabicyclo[2.2.2]oct-3-yl)-4-(4-fluorophenyl)-1H-pyrazol-3-ol hydrochloride in the form of a white solid. Mass spectrum (EI): 287(+)=M(+). ¹H NMR spectrum (300 MHz)—δ in ppm—in DMSO-d6: from 1.66 to 2.03 (m, 4H); 2.42 (m, 1H);

from 3.20 to 3.49 (m, 4H); 3.79 (m, 2H); 4.66 (m, 1H); 7.19 (broad t, J=9.0 Hz, 2H); 7.71 (broad dd, J=6.0 and 9.0 Hz, 2H); 8.17 (s, 1H); 10.15 (broad m, 1H); 10.5 (s, 1H). [α]$^{20}_D$=−14.9+/−0.7° (c 0.5, MeOH).

The (+)-3-[3-benzyloxy-4-(4-fluorophenyl)pyrazol-1-yl]-1-azabicyclo[2.2.2]octane and the (−)-3-[3-benzyloxy-4-(4-fluorophenyl)pyrazol-1-yl]-1-azabicyclo[2.2.2]octane can be prepared in the following way:

A solution of 2 g of 3-benzyloxy-4-(4-fluorophenyl)-1H-pyrazole and of 1 g of potassium tert-butoxide in 20 cm$^3$ of dimethylformamide, under an inert atmosphere, is stirred for 1 h 30 min at a temperature in the region of 20° C., and then a solution of 2.3 g of toluene-4-sulfonic acid 1-azabicyclo[2.2.2]oct-3-yl ester in 25 cm$^3$ of dimethylformamide is added thereto. After heating for 15 h at 100° C., the reaction medium is poured into water, and the mixture is extracted with two times ethyl acetate. The combined organic phases are washed successively with two times water and a saturated aqueous sodium chloride solution, dried over magnesium sulfate and evaporated under reduced pressure (2.7 kPa). The orange oil obtained (2.3 g) is purified by flash chromatography on alumina CTB1 under an argon pressure (50 kPa) [eluent: ethyl acetate then ethyl acetate/methanol (98/2 by volume)]. After concentrating the fractions under reduced pressure (2.7 kPa), an orange oil is obtained (1.5 g), which is purified by flash chromatography on silica under an argon pressure (50 kPa) [eluent: ethyl acetate/methanol (95/5 by volume) then dichloromethane/methanol (98/2, 95/5 then 90/10 by volume)]. Concentrating the appropriate fractions under reduced pressure (2.7 kPa) gives an orange oil (500 mg) which is again purified by flash chromatography on alumina CTB1 under an argon pressure (50 kPa) [eluent: cyclohexane/ethyl acetate (10/90 by volume)]. After concentrating the fractions under reduced pressure (2.7 kPa), 290 mg of (R,S)-3-[3-benzyl-oxy-4-(4-fluorophenyl)pyrazol-1-yl]-1-azabicyclo[2.2.2]-octane are obtained in the form of a pale yellow oil. $^1$H NMR spectrum (300 MHz)—δ in ppm—in DMSO-d6: 1.28 (m, 1H); from 1.49 to 1.71 (m, 3H); 2.08 (m, 1H); from 2.65 to 2.79 (m, 3H); 2.98 (m, 1H); from 3.14 to 3.44 (m, 2H); 4.25 (m, 1H); 5.33 (m, 2H); 7.18 (broad t, J=9.0 Hz, 2H); from 7.30 to 7.44 (m, 3H); 7.50 (broad d, J=7.5 Hz, 2H); 7.71 (broad dd, J=6.0 and 9.0 Hz, 2H); 8.20 (s, 1H).

An ethanolic solution containing 0.29 g of (+/−)-3-[3-benzyloxy-4-(4-fluorophenyl)pyrazol-1-yl]-1-azabicyclo-[2.2.2]octane is introduced onto a column, 8 cm in diameter, containing 1180 g of Chiralpak AD™ chiral stationary phase. The elution is carried out by means of a mixture of heptane, of ethanol, of methanol and of triethylamine (80/10/10/0.1 by volume), the flow rate of the mobile phase being 120 ml/min. The dextro-rotatory enantiomer is eluted in the first position, the solution is evaporated to dryness under reduced pressure (2.7 kPa) to give 0.135 g of (+)-3-[3-benzyl-oxy-4-(4-fluorophenyl)pyrazol-1-yl]-1-azabicyclo[2.2.2]-octane in the form of an oil.

$^1$H NMR spectrum (300 MHz)—δ in ppm—in DMSO-d6: 1.30 (m, 1H); from 1.50 to 1.71 (m, 3H); 2.08 (m, 1H); from 2.64 to 2.80 (m, 3H); 2.99 (m, 1H); from 3.16 to 3.43 (m, 2H); 4.26 (m, 1H); 5.33 (m, 2H); 7.17 (broad t, J=9.0 Hz, 2H); from 7.30 to 7.44 (m, 3H); 7.50 (broad d, J=7.5 Hz, 2H); 7.71 (broad dd, J=6.0 and 9.0 Hz, 2H); 8.20 (s, 1H). [α]$^{20}_D$=+21.5+/−0.5° (c 0.5, MeOH). The solution containing the levorotatory enantiomer eluted in the second position is evaporated to dryness under reduced pressure (2.7 kPa), so as to obtain 0.137 g of (−)-3-[3-benzyloxy-4-(4-fluorophenyl)-pyrazol-1-yl]-1-azabicyclo[2.2.2]octane oil.

$^1$H NMR spectrum (300 MHz)—δ in ppm—in DMSO-d6: 1.30 (m, 1H); from 1.49 to 1.71 (m, 3H); 2.08 (m, 1H); from 2.65 to 2.80 (m, 3H); 2.98 (m, 1H); from 3.15 to 3.42 (m, 2H); 4.25 (m, 1H); 5.33 (m, 2H); 7.18 (broad t, J=9.0 Hz, 2H); from 7.30 to 7.44 (m, 3H); 7.50 (broad d, J=7.5 Hz, 2H); 7.71 (broad dd, J=6.0 and 9.0 Hz, 2H); 8.20 (s, 1H). [α]$^{20}_D$=−20.2+/−0.6° (c 0.5, MeOH).

The 3-benzyloxy-4-(4-fluorophenyl)-1H-pyrazole can be prepared in the following way:

20 cm$^3$ of a 1N solution of tetrabutylammonium fluoride in tetrahydrofuran are added to a solution, under an argon atmosphere and with stirring, of 3.5 g of 3-benzyloxy-4-(4-fluorophenyl)-1-(toluene-4-sulfonyl)-1H-pyrazole in 50 cm$^3$ of tetrahydrofuran. After heating for 15 h at the reflux of the solvent, the reaction medium is evaporated under reduced pressure (2.7 kPa) and ethyl acetate is added to the residue. The organic phase is washed successively with two times water and a saturated aqueous sodium chloride solution; it is dried over magnesium sulfate and evaporated under reduced pressure (2.7 kPa). The yellow solid obtained (2.3 g) is purified by flash chromatography on silica under an argon pressure (50 kPa) [eluent: cyclohexane/ethyl acetate (70/30 by volume)]. After concentrating the fractions under reduced pressure (2.7 kPa), 2 g of 3-benzyloxy-4-(4-fluorophenyl)-1H-pyrazole are obtained in the form of a white solid. Mass spectrum (EI): 268(+)=M(+).

The 3-benzyloxy-4-(4-fluorophenyl)-1-(toluene-4-sulfonyl)-1H-pyrazole can be prepared in the following way:

4.5 g of 4-fluorophenylboronic acid, 15 cm$^3$ of a 2N aqueous potassium carbonate solution and 1.6 g of tetrakis(triphenylphosphine)palladium are added to a solution, under an argon atmosphere and with stirring, of 4.8 g of 3-benzyloxy-4-iodo-1-(toluene-4-sulfonyl)-1H-pyrazole in 40 cm$^3$ of toluene to which 10 cm$^3$ of ethanol have been added. After heating for 5 h at 100° C. and for 16 h at a temperature in the region of 20° C., the reaction medium is evaporated under reduced pressure (2.7 kPa). Ethyl acetate, water and carbon black are added to the residue, which is filtered through supercel. The filtrate is separated by settling out, and the organic phase is then washed successively with three times water and a saturated aqueous sodium chloride solution; it is dried over magnesium sulfate and evaporated under reduced pressure (2.7 kPa). The yellow solid obtained (9 g) is purified by flash chromatography on silica under an argon pressure (50 kPa) [eluent: cyclohexane/ethyl acetate (95/5 by volume)]. After concentrating the fractions under reduced pressure (2.7 kPa), 3.5 g of 3-benzyloxy-4-(4-fluorophenyl)-1-(toluene-4-sulfonyl)-1H-pyrazole are obtained in the form of a yellow solid. Mass spectrum (EI): 422(+)=M(+); 267(+)=422(+)−Ts; 91(+)=C$_7$H$_7$(+).

EXAMPLE 93

(+)-1-(1-Azabicyclo[2.2.2]oct-3-yl)-4-(4-fluorophenyl)-1H-pyrazol-3-ol hydrochloride 5 cm$^3$ of 12N hydrochloric acid are added to a stirred solution of 137 mg of (−)-3-[3-benzyloxy-4-(4-fluoro-phenyl)pyrazol-1-yl]-1-azabicyclo[2.2.2]octane in 5 cm$^3$ of ethanol. After 7 h at the reflux of the solvent, the reaction medium is cooled to a temperature in the region of 20° C. and evaporated to dryness under reduced pressure (2.7 kPa). The residue is triturated in diisopropyl ether, filtered, and dried under reduced pressure (2.7 kPa), to give 99 mg of (+)-1-(1-azabicyclo[2.2.2]oct-3-yl)-4-(4-fluorophenyl)-1H-pyrazol-3-ol hydrochloride in the form of a white solid. Mass spectrum (EI): 287(+)=M(+). $^1$H NMR spectrum (300 MHz)—δ in ppm—in DMSO-d6: from 1.69 to 2.03 (m, 4H); 2.41 (m, 1H); from 3.19 to 3.50 (m, 4H); 3.79 (m, 2H); 4.65 (m, 1H); 7.19

(broad t, J=9.0 Hz, 2H); 7.71 (broad dd, J=6.0 and 9.0 Hz, 2H); 8.17 (s, 1H); from 10.1 to 10.3 (very broad m, 1H); 10.5 (s, 1H). $[\alpha]^{20}_D$=+ 15.3+/−0.6° (c 0.5, MeOH).

EXAMPLE 94

3-[4-(4-Chlorophenyl)pyrazol-1-yl]-1-azabicyclo[2.2.2]-octane hydrochloride

A solution of 600 mg of 4-(4-chlorophenyl)-1H-pyrazole and of 420 mg of potassium tert-butoxide in 20 cm³ of dimethylformamide, in an inert atmosphere, is stirred for 2 h at a temperature in the region of 20° C., and then a solution of 1.1 g of toluene-4-sulfonic acid 1-azabicyclo[2.2.2]oct-3-yl ester in 20 cm³ of dimethyl-formamide is added thereto. After heating for 15 h at 100° C., reaction medium is poured into water, and the mixture is extracted with two times ethyl acetate. The combined organic phases are washed successively with two times water and a saturated aqueous sodium chloride solution, dried over magnesium sulfate, and evaporated under reduced pressure (2.7 kPa). The orange oil obtained (1 g) is purified by flash chromatography on alumina CTB1 under an argon pressure (50 kPa) [eluent: ethyl acetate then ethyl acetate/methanol (95/5 by volume)]. After concentrating the fractions under reduced pressure (2.7 kPa), an orange oil is obtained (840 mg) which is purified by flash chromatography on silica under an argon pressure (50 kPa) [eluent: ethyl acetate, ethyl acetate/methanol (80/20 by volume) then dichloromethane/methanol (80/20 by volume)]. Concen-trating the appropriate fractions under reduced pressure (2.7 kPa) gives a cream solid (250 mg) which is dissolved in ethyl acetate. 0.85 cm³ of 1N hydro-chloric ether is added to the solution, which is then evaporated to dryness under reduced pressure (2.7 kPa). The residue is triturated in diisopropyl ether and the resulting solid is filtered and then dried under reduced pressure (2.7 kPa), to give 239 mg of 3-[4-(4-chlorophenyl)pyrazol-1-yl]-1-azabicyclo[2.2.2]octane hydrochloride in the form of a cream solid. Mass spectrum (EI): 287(+)/ . . . =M(+)/ . . . (1 Cl); 36(+)/38(+)=HCl(+)= salification via HCl. ¹H NMR spectrum (400 MHz)—δ in ppm—in DMSO-d6: 1.71 (m, 2H); 1.98 (m, 2H); 2.41 (m, 1H); from 3.20 to 3.46 (m, 4H); 3.78 (m, 1H); 3.92 (m, 1H); 4.89 (m, 1H); 7.44 (broad d, J=8.5 Hz, 2H); 7.64 (broad d, J=8.5 Hz, 2H); 8.05 (s, 1H); 8.46 (s, 1H); from 10.05 to 10.35 (very broad m, 1H).

The 4-(4-chlorophenyl)-1H-pyrazole can be prepared in the following way:

21 cm³ of a 1N solution of tetrabutylammonium fluoride in tetrahydrofuran are added to a solution, under an argon atmosphere and with stirring, of 2.8 g of 4-(4-chlorophenyl)-1-(toluene-4-sulfonyl)-1H-pyrazole in 30 cm³ of tetrahydrofuran. After heating for 8 h at the reflux of the solvent, the reaction medium is evaporated under reduced pressure (2.7 kPa) and ethyl acetate is added to the residue. The organic phase is washed successively with two times water and a saturated aqueous sodium chloride solution; it is dried over magnesium sulfate and evaporated under reduced pressure (2.7 kPa). The yellow solid obtained (2.1 g) is purified by flash chromatography on silica under an argon pressure (50 kPa) [eluent: cyclohexane/ethyl acetate (50/50 by volume)]. After concentrating the fractions under reduced pressure (2.7 kPa), 1.2 g of 4-(4-chlorophenyl)-1H-pyrazole are obtained in the form of a white solid. Mass spectrum (EI): m/z=178 (M⁺·) base peak, m/z=151 [(M−HCN)⁺·], m/z=116 [(m/z=151−Cl)⁺], m/z=89 [(m/z=116−HCN)⁺].

The 4-(4-chlorophenyl)-1-(toluene-4-sulfonyl)-1H-pyrazole can be prepared in the following way:

6.1 g of 4-chlorophenylboronic acid, 20 cm³ of a 2N aqueous potassium carbonate solution and 2.1 g of tetrakis(triphenylphosphine)palladium are added to a solution, under an argon atmosphere and with stirring, of 5 g of 4-iodo-1-(toluene-4-sulfonyl)-1H-pyrazole in 60 cm³ of toluene to which 15 cm³ of ethanol have been added. After heating for 3 h at 100° C. and for 16 h at a temperature in the region of 20° C., the reaction medium is evaporated under reduced pressure (2.7 kPa). Ethyl acetate, water and carbon black are added to the residue, which is filtered through supercel. The filtrate is separated by settling out, and the organic phase is then washed successively with two times water and a saturated aqueous sodium chloride solution; it is dried over magnesium sulfate and evaporated under reduced pressure (2.7 kPa). The oil obtained (10.7 g) is purified by flash chromatography on silica under an argon pressure (50 kPa) [eluent: cyclohexane/ethyl acetate (90/10 by volume)]. After concentrating the fractions under reduced pressure (2.7 kPa), the resulting solid is triturated in diisopropyl ether. After filtration and drying under reduced pressure (2.7 kPa), 2.8 g of 4-(4-chlorophenyl)-1-(toluene-4-sulfonyl)-1H-pyrazole are obtained in the form of an orange solid. ¹H NMR spectrum (300 MHz)—δ in ppm—in DMSO-d6: 2.41 (s, 3H); from 7.44 to 7.53 (m, 4H); 7.80 (broad d, J=9.0 Hz, 2H); 7.92 (broad d, J=9.0 Hz, 2H); 8.42 (s, 1H); 9.04 (s, 1H).

EXAMPLE 95

3-[4-(4-Chlorophenyl)pyrazol-1-ylmethyl]-1-azabicyclo-[2.2.2]octane hydrochloride A solution of 640 mg of 4-(4-chlorophenyl)-1H-pyrazole in 25 cm³ of dimethylformamide is added gradually, under an argon atmosphere and at a temperature in the region of 20° C., to a suspension of 345 mg of sodium hydride (at 75% by mass in liquid petroleum jelly) in 15 cm³ of dimethylformamide. After stirring for 45 min at a temperature in the region of 50° C., 1.4 g of 3-chloro-methyl-1-azabicyclo[2.2.2]octane hydrochloride are added, in small portions, and the mixture is then heated for 15 hours at a temperature in the region of 100° C. The mixture is cooled to a temperature in the region of 20° C. and is then poured into water. The aqueous phase is extracted with two times ethyl acetate. The combined organic phases can be washed with two times water and brine, and are then dried over magnesium sulfate, filtered, and concentrated to dryness under reduced pressure (2.7 kPa). The orange oil obtained (1.3 g) is purified by flash chromatography on alumina CTB1 under an argon pressure (50 kPa) [eluent: ethyl acetate then ethyl acetate/methanol (99/1 then 97/3 by volume)]. After concentrating the fractions under reduced pressure (2.7 kPa), an oil is obtained (520 mg) which is purified by flash chromatography on silica under an argon pressure (50 kPa) [eluent: dichloromethane/7N ammoniacal methanol (97/3 by volume)]. Concentrating the appropriate fractions under reduced pressure (2.7 kPa) gives a pale yellow oil (330 mg) which is dissolved in ethyl acetate. 0.985 cm³ of 1N hydrochloric ether is added to the solution, which is then evaporated to dryness under reduced pressure (2.7 kPa). The residue is triturated in diisopropyl ether and the resulting solid is filtered and then dried under reduced pressure (2.7 kPa), to give 353 mg of 3-[4-(4-chlorophenyl)pyrazol-1-ylmethyl]-1-azabicyclo[2.2.2]-octane hydrochloride in the form of a white solid. Mass spectrum (EI): 301(+)/ . . . =M(+)/ . . . (1 Cl). ¹H NMR spectrum (300 MHz)—δ in ppm—in DMSO-d6: from 1.65 to 2.13 (m, 5H); 2.58 (m, 1H); 2.93 (m, 1H); from 3.09 to 3.63 (m, 5H); from 4.22 to 4.34 (m, 2H); 7.42 (broad d, J=9.0 Hz, 2H); 7.62 (broad d, J=9.0 Hz, 2H); 7.95 (s, 1H); 8.28 (s, 1H); from 9.90 to 10.2 (very broad m, 1H).

EXAMPLE 96

3-[4-(3-Chloro-4-methoxyphenyl)pyrazol-1-ylmethyl]-1-azabicyclo[2.2.2]octane

A solution of 1.1 g of 4-(3-chloro-4-methoxyphenyl)-1H-pyrazole in 25 cm³ of dimethylformamide is added gradually, under an argon atmosphere and at a temperature in the region of 20° C., to a suspension of 530 mg of sodium hydride (at 75% by mass in liquid petroleum jelly) in 15 cm³ of dimethylformamide. After stirring for 1 h at a temperature in the region of 50° C., 2.07 g of 3-chloromethyl-1-azabicyclo [2.2.2]octane hydrochloride are added in small portions, and the mixture is then heated for 15 hours at a temperature in the region of 100° C. The mixture is cooled to a temperature in the region of 20° C. and is then poured into water. The aqueous phase is extracted with two times ethyl acetate. The combined organic phases are washed with two times water and brine, and then dried over magnesium sulfate, filtered, and concentrated to dryness under reduced pressure (2.7 kPa). The orange oil obtained (1.8 g) is purified by flash chromatography on alumina CTB1 under an argon pressure (50 kPa) [eluent: ethyl acetate then ethyl acetate/methanol (98/2 then 95/5 by volume)]. After concentrating the fractions under reduced pressure (2.7 kPa), an oil is obtained (550 mg) which is purified by flash chromato-graphy on silica under an argon pressure (50 kPa) [eluent: dichloromethane/7N ammoniacal methanol (98/2 by volume)]. Concentrating the appropriate fractions under reduced pressure (2.7 kPa) gives a pale yellow oil (400 mg) which is again purified by flash chromatography on alumina CTB1 under an argon pressure (50 kPa) [eluent: ethyl acetate/methanol (95/5 by volume) then dichloromethane/methanol (80/20 by volume)]. After concentrating the fractions under reduced pressure (2.7 kPa), 140 mg of 3-[4-(3-chloro-4-methoxyphenyl)pyrazol-1-ylmethyl]-1-azabicyclo[2.2.2]octane are obtained in the form of a white solid. Mass spectrum (CI): 332(+)/ . . . =(M+H)(+)/ . . . (1 Cl); 349(+)=(M+NH$_4$)(+)/ . . . ¹H NMR spectrum (400 MHz)—δ in ppm—in DMSO-d6: from 1.28 to 1.57 (m, 4H); 1.77 (m, 1H); 2.15 (m, 1H); 2.36 (m, 1H); from 2.58 to 2.88 (m, 5H); 3.85 (s, 3H); 4.10 (d, J=8.0 Hz, 2H); 7.12 (d, J=8.0 Hz, 1H); 7.50 (dd, J=2.0 and 8.0 Hz, 1H); 7.64 (d, J=2.0 Hz, 1H); 7.85 (s, 1H); 8.08 (s, 1H).

The 4-(3-chloro-4-methoxyphenyl)-1H-pyrazole can be prepared in the following way:

35 cm³ of a 1N solution of tetrabutylammonium fluoride in tetrahydrofuran are added to a solution, under an argon atmosphere and with stirring, of 5.2 g of 4-(3-chloro-4-methoxyphenyl)-1-(toluene-4-sulfonyl)-1H-pyrazole in 50 cm³ of tetrahydrofuran. After heating for 6 h at the reflux of the solvent, the reaction medium is evaporated under reduced pressure (2.7 kPa) and ethyl acetate is added to the residue. The organic phase is washed successively with two times water and the saturated aqueous sodium chloride solution; it is dried over magnesium sulfate and evaporated under reduced pressure (2.7 kPa). The orange solid obtained (5.1 g) is purified by flash chromatography on silica under an argon pressure (50 kPa) [eluent: cyclohexane/ethyl acetate (50/50 by volume)]. After concentrating the fractions under reduced pressure (2.7 kPa), 1.84 g of 4-(3-chloro-4-methoxyphenyl)-1H-pyrazole are obtained in the form of a pale yellow solid. Mass spectrum (EI): 208(+)/ . . . =M(+)/ . . . (1 Cl); 193 (+)/ . . . =M(+)/ . . . —CH$_3$.

The 4-(3-chloro-4-methoxyphenyl)-1-(toluene-4-sulfonyl)-1H-pyrazole can be prepared in the following way:

9 g of 4-chloro-3-methoxyphenylboronic acid, 24 cm³ of a 2N aqueous potassium carbonate solution and 2.45 g of tetrakis(triphenylphosphine)palladium are added to a solution, under an argon atmosphere and with stirring, of 5.6 g of 4-iodo-1-(toluene-4-sulfonyl)-1H-pyrazole in 60 cm³ of toluene to which 15 cm³ of ethanol have been added. After heating for 3 h at 100° C. and for 16 h at a temperature in the region of 20° C., the reaction medium is evaporated under reduced pressure (2.7 kPa). Ethyl acetate, water and carbon black are added to the residue, which is filtered through supercel. The filtrate is separated by settling out, and the organic phase is then washed successively with two times water and a saturated aqueous sodium chloride solution; it is dried over magnesium sulfate and evaporated under reduced pressure (2.7 kPa). The solid obtained is triturated in ethyl acetate, filtered and dried under reduced pressure (2.7 kPa), to give 5.2 g of 4-(3-chloro-4-methoxyphenyl)-1-(toluene-4-sulfonyl)-1H-pyrazole in the form of a beige solid that is used without any other purification in the subsequent step.

¹H NMR spectrum (300 MHz)—δ in ppm—in DMSO-d6 for 70% of the mixture: 2.40 (m, 3H); 3.88 (broad s, 3H); 7.19 (d, J=8.5 Hz, 1H); 7.50 (broad d, J=8.5 Hz, 2H); 7.71 (dd, J=2.0 and 8.5 Hz, 1H); from 7.88 to 7.93 (m, 3H); 8.41 (s, 1H); 8.99 (s, 1H) (purity evaluated at 70% by ¹H NMR+ starting boronic acid).

EXAMPLE 97

4-[1-(1-Azabicyclo[2.2.2]oct-3-ylmethyl)-1H-pyrazol-4-yl]-2-chlorophenol dihydrochloride A solution, under an argon atmosphere and with stirring, of 470 mg of 3-[4-(3-chloro-4-methoxyphenyl)-pyrazol-1-ylmethyl]-1-azabicyclo[2.2.2]octane in 20 cm³ of dichloromethane is cooled in an ice-cold bath and 12 cm³ of a 1N solution of boron tribromide in dichloro-methane are then added thereto. After having allowed the reaction medium to return to a temperature in the region of 20° C., the reaction is continued for 15 h at this temperature and then the mixture is poured into water to which dichloromethane has been added. The solution is brought to a pH in the region of 8 by adding 1N sodium hydroxide. The precipitate formed is filtered off, and taken up in ethanol under hot conditions. After filtration of the suspension under hot conditions, water and carbon black are added to the filtrate, which is filtered through Wattman® paper and evaporated to dryness under reduced pressure (2.7 kPa). The resulting beige solid (330 mg) is dissolved in 10 cm³ of ethanol and 10 cm³ of 12N hydrochloric acid. After heating for 12 h at the reflux of the solvent, the mixture is cooled to a temperature in the region of 20° C., and evaporated to dryness under reduced pressure (2.7 kPa). The solid obtained is, three times, successively dissolved in ethanol and evaporated to dryness under reduced pressure (2.7 kPa), and is then triturated in diisopropyl ether, filtered and dried under vacuum (2.7 kPa), to give 370 mg of 4-[1-(1-azabicyclo [2.2.2]oct-3-ylmethyl)-1H-pyrazol-4-yl]-2-chlorophenol dihydrochloride in the form of a cream solid. Mass spectrum (ESP): 318(+)/ . . . =(M+H)(+). ¹H NMR spectrum (300 MHz)—δ in ppm—in DMSO-d6: from 1.66 to 1.92 (m, 4H); 2.07 (m, 1H); 2.60 (m, 1H); 2.94 (m, 1H); from 3.10 to 3.39 (m, 5H); from 4.15 to 4.32 (m, 2H); 7.00 (d, J=8.5 Hz, 1H); 7.34 (dd, J=2.5 and 8.5 Hz, 1H); 7.56 (d, J=2.5 Hz, 1H); 7.85 (s, 1H); 8.16 (s, 1H); from 9.80 to 10.3 (very broad m, 2H).

EXAMPLE 98

4-[1-(1-Azabicyclo[2.2.2]oct-3-yl)-1H-pyrazol-4-yl]-2-chlorophenol

A solution, under an argon atmosphere and with stirring, of 750 mg of 3-[4-(3-chloro-4-methoxyphenyl)-pyrazol-1-yl]-1-azabicyclo[2.2.2]octane in 25 cm$^3$ of dichloromethane is cooled in an ice-cold bath and 11 cm$^3$ of a 1N solution of boron tribromide in dichloromethane are then added thereto. After reaction for 30 min at a temperature in the region of 0° C., and heating for 3 h at 40° C. then for 15 h at a temperature in the region of 20° C., the reaction mixture is poured into water to which dichloromethane has been added. The resulting suspension is filtered and the solid is taken up in water. The mixture is adjusted to pH 8 and then extracted with ethyl acetate. The organic phase is washed successively with two times water and a saturated aqueous sodium chloride solution, dried over magnesium sulfate, and evaporated under reduced pressure (2.7 kPa). The beige solid obtained (800 mg) is purified by flash chromatography on silica under an argon pressure (50 kPa) [eluent: dichloromethane/methanol (80/20 by volume)]. Concentrating the appro-priate fractions under reduced pressure (2.7 kPa) gives a residue which is triturated in diisopropyl ether, filtered and dried under reduced pressure (2.7 kPa), to give 240 mg of 4-[1-(1-azabicyclo[2.2.2]oct-3-yl)-1H-pyrazol-4-yl]-2-chlorophenol in the form of a white solid. Mass spectrum (EI): 303(+)/ . . . =M(+)/ . . . (1 Cl). $^1$H NMR spectrum (400 MHz)—δ in ppm—in DMSO-d6: 1.32 (m, 1H); 1.54 (m, 1H); 1.70 (m, 2H); 2.02 (m, 1H); 2.77 (m, 3H); 2.98 (m, 1H); from 3.20 to 3.50 (m, 2H); 4.42 (m, 1H); 6.98 (d, J=9.0 Hz, 1H); 7.40 (dd, J=2.0 and 9.0 Hz, 1H); 7.62 (d, J=2.0 Hz, 1H); 7.87 (s, 1H); 8.28 (s, 1H); 10.05 (broad m, 1H).

The 3-[4-(3-chloro-4-methoxyphenyl)pyrazol-1-yl]-1-aza-bicyclo[2.2.2]octane can be prepared in the following way:

A solution of 1.35 g of 4-(3-chloro-4-methoxyphenyl)-1H-pyrazole and of 800 mg of potassium tert-butoxide in 20 cm$^3$ of dimethylformamide, under an inert atmosphere, is stirred for 1 h at a temperature in the region of 20° C. and a solution of 2 g of toluene-4-sulfonic acid 1-azabicyclo[2.2.2]oct-3-yl ester in 20 cm$^3$ of dimethyl-formamide is then added thereto. After heating for 18 h at 100° C., the reaction medium is poured into water, and the mixture is extracted with two times ethyl acetate. The combined organic phases are washed successively with two times water and a saturated aqueous sodium chloride solution, dried over magnesium sulfate, and evaporated under reduced pressure (2.7 kPa). The orange oil obtained (2 g) is purified by flash chromatography on silica under an argon pressure (50 kPa) [eluent: ethyl acetate, ethyl acetate/methanol (80/20 by volume) then dichloromethane/methanol (80/20 by volume)]. After concentrating the fractions under reduced pressure (2.7 kPa), 480 mg of 3-[4-(3-chloro-4-methoxyphenyl)-pyrazol-1-yl]-1-azabicyclo[2.2.2]octane are obtained in the form of an orange oil. Mass spectrum (EI): m/z=317 (M$^{+\cdot}$), m/z=234 [(M-C$_5$H$_9$N)$^{+\cdot}$], m/z=109 [C$_7$H$_{11}$N$^{+\cdot}$], m/z=97 [C$_6$H$_{11}$N$^{+\cdot}$] base peak.

EXAMPLES 99 AND 100

(−)-4-[1-(1-Azabicyclo[2.2.2]oct-3-yl)-1H-pyrazol-4-yl]-2-chlorophenol and (+)-4-[1-(1-azabicyclo[2.2.2]oct-3-yl)-1H-pyrazol-4-yl]-2-chlorophenol An ethanolic solution containing 0.173 g of 4-[1-(1-aza-bicyclo[2.2.2]oct-3-yl)-1H-pyrazol-4-yl]-2-chlorophenol is introduced onto a column, 8 cm in diameter, containing 1180 g of Chiralpak AD™ chiral stationary phase. The elution is carried out by means of a mixture of heptane, of ethanol, of methanol and of triethyl-amine (80/10/10/0.1 by volume), the flow rate of the mobile phase being 120 ml/min. The levorotatory enantiomer is eluted in the first position, the solution is evaporated to dryness under reduced pressure (2.7 kPa), to give 0.093 g of (−)-4-[1-(1-aza-bicyclo[2.2.2]oct-3-yl)-1H-pyrazol-4-yl]-2-chlorophenol in the form of an oil.

Mass spectrum (EI): 303(+)/ . . . =M(+)/ . . . (1 Cl). $^1$H NMR spectrum (400 MHz)—δ in ppm—in DMSO-d6: 1.31 (m, 1H); 1.53 (m, 1H); 1.68 (m, 2H); 2.09 (m, 1H); from 2.67 to 2.80 (m, 3H); 2.97 (m, 1H); from 3.18 to 3.48 (m, 2H); 4.39 (m, 1H); 6.95 (d, J=8.5 Hz, 1H); 7.38 (dd, J=2.5 and 8.5 Hz, 1H); 7.60 (d, J=2.5 Hz, 1H); 7.85 (s, 1H); 8.23 (s, 1H); from 9.98 to 10.15 (very broad m, 1H). [α]$^{20}_D$=−4.1+/−0.6° (c 0.5, MeOH).

The solution containing the dextrorotatory enantiomer eluted in the second position is evaporated to dryness under reduced pressure (2.7 kPa), to give 0.102 g of (+)-4-[1-(1-azabicyclo[2.2.2]oct-3-yl)-1H-pyrazol-4-yl]-2-chlorophenol in the form of an oil.

Mass spectrum (EI): 303(+)/ . . . =M(+)/ . . . (1 Cl). $^1$H NMR spectrum (400 MHz)—δ in ppm—in DMSO-d6: 1.35 (m, 1H); 1.54 (m, 1H); 1.70 (m, 2H); 2.12 (m, 1H); from 2.70 to 2.83 (m, 3H); 3.00 (m, 1H); from 3.21 to 3.51 (m, 2H); 4.43 (m, 1H); 6.95 (d, J=8.5 Hz, 1H); 7.38 (dd, J=2.5 and 8.5 Hz, 1H); 7.61 (d, J=2.5 Hz, 1H); 7.87 (s, 1H); 8.27 (s, 1H); 10.05 (broad m, 1H). [α]$^{20}_D$=+5.3+/−0.4° (c 0.5, MeOH).

EXAMPLES 101 AND 102

(+)-1-(1-Azabicyclo[2.2.2]oct-3-yl)-4-pyridin-2-yl-1H-pyrazol-3-ol and (−)-1-(1-azabicyclo[2.2.2]oct-3-yl)-4-pyridin-2-yl-1H-pyrazol-3-ol An ethanolic solution containing 0.3 g of (+/−)-1-(1-azabicyclo[2.2.2]oct-3-yl)-4-pyridin-2-yl-1H-pyrazol-3-ol is introduced onto a column, 8 cm in diameter, containing 1180 g of 20 μM Chiralpak AD™ chiral stationary phase. The elution is carried out by means of a mixture of heptane, of ethanol, of methanol and of triethylamine (70/15/15/0.2 by volume), the flow rate of the mobile phase being 120 ml/min. The levorotatory enantiomer is eluted in the first position, the solution is evaporated to dryness under reduced pressure (2.7 kPa), to give 0.109 g of (−)-1-(1-aza-bicyclo[2.2.2]oct-3-yl)-4-pyridin-2-yl-1H-pyrazol-3-ol in the form of an oil.

Mass spectrum (EI): m/z=270 (M$^{+\cdot}$), m/z=187 [(M-C$_5$H$_9$N)$^+$] base peak. $^1$H NMR spectrum (400 MHz)—δ in ppm—in DMSO-d6 (referenced at 2.50 ppm): 1.31 (m, 1H); from 1.55 to 1.70 (m, 3H); 2.07 (m, 1H); from 2.65 to 2.75 (m, 2H); 2.90 (m, 1H); from 3.14 to 3.39 (partially masked m, 3H); 4.21 (m, 1H); 7.14 (m, 1H); 7.72 (broad d, J=7.5 Hz, 1H); 7.78 (m, 1H); 8.26 (s, 1H); 8.45 (broad d, J=5.0 Hz, 1H); from 10.9 to 11.1 (broad m, 1H). [α]$^{20}_D$=−40.7+/−0.8° (c 0.5, dimethylformamide).

The solution containing the dextrorotatory enantiomer eluted in the second position is evaporated to dryness under reduced pressure (2.7 kPa), to give 0.113 g of (+)-1-(1-azabicyclo[2.2.2]oct-3-yl)-4-pyridin-2-yl-1H-pyrazol-3-ol in the form of an oil.

Mass spectrum (EI): m/z=270 (M$^{+\cdot}$), m/z=187 [(M-C$_5$H$_9$N)$^+$] base peak. $^1$H NMR spectrum (400 MHz)—δ in ppm—in DMSO-d6 (referenced at 2.50 ppm): 1.32 (m, 1H); from 1.56 to 1.68 (m, 3H); 2.08 (m, 1H); from 2.66 to 2.76 (m, 2H); 2.92 (m, 1H); from 3.14 to 3.42 (partially masked m, 3H); 4.22 (m, 1H); 7.14 (m, 1H); 7.71 (broad d, J=7.5 Hz, 1H); 7.78 (m, 1H); 8.27 (s, 1H); 8.47 (broad d, J=5.0 Hz, 1H); from 10.8 to 11.15 (broad m, 1H). $[\alpha]^{20}_D$=+35.4+/−0.8° (c 0.5, dimethylformamide).

The (+/−)-1-(1-azabicyclo[2.2.2]oct-3-yl)-4-pyridin-2-yl-1H-pyrazol-3-ol hydrochloride can be prepared in the following way:

7 cm$^3$ of 4N hydrochloric dioxane are added to a solution of 330 mg of 3-[3-(cyclohex-2-enyloxy)-4-pyridin-2-yl-pyrazol-1-yl]-1-azabicyclo[2.2.2]octane in 7 cm$^3$ of dioxane. After stirring for 15 h at a temperature in the region of 20° C., the insoluble material formed is filtered off, rinsed with diisopropyl ether and dried under reduced pressure (2.7 kPa), to give 300 mg of (+/−)-1-(1-azabicyclo[2.2.2]oct-3-yl)-4-pyridin-2-yl-1H-pyrazol-3-ol hydrochloride in the form of a white solid. Mass spectrum (EI): m/z=270 (M$^{+\cdot}$), m/z=187 [(M−C$_5$H$_9$N)$^+$] base peak, m/z=36 (HCl$^{+\cdot}$).

The 3-[3-(cyclohex-2-enyloxy)-4-pyridin-2-ylpyrazol-1-yl]-1-azabicyclo[2.2.2]octane can be prepared in the following way:

A solution of 2.5 g of 2-[3-(cyclohex-2-enyloxy)-1H-pyrazol-4-yl]pyridine and of 1.4 g of potassium tert-butoxide in 20 cm$^3$ of dimethylformamide, under an inert atmosphere, is stirred for 1 h at 50° C. and a solution of 4 g of toluene-4-sulfonic acid 1-azabicyclo[2.2.2]-oct-3-yl ester in 20 cm$^3$ of dimethylformamide is then added thereto. After heating for 15 h at 100° C., the reaction medium is poured into water, and the mixture is extracted with two times ethyl acetate. The combined organic phases are washed successively with two times water and a saturated aqueous sodium chloride solution, dried over magnesium sulfate, and evaporated under reduced pressure (2.7 kPa). The orange oil obtained (5.3 g) is purified by flash chromatography on alumina CTB1 under an argon pressure (50 kPa) [eluent: cyclo-hexane/ethyl acetate (60/40 by volume), ethyl acetate then ethyl acetate/methanol (95/5 by volume)]. After concentrating the fractions under reduced pressure (2.7 kPa), an oil is obtained which is purified by flash chromatography on silica under an argon pressure (50 kPa) [eluent: dichloromethane/methanol (95/5 then 70/30 by volume)]. Concentrating the appropriate fractions under reduced pressure (2.7 kPa) gives 370 mg of 3-[3-(cyclohex-2-enyloxy)-4-pyridin-2-ylpyrazol-1-yl]-1-azabicyclo[2.2.2]octane in the form of a pale yellow oil. $^1$H NMR spectrum (400 MHz)—δ in ppm—in DMSO-d6 (referenced at 2.50 ppm): 1.35 (m, 1H); from 1.59 to 1.70 (m, 4H); 1.78 (m, 1H); from 1.86 to 2.17 (m, 5H); from 2.67 to 2.78 (m, 3H); 2.96 (m, 1H); 3.19 (m, 1H); from 3.27 to 3.37 (masked m, 1H); 4.30 (m, 1H); 5.20 (m, 1H); from 5.95 to 6.04 (m, 2H); 7.10 (m, 1H); 7.74 (m, 2H); 8.18 (s, 1H); 8.47 (broad d, J=5.0 Hz, 1H).

EXAMPLES 103 AND 104

(+)-1-(1-Azabicyclo[2.2.2]oct-3-yl)-4-phenyl-1H-pyrazol-3-ylamine and (−)-1-(1-azabicyclo[2.2.2]oct-3-yl)-4-phenyl-1H-pyrazol-3-ylamine An ethanolic solution containing 0.13 g of (+/−)-1-(1-azabicyclo[2.2.2]oct-3-yl)-4-phenyl-1H-pyrazol-3-ylamine is introduced onto a column, 8 cm in diameter, containing 1180 g of 20 μM Chiralpak AD™ chiral stationary phase. The elution is carried out by means of a mixture of heptane, of ethanol and of triethyl-amine (50/50/0.1 by volume), the flow rate of the mobile phase being 120 ml/min. The levorotatory enantiomer is eluted in the first position, the solution is evaporated to dryness under reduced pressure (2.7 kPa), to give 0.035 g of (−)-1-(1-aza-bicyclo[2.2.2]oct-3-yl)-4-phenyl-1H-pyrazol-3-ylamine in the form of an oil.

Mass spectrum (EI): m/z=268 (M$^{+\cdot}$) base peak, m/z=185 [(M−C$_5$H$_9$N)$^+$], m/z=109 (C$_7$H$_{11}$N$^{+\cdot}$). $^1$H NMR spectrum (300 MHz)—δ in ppm—in DMSO-d6 (referenced at 2.50 ppm): 1.37 (m, 1H); from 1.61 to 1.74 (m, 3H); 2.11 (m, 1H); from 2.71 to 2.85 (m, 3H); 3.00 (m, 1H); from 3.12 to 3.53 (partially masked m, 2H); 4.21 (m, 1H); 4.65 (broad m, 2H); 7.13 (tt, J=1.5 and 7.5 Hz, 1H); 7.32 (broad t, J=7.5 Hz, 2H); 7.52 (broad d, J=7.5 Hz, 2H); 7.90 (s, 1H). $[\alpha]^{20}_D$=−(dimethyl-formamide).

The solution containing the dextrorotatory enantiomer eluted in the second position is evaporated under reduced pressure (2.7 kPa), to give 0.039 g of (+)-1-(1-azabicyclo[2.2.2]oct-3-yl)-4-phenyl-1H-pyrazol-3-ylamine in the form of an oil.

Mass spectrum (EI): m/z=268 (M$^{+\cdot}$), m/z=185 [(M−C$_5$H$_9$N)$^+$], m/z=109 (C$_7$H$_{11}$N$^{+\cdot}$) base peak. $^1$H NMR spectrum (300 MHz)—δ in ppm—in DMSO-d6 (referenced at 2.50 ppm): 1.34 (m, 1H); from 1.60 to 1.73 (m, 3H); 2.09 (m, 1H); from 2.68 to 2.82 (m, 3H); from 2.90 to 3.53 (partially masked m, 3H); 4.19 (m, 1H); 4.63 (broad m, 2H); 7.12 (broad t, J=7.5 Hz, 1H); 7.32 (broad t, J=7.5 Hz, 2H); 7.51 (broad d, J=7.5 Hz, 2H); 7.89 (s, 1H). $[\alpha]^{20}_D$=+(dimethylformamide).

The (+/−)-1-(1-azabicyclo[2.2.2]oct-3-yl)-4-phenyl-1H-pyrazol-3-ylamine can be prepared in the following way:

1.1 g of 1,3-dimethylbarbituric acid and 50 mg of tetrakis(triphenylphosphine)palladium are added to a solution of 280 mg of diallyl-[1-(1-azabicyclo[2.2.2]-oct-3-yl)-4-phenyl-1H-pyrazol-3-yl]amine in 10 cm$^3$ of dichloromethane, under argon and with stirring. After heating for 15 h at the reflux of the reaction medium, the mixture is evaporated to dryness under reduced pressure (2.7 kPa). The residue is taken up with 1N hydrochloric acid and the solution is washed with two times ethyl acetate. The resulting aqueous phase is alkylinized with 1N sodium hydroxide and extracted with two times ethyl acetate. The combined organic phases are washed with a saturated aqueous sodium chloride solution, dried over magnesium sulfate and evaporated under reduced pressure (2.7 kPa). The residue is taken up with dichloromethane and the solution is treated with carbon black, filtered through supercel, and evaporated under reduced pressure (2.7 kPa), to give 130 mg of (+/−)-1-(1-azabicyclo[2.2.2]oct-3-yl)-4-phenyl-1H-pyra-zol-3-ylamine in the form of an orange oil. $^1$H NMR spectrum (300 MHz)—δ in ppm—in DMSO-d6 (referenced at 2.50 ppm): from 1.20 to 1.38 (m, 1H); from 1.58 to 1.71 (m, 3H); 2.07 (m, 1H); from 2.62 to 2.79 (m, 3H); from 2.88 to 3.63 (partially masked m, 3H); 4.16 (m, 1H); 4.63 (broad s, 2H); 7.13 (broad t, J=7.5 Hz, 1H); 7.32 (broad t, J=7.5 Hz, 2H); 7.52 (broad d, J=7.5 Hz, 2H); 7.89 (s, 1H).

The diallyl-[1-(1-azabicyclo[2.2.2]oct-3-yl)-4-phenyl-1H-pyrazol-3-yl]amine can be prepared in the following way:

A solution of 1.3 g of diallyl-(4-phenyl-1H-pyrazol-3-yl)amine and of 730 mg of potassium tert-butoxide in 20 cm$^3$ of dimethylformamide, under an argon atmosphere, is stirred for 45 min at 45° C. and then a solution of 2.3 g of toluene-4-sulfonic acid 1-azabicyclo[2.2.2]-oct-3-yl ester in 15 cm$^3$ of dimethylformamide is added thereto. After heating for 15 h at 100° C., the reaction medium is poured into water, and the mixture is extracted with two times ethyl acetate. The combined organic phases are washed successively with two times water and a saturated aqueous sodium chloride solution, dried over magnesium sulfate, and evaporated under reduced pressure (2.7 kPa). The orange oil obtained (1.8 g) is purified by flash chromatography on alumina CTB1 under an argon pressure (50 kPa) [eluent: cyclo-hexane/ethyl acetate (60/40 by volume)]. After concentrating the fractions under reduced pressure (2.7 kPa), an oil is obtained which is purified by flash chromatography on silica under an argon pressure (50 kPa) [eluent: dichloromethane/methanol (50/50 by volume)]. Concentrating the appropriate fractions under reduced pressure (2.7 kPa) gives 280 mg of diallyl-[1-(1-azabicyclo[2.2.2]oct-3-yl)-4-phenyl-1H-pyrazol-3-yl]amine containing 20% (estimated by $^1$H NMR) of diallyl-(4-phenyl-1H-pyrazol-3-yl)amine in the form of a pale yellow oil. $^1$H NMR spectrum (300 MHz)—δ in ppm—in DMSO-d6 (referenced at 2.50 ppm): 1.29 (m, 1H); from 1.53 to 1.69 (m, 3H); 2.03 (m, 1H); from 2.62 to 2.80 (m, 3H); 2.97 (m, 1H); 3.17 (m, 1H); 2.39 (m, 1H); from 3.52 to 3.52 (m, 4H); 4.24 (m, 1H); from 4.98 to 5.17 (m, 4H); from 5.75 to 5.91 (m, 2H); 7.17 (tt, J=1.5 and 7.5 Hz, 1H); 7.33 (broad t, J=7.5 Hz, 2H); 7.61 (broad d, J=7.5 Hz, 2H); 7.93 (s, 1H).

The diallyl-(4-phenyl-1H-pyrazol-3-yl)amine can be prepared in the following way:

22 cm$^3$ of a 1N solution of tetrabutylammonium fluoride in tetrahydrofuran are added to a solution, under an argon atmosphere and with stirring, of 2.9 g of diallyl-[4-phenyl-1-(2-trimethylsilanylethoxymethyl)-1H-pyrazol-3-yl]amine in 25 cm$^3$ of tetrahydrofuran. After heating to 18 h at the reflux of the solvent, 6.3 cm$^3$ of 1N tetrabutylammonium fluoride solution are added and the heating is continued for 4 h. After evaporation of the reaction medium to dryness under reduced pressure (2.7 kPa), ethyl acetate is added to the residue and the organic phase is washed successively with two times water and a saturated aqueous sodium chloride solution; it is dried over magnesium sulfate and evaporated under reduced pressure (2.7 kPa). The brown oil obtained (1.8 g) is purified by flash chromatography on silica under an argon pressure (50 kPa) [eluent: cyclohexane/ethyl acetate (70/30 by volume)]. After concentrating the fractions under reduced pressure (2.7 kPa), 1.3 g of diallyl-(4-phenyl-1H-pyrazol-3-yl)amine are obtained in the form of an orange oil. Mass spectrum (EI): m/z=239 (M$^{+\cdot}$) base peak, m/z=198 [(M–C$_3$H$_5$)$^+$], m/z=41 (C$_3$H$_5^+$).

The diallyl-[4-phenyl-1-(2-trimethylsilanylethoxymethyl)-1H-pyrazol-3-yl]amine can be prepared in the following way:

8.17 g of cesium carbonate and 4.35 cm$^3$ of allyl bromide are added to a solution, under an argon atmosphere and with stirring, of 2.9 g of 4-phenyl-1-(2-trimethyl-silanylethoxymethyl)-1H-pyrazol-3-ylamine in 60 cm$^3$ of acetonitrile. After heating for 15 h at the reflux of the solvent, the reaction medium is evaporated to dryness under reduced pressure (2.7 kPa) and the residue is taken up with ethyl acetate. The organic solution is washed successively with two times water and a saturated aqueous sodium chloride solution; it is dried over magnesium sulfate and evaporated under reduced pressure (2.7 kPa). The orange oil obtained (4 g) is purified by flash chromatography on silica under an argon pressure (50 kPa) [eluent: cyclohexane/ethyl acetate (93/7 by volume)]. After concentrating the fractions under reduced pressure (2.7 kPa), 2.9 g of diallyl-[4-phenyl-1-(2-trimethylsilanylethoxymethyl)-1H-pyrazol-3-yl]amine are obtained in the form of an orange oil. $^1$H NMR spectrum (300 MHz)—δ in ppm—in DMSO-d6 (referenced at 2.50 ppm): –0.03 (s, 9H); 0.83 (m, 2H); from 3.52 to 3.63 (m, 6H); from 5.04 to 5.15 (m, 4H); 5.24 (s, 2H); from 5.74 to 5.90 (m, 2H); 7.21 (tt, J=1.5 and 7.5 Hz, 1H); 7.36 (broad t, J=7.5 Hz, 2H); 7.58 (broad d, J=7.5 Hz, 2H); 7.96 (s, 1H).

The 4-phenyl-1-(2-trimethylsilanylethoxymethyl)-1H-pyra-zol-3-ylamine can be prepared in the following way:

3.7 g of iron, 1.8 g of ammonium chloride and then a solution of 3.5 g of 3-nitro-4-phenyl-1-(2-trimethyl-sila-nylethoxymethyl)-1H-pyrazole in 50 cm$^3$ of ethanol are added to a mixture of 50 cm$^3$ of ethanol and 50 cm$^3$ of water. After heating for 8 h at the reflux of the solvent and with stirring, and for 15 h at a temperature in the region of 20° C., the reaction medium is filtered through supercel and the filtrate is evaporated to dryness under reduced pressure (2.7 kPa). The residue is taken up with ethyl acetate and the organic solution is washed successively with two times water and a saturated aqueous sodium chloride solution, and is then dried over magnesium sulfate and evaporated under reduced pressure (2.7 kPa), to give 2.9 g of 4-phenyl-1-(2-trimethyl-silanylethoxymethyl)-1H-pyrazol-3-ylamine in the form of an orange oil. $^1$H NMR spectrum (400 MHz)—δ in ppm—in DMSO-d6 (referenced at 2.50 ppm): –0.01 (s, 9H); 0.86 (m, 2H); 3.56 (m, 2H); 4.75 (broad s, 2H); 5.17 (s, 2H); 7.18 (broad t, J=7.5 Hz, 1H); 7.35 (broad t, J=7.5 Hz, 2H); 7.50 (broad d, J=7.5 Hz, 2H); 7.88 (s, 1H).

The 3-nitro-4-phenyl-1-(2-trimethylsilanylethoxymethyl)-1H-pyrazole can be prepared in the following way:

8.8 g of phenylboronic acid, 36 cm$^3$ of a 2N aqueous potassium carbonate solution and 3.6 g of tetrakis(tri-phe-nylphosphine)palladium are added to a solution, under an argon atmosphere and with stirring, of 7.8 g of 4-iodo-3-nitro-1-(2-trimethylsilanylethoxymethyl)-1H-pyrazole in 120 cm$^3$ of toluene to which 30 cm$^3$ of ethanol have been added. After heating for 15 h at 100° C., the reaction medium is cooled to a temperature in the region of 20° C. and is then evaporated under reduced pressure (2.7 kPa). The residue is taken up with ethyl acetate and the organic solution is washed successively with two times water and a saturated aqueous sodium chloride solution; it is dried over magnesium sulfate and evaporated under reduced pressure (2.7 kPa), to give 14.3 g of a brown oil which is purified by flash chromatography on silica under an argon pressure (50 kPa) [eluent: cyclohexane/ethyl acetate (90/10 then 70/30 by volume)]. Concentrating the appropriate fractions under reduced pressure (2.7 kPa) gives 4.5 g of 3-nitro-4-phenyl-1-(2-tri-methylsilanylethoxymethyl)-1H-pyrazole in the form of a yellow oil. Mass spectrum (EI): m/z=319 (M$^{+\cdot}$), m/z=246 [(M–C$_3$H$_9$Si)$^+$] base peak, m/z=73 (C$_3$H$_9$Si$^+$).

The 4-iodo-3-nitro-1-(2-trimethylsilanylethoxymethyl)-1H-pyrazole can be prepared in the following way:

10 g of 3-nitro-4-phenyl-1H-pyrazole are added, portionwise, to a suspension of 1.7 g of sodium hydride (at 75% in liquid petroleum jelly) in 120 cm$^3$ of dimethylformamide under an argon atmosphere and with stirring. The mixture is stirred for 45 min at a temperature in the region of 20° C. and 14 cm$^3$ of 2-trimethylsilanylethoxymethyl chloride are then slowly added thereto. After stirring for 15 h at a temperature in the region of 20° C., the reaction medium is poured into 500 cm$^2$ of water and the mixture is extracted with three times 500 cm$^3$ of ethyl acetate. The organic phases are combined, washed successively with two times water and a saturated aqueous sodium chloride solution, dried over magnesium sulfate, filtered and evaporated under reduced pressure (2.7 kPa), to give an orange oil (22 g) which is purified by flash chromatography on silica under an argon pressure (50 kPa) [eluent: cyclohexane/ethyl acetate (85/15 by volume)]. After concentrating the fractions under reduced pressure, 7.8 g of 4-iodo-3-nitro-1-(2-trimethylsilanylethoxy-methyl)-1H-pyrazole are obtained in the form of a pale yellow oil. $^1$H NMR spectrum (300 MHz)—δ in ppm—in DMSO-d6 (referenced at 2.50 ppm): –0.03 (s, 9H); 0.87 (m, 2H); 3.61 (m, 2H); 5.51 (s, 2H); 8.52 (s, 1H).

EXAMPLES 105 AND 106

1-(1-Azabicyclo[2.2.2]oct-3-yl)-4-(1H-indol-4-yl)-1H-pyrazole hydrochloride, enantiomers A and B The procedure is carried out as in example 38, but with 0.78 g of 1-(1-azabicyclo[2.2.2]oct-3-yl)-4-iodo-1H-pyrazole, 0.51 g of 1H-indol-4-yl boronic acid pinacolic ester, 0.475 g of sodium carbonate, 0.13 g of 1,1'-di-chlorobis(diphenylphosphinoferrocene)palladium in 35 cm³ of dioxane and 5 cm³ of water. After purification by chromatography under a nitrogen pressure of 50 kPa on a basic alumina cartridge (Merck), eluting with a mixture of cyclohexane and of ethyl acetate (50/50 then 25/75 then 10/90 by volume) and then with a mixture of ethyl acetate and of methanol (95/5 by volume), fractions 49 to 120 are combined, and concentrated to dryness under reduced pressure (3 kPa). Fractions 192 to 205 are combined, washed with 5 cm³ of water and concentrated to dryness under reduced pressure (3 kPa). The 2 batches, in the form of an orange powder, are combined (266 mg) and purified by HPLC in order to separate the enantiomers on a 20 μm Chiralcel OD column with, as eluent, a mixture of heptane, of methanol, of ethanol and of triethylamine (60/10/30/0.2 by volume); each enantiomer is then taken up with 10 cm³ of dichloromethane and 5 cm³ of water. The organic phase is washed with a saturated aqueous sodium chloride solution, dried over magnesium sulfate, filtered, and concentrated to dryness under reduced pressure (3 kPa). Each white powder thus obtained is then taken up with 20 cm³ of absolute ethanol and then brought to the reflux of the solvent for 20 minutes. Each solution is filtered and washed with 5 cm³ of absolute ethanol, and 1 cm³ of a 1N solution of hydrochloric diethyl ether is added thereto. The solutions are concentrated to dryness under reduced pressure, taken up with 5 cm³ of ethanol and again concentrated to dryness under reduced pressure; the residues are precipitated from 5 cm³ of diisopropyl ether and then filtered through sintered glass. 45 mg of (+)-1-(1-azabicyclo[2.2.2]oct-3-yl)-4-(1H-indol-4-yl)-1H-pyrazole hydrochloride, enantiomer A, in the form of a beige powder ($[\alpha]^{20}_D$=+21.0°, solvent: dimethyl sulfoxide, concentration: 0.5) and 39 mg of (−)-1-(1-azabicyclo[2.2.2]oct-3-yl)-4-(1H-indol-4-yl)-1H-pyrazole hydrochloride, enantiomer B, in the form of a beige powder ($[\alpha]^{20}_D$=−22.7°, solvent: dimethyl sulfoxide, concentration: 0.5) are thus obtained.

The pharmaceutical compositions according to the invention consist of a compound of formula (I) or a salt of such a compound, in the pure state or in the form of a composition in which it is combined with any other pharmaceutically compatible product, which may be inert or physiologically active. The medicinal products according to the invention can be used orally, parenterally, rectally or topically.

As solid compositions for oral administration, use may be made of tablets, pills, powders (gelatin capsules, wafer capsules) or granules. In these compositions, the active principle according to the invention is mixed with one or more inert diluents such as starch, cellulose, sucrose, lactose or silica, under a stream of argon. These compositions may also contain substances other than diluents, for example one or more lubricants such as magnesium stearate or talc, a dye, a coating (sugar-coated tablets) or a varnish.

As liquid compositions for oral administration, use may be made of pharmaceutically acceptable solutions, suspensions, emulsions, syrups and elixirs, containing inert diluents such as water, ethanol, glycerol, plant oils or liquid paraffin. These compositions may comprise substances other than diluents, for example wetting, sweetening, thickening, flavoring or stabilizing products.

The sterile compositions for parenteral administration may preferably be aqueous or nonaqueous solutions, suspensions or emulsions. As a solvent or vehicle, use may be made of water, propylene glycol, a polyethylene glycol, plant oils, in particular olive oil, injectable organic esters, for example ethyl oleate, or other suitable organic solvents. These compositions may also contain adjuvants, in particular wetting agents, tonicity agents, emulsifiers, dispersants and stabilizing agents. The sterilization may be carried out in several ways, for example by aseptic filtration, by incorporating sterilizing agents into the composition, by irradiation or by heating. They may also be prepared in the form of sterile solid compositions which can be dissolved at the time of use in sterile water or any other sterile injectable medium.

The compositions for rectal administration are suppositories or rectal capsules which contain, besides the active product, excipients such as cocoa butter, semisynthetic glycerides or polyethylene glycols.

The compositions for topical administration may, for example, be creams, lotions, eye washes, throat sprays, nasal drops or aerosols.

The doses depend on the desired effect, on the duration of the treatment and on the route of administration used; they are generally between 5 mg and 1 000 mg per day orally for an adult, with single doses ranging from 1 mg to 250 mg of active substance.

In general, the physician will determine the appropriate dosage in accordance with the age, the weight and all the other factors specific to the individual to be treated.

The compounds of formula (I) according to the invention will be useful as a medicinal product in the treatment of diseases due to a dysfunction of alpha-7 nicotinic receptors or responding favorably to a modulation thereof; in the treatment, prevention, diagnosis and/or monitoring of the evolution of psychiatric disorders or diseases or neurological disorders or diseases of the central nervous system involving an impairment of cognitive functions or of the processing of sensory information.

More particularly, the diseases or the disorders treated concern cognitive abilities and attention capacity, the ability to concentrate, to learn and/or to memorize, Alzheimer's disease and related cognitive disorders, senile dementia, vascular dementia, slight cognitive impairments, age-related amnesic deficits, cognitive impairments related to bacterial or viral infections, attention deficit hyperactivity disorders, schizophrenia, the treatment of inflammatory syndromes, ulcerative colitis, Crohn's disease, irritable bowel syndrome, arthritis, the treatment of acute or chronic pain, fibromyalgia, the treatment of acute neurone degeneration subsequent to a trauma, to strokes, to ischemia or to brain hypoxia, the treatment of chronic neural degeneration observed during Parkinson's disease, Huntington's chorea, multisystem atrophy, progressive supranuclear paralysis or amyotrophic lateral sclerosis, the treatment of epilepsy, the treatment of depression, of anxiety, of manic depressive psychoses, of obsessive/compulsive disorders, of phobias, of post-traumatic stress syndromes, of panic attacks, of Tourette's syndrome, of anorexia and of bulimia, and sleep disorders.

The compounds of formula (I) can also be used for establishing a decrease in the consumption of addictive substances, for helping to maintain an abstinence with respect to said substances or for reducing the symptoms of withdrawal therefrom.

The compounds of formula (I) can also be used as a diagnostic agent.

The following examples illustrate compositions according to the invention:

EXAMPLE A

Gelatin capsules containing a dose of 50 mg of active product, having the following composition, are prepared according to the conventional technique:

|  |  |
|---|---|
| Compound of formula (I) | 50 mg |
| Cellulose | 18 mg |
| Lactose | 55 mg |
| Colloidal silica | 1 mg |
| Sodium carboxymethylstarch | 10 mg |
| Talc | 10 mg |
| Magnesium stearate | 1 mg |

EXAMPLE B

Tablets containing a dose of 50 mg of active product, having the following composition, are prepared according to the conventional technique:

|  |  |
|---|---|
| Compound of formula (I) | 50 mg |
| Lactose | 104 mg |
| Cellulose | 40 mg |
| Polyvidone | 10 mg |
| Sodium carboxymethylstarch | 22 mg |
| Talc | 10 mg |
| Magnesium stearate | 2 mg |
| Colloidal silica | 2 mg |
| Mixture of hydroxymethylcellulose, glycerol, titanium oxide (72-3.5-24.5) qs 1 film-coated tablet with a final weight of 245 mg |  |

EXAMPLE C

An injectable solution containing 10 mg of active product, having the following composition, is prepared:

|  |  |
|---|---|
| Compound of formula (I) | 10 mg |
| Benzoic acid | 80 mg |
| Benzyl alcohol | 0.06 ml |
| Sodium benzoate | 80 mg |
| 95% ethanol | 0.4 ml |
| Sodium hydroxide | 24 mg |
| Propylene glycol | 1.6 ml |
| water | qs. 4 ml |

We claim:

1. A compound of formula (I):

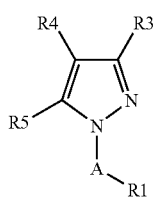

wherein:
A is a bond;
R1 is azetidinyl, pyrrolidinyl, (C5-C7) azacycloalkenyl, (C5-C9) azabicycloalkyl or (C5-C9) azabicycloalkenyl, these groups being optionally substituted with one or more substituents selected from the group consisting of (C1-C5) alkyl, (C3-C5) cycloalkyl and halogen;
A-R1 is such that the nitrogen of R1 and the nitrogen in the 1-position of the pyrazole are necessarily separated by at least two carbon atoms;

R3 is H, halogen, OH, SH, $NH_2$, ORc, SRc, SORa, $SO_2Ra$, NHCHO, NRaRb, NHC(O)Ra, NHC(S)Ra or $NHSO_2Ra$;

R4 is phenyl or heteroaryl selected from the group consisting of thienyl, pyridinyl, benzothienyl, and indolyl, wherein said phenyl and heteroaryl are optionally substituted with one or more substituents selected from the group consisting of halogen, CN, $NO_2$, $NH_2$, OH, SH, COOH, CHO, $C(O)NH_2$, $C(S)NH_2$, $SO_2H$, $SO_2NH_2$, NHCHO, C(O)Ra, C(O)ORa, C(O)NRaRb, C(S)NRaRb, S(O)Ra, $SO_2Ra$, $SO_2NRaRb$, ORc, SRc, O—C(O)Ra, —O—C(S)Ra, NRaRb, NHC(O)Ra, NHC(S)Ra, $NHCONH_2$, NHCONRaRb, $NHSO_2Ra$, aryl, heteroaryl, (C4-C7) heterocycloalkyl, polyfluoroalkyl, trifluoromethylsulfanyl, trifluoromethoxy, linear or branched (C1-C6) alkyl, (C2-C6) alkenyl and (C2-C6) alkynyl, these substituents being optionally substituted with one or more substituents selected from the group consisting of alkyl, halogen, OH, and methoxy;

R5 is H, halogen, $CF_3$, $CHF_2$, $CH_2F$, linear or branched (C1-C6) alkyl or (C3-C7) cycloalkyl;

Ra is linear or branched (C1-C6) alkyl, alkenyl, alkynyl, (C3-C7) cycloalkyl, (C5-C7) cycloalkenyl, (C4-C7) heterocycloalkyl, arylalkyl, heteroarylalkyl, aryl, heteroaryl or polyfluoroalkyl;

Rb is, independently of Ra, a hydrogen, linear or branched (C1-C6) alkyl, alkenyl, alkynyl, (C3-C7) cycloalkyl, (C5-C7) cycloalkenyl, (C4-C7) heterocycloalkyl, arylalkyl, heteroaryl-alkyl, aryl, heteroaryl or polyfluoroalkyl; or Ra and Rb taken together with the nitrogen atom to which they are attached form a saturated or unsaturated ring containing 5, 6 or 7 ring members, optionally containing one or more additional heteroatoms, wherein said heteroatoms are O, S or N, and wherein said ring is optionally substituted with one or more substituents selected from alkyl and halogen;

Rc is linear or branched (C1-C6) alkyl, (C3-C6) alkenyl, (C3-C6) alkynyl, (C3-C7) cycloalkyl, (C5-C7) cycloalkenyl, (C4-C7) heterocycloalkyl, heteroarylalkyl, heteroaryl, polyfluoroalkyl, C(O)R8, C(S)R8 or $SO_2R8$;

R6 and R7 are, independently of one another, a hydrogen, (C1-C6) alkyl, (C3-C6) alkenyl, (C3-C6) alkynyl, (C3-C7) cycloalkyl, (C5-C7) cycloalkenyl, (C4-C7) heterocycloalkyl, an arylalkyl or heteroarylalkyl; or R6 and R7 taken together with the nitrogen atom to which they are attached form a saturated or unsaturated ring with 5, 6 or 7 ring members, optionally containing one or more additional heteroatoms, wherein said heteroatoms are O, S or N and wherein said ring is optionally substituted with one or more substituents selected from alkyl and halogen; and R8 is Ra or NRaRb, or a racemate, an enantiomer or a diastereoisomer, or a mixture in any combination thereof, a tautomer or a pharmaceutically acceptable salt thereof 2. The compound of claim 1 wherein A is a bond;
R1 is azetidinyl, pyrrolidinyl, (C5-C7) azacycloalkenyl, (C5-C9) azabicycloalkyl or (C5-C9) azabicycloalkenyl, these groups being optionally substituted with one or more substituents selected from the group consisting of (C1-C5) alkyl, (C3-C5) cycloalkyl and halogen;
A-R1 is such that the nitrogen of R1 and the nitrogen in the 1-position of the pyrazole are necessarily separated by at least two carbon atoms;

R3 is OH, NH₂, OCH₃ or H;
R4 is phenyl or heteroaryl selected from the group consisting of thienyl, pyridinyl, benzothienyl, and indolyl, wherein said phenyl and heteroaryl are optionally substituted with one or more substituents selected from the group consisting of halogen, CN, NO₂, NH₂, OH, SH, COOH, CHO, C(O)NH₂, C(S)NH₂, SO₂H, SO₂NH₂, NHCHO, C(O)Ra, C(O)ORa, C(O)NRaRb, C(S)NRaRb, S(O)Ra, SO₂Ra, SO₂NRaRb, ORc, SRc, O—C(O)Ra, —O—C(S)Ra, NRaRb, NHC(O)Ra, NHC(S)Ra, NHCONH₂, NHCONRaRb, NHSO₂Ra, aryl, heteroaryl, (C4-C7) heterocycloalkyl, polyfluoroalkyl, trifluoromethylsulfanyl, trifluoromethoxy, linear or branched (C1-C6) alkyl, (C2-C6) alkenyl and (C2-C6) alkynyl, these substituents being optionally substituted with one or more alkyl, halogen, OH, or methoxy substituents;
R5 is hydrogen or methyl;
Ra is linear or branched (C1-C6) alkyl, alkenyl, alkynyl, (C3-C7) cycloalkyl, (C5-C7) cycloalkenyl, (C4-C7) heterocycloalkyl, arylalkyl, heteroarylalkyl, aryl, heteroaryl or polyfluoroalkyl;
Rb is, independently of Ra, a hydrogen, linear or branched (C1-C6) alkyl, alkenyl, alkynyl, (C3-C7) cycloalkyl, (C5-C7) cycloalkenyl, (C4-C7) heterocycloalkyl, arylalkyl, heteroaryl -alkyl, aryl, heteroaryl or polyfluoroalkyl; or
Ra and Rb taken together with the nitrogen atom to which they are attached form a saturated or unsaturated ring containing 5, 6 or 7 ring members, optionally containing one or more additional heteroatoms wherein said heteroatoms are O, S or N, and wherein said ring is optionally substituted with one or more substituents selected from alkyl and halogen;
Rc is a linear or branched (C1-C6) alkyl, (C3-C6) alkenyl, (C3-C6) alkynyl, (C3-C7) cycloalkyl, (C5-C7) cycloalkenyl, (C4-C7) heterocycloalkyl, heteroarylalkyl, heteroaryl, polyfluoroalkyl, C(O)R8, C(S)R8 or SO₂R8;
R6 and R7 are, independently of one another, hydrogen, (C1-C6) alkyl, (C3-C6) alkenyl, (C3-C6) alkynyl, (C3-C7) cycloalkyl, (C5-C7) cycloalkenyl, (C4-C7) heterocycloalkyl, arylalkyl or heteroarylalkyl;
R6 and R7 taken together with the nitrogen atom to which they are attached form a saturated or unsaturated ring with 5, 6 or 7 ring members, optionally containing one or more additional heteroatoms wherein said heteroatoms are O, S or N and wherein said ring is optionally substituted with one or more substituents selected from alkyl and halogen; and
R8 is an Ra or NRaRb;
or a racemate, an enantiomer or a diastereoisomer, or a mixture in any combination thereof, a tautomer or a pharmaceutically acceptable salt thereof.

3. The compound of claim 1 wherein A is a bond;
R1 is azetidinyl, pyrrolidinyl, (C5-C7) azacycloalkenyl, (C5-C9) azabicycloalkyl or (C5-C9) azabicycloalkenyl optionally substituted with one or more substituents selected from the group consisting of (C1-C5) alkyl, (C3-C5) cycloalkyl and halogen;
A-R1 is such that the nitrogen of R1 and the nitrogen in the 1-position of the pyrazole are necessarily separated by at least two carbon atoms;
R3 is OH, NH₂, OCH₃ or H;
R4 is phenyl or heteroaryl selected from the group consisting of thienyl, pyridinyl, benzothienyl, and indolyl, wherein said phenyl and heteroaryl are optionally substituted with one or more substituents selected from the group consisting of halogen, CN, NO₂, NH₂, OH, SH, COOH, CHO, C(O)NH₂, C(S)NH₂, SO₂H, SO₂NH₂, NHCHO, C(O)Ra, C(O)ORa, C(O)NRaRb, C(S)NRaRb, S(O)Ra, SO₂Ra, SO₂NRaRb, ORc, SRc, O—C(O)Ra, —O—C(S)Ra, NRaRb, NHC(O)Ra, NHC(S)Ra, NHCONH₂, NHCONRaRb, NHSO₂Ra, aryl, heteroaryl, (C4-C7) heterocycloalkyl, polyfluoroalkyl, trifluoromethylsulfanyl, trifluoromethoxy, linear or branched (C1-C6) alkyl, (C2-C6) alkenyl and (C2-C6) alkynyl, these substituents being optionally substituted with one or more alkyl, halogen, OH, or methoxy substituents;
R5 is hydrogen,
Ra is linear or branched (C1-C6) alkyl, alkenyl, alkynyl, (C3-C7) cycloalkyl, (C5-C7) cycloalkenyl, (C4-C7) heterocycloalkyl, arylalkyl, heteroarylalkyl, aryl, heteroaryl or polyfluoroalkyl;
Rb is, independently of Ra, a hydrogen, linear or branched (C1-C6) alkyl, alkenyl, alkynyl, (C3-C7) cycloalkyl, (C5-C7) cycloalkenyl, (C4-C7) heterocycloalkyl, arylalkyl, heteroaryl-alkyl, aryl, heteroaryl or polyfluoroalkyl; or
Ra and Rb taken together with the nitrogen atom to which they are attached form a saturated or unsaturated ring containing 5, 6 or 7 ring members, optionally containing one or more additional heteroatoms wherein said heteroatoms are O, S or N, and wherein said ring is optionally substituted with one or more substituents selected from alkyl and halogen;
Rc is linear or branched (C1-C6) alkyl, (C3-C6) alkenyl, (C3-C6) alkynyl, (C3-C7) cycloalkyl, (C5-C7) cycloalkenyl, (C4-C7) heterocycloalkyl, heteroarylalkyl, heteroaryl, polyfluoroalkyl, C(O)R8, C(S)R8 or SO₂R8;
R6 and R7 are, independently of one another, hydrogen, (C1-C6) alkyl, (C3-C6) alkenyl, (C3-C6) alkynyl, (C3-C7) cycloalkyl, (C5-C7) cycloalkenyl, (C4-C7) heterocycloalkyl, arylalkyl or heteroarylalkyl; or
R6 and R7 taken together with the nitrogen atom to which they are attached form a saturated or unsaturated ring with 5, 6 or 7 ring members, optionally containing one or more additional heteroatoms wherein said heteroatoms are O, S or N and wherein said ring is optionally substituted with one or more substituents selected from alkyl and halogen; and
R8 is Ra or NRaRb,
or a racemate, an enantiomer or a diastereoisomer, or a mixture in any combination thereof, a tautomer or a pharmaceutically acceptable salt thereof.

4. A compound selected from the group consisting of:
1-(1-Azabicyclo[2.2.2]oct-3-yl)-4-phenyl-1H-pyrazol-3-ol;
3-(3-Methoxy-4-phenylpyrazol-1-yl)-1-azabicyclo[2.2.2]octane;
1-(1-Azabicyclo[2.2.2]oct-3-yl)-4-(4-chlorophenyl)-1H-pyrazol-3-ol;
1-(1-Azabicyclo[2.2.2]oct-3-yl)-4-(3-chlorophenyl)-1H-pyrazol-3-ol;
1-(1-Azabicyclo[2.2.2]oct-3-yl)-4-(3-fluorophenyl)-1H-pyrazol-3-ol;
1-(1-Methylpyrrolidin-3-yl)-4-phenyl-1H-pyrazol-3-ol;
1-(Pyrrolidin-3-yl)-4-phenyl-1H-pyrazol-3-ol;
1-(1-Methylazepan-3-yl)-4-phenyl-1H-pyrazol-3-ol;
1-(1-Azabicyclo[2.2.2]oct-3-yl)-4-(1H-indol-5-yl)-1H-pyrazole;

(+)-1-(Azabicyclo[2.2.2]oct-3-yl)-4-(1H-indol-5-yl)-1H-pyrazole;
(−)-1-(Azabicyclo[2.2.2]oct-3-yl)-4-(1H-indol-5-yl)-1H-pyrazole;
1-(1-Azabicyclo[2.2.2]oct-3-yl)-4-(5-chlorothiophen-2-yl)-1H-pyrazol-3-ol;
1-(1-Azabicyclo[2.2.2]oct-3-yl)-4-(5-chlorothiophen-2-yl)-1H-pyrazol-3-ol;
3-[4-(3,5-Difluorophenyl)pyrazol-1-yl]-1-azabicyclo[2.2.2]octane;
(−)-1-(1-Azabicyclo[2.2.2]oct-3-yl)-4-phenyl-1H-pyrazol-3-ol;
(+)-1-(1-Azabicyclo[2.2.2]oct-3-yl)-4-phenyl-1H-pyrazol-3-ol;
(−)-1-(1-Azabicyclo[2.2.2]oct-3-yl)-4-(4-chlorophenyl)-1H-pyrazol-3-ol;
(+)-1-(1-Azabicyclo[2.2.2]oct-3-yl)-4-(4-chlorophenyl)-1H-pyrazol-3-ol;
(−)-1-(1-Azabicyclo[2.2.2]oct-3-yl)-4-(4-fluorophenyl)-1H-pyrazol-3-ol;
(+)-1-(1-Azabicyclo[2.2.2]oct-3-yl)-4-(4-fluorophenyl)-1H-pyrazol-3-ol;
3-[4-(4-Chlorophenyl)pyrazol-1-yl]-1-azabicyclo[2.2.2]octane;
4-[1-(1-Azabicyclo [2.2.2]oct-3-yl)-1H-pyrazol-4-yl]-2-chlorophenol;
(−)-4-[1-(1-Azabicyclo[2.2.2]oct-3-yl)-1H-pyrazol-4-yl]-2-chlorophenol;
(+)-4-[1-(1-Azabicyclo[2.2.2]oct-3-yl)-1H-pyrazol-4-yl]-2-chlorophenol;
(+)-1-(1-Azabicyclo[2.2.2]oct-3-yl)-4-pyridin-2-yl-1H-pyrazol-3-ol;
(−)-1-(1-Azabicyclo[2.2.2]oct-3-yl)-4-pyridin-2-yl-1H-pyrazol-3-ol;
(+)-1-(1-Azabicyclo[2.2.2]oct-3-yl)-4-phenyl-1H-pyrazol-3-ylamine;
(−)-1-(1-Azabicyclo[2.2.2]oct-3-yl)-4-phenyl-1H-pyrazol-3-ylamine;
(+)-1-(1-Azabicyclo[2.2.2]oct-3-yl)-4-(1H-indol-4-yl)-1H-pyrazole; and
(−)-1-(1-Azabicyclo[2.2.2]oct-3-yl)-4-(1H-indol-4-yl)-1H-pyrazole;

or a racemate, an enantiomer or a diastereoisomer or a mixture in any combination thereof, a tautomer or a pharmaceutically acceptable salt thereof.

5. A method of modulating α7 nicotinic receptors to treat a disease or disorder selected from the group consisting of Alzheimer's disease and schizophrenia, comprising administering to a patient in need of said treatment an effective α7 nicotinic receptor modulating amount of a compound of formula (I):

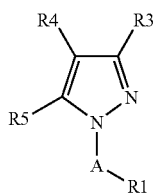

(I)

wherein:
A is a bond;
R1 is azetidinyl, pyrrolidinyl, (C5-C7) azacycloalkenyl, (C5-C9) azabicycloalkyl or (C5-C9) azabicycloalkenyl; these groups being optionally substituted with one or more substituents selected from the group consisting of (C1-5) alkyl, (C3-C5) cycloalkyl and halogen;
A-R1 is such that the nitrogen of R1 and the nitrogen in the 1-position of the pyrazole are necessarily separated by at least two carbon atoms;
R3 is H, halogen, OH, SH, $NH_2$, ORc, SRc, SORa, $SO_2Ra$, NHCHO, NRaRb, NHC(O)Ra, NHC(S)Ra or $NHSO_2Ra$;
R4 is phenyl or heteroaryl selected from the group consisting of thienyl, pyridinyl, benzothienyl, and indolyl, wherein said phenyl and heteroaryl are optionally substituted with one or more substituents selected from the group consisting of halogen, CN, $NO_2$, $NH_2$, OH, SH, COOH, CHO, $C(O)NH_2$, $C(S)NH_2$, $SO_2H$, $SO_2NH_2$, NHCHO, C(O)Ra, C(O)ORa, C(O)NRaRb, C(S)NRaRb, S(O)Ra, $SO_2Ra$, $SO_2NRaRb$, ORc, SRc, O—C(O)Ra, —O—C(S)Ra, NRaRb, NHC(O)Ra, NHC(S)Ra, $NHCONH_2$, NHCONRaRb, $NHSO_2Ra$, aryl, heteroaryl, (C4-C7) heterocycloalkyl, polyfluoroalkyl, trifluoromethylsulfanyl, trifluoromethoxy, linear or branched (C1-C6) alkyl, (C2-C6) alkenyl and (C2-C6) alkynyl, these substituents being optionally substituted with one or more substituents selected from the group consisting of alkyl, halogen, OH, and methoxy;
R5 is H, halogen, $CF_3$, $CHF_2$, $CH_2F$, linear or branched (C1-C6) alkyl or (C3-C7) cycloalkyl;
Ra is linear or branched (C1-C6) alkyl, alkenyl, alkynyl, (C3-C7) cycloalkyl, (C5-C7) cycloalkenyl, (C4-C7) heterocycloalkyl, arylalkyl, heteroarylalkyl, aryl, heteroaryl or polyfluoroalkyl;
Rb is, independently of Ra, hydrogen, linear or branched (C1-C6) alkyl, alkenyl, alkynyl, (C3-C7) cycloalkyl, (C5-C7) cycloalkenyl, (C4-C7) heterocycloalkyl, arylalkyl, heteroaryl-alkyl, aryl, heteroaryl or polyfluoroalkyl; or
Ra and Rb taken together with the nitrogen atom to which they are attached form a saturated or unsaturated ring containing 5, 6 or 7 ring members, optionally containing one or more additional heteroatoms wherein said heteroatoms are O, S or N, and wherein said ring is optionally substituted with one or more substituents selected from alkyl and halogen;
Rc is a linear or branched (C1-C6) alkyl, (C3-C6) alkenyl, (C3-C6) alkynyl, (C3-C7) cycloalkyl, (C5-C7) cycloalkenyl, (C4-C7) heterocycloalkyl, heteroarylalkyl, heteroaryl, polyfluoroalkyl, C(O)R8, C(S)R8 or $SO_2R8$;
R6 and R7 are, independently of one another, a hydrogen, (C1-C6) alkyl, (C3-C6) alkenyl, (C3-C6) alkynyl, (C3-C7) cycloalkyl, (C5-C7) cycloalkenyl, (C4-C7) heterocycloalkyl, arylalkyl or heteroarylalkyl; or
R6 and R7 taken together with the nitrogen atom to which they are attached form a saturated or unsaturated ring with 5, 6 or 7 ring members, optionally containing one or more additional heteroatoms wherein said heteroatoms are O, S or N and wherein said ring is optionally substituted with one or more substituents selected from alkyl and halogen; and
R8 is an Ra or NRaRb;
or a racemate, an enantiomer or a diastereoisomer, or a mixture in any combination thereof, a tautomer or a pharmaceutically acceptable salt thereof.

6. The method of claim 5 wherein A is a bond;
R1 is azetidinyl, pyrrolidinyl, (C5-C7) azacycloalkenyl, (C5-C9) azabicycloalkyl or (C5-C9) azabicycloalkenyl, these groups being optionally substituted with one or more substituents selected from the group consisting of (C1-C5) alkyl, (C3-C5) cycloalkyl and halogen, A-R1 is such that the nitrogen of R1 and the nitrogen in the 1-position of the pyrazole are necessarily separated by at least two carbon atoms;

R3 is OH, NH$_2$, OCH$_3$ or H;

R4 is phenyl or heteroaryl selected from the group consisting of thienyl, pyridinyl, benzothienyl, and indolyl, wherein said phenyl and heteroaryl are optionally substituted with one or more substituents selected from the group consisting of halogen, CN, NO$_2$, NH$_2$, OH, SH, COOH, CHO, C(O)NH$_2$, C(S)NH$_2$, SO$_2$H, SO$_2$NH$_2$, NHCHO, C(O)Ra, C(O)ORa, C(O)NRaRb, C(S)NRaRb, S(O)Ra, SO$_2$Ra, SO$_2$NRaRb, ORc, SRc, O—C(O)Ra, —O—C(S)Ra, NRaRb, NHC(O)Ra, NHC(S)Ra, NHCONH$_2$, NHCONRaRb, NHSO$_2$Ra, aryl, heteroaryl, (C4-C7) heterocycloalkyl, polyfluoroalkyl, trifluoromethylsulfanyl, trifluoromethoxy, linear or branched (C1-C6) alkyl, (C2-C6) alkenyl and (C2-C6) alkynyl, these substituents being optionally substituted with one or more alkyl, halogen, OH, or methoxy substituents;

R5 is a hydrogen or methyl;

Ra is linear or branched (C1-C6) alkyl, alkenyl, alkynyl, (C3-C7) cycloalkyl, (C5-C7) cycloalkenyl, (C4-C7) heterocycloalkyl, arylalkyl, heteroarylalkyl, aryl, heteroaryl or polyfluoroalkyl;

Rb is, independently of Ra, a hydrogen, linear or branched (C1-C6) alkyl, alkenyl, alkynyl, (C3-C7) cycloalkyl, (C5-C7) cycloalkenyl, (C4-C7) heterocycloalkyl, arylalkyl, heteroaryl-alkyl, aryl, heteroaryl or polyfluoroalkyl; or Ra and Rb taken together with the nitrogen atom to which they are attached form a saturated or unsaturated ring containing 5, 6 or 7 ring members, optionally containing one or more additional heteroatoms wherein said heteroatoms are O, S or N, and wherein said ring is optionally substituted with one or more substituents selected from alkyl and halogen;

Rc is a linear or branched (C1-C6) alkyl, (C3-C6) alkenyl, (C3-C6) alkynyl, (C3-C7) cycloalkyl, (C5-C7) cycloalkenyl, (C4-C7) heterocycloalkyl, heteroarylalkyl, heteroaryl, polyfluoroalkyl, C(O)R8, C(S)R8 or SO$_2$R8;

R6 and R7 are, independently of one another, a hydrogen, (C1-C6) alkyl, (C3-C6) alkenyl, (C3-C6) alkynyl, (C3-C7) cycloalkyl, (C5-C7) cycloalkenyl, (C4-C7) heterocycloalkyl, arylalkyl or heteroarylalkyl; or R6 and R7 taken together with the nitrogen atom to which they are attached form a saturated or unsaturated ring with 5, 6 or 7 ring members, optionally containing one or more additional heteroatoms wherein said heteroatoms are O, S or N and wherein said ring is optionally substituted with one or more substituents selected from alkyl and halogen; and R8 is an Ra or NRaRb;

or a racemate, an enantiomer or a diastereoisomer, or a mixture in any combination thereof, a tautomer or a pharmaceutically acceptable salt thereof.

7. The method of claim 5 wherein A is a bond;

R1 is azetidinyl, pyrrolidinyl, (C5-C7) azacycloalkenyl, (C5-C9) azabicycloalkyl or (C5-C9) azabicycloalkenyl, these groups being optionally substituted with one or more substituents selected from the group consisting of (C1-C5) alkyl, (C3-C5) cycloalkyl and halogen;

A-R1 is such that the nitrogen of R1 and the nitrogen in the 1-position of the pyrazole are necessarily separated by at least two carbon atoms;

R3 is OH, NH$_2$, OCH$_3$ or H;

R4 is phenyl or heteroaryl selected from the group consisting of thienyl, pyridinyl, benzothienyl, and indolyl, wherein said phenyl and heteroaryl are optionally substituted with one or more substituents selected from the group consisting of halogen, CN, NO$_2$, NH$_2$, OH, SH, COOH, CHO, C(O)NH$_2$, C(S)NH$_2$, SO$_2$H, SO$_2$NH$_2$, NHCHO, C(O)Ra, C(O)ORa, C(O)NRaRb, C(S)NRaRb, S(O)Ra, SO$_2$Ra, SO$_2$NRaRb, ORc, SRc, O—C(O)Ra, —O—C(S)Ra, NRaRb, NHC(O)Ra, NHC(S)Ra, NHCONH$_2$, NHCONRaRb, NHSO$_2$Ra, aryl, heteroaryl, (C4-C7) heterocycloalkyl, polyfluoroalkyl, trifluoromethylsulfanyl, trifluoromethoxy, linear or branched (C1-C6) alkyl, (C2-C6) alkenyl and (C2-C6) alkynyl, these substituents being optionally substituted with one or more alkyl, halogen, OH, or methoxy substituents;

R5 is hydrogen;

Ra is linear or branched (C1-C6) alkyl, alkenyl, alkynyl, (C3-C7) cycloalkyl, (C5-C7) cycloalkenyl, (C4-C7) heterocycloalkyl, arylalkyl, heteroarylalkyl, aryl, heteroaryl or polyfluoroalkyl;

Rb is, independently of Ra, a hydrogen, linear or branched (C1-C6) alkyl, alkenyl, alkynyl, (C3-C7) cycloalkyl, (C5-C7) cycloalkenyl, (C4-C7) heterocycloalkyl, arylalkyl, heteroaryl-alkyl, aryl, heteroaryl or polyfluoroalkyl; or Ra and Rb taken together with the nitrogen atom to which they are attached form a saturated or unsaturated ring containing 5, 6 or 7 ring members, optionally containing one or more additional heteroatoms wherein said heteroatoms are O, S or N, and wherein said ring is optionally substituted with one or more substituents selected from alkyl and halogen;

Rc is a linear or branched (C1-C6) alkyl, (C3-C6) alkenyl, (C3-C6) alkynyl, (C3-C7) cycloalkyl, (C5-C7) cycloalkenyl, (C4-C7) heterocycloalkyl, heteroarylalkyl, heteroaryl, polyfluoroalkyl, C(O)R8, C(S)R8 or SO$_2$R8;

R6 and R7 are, independently of one another, a hydrogen, (C1-C6) alkyl, (C3-C6) alkenyl, (C3-C6) alkynyl, (C3-C7) cycloalkyl, (C5-C7) cycloalkenyl, (C4-C7) heterocycloalkyl, arylalkyl or heteroarylalkyl; or R6 and R7 taken together with the nitrogen atom to which they are attached form a saturated or unsaturated ring with 5, 6 or 7 ring members, optionally containing one or more heteroatoms wherein said heteroatoms are O, S or N and wherein said ring is optionally substituted with one or more substituents selected from alkyl and halogen; and R8 is an Ra or NRaRb;

or a racemate, an enantiomer or a diastereoisomer, or a mixture in any combination thereof, a tautomer or a pharmaceutically acceptable salt thereof.

8. The method of claim 5 wherein the disease is Alzheimer's disease.

9. The method of claim 5 wherein the disease is schizophrenia.

10. A method of treating drug addiction, in a patient in need thereof comprising administering to said patient a therapeutically effective amount of a compound of formula (I):

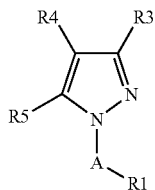

wherein:

A is a bond;

R1 is azetidinyl, pyrrolidinyl, (C5-C7) azacycloalkenyl, (C5-C9) azabicycloalkyl or (C5-C9) azabicycloalkenyl; these groups being optionally substituted with one or more substituents selected from the group consisting of (C1-C5) alkyl, (C3-C5) cycloalkyl and halogen;

A-R1 is such that the nitrogen of R1 and the nitrogen in the 1-position of the pyrazole are necessarily separated by at least two carbon atoms;

R3 is H, halogen, OH, SH, $NH_2$, ORc, SRc, SORa, $SO_2Ra$, NHCHO, NRaRb, NHC(O)Ra, NHC(S)Ra or $NHSO_2Ra$;

R4 is phenyl or heteroaryl selected from the group consisting of thienyl, pyridinyl, benzothienyl, and indolyl, wherein said phenyl and heteroaryl are optionally substituted with one or more substituents selected from the group consisting of halogen, CN, $NO_2$, $NH_2$, OH, SH, COOH, CHO, $C(O)NH_2$, $C(S)NH_2$, $SO_2H$, $SO_2NH_2$, NHCHO, C(O)Ra, C(O)ORa, C(O)NRaRb, C(S)NRaRb, S(O)Ra, $SO_2Ra$, $SO_2NRaRb$, ORc, SRc, O—C(O)Ra, —O—C(S)Ra, NRaRb, NHC(O)Ra, NHC(S)Ra, $NHCONH_2$, NHCONRaRb, $NHSO_2Ra$, aryl, heteroaryl, (C4-C7) heterocycloalkyl, polyfluoroalkyl, trifluoromethylsulfanyl, trifluoromethoxy, linear or branched (C1-C6) alkyl, (C2-C6) alkenyl and (C2-C6) alkynyl, these substituents being optionally substituted with one or more substituents selected from the group consisting of alkyl, halogen, OH, and methoxy;

R5 is H, halogen, $CF_3$, $CHF_2$, $CH_2F$, linear or branched (C1-C6) alkyl or (C3-C7) cycloalkyl;

Ra is linear or branched (C1-C6) alkyl, alkenyl, alkynyl, (C3-C7) cycloalkyl, (C5-C7) cycloalkenyl, (C4-C7) heterocycloalkyl, arylalkyl, heteroarylalkyl, aryl, heteroaryl or polyfluoroalkyl;

Rb is, independently of Ra, hydrogen, linear or branched (C1-C6) alkyl, alkenyl, alkynyl, (C3-C7) cycloalkyl, (C5-C7) cycloalkenyl, (C4-C7) heterocycloalkyl, arylalkyl, heteroaryl-alkyl, aryl, heteroaryl or polyfluoroalkyl; or Ra and Rb taken together with the nitrogen atom to which they are attached form a saturated or unsaturated ring containing 5, 6 or 7 ring members, optionally containing one or more additional heteroatoms wherein said heteroatoms are O, S or N, and wherein said ring is optionally substituted with one or more substituents selected from alkyl and halogen;

Rc is a linear or branched (C1-C6) alkyl, (C3-C6) alkenyl, (C3-C6) alkynyl, (C3-C7) cycloalkyl, (C5-C7) cycloalkenyl, (C4-C7) heterocycloalkyl, heteroarylalkyl, heteroaryl, polyfluoroalkyl, C(O)R8, C(S)R8 or $SO_2R8$;

R6 and R7 are, independently of one another, a hydrogen, (C1-C6) alkyl, (C3-C6) alkenyl, (C3-C6) alkynyl, (C3-C7) cycloalkyl, (C5-C7) cycloalkenyl, (C4-C7) heterocycloalkyl, arylalkyl or heteroarylalkyl; or R6 and R7 taken together with the nitrogen atom to which they are attached form a saturated or unsaturated ring with 5, 6 or 7 ring members, optionally containing one or more additional heteroatoms wherein said heteroatoms are O, S or N and wherein said ring is optionally substituted with one or more substituents selected from alkyl and halogen; and R8 is an Ra or NRaRb;

or a racemate, an enantiomer or a diastereoisomer, or a mixture in any combination thereof, a tautomer or a pharmaceutically acceptable salt thereof.

11. A pharmaceutical composition, comprising a compound of formula (I) according to claim 1 and a pharmaceutically acceptable medium.

12. A pharmaceutical composition, comprising a compound of formula (I) according to claim 4 and a pharmaceutically acceptable medium.

13. A process for preparing a compound of formula (I) as defined in claim 1 wherein R3 is OH, from a compound of formula(II)

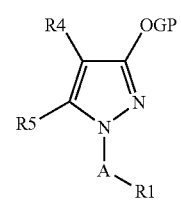

wherein GP is a hydroxyl function-protecting group, comprising removing the hydroxyl function-protecting group and optionally converting the product into a pharmaceutically acceptable salt.

14. A process for preparing the compounds of formula (I) as defined in claim 1, wherein R3 is ORc, H or $NH_2$, comprising the steps of:

1.) alkylating a pyrazole of formula (III)

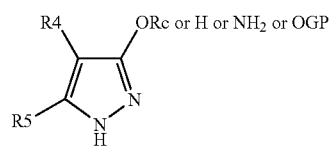

wherein GP is an OH function-protecting group, with a compound of formula (IV) R1-A-X wherein X is Cl, Br, I, OTs, OMs or OTf, in basic medium in an aprotic solvent, 2.) optionally removing the OH function-protecting group from the product of step 1; and 3.) optionally forming a pharmaceutically acceptable salt.

15. A pharmaceutical composition, comprising a compound of formula (I) according to claim 2 and a pharmaceutically acceptable medium.

16. A pharmaceutical composition, comprising a compound of formula (I) according to claim 3 and a pharmaceutically acceptable medium.

17. A compound of formula (Ia):

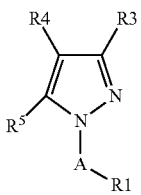

wherein:
A is a bond;
R1 is (C4-C7) azacycloalkyl, (C5-C7) azacycloalkenyl, (C5-C9) azabicycloalkyl or (C5-C9) azabicycloalkenyl, these groups being optionally substituted with one or more substituents selected from the group consisting of (C1-C5) alkyl, (C3-C5) cycloalkyl and halogen;
A-R1 is such that the nitrogen of R1 and the nitrogen in the 1-position of the pyrazole are necessarily separated by at least two carbon atoms;
R3 is H, halogen, OH, SH, $NH_2$, ORc, SRc, SORa, $SO_2Ra$, NHCHO, NRaRb, NHC(O)Ra, NHC(S)Ra or $NHSO_2Ra$;
R4 is phenyl or heteroaryl selected from the group consisting of thienyl, pyridinyl, benzothienyl, and indolyl, wherein said phenyl and heteroaryl are optionally substituted with one or more substituents selected from the group consisting of halogen, CN, $NO_2$, $NH_2$, OH, SH, COOH, CHO, $C(O)NH_2$, $C(S)NH_2$, $SO_2H$, $SO_2NH_2$, NHCHO, C(O)Ra, C(O)ORa, C(O)NRaRb, C(S)NRaRb, S(O)Ra, $SO_2Ra$, $SO_2NRaRb$, ORc, SRc, O—C(O)Ra, —O—C(S)Ra, NRaRb, NHC(O)Ra, NHC(S)Ra, $NHCONH_2$, NHCONRaRb, $NHSO_2Ra$, aryl, heteroaryl, (C4-C7) heterocycloalkyl, polyfluoroalkyl, trifluoromethylsulfanyl, trifluoromethoxy, linear or branched (C1-C6) alkyl, (C2-C6) alkenyl and (C2-C6) alkynyl, these substituents being optionally substituted with one or more substituents selected from the group consisting of alkyl, halogen, OH, and methoxy;
R5 is H, halogen, $CF_3$, $CHF_2$, $CH_2F$, or (C3-C7) cycloalkyl;
Ra is linear or branched (C1-C6) alkyl, alkenyl, alkynyl, (C3-C7) cycloalkyl, (C5-C7) cycloalkenyl, (C4-C7) heterocycloalkyl, arylalkyl, heteroarylalkyl, aryl, heteroaryl or polyfluoroalkyl;
Rb is, independently of Ra, a hydrogen, linear or branched (C1-C6) alkyl, alkenyl, alkynyl, (C3-C7) cycloalkyl, (C5-C7) cycloalkenyl, (C4-C7) heterocycloalkyl, arylalkyl, heteroaryl-alkyl, aryl, heteroaryl or polyfluoroalkyl; or
Ra and Rb taken together with the nitrogen atom to which they are attached form a saturated or unsaturated ring containing 5, 6 or 7 ring members, optionally containing one or more additional heteroatoms, wherein said heteroatoms are O, S or N, and wherein said ring is optionally substituted with one or more substituents selected from alkyl and halogen;
Rc is linear or branched (C1-C6) alkyl, (C3-C6) alkenyl, (C3-C6) alkynyl, (C3-C7) cycloalkyl, (C5-C7) cycloalkenyl, (C4-C7) heterocycloalkyl, heteroarylalkyl, heteroaryl, polyfluoroalkyl, C(O)R8, C(S)R8 or $SO_2R8$;
R6 and R7 are, independently of one another, a hydrogen, (C1-C6) alkyl, (C3-C6) alkenyl, (C3-C6) alkynyl, (C3-C7) cycloalkyl, (C5-C7) cycloalkenyl, (C4-C7) heterocycloalkyl, an arylalkyl or heteroarylalkyl; or
R6 and R7 taken together with the nitrogen atom to which they are attached form a saturated or unsaturated ring with 5, 6 or 7 ring members, optionally containing one or more additional heteroatoms, wherein said heteroatoms are O, S or N and wherein said ring is optionally substituted with one or more substituents selected from alkyl and halogen; and
R8 is Ra or NRaRb,
or a racemate, an enantiomer or a diastereoisomer, or a mixture in any combination thereof, a tautomer or a pharmaceutically acceptable salt thereof.

* * * * *